US008895535B2

(12) United States Patent
Heinrich et al.

(10) Patent No.: US 8,895,535 B2
(45) Date of Patent: Nov. 25, 2014

(54) PYRROLIDINONES AS METAP-2 INHIBITORS

(75) Inventors: Timo Heinrich, Gross-Umstadt (DE); Frank Zenke, Darmstadt (DE); Michel Calderini, Darmstadt (DE); Djordje Musil, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/878,574

(22) PCT Filed: Sep. 14, 2011

(86) PCT No.: PCT/EP2011/004608
§ 371 (c)(1),
(2), (4) Date: Apr. 10, 2013

(87) PCT Pub. No.: WO2012/048775
PCT Pub. Date: Apr. 19, 2012

(65) Prior Publication Data
US 2013/0296274 A1 Nov. 7, 2013

(30) Foreign Application Priority Data

Oct. 13, 2010 (DE) .................. 10 2010 048 374

(51) Int. Cl.
| | | |
|---|---|---|
| *C07D 401/14* | (2006.01) | |
| *C07D 409/12* | (2006.01) | |
| *C07D 413/12* | (2006.01) | |
| *C07D 401/10* | (2006.01) | |
| *C07F 5/02* | (2006.01) | |
| *A61K 31/4025* | (2006.01) | |
| *A61K 31/422* | (2006.01) | |
| *A61K 31/433* | (2006.01) | |
| *A61K 31/4709* | (2006.01) | |
| *A61K 31/5377* | (2006.01) | |
| *A61K 31/69* | (2006.01) | |
| *A61K 45/06* | (2006.01) | |
| *C07D 405/12* | (2006.01) | |
| *C07D 403/04* | (2006.01) | |
| *C07D 417/12* | (2006.01) | |
| *C07D 405/14* | (2006.01) | |
| *A61K 31/4245* | (2006.01) | |
| *C07D 401/04* | (2006.01) | |
| *A61K 31/4439* | (2006.01) | |
| *C07D 403/12* | (2006.01) | |
| *C07D 207/277* | (2006.01) | |
| *C07D 401/12* | (2006.01) | |
| *C07D 413/10* | (2006.01) | |
| *C07D 401/06* | (2006.01) | |
| *C07D 405/04* | (2006.01) | |

(52) U.S. Cl.
CPC ............ *C07D 401/14* (2013.01); *A61K 31/422* (2013.01); *C07D 405/12* (2013.01); *C07D 403/04* (2013.01); *C07D 417/12* (2013.01); *C07D 405/14* (2013.01); *C07D 409/12* (2013.01); *A61K 31/4709* (2013.01); *A61K 31/4245* (2013.01); *A61K 31/69* (2013.01); *C07D 401/04* (2013.01); *A61K 31/4439* (2013.01); *C07D 403/12* (2013.01); *A61K 31/4025* (2013.01); *C07D 401/10* (2013.01); *C07D 207/277* (2013.01); *C07D 401/12* (2013.01); *C07D 413/12* (2013.01); *A61K 31/5377* (2013.01); *C07D 413/10* (2013.01); *C07F 5/025* (2013.01); *A61K 31/433* (2013.01); *C07D 401/06* (2013.01); *C07D 405/04* (2013.01); *A61K 45/06* (2013.01)
USPC ............ 514/64; 514/422; 514/374; 514/364; 514/363; 514/343; 514/314; 514/312; 514/235.5; 548/527; 548/235; 548/131; 548/405; 546/171; 546/158

(58) Field of Classification Search
USPC ........... 514/64, 422, 374, 364, 363, 343, 314, 514/312, 235.5; 548/527, 235, 131, 405; 546/171, 158
See application file for complete search history.

(56) References Cited

U.S. PATENT DOCUMENTS

| | | |
|---|---|---|
| 7,355,053 B2 | 4/2008 | Reinhard et al. |
| 2006/0019831 A1 | 1/2006 | Reinhard et al. |
| 2007/0123508 A1 | 5/2007 | Olsson et al. |
| 2009/0264650 A1 | 10/2009 | Cho et al. |
| 2011/0313156 A1 | 12/2011 | Engelhardt et al. |

FOREIGN PATENT DOCUMENTS

| | | |
|---|---|---|
| EP | 1864971 A1 | 12/2007 |
| WO | 2004037787 A1 | 5/2004 |
| WO | 2006127396 A1 | 11/2006 |
| WO | 2010007114 A2 | 1/2010 |

OTHER PUBLICATIONS

International Search Report for PCT/EP2011/004608 dated Dec. 20, 2011.
Xiaochun Chen et al. "Fumagillin and Fumarranol Interact with *P. falciparum* Methionine Aminopeptidase 2 and Inhibit Malaria Parasite Growth In Vitro and In Vivo" Chemistry & Biology 16, pp. 193-202, Feb. 27, 2009.
Henri R. Lijnen et al. "Fumagillin Reduces Adipose Tissue Formation in Murine Models of Nutritionally Induced Obesity" Adipocyte Biology, Obesity, vol. 18, No. 12, Dec. 2010, pp. 2241-2246.
Tanja Y. Reuter "Diet-induced models for obesity and type 2 diabetes" Elsevier, Drug Discovery Today: Disease Models, vol. 4, No. 1, 2007, pp. 3-8.

*Primary Examiner* — Samantha Shterengarts
*Assistant Examiner* — Amanda L Aguirre
(74) *Attorney, Agent, or Firm* — Millen, White, Zelano & Branigan, P.C.

(57) ABSTRACT

Compounds of the formula I in which $R^1$, $R^2$, $R^3$ and $R^4$ have the meanings indicated in Claim 1, are inhibitors of methionine aminopeptidase and can be employed for the treatment of tumors.

15 Claims, No Drawings

PYRROLIDINONES AS METAP-2 INHIBITORS

The invention relates to compounds of the formula I

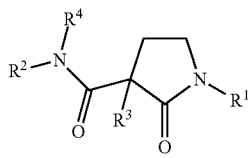

in which
$R^1$ denotes $(CH_2)_nAr^1$, $(CH_2)_n$Het, $(CH_2)_n$Cyc,

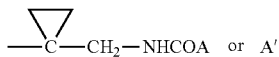

$R^2$ denotes $(CH_2)_nAr^2$, $CH[B(OH)_2]CH_2$Het,

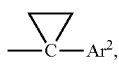

CH(C≡CH)phenyl, $(CH_2)_n$Het, $(CH_2)_n$Cyc or A,
$R^3$ denotes OH, Hal, $NH_2$, CN, $CF_3$, $CHF_2$ or $N_3$,
$R^4$ denotes H or alkyl having 1, 2, 3 or 4 C atoms,
$R^2$ and $R^4$ together also denote alkylene having 2, 3, 4 or 5 C atoms, where one $CH_2$ group may also be replaced by NH, NA, N—COA, N—$(CH_2)_nAr^3$, N—$(CH_2)_n$Het$^2$, CH-A, CH—O—$(CH_2)_nAr^3$, N—$SO_2$A or O and/or may be substituted by A,
$Ar^1$ denotes phenyl, naphthyl or biphenyl, each of which is unsubstituted or mono-, di-, tri-, tetra- or pentasubstituted by Hal, A, OH, OA, $NH_2$, NHA, $NA_2$, $NO_2$, CN, COOH, COOA, $CONH_2$, CONHA, $CONA_2$, NHCOA, $NHSO_2A$, COA, CHO, Het$^1$, $SO_2NH_2$ and/or $SO_2A$,
$Ar^2$ denotes phenyl, naphthyl or biphenyl, each of which is unsubstituted or mono-, di-, tri-, tetra- or pentasubstituted by Hal, A, OH, OA, $NH_2$, NHA, $NA_2$, $NO_2$, CN, COOH, COOA, $CONH_2$, CONHA, $CONA_2$, NHCOA, $NHSO_2A$, COA, CHO, Het$^1$, $SO_2NH_2$ and/or $SO_2A$,
$Ar^3$ denotes phenyl which is unsubstituted or mono-, di- or trisubstituted by Hal, OH, OA and/or A,
Het denotes a mono- or bicyclic saturated, unsaturated or aromatic heterocycle having 1 to 4 N, and/or O and/or S atoms which is unsubstituted or mono-, di- or trisubstituted by Hal, A, OH, OA, $NH_2$, NHA, $NA_2$, $NO_2$, CN, COOH, COOA, $(CH_2)_nCONH_2$, $(CH_2)_nCONHA$, $(CH_2)_nCONA_2$, NHCOA, $NHSO_2A$, COA, CHO, Het$^1$, $SO_2NH_2$, $SO_2A$ and/or =O,
Het$^1$ denotes a monocyclic saturated, unsaturated or aromatic heterocycle having 1 to 4 N, and/or O and/or S atoms which is unsubstituted or mono-, di- or trisubstituted by Hal, A, OH, OA, $NH_2$, NHA, $NA_2$, $NO_2$, CN, COOH and/or COOA,
Het$^2$ denotes pyridyl, pyrimidinyl, furyl, thienyl, imidazolyl, pyrrolyl, oxazolyl, oxadiazolyl, isoxazolyl, thiazolyl, triazolyl, tetrazolyl or thiadiazole,
A denotes unbranched or branched alkyl having 1-10 C atoms, in which 1-7H atoms may be replaced by F, Cl, Br, OH, CHO, COA, COOA, CN, $CONA_2$, CONHA and/or $CONH_2$,
and/or in which one or two non-adjacent CH and/or $CH_2$ groups may be replaced by O, N and/or $NR^4$,
or Cyc,
Cyc denotes cyclic alkyl having 3-7 C atoms,
Hal denotes F, Cl, Br or I,
n denotes 0, 1, 2, 3 or 4,
and pharmaceutically usable salts, tautomers and stereoisomers thereof, including mixtures thereof in all ratios.

The invention was based on the object of finding novel compounds having valuable properties, in particular those which can be used for the preparation of medicaments.

It has been found that the compounds of the formula I and salts thereof have very valuable pharmacological properties while being well tolerated.

In particular, they exhibit a regulatory, modulatory and/or inhibiting action on metal proteases, preferably on methionine aminopeptidase (MetAP), particularly on the sub-type MetAP-2.

They can be used as medicaments against cancer, but also as medicaments which positively influence fat metabolism, but also as medicaments against inflammation.

It has been found that the S enantiomer of the compounds according to the invention is significantly more active against MetAP-2 than the mirror image (R enantiomer).

Other hydroxyl-substituted pyrrolidinones are known from:
Zeitschrift für Naturforschung, B: Chemical Sciences (1994), 49(11), 1586-95;
Analytica Chimica Acta (1987), 202, 167-74;
Journal of Electroanalytical Chemistry and Interfacial Electrochemistry (1988), 239(1-2), 161-73;
Zeitschrift fuer Naturfor. Part B: Anorg. Chem. Org. Chem. (1978), 33B(12), 1540-6;
J. Chem. Soc. (1965), (October), 5556-62;
J. Chem. Soc. (1965), (October), 5551-6.

WO 01/79157 describes substituted hydrazides and N-alkoxyamides which have MetAP-2 inhibitory activity and can be used for the inhibition of angiogenesis, in particular for the treatment of diseases, such as, for example, cancer, whose development is dependent on angiogenesis.

WO 02/081415 describes MetAP-2 inhibitors which can be used for the treatment of cancer, haemangioma, proliferative retinopathy, rheumatoid arthritis, atherosclerotic neovascularisation, psoriasis, ocular neovascularisation and obesity.

WO 2008/011114 describes compounds as angiogenesis inhibitors and MetAP-2 inhibitors which can be used for the treatment of lymphoid leukaemia and lymphoma.

The action of the compounds according to the invention against cancer lies in particular in their action against angiogenesis. Angiogenesis inhibition has proven helpful in more than 70 diseases, such as, for example, ovarian cancer (F. Spinella et al. J. Cardiovasc. Pharmacol. 2004, 44, S140), breast cancer (A. Morabito et al. Crit. Rev. Oncol./Hematol. 2004, 49, 91), prostate cancer (B. Nicholson et al. Cancer Metastas. Rev. 2001, 20, 297), diabetic blindness, psoriasis and macular degeneration (E. Ng et al. Can. J. Ophthalmol. 2005, 23, 3706).

Proteases regulate many different cell processes, particularly the modulation of peptides and proteins, particularly protein conversion, protein ripening and signal peptide processing, the breakdown of abnormal proteins and the deactivation/activation of regulatory proteins. In particular, the amino-terminal modification of nascent polypeptides represents the most frequent modulation. Aminoproteases are metalloproteases which cleave off amino acids from the unprotected N terminus of peptides or proteins, which can be carried out in either a co- or post-translatory manner.

Methionine aminopeptidase (MetAP) cleaves terminal methionine of nascent peptides in particular if the penultimate amino acid is small and uncharged (for example Gly, Ala, Ser, Thr, Val, Pro or Cys).

In many disease processes, angiogenesis is either causally at the centre of the disease or has a worsening effect on the progression of the disease. In cancer events, for example, angiogenesis results in the tumour increasing in size and being able to enter other organs. Other diseases in which angiogenesis plays an important role are psoriasis, arthrosis, arteriosclerosis and eye diseases, such as diabetic retinopathy, age-induced macular degeneration, rubeosis iridis or neovascular glaucoma, furthermore in inflammations. The compounds of the formula I on which this invention is based, compositions which comprise these compounds, and the processes described can thus be employed for the treatment of these diseases.

Accordingly, the compounds according to the invention or a pharmaceutically acceptable salt thereof are administered for the treatment of cancer, including solid carcinomas, such as, for example, carcinomas (of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an anti-carcinogenic action. The compounds according to the invention are administered to a patient having a disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined. The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

It has been found that the compounds according to the invention cause specific inhibition of MetAP-2. The compounds according to the invention preferably exhibit an advantageous biological activity which can be detected in the tests described, for example, herein. In such tests, the compounds according to the invention exhibit and cause an inhibiting effect, which is usually documented by $IC_{50}$ values in a suitable range, preferably in the micromolar range and more preferably in the nanomolar range.

In addition, the compounds according to the invention can be used to achieve additive or synergistic effects in certain existing cancer chemotherapies and radiotherapies and/or to restore the efficacy of certain existing cancer chemotherapies and radiotherapies.

The compounds according to the invention can also be used for the treatment of obesity. Henri R. Lijnen et al. in Obesity, Vol. 18 no. 12, 2241-2246 (2010) describes the use of fumagillin, an Met-AP2 inhibitor, in the reduction of adipose tissue. The use of Met-AP2 inhibitors (compounds of the fumagillin type) for the treatment of obesity is also described in WO 2011/085201 A1.

The compounds according to the invention can also be used for the treatment of malaria. X. Chem et al. in Chemistry & Biology, Vol. 16, 193-202 (2009) describes the use of fumagillin, an Met-AP2 inhibitor, for the treatment of malaria.

The compounds according to the invention can also be used for the treatment of benign prostate hypertrophy.

The use of Met-AP2 inhibitors (compounds of the fumagillin type) for the treatment of benign prostate hypertrophy is described in WO 2011/085198 A1.

Compounds of the formula I are also taken to mean the hydrates and solvates of these compounds, furthermore pharmaceutically usable derivatives.

The invention also relates to the optically active forms (stereoisomers), salts, the enantiomers, the racemates, the diastereomers and the hydrates and solvates of these compounds. The term solvates of the compounds is taken to mean adductions of inert solvent molecules onto the compounds which form owing to their mutual attractive force. solvates are, for example, mono- or dihydrates or alkoxides.

The term pharmaceutically usable derivatives is taken to mean, for example, the salts of the compounds according to the invention and also so-called prodrug compounds. The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that
a) a compound of the formula II

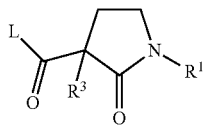

II in which $R^1$ and $R^3$ have the meanings indicated in claim 1, and L denotes Cl, Br, I or a free or reactively functionally modified OH group, is reacted with a compound of the formula III

 III in which $R^2$ and $R^4$ have the meanings indicated in claim 1, or
b) for the preparation of compounds of the formula I in which $R^3$ denotes OH,
a compound of the formula IV

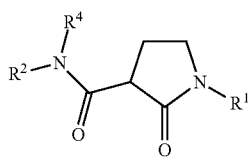

IV in which $R^1$, $R^2$ and $R^4$ have the meanings indicated in claim 1,
is oxidised,
or
c) a radical $R^3$ is converted into another radical $R^3$ by replacing an OH group with a halogen atom,
or replacing a halogen atom with $N_3$,
and/or a base or acid of the formula I is converted into one of its salts.

Above and below, the radicals $R^1$, $R^2$ and $R^3$ have the meanings indicated for the formula I, unless expressly indicated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A preferably denotes unbranched or branched alkyl having 1-6 C atoms, in which 1-7H atoms may be replaced by F, Cl, Br and/or OH,
or Cyc.

Furthermore, A preferably denotes unbranched or branched alkyl having 1-10 C atoms, in which 1-7H atoms may be replaced by F, Cl, Br, OH, CHO, COA, COOA, CN, $CONA_2$, CONHA and/or $CONH_2$,
and/or in which one or two non-adjacent CH and/or $CH_2$ groups may be replaced by O,
N and/or $NR^4$,
or Cyc.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl preferably denotes cyclopropyl, cyclobutyl, cyclopentyl, cyclohexyl or cycloheptyl.

$R^1$ preferably denotes phenyl, benzyl, naphthyl or biphenyl, each of which is unsubstituted or mono-, di-, tri-, tetra- or pentasubstituted by Hal, CN, NHCOA, $NHSO_2A$, $SO_2A$ and/or $CONH_2$;
A or $(CH_2)_n$Het.

$R^2$ preferably denotes $[C(R^4)_2]_nAr^2$, $(CH_2)_n$Cyc,

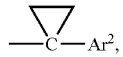
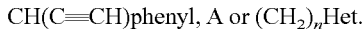

$CH(C\equiv CH)$phenyl, A or $(CH_2)_n$Het.
$R^3$ preferably denotes OH, $N_3$, $NH_2$ or F.
$R^4$ preferably denotes H, methyl, ethyl or propyl.
$Ar^1$ denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromo-phenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl; furthermore naphthyl or biphenyl.

$Ar^1$ furthermore preferably denotes phenyl, naphthyl or biphenyl, each of which is unsubstituted or mono-, di-, tri-, tetra- or pentasubstituted by Hal.

$Ar^2$ denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-aminocarbonylphenyl, o-, m- or p-carboxyphenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromo-phenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl; furthermore naphthyl or biphenyl.

Ar² furthermore preferably denotes phenyl which is unsubstituted or mono-, di-, tri-, tetra- or pentasubstituted by A, Hal, CN, OH and/or OA.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Unsubstituted Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, 2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)-phenyl or also 3,4-dihydro-2H-1,5-benzodioxepin-6- or -7-yl, furthermore preferably 2,3-dihydrobenzofuranyl or 2,3-dihydro-2-oxofuranyl.

Het furthermore preferably denotes pyridazinyl, pyrazolyl, benzimidazolyl, pyridyl, dibenzofuranyl, carbazolyl, indolyl, dihydroindolyl, benzofuranyl, dihydro-benzofuranyl, 2,3-dihydrobenzo-1,4-dioxinyl, chromanyl, piperazinyl, morpholinyl, tetrahydropyranyl, quinolinyl, isoquinolinyl, isoindolyl, dihydroquinolinyl, dihydroisoquinolinyl, tetrahydroquinolinyl, tetrahydroisoquinolinyl, quinazolinyl, quinoxalinyl, phthalazinyl, purinyl, naphthyridinyl, pyrimidinyl, indazolyl, furyl, thienyl, imidazolyl, pyrrolyl, oxazolyl, oxadiazolyl, isoxazolyl, thiazolyl, triazolyl, tetrazolyl, thiadiazol, benzothiazolyl, imidazo[1,2-a]pyridinyl, 1,3-benzodioxolyl, benzoxazolyl, piperidin-1-yl, pyrrolidin-1-yl, 1,2-oxazinan-2-yl, 1,2,5-oxadiazinan-2-yl, -1,3-oxazinan-3-yl or hexahydropyrimidinyl, each of which is unsubstituted or mono-, di- or trisubstituted by A, OA, COOA, COA, CHO, $(CH_2)_nCONH_2$, $SO_2A$, $NHSO_2A$, =O and/or Het¹.

Het particularly preferably denotes dihydroindolyl, benzofuranyl, dihydro-benzofuranyl, 2,3-dihydrobenzo-1,4-dioxinyl, chromanyl, oxazolyl, oxadiazolyl, tetrazolyl, oxadiazolyl, thiazolyl, thiadiazolyl, thienyl, furanyl, tetrahydropyranyl, pyrazolyl, pyridyl, benzothiazolyl, 2,3-dihydrobenzo-1,4-dioxinyl, quinolyl, iso-quinolyl or pyrrolidinyl, each of which is unsubstituted or mono- or disubstituted by A, COOA, COA, CHO, $(CH_2)_nCONH_2$, $(CH_2)_nCONHA$, $(CH_2)_nCONA_2$, $SO_2A$, $NHSO_2A$, =O and/or pyrrolidinyl.

Irrespective of further substitutions, Het¹ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl.

The heterocyclic radicals may also be partially or fully hydrogenated.

Unsubstituted Het¹ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, 2-, -3-, -4- or -5-pyrazolyl, tetrahydro-1,1-3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl or 1-, 2- or 3-piperazinyl.

Het¹ furthermore preferably denotes pyridazinyl, pyrazolyl, pyridyl, piperazinyl, morpholinyl, pyrimidinyl, furyl, thienyl, imidazolyl, pyrrolyl, oxazolyl, isoxazolyl, thiazolyl, triazolyl, tetrazolyl, thiadiazol, piperidin-1-yl, pyrrolidin-1-yl, tetrahydro-pyranyl, 1,2-oxazinan-2-yl, 1,2,5-oxadiazinan-2-yl, -1,3-oxazinan-3-yl or hexahydropyrimidinyl, each of which is unsubstituted or mono-, di- or trisubstituted by A and/or OA.

Het¹ particularly preferably denotes imidazolyl, thiazolyl or pyrrolidinyl, each of which is unsubstituted or monosubstituted by A.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above.

Some preferred groups of compounds may be expressed by the following sub-formulae Ia to If, which conform to the formula I and in which the radicals not designated in greater detail have the meaning indicated for the formula I, but in which
in Ia
  $R^1$ denotes phenyl, benzyl, naphthyl or biphenyl, each of which is unsubstituted or mono-, di-, tri-, tetra- or pentasubstituted by Hal, CN, NHCOA, NHSO$_2$A, SO$_2$A and/or CONH$_2$;
  A or (CH$_2$)$_n$Het;
in Ib
  $R^2$ denotes [C(R$^4$)$_2$]$_n$Ar$^2$, (CH$_2$)$_n$Cyc, CH[B(OH)$_2$] CH$_2$Het,

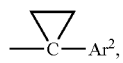

CH(C≡CH)phenyl, A or (CH$_2$)$_n$Het;
in Ic
  $R^3$ denotes OH, N$_3$, NH$_2$ or F;
in Id
  Het denotes pyridazinyl, pyrazolyl, benzimidazolyl, pyridyl, dibenzofuranyl, carbazolyl, indolyl, dihydroindolyl, benzofuranyl, dihydro-benzofuranyl, 2,3-dihydrobenzo-1,4-dioxinyl, chromanyl, piperazinyl, morpholinyl, tetrahydropyranyl, quinolinyl, isoquinolinyl, isoindolyl, dihydroquinolinyl, dihydroisoquinolinyl, tetrahydroquinolinyl, tetrahydroisoquinolinyl, quinazolinyl, quinoxalinyl, phthalazinyl, purinyl, naphthyridinyl, pyrimidinyl, indazolyl, furyl, thienyl, imidazolyl, pyrrolyl, oxazolyl, oxadiazolyl, isoxazolyl, thiazolyl, triazolyl, tetrazolyl, thiadiazole, benzothiazolyl, imidazo[1,2-a]pyridinyl, 1,3-benzodioxolyl, benzoxazolyl, piperidin-1-yl, pyrrolidin-1-yl, 1,2-oxazinan-2-yl, 1,2,5-oxadiazinan-2-yl, 1,3-oxazinan-3-yl or hexahydropyrimidinyl, each of which is unsubstituted or mono-, di- or trisubstituted by A, OA, COOA, COA, CHO, (CH$_2$)$_n$CONH$_2$, (CH$_2$)$_n$CONHA, (CH$_2$)$_n$CONA$_2$, SO$_2$A, NHSO$_2$A, =O and/or Het$^1$;
in Ie
  Het$^1$ denotes pyridazinyl, pyrazolyl, pyridyl, piperazinyl, morpholinyl, pyrimidinyl, furyl, thienyl, imidazolyl, pyrrolyl, oxazolyl, isoxazolyl, thiazolyl, triazolyl, tetrazolyl, thiadiazole, piperidin-1-yl, pyrrolidin-1-yl, tetrahydropyranyl, 1,2-oxazinan-2-yl, 1,2,5-oxadiazinan-2-yl, 1,3-oxazinan-3-yl or hexahydropyrimidinyl, each of which is unsubstituted or mono-, di- or trisubstituted by A and/or OA;
in If
  $R^1$ denotes phenyl, benzyl, naphthyl or biphenyl, each of which is unsubstituted or mono-, di-, tri-, tetra- or pentasubstituted by Hal, CN, NHCOA, NHSO$_2$A, SO$_2$A and/or CONH$_2$;
  A or (CH$_2$)$_n$Het,
  $R^2$ denotes [C(R$^4$)$_2$]$_n$Ar$^2$, CH[B(OH)$_2$]CH$_2$Het, (CH$_2$)$_n$Cyc,

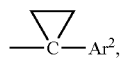

CH(C≡CH)phenyl, A or (CH$_2$)$_n$Het,
  $R^3$ denotes OH, N$_3$, NH$_2$ or F,
  $R^4$ denotes H or alkyl having 1, 2, 3 or 4 C atoms, $R^2$ and $R^4$ together also denote alkylene having 2, 3, 4 or 5 C atoms, where one CH$_2$ group may also be replaced by NH, NA, N—COA, N—(CH$_2$)$_n$Ar$^3$, N—(CH$_2$)$_n$Het$^2$, CH-A, CH—O—(CH$_2$)$_n$Ar$^3$, N—SO$_2$A or O and/or may be substituted by A,
Het denotes pyridazinyl, pyrazolyl, benzimidazolyl, pyridyl, dibenzofuranyl, carbazolyl, indolyl, dihydroindolyl, benzofuranyl, dihydrobenzofuranyl, 2,3-dihydrobenzo-1,4-dioxinyl, chromanyl, piperazinyl, morpholinyl, tetrahydropyranyl, quinolinyl, isoquinolinyl, isoindolyl, dihydroquinolinyl, dihydroisoquinolinyl, tetrahydroquinolinyl, tetrahydroisoquinolinyl, quinazolinyl, quinoxalinyl, phthalazinyl, purinyl, naphthyridinyl, pyrimidinyl, indazolyl, furyl, thienyl, imidazolyl, pyrrolyl, oxazolyl, oxadiazolyl, isoxazolyl, thiazolyl, triazolyl, tetrazolyl, thiadiazole, benzothiazolyl, imidazo[1,2-a]pyridinyl, 1,3-benzodioxolyl, benzoxazolyl, piperidin-1-yl, pyrrolidin-1-yl, 1,2-oxazinan-2-yl, 1,2,5-oxadiazinan-2-yl, 1,3-oxazinan-3-yl or hexahydropyrimidinyl, each of which is unsubstituted or mono-, di- or trisubstituted by A, OA, COOA, COA, CHO, (CH$_2$)$_n$CONH$_2$, (CH$_2$)$_n$CONHA, (CH$_2$)$_n$CONA$_2$, SO$_2$A, NHSO$_2$A, =O and/or Het$^1$,
Het$^1$ denotes pyridazinyl, pyrazolyl, pyridyl, piperazinyl, morpholinyl, pyrimidinyl, furyl, thienyl, imidazolyl, pyrrolyl, oxazolyl, isoxazolyl, thiazolyl, triazolyl, tetrazolyl, thiadiazole, piperidin-1-yl, pyrrolidin-1-yl, tetrahydropyranyl, 1,2-oxazinan-2-yl, 1,2,5-oxadiazinan-2-yl, 1,3-oxazinan-3-yl or hexahydropyrimidinyl, each of which is unsubstituted or mono-, di- or trisubstituted by A and/or OA,
Het$^2$ denotes pyridyl, pyrimidinyl, furyl, thienyl, imidazolyl, pyrrolyl, oxazolyl, oxadiazolyl, isoxazolyl, thiazolyl, triazolyl, tetrazolyl or thiadiazole,
A denotes unbranched or branched alkyl having 1-10 C atoms, in which 1-7H atoms may be replaced by F, Cl, Br, OH, CHO, COA, COOA, CN, CONA$_2$, CONHA and/or CONH$_2$, and/or in which one or two non-adjacent CH and/or CH$_2$ groups may be replaced by O, N and/or NR$^4$, or Cyc,
Ar$^2$ denotes phenyl which is unsubstituted or mono-, di-, tri-, tetra- or pentasubstituted by A, Hal, CN, OH and/or OA,
Ar$^3$ denotes phenyl which is unsubstituted or mono-, di- or trisubstituted by Hal, OH, OA and/or A,
Cyc denotes cyclic alkyl having 3-7 C atoms,
Hal denotes F, Cl, Br or I,
n denotes 0, 1, 2, 3 or 4;
and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting compounds of the formula II with a compound of the formula III.

The compounds of the formula II and of the formula III are generally known. If they are novel, however, they can be prepared by methods known per se.

In the compounds of the formula II, L preferably denotes Cl, Br, I or a free or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

The reaction preferably succeeds in the presence of a dehydrating agent, such as, for example, a carbodiimide, such as N,N'-dicyclohexylcarbodiimide ("DCCI"), 1,1'-carbonyldiimidazole or N-3-dimethylaminopropyl-N'-ethylcarbodiimide ("DAPECI"), furthermore propanephosphonic anhydride T3P (cf. Angew. Chem. 92, 129 (1980)), diphenylphosphoryl azide or 2-ethoxy-N-ethoxycarbonyl-1,2-dihydroquinoline, optionally in the presence of N-hydroxybenzotriaole;

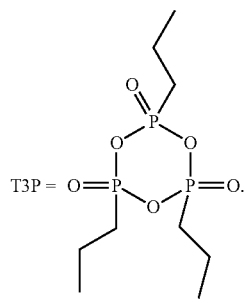 [SMILES: CCCP1(=O)OP(=O)(CCC)OP(=O)(CCC)O1]

The reaction is carried out in an inert solvent and is generally carried out in the presence of an acid-binding agent, preferably an organic base, such as DIPEA, triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and 14 days, the reaction temperature is between about −15° and 150°, normally between 40° and 130°, particularly preferably between 60° and 110° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to glycol ethers, such as ethylene glycol monomethyl ether, THF, dichloromethane and/or DMF.

Compounds of the formula I can furthermore preferably be obtained by oxidising compounds of the formula IV.

The oxidation is preferably carried out using tert-butyl hydroperoxide.

Depending on the conditions used, the reaction time is between a few minutes and 14 days, the reaction temperature is between about −15° and 150°, normally between 40° and 130°, particularly preferably between 60° and 110° C.

The solvent is preferably water, where the addition of an alkali or alkaline-earth metal hydroxide, carbonate or bicarbonate or another salt of a weak acid of the alkali or alkaline-earth metals, preferably of potassium, sodium, calcium or caesium, is also favourable.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are like-wise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoaryl-sulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzene-sulfonate (besylate), bisulfate, bisulfite, bromide, butyrate, camphorate, camphor-sulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxy-methyl)methylamine(tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxy-butyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated;

and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts and stereoisomers thereof, including mixtures thereof in all ratios, and at least one further medicament active compound.

The invention also relates to a set (kit) consisting of separate packs of (a) an effective amount of a compound of the formula I and/or pharmaceutically usable salts and stereoisomers thereof, including mixtures thereof in all ratios, and (b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable salts and stereoisomers thereof, including mixtures thereof in all ratios, and an effective amount of a further medicament active compound in dissolved or lyophilised form.

The invention relates to the compounds of the formula I according to claim 1-8, and pharmaceutically usable salts, tautomers and stereoisomers thereof, including mixtures thereof in all ratios, for use for the treatment of tumours, tumour metastases, proliferative diseases of the mesangial cells, haemangioma, proliferative retinopathy, rheumatoid arthritis, atherosclerotic neovascularisation, psoriasis, ocular neovascularisation, osteoporosis, diabetes and obesity, lymphoid leukaemia, lymphoma, malaria and prostate hypertrophy Use The present compounds are suitable as pharmaceutical active compounds for mammals, especially for humans, in the treatment and control of diseases. These diseases include the proliferation of tumour cells, pathological neovascularisation (or angiogenesis), which promotes the growth of solid tumours, neovascularisation in the eye (diabetic retinopathy, age-induced macular degeneration and the like) and inflammation (psoriasis, rheumatoid arthritis and the like), and proliferative diseases of the mesangial cells.

The present invention encompasses the use of the compounds of the formula I and/or physiologically acceptable salts and solvates thereof for the preparation of a medicament for the treatment or prevention of tumours, tumour diseases and/or tumour metastases.

The tumour disease is preferably selected from the group tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma.

Likewise encompassed is the use of the compounds according to claim 1 according to the invention and/or physiologically acceptable salts and solvates thereof for the preparation of a medicament for the treatment of osteoporosis, diabetes and obesity.

Likewise encompassed is the use of the compounds according to claim 1 according to the invention and/or physiologically acceptable salts and solvates thereof for the preparation of a medicament for the treatment or prevention of a disease in which angiogenesis is involved.

A disease of this type in which angiogenesis is involved is an eye disease, such as retina vascularisation, diabetic retinopathy, age-induced macular degeneration and the like.

The angiogenic disease is preferably selected from the group diabetic retinopathy, arthritis, cancer, psoriasis, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome.

The proliferative disease of the mesangial cells is preferably selected from the group glomerulonephritis, diabetic nephropathy, malignant nephrosclerosis, thrombotic microangiopathy syndrome, transplant rejection, glomerulopathy.

The use of compounds of the formula I and/or physiologically acceptable salts and solvates thereof for the preparation of a medicament for the treatment or prevention of inflammatory diseases likewise falls within the scope of the present invention. Examples of such inflammatory diseases include rheumatoid arthritis, psoriasis, contact dermatitis, delayed hypersensitivity reaction and the like.

The inflammatory disease is preferably selected from the group inflammatory bowel disease, arthritis, atherosclersosis, asthma, allergies, inflammatory kidney diseases, multiple sclerosis, chronic obstructive pulmonary disease, inflammatory skin diseases, pardontal diseases, psoriasis, T-cell-promoted immune disease.

The inflammatory bowel disease is preferably selected from the group ulcerative colitis, Crohn's disease, non-specific colitis.

The T-cell-promoted immune disease is preferably selected from the group
allergic encephalomyelitis, allergic neuritis, transplant rejection, graft-versus-host reaction, myocarditis, thyroiditis, nephritis, systemic lupus erythematosus, insulin-dependent diabetes mellitus.

The arthritis disease is preferably selected from the group rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome.

The inflammatory kidney disease is preferably selected from the group glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease.

The inflammatory skin disease is preferably selected from the group psoriasis, atopic dermatitis, contact sensitivity, acne.

Likewise encompassed is the use of the compounds of the formula I and/or physiologically acceptable salts and solvates thereof for the preparation of a medicament for the treatment or prevention of a disease or condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Likewise encompassed is the use of the compounds of the formula I and/or physiologically acceptable salts thereof for the preparation of a medicament for the treatment and/or combating of a tumour-induced disease in a mammal, in which to this method a therapeutically effective amount of a compound according to the invention is administered to a sick mammal in need of such treatment. The therapeutic amount varies according to the specific disease and can be determined by the person skilled in the art without undue effort.

The disclosed compounds of the formula I can be administered in combination with other therapeutic agents, including anticancer agents. As used here, the term "anticancer agent" relates to any agent which is administered to a patient with cancer for the purposes of treating the cancer.

The compounds of the formula I may also be administered together with other well-known therapeutic agents that are selected for their particular suitability for the condition being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamine-platinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxy-phenyl)benzenesulfonamide, anhydrovinblastine, N,N-dimethyl-L-valyl-L-valyl-N-methyl-L-valyl-L-prolyl-L-proline-t-butylamide, TDX258 and BMS 188797. Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]-pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(di-methylamino)ethyl]-N-methylamino]ethyl]-5-[4-hydroxy-3,5-dimethoxyphenyl]-5,5a,6,8,8a,9-hexohydrofuro(3',':6,7) naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropyl-amino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-yl-methyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diaza-tetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation/Vitality of Tumour Cells In Vitro 1.0 Background In the present experiment description, the inhibition of tumour cell proliferation/tumour cell vitality by active compounds is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2.0 Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active compounds and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

$$\frac{100*(\text{value with cells and test substance} - \text{value of medium control})}{(\text{value with cells} - \text{value of medium control})}$$

$IC_{50}$ values (50% inhibition) are determined with the aid of statistics programs, such as, for example, RS1.

$IC_{50}$ data for compounds according to the invention are shown in Table 1.

| Material | Order No. | Manufacturer |
|---|---|---|
| Microtitre plates for cell culture (Nunclon Surface 96-well plate) | | 167008 Nunc |
| DMEM | P04-03550 | Pan Biotech |
| PBS (10x) Dulbecco | 14200-067 | Gibco |
| 96-well plates (polypropylene) | | 267334 Nunc |
| AlamarBlue ™ | BUF012B | Serotec |
| FCS | 1302 | Pan Biotech GmbH |
| Trypsin/EDTA solution 10x | L 2153 | Biochrom AG |
| 75 cm² culture bottles | 353136 | BD Falcon |
| A2780 | 93112519 | ECACC |

-continued

| Material | Order No. | Manufacturer |
|---|---|---|
| Colo205 | CCL222 | ATCC |
| MCF7 | HTB22 | ATCC |
| PC3 | CRL-1435 | ATCC |

Determination of the Proliferation Inhibition by Inhibitors of Methionine Aminopeptidase 2 in the BrdU Proliferation Test (Cellular Assay)

The inhibition of proliferation is determined by incorporation of bromodesoxyuridine (BrdU) into human umbilical vein endothelial cells (HUVECs, PromoCell, C-12200). The HUVECs are cultivated at 37° C. and 5% $CO_2$ in basal medium (PromoCell, C-22200) with supplement mix (PromoCell, C-39225). After detachment of the cells by means of trypsin/EDTA, the number of living cells is determined, and the cells are sown in a density of 1000 cells per cavity in a total volume of 175 μl (cavities are coated in advance either with supplemented culture medium for 1-2 hours at 37° C. or with 1.5% gelatine for 0.5-2 hours at 37° C.). After cultivation for 24 hours, the test substances are added in various concentrations (for example final concentrations 30 μM to 0.03 nM in 10-fold dilution steps) and a volume of 25 μl. The DMSO concentration is kept constant at 0.3%. After cultivation for a total of 48 or 72 hours, 20 μl of bromodesoxyuridine (Roche, #11647229001 diluted 1:1000 in culture medium, final concentration 10 μM) are added, and cultivation is continued for a further 20 to 24 hours. After incubation with test substances for a total of 72 or 96 hours, the culture medium is removed, and an immunohistochemical determination is carried out for detection of BrdU incorporation (BrdU ELISA, Roche, #11647229001). To this end, the cells are treated with a fixative for 30 min at room temperature and subsequently incubated with a peroxidase-labelled anti-BrdU antibody (diluted 1:100 in antibody dilution buffer) for 60 min at room temperature. After washing three times with 1-fold-concentrated DPBS buffer (Gibco, #14200), the enzymatic reaction is initiated in TMB substrate solution. The colour development is stopped after 15 min by addition of 25 μl of a 1M sulfuric acid solution. A determination of the optical density is carried out within 5 min by measurement at a wavelength of 450 nM. The controls used are cavities containing DMSO-treated cells (100% control) or empty cavities (blank value). The sensitivity of this test to inhibitors of methionine aminopeptidase is checked and confirmed using the inhibitor fumagillin.

MetAP-2 Activity Measurement

The MetAP-2 activity is determined by coupling enzymatic reactions. The $_{tripeptide}$ Met-Arg-Ser (MAS) is employed as substrate. The methionine liberated is firstly converted into $Met_{ox}$ and $H_2O_2$ by L-aminooxidase (AAO). In the second step, the peroxidase (POD) with the aid of the $H_2O_2$ catalyses the oxidation of the leukodye dianisidine to $dianisidine_{ox}$, the increase of which is detected photometrically at 450 nm.

MetAP-2 activity can be recorded continuously as kinetics. The reaction scheme illustrates that one mol of $dianisidine_{ox}$ is formed per mol of methionene. The MetAP-2 enzyme activity can therefore be calculated directly as Δ absorption per time unit. Qualification of the MetAP-2 activity (mol of Met/time unit) is possible with the aid of the $dianisidine_{ox}$ extinction coefficient.

The change in extinction per time unit is depicted graphically and a slope calculation is carried out in the visually linear region of the reaction.

The activities of the compounds are summarised in Table 1.

Solubility Measurement

Determination by Shake Flask Solubility Measurement

Eluent Preparation:

Eluent A: 2 ml of diethylamine, for synthesis+1000 ml of methanol, LiChrosolv

Eluent B: 5 g of ammonium acetate, for analysis+5 ml of methanol, LiChrosolv+995 ml of ultrapure water Sample Solvent:

Buffer: 3.954 g of sodium dihydrogenphosphate monohydrate+6.024 g of sodium chloride+950 ml of ultrapure water the pH is adjusted using 0.1 M NaOH or 0.1 M HCl.

Sample Preparation:

The samples are shaken at 37° C. and 450 rpm for 24 h.

After about 7 h, the pH of the samples is checked and adjusted if necessary.

It is also checked whether the sample is still present in excess.

Just before the end of the 24 h shaking time, the samples are again checked for pH and a precipitate.

Ultrapure water unit: MilliQ gradient, Millipore, instrument: F3PN37462D

Shaker: TiMix control, Bühler

Incubation hood: TH 15 Bühler pH meter: 766 Calimatic Knick instrument: pH 1 pH electrode: InLab 423 Mettler

APCI-MS (atmospheric pressure chemical ionisation-mass spectrometry) $(M+H)^+$.

The racemic end products of the compounds according to the invention or the racemic intermediates can be separated simply and both on an analytical and also on a preparative scale via a chiral HPLC or SFC column.

§

NMR Spectrum after Addition of Deuterated Trifluoroacetic Acid

Methods:

%

HPLC-MS Analysis Conditions:

1. Column: Acquity BEH C-18 (2.1×100 mm, 1.7 μm)
2. Mobile phase: A—5 mM ammonium acetate in water B—acetonitrile
3. Flow mode: gradient

| % A | % | B | |
|---|---|---|---|
| 0.0 | 0.3 | 90 | 10 |
| 1.0 | 0.3 | 90 | 10 |
| 2.0 | 0.3 | 85 | 15 |
| 4.5 | 0.3 | 45 | 55 |
| 6.0 | 0.3 | 10 | 90 |
| 8.0 | 0.3 | 10 | 90 |
| 9.0 | 0.3 | 90 | 10 |
| 10.0 | 0.3 | 90 | 10 |

4. Flow rate: 0.3 ml/min.
5. UV max.: 254.0 nm
6. Column temp.: 30.0 deg.
7. Sample preparation: acetonitrile+water
   *HPLC: La Chrom Unit
   Chromolite Performance RP18-e 100-4.6 mm
   Gradient: acetonitrile/$_{H2O}$ comprising 0.01% of formic acid
   Method: Chromolith/Chromolith (extended)
   Flow rate: 3 ml/min Column: XBridge C8, 3.5 μm, 4.6×50 mm;
Solvent A: water+0.1% of TFA;
Solvent B: acetonitrile+0.1% of TFA;
Flow rate: 2 ml/min;
Gradient: 0 min: 5% of B, 8 min: 100% of B, 8.1 min: 10%;
Detection at 254 nm

[1])
Enantiomer Separation:
Separation on Chiralcel OD-H with n-heptane/ethanol=70/30.

The substance is dissolved in 10 ml of n-heptane/EtOH=1/1 and separated via 5×25 cm Chiralcel OD column with 20 μm material at a flow rate of 100 ml/min of n-heptane/ethanol=70/30.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

M.p.: melting point

Mass spectrometry (MS): EI (electron impact ionisation) $M^+$

FAB (fast atom bombardment) $(M+H)^+$

ESI (electrospray ionisation) $(M+H)^+$

APCI-MS (atmospheric pressure chemical ionisation-mass spectrometry) $(M+H)^+$.

Synthesis Schemes for the Preparation of Compounds of the Formula I:

Route 1

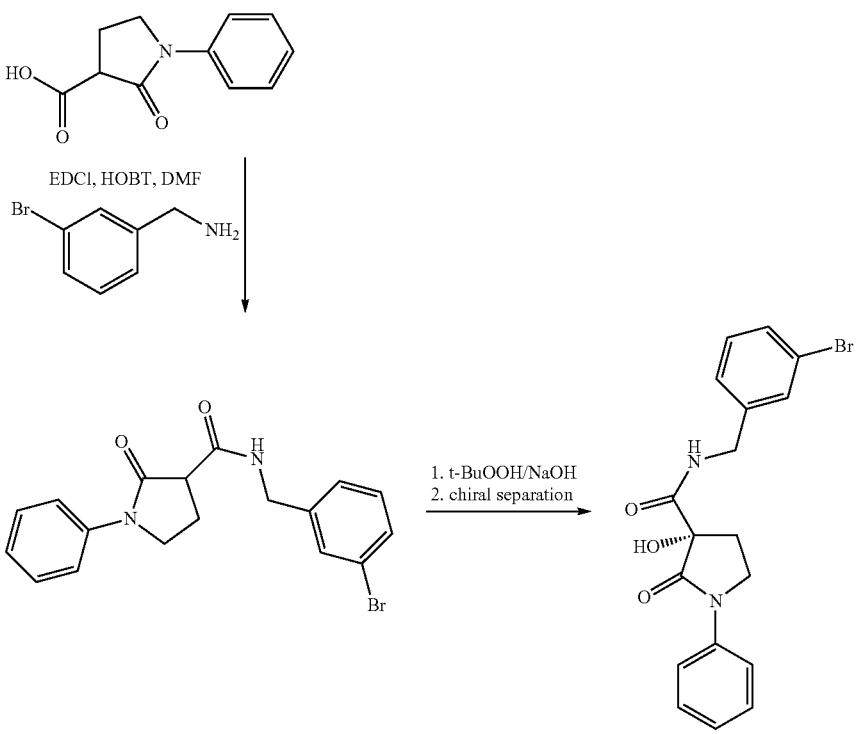

a)

Route 2

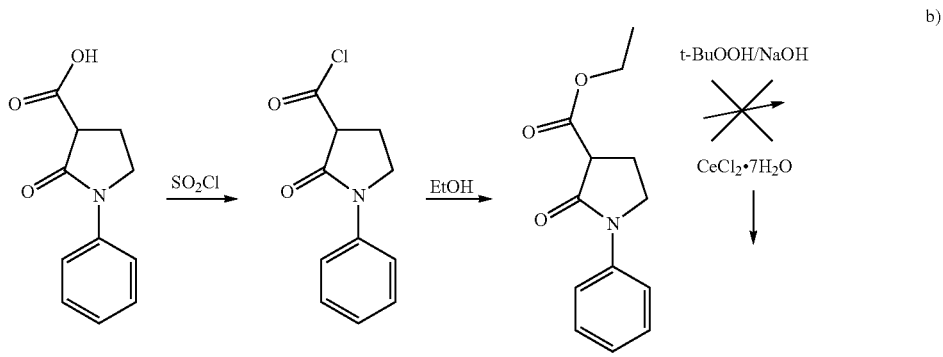

b)

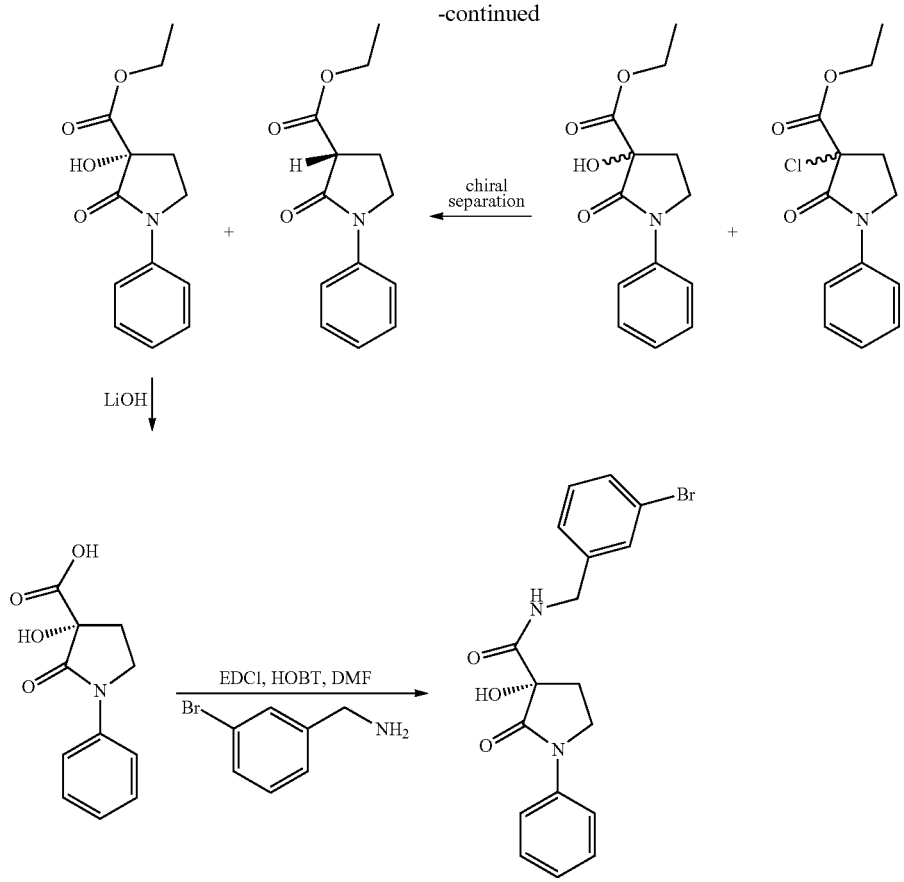

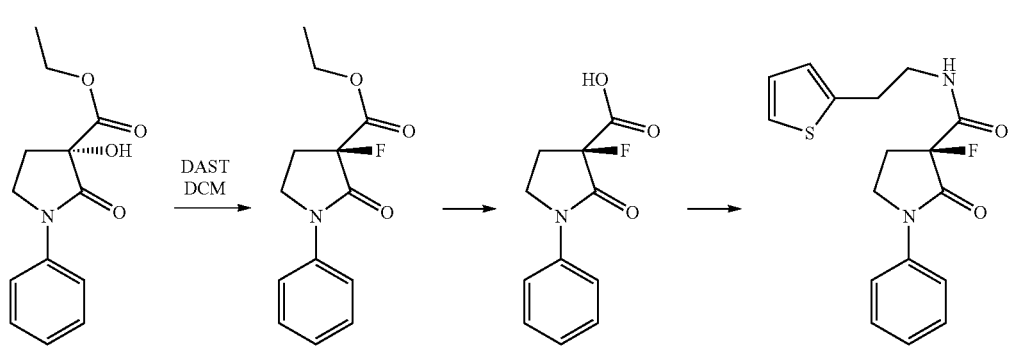

a) Route 1: The acid is converted into the corresponding amide in an amide coupling and then oxidised on the carbon between the two carboxyl groups using tertiary butyl hydroperoxide in a basic environment to give the alcohol (followed by enantiomer separation via chromatography).

b) Route 2: Alternatively, it has been found that, under the same oxidative conditions as described in route 1 for the amide, the ethyl ester of the starting acid cannot be oxidised. However, this does succeed with cerium chloride. The chlorine derivative obtained with 30% can be separated into the enantiomers analogously to the alcohols and then derivatised further. (further reactions not shown here, products are then, however, for example, "A39", "A43" and "A61")

c) However, the use of cerium fluoride does not give the analogous fluorine derivative. The reaction of the alcohol compound with DAST (diethylaminosulfur trifluoride) in dichloromethane results in the desired fluorine analogue. Testing confirms the inversion at the centre of asymmetry which is expected from mechanistic considerations of the fluorination of alcohols using DAST.

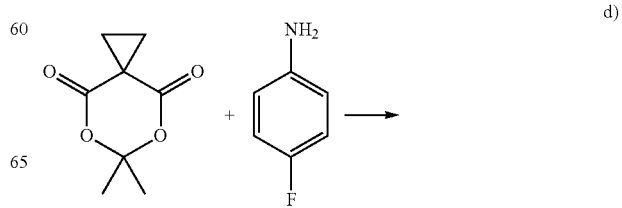

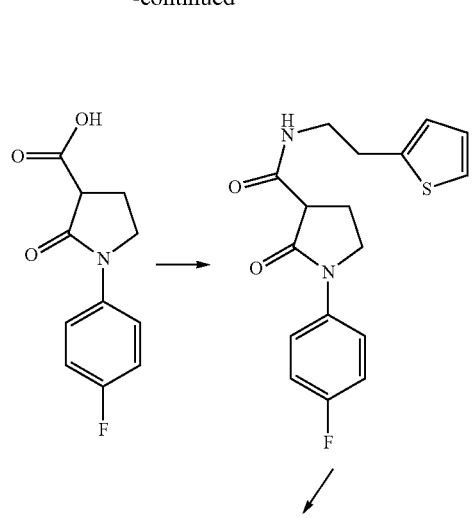
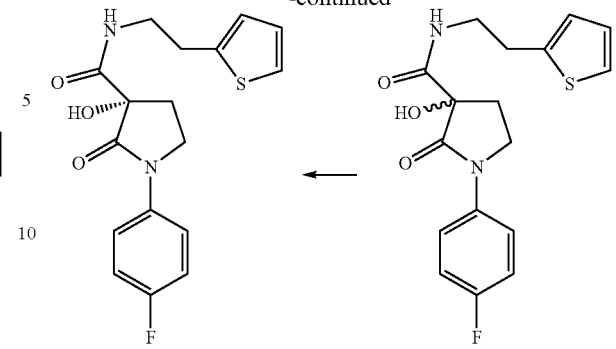

It is shown in d) how N-aryllactamcarboxylic acids can be prepared. This route can easily be carried out if the nitrogen compound is a liquid. It is found that joint melting of the starting materials, if the nitrogen-aryl compound is not liquid, is not advantageous. However, the desired product is obtained if the nitrogen-aryl compound is melted and the dicarboxylic acid ester (Meldrum's acid) is added to this melt.

e)

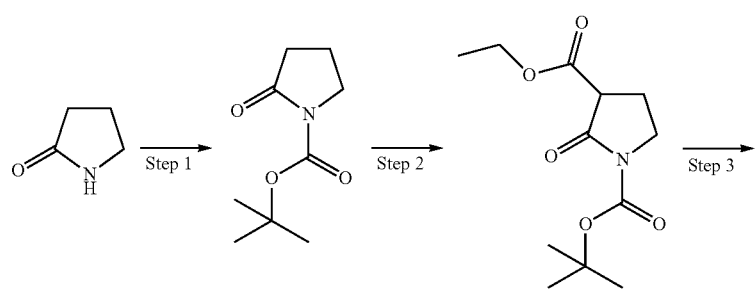

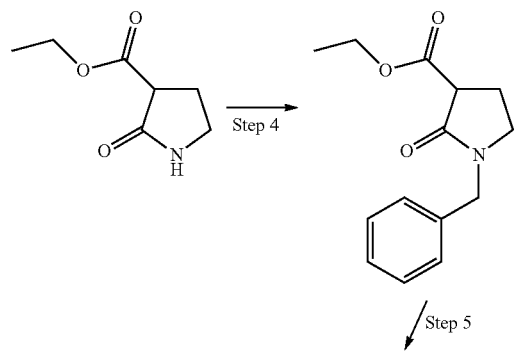

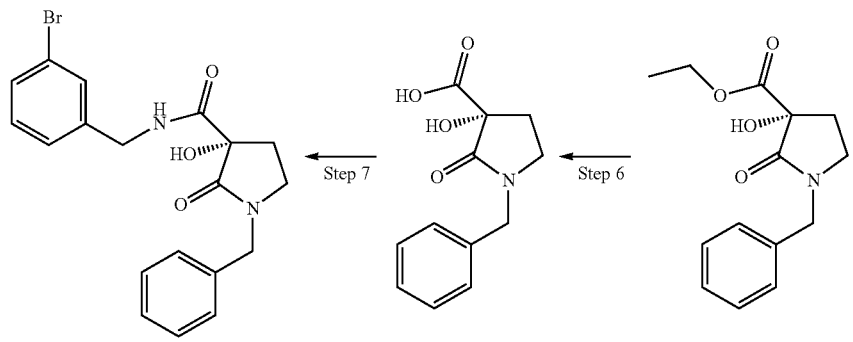

e) shows a route for the preparation of the N-alkaryllactam-carboxylic acid.

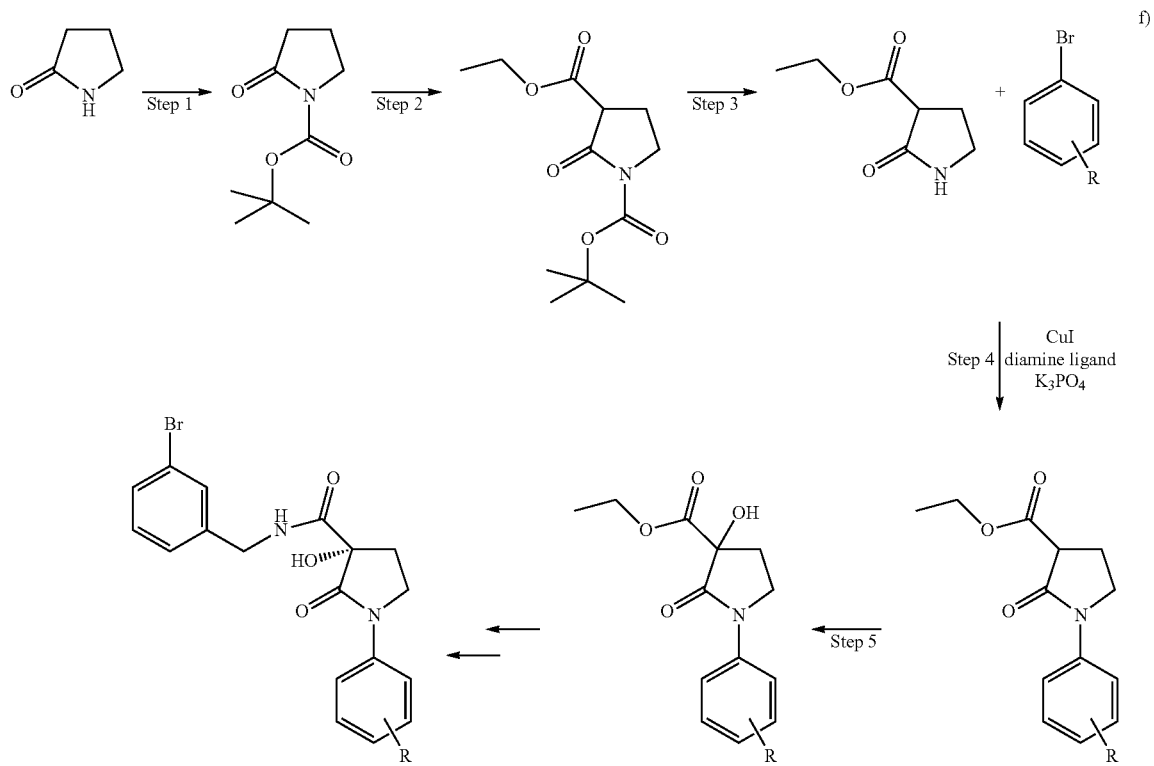

f) shows a further alternative, which is carried out in order to make available aryl radicals on the lactam nitrogen in which the analogous nitrogen compound is not a liquid. Here, the lactam nitrogen is coupled to an aryl halide, a step which is preferably catalysed by transition-metal compounds.

EXAMPLE 1

Synthesis of 3-hydroxy-2-oxo-1-phenylpyrrolidine-3-carboxylic acid (2-thiophen-2-yl-ethyl)amide ("A65") [analogous to Synthesis Scheme a); route 1]

a) 2-Oxo-1-phenylpyrrolidine-3-carboxylic acid (2-thiophen-2-ylethyl)amide

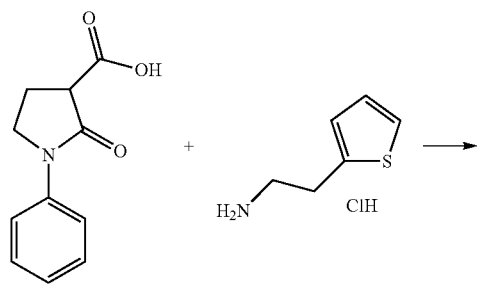

-continued

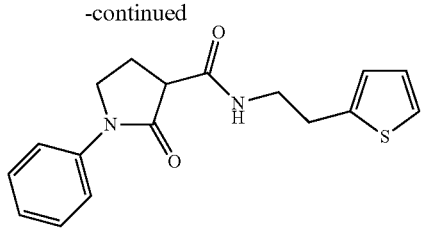

200 mg of 1-phenyl-2-oxo-3-pyrrolidinecarboxylic acid, 155 mg of 2-thiophen-ethylamine hydrochloride, 550 mg of N-(3-diemethylaminopyroyl)-N'-ethyl-carbodiimide hydrochloride, 190 mg of hydroxybenzotriazole, 132 µl of triethylamine and 5 ml of DMF are combined in a microwave vessel. After the vessel has been sealed using a septum, the mixture is heated by means of microwaves (Emrys Optimiser, PersonalChemistry) (160° C., 5 min). Water is added to the batch. A precipitate is formed. Water is added until no further precipitate is formed. The precipitate is filtered off with suction and dried.

Yield: 239 mg;
Appearance: white solid;
Purity: 100% (220 nm, UV track of the LC-MS);
LC-MS: 315(M+H);
HPLC: 3.03 (Rt/min);
HPLC method: 1__100__2 (instrument: LaChrom)
Column: Chromolith Performance RP18e 100-3 mm
Flow rate: 2 ml/min (pump: L-7100)
Solvent A: water+0.05% of HCOOH
Solvent B: acetonitrile+0.04% of HCOOH
Wavelength: 220 nm (detector: L-7455)

Gradient: 0-0.2 min: 99% of A, 0.2-3.8 min: 99% of A→100% of B, 3.8-4.4 min: 100% of B, 4.4-4.5 min: 100% of B→99% of A, 4.5-5.1 min: 99% of A;
LC-MS method: (instrument: Agilent 1100 series)
Column: Chromolith Speed Rod RP18e-50-4.6
Flow rate: 2.4 ml/min
Solvent A: water+0.05% of HCOOH
Solvent B: acetonitrile+0.04% of HCOOH
WL: 220 nm
Gradient: 0-2.8 min: 4% of B to 100% of B, 2.8-3.3 min: 100% of B.

b) 3-Hydroxy-2-oxo-1-phenylpyrrolidine-3-carboxylic acid (2-thiophen-2-ylethyl)amide ("A65")

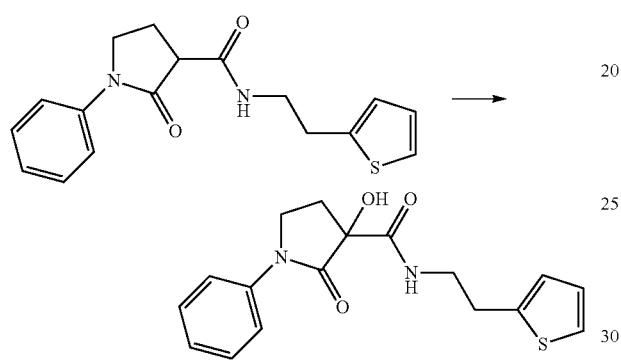

100 mg of the amide prepared under a) are dissolved in 10 ml of tert-butanol, and 60 mg of tert-butyl hydroperoxide (70% in water) and 0.2 ml of sodium ethoxide (20% in ethanol) are added, The mixture is then stirred at 90° C. for 4 h. The batch is evaporated virtually to dryness. Water and EA (ethyl acetate) are added to the residue, and the mixture is extracted by shaking. The organic phase is dried over $Na_2SO_4$, filtered off with suction and evaporated to dryness in vacuo, giving 80 mg. The residue is dissolved in DMSO and purified by preparative HPLC. The product fractions are combined and evaporated to dryness in vacuo, giving 57 mg (54%) of "A65";
Appearance: White Solid;
Purity: 100% (220 nm, UV track of the LC-MS);
LC-MS: 331 (M+H);
HPLC: 2.88 (Rt/min);
HPLC method: 1__100__2 (instrument: LaChrom)
Column: Chromolith Performance RP18e 100-3 mm
Flow rate: 2 ml/min (pump: L-7100)
Solvent A: water+0.05% of HCOOH
Solvent B: acetonitrile+0.04% of HCOOH
Wavelength: 220 nm (detector: L-7455)
Gradient: 0-0.2 min: 99% of A, 0.2-3.8 min: 99% of A→100% of B, 3.8-4.4 min: 100% of B, 4.4-4.5 min: 100% of B→99% of A, 4.5-5.1 min: 99% of A;
LC-MS method: (instrument: Agilent 1100 series)
Column: Chromolith Speed Rod RP18e-50-4.6
Flow rate: 2.4 ml/min
Solvent A: water+0.05% of HCOOH
Solvent B: acetonitrile+0.04% of HCOOH
WL: 220 nm
Gradient: 0-2.8 min: 4% of B to 100% of B, 2.8-3.3 min: 100% of B;
Prep. HPLC method: 15__35__10__50 ml_empfind_o_equi.M (instrument: Agilent 1100 series)
Column: Chromolith Prep Rod RP18e
Flow rate: 50 ml/min
Solvent A: acetonitrile+0.1% of TFA
Solvent B: water+0.1% of TFA
WL: 220 nm
Gradient: from 1-15% of ACN in 2 min, from 15-35% of ACN in 8 min, collection from 2 min to 11 min.

Separation of the Racemate into the Enantiomers:

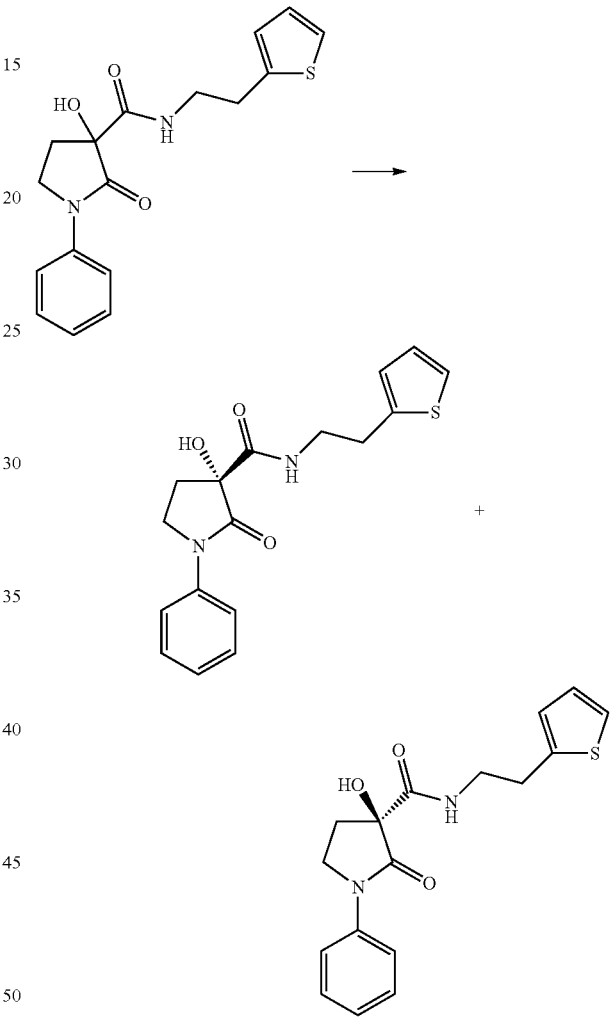

Analytical separation on Chiralcel OD-H with n-heptane/ethanol=70:30.

40 mg of the racemate are dissolved in 10 ml of n-heptane/EtOH=1:1 and separated via 5×25 cm Chiralcel OD column with 20 μm material at a flow rate of 100 ml/min of n-heptane/ethanol=70:30.

2 fractions were collected and evaporated.

Fraction 1: m=20 mg of enantiomer 1:
enantiomerically pure

Fraction 2: m=20 mg of enantiomer 2:
enantiomer ratio:
enantiomer 1: 0.6%:99.4% of enantiomer 2

EXAMPLE 2

Preparation of
3-hydroxy-2-oxo-1-phenylpyrrolidine-3-carboxylic acid [intermediate for Synthesis Scheme b); route 2]

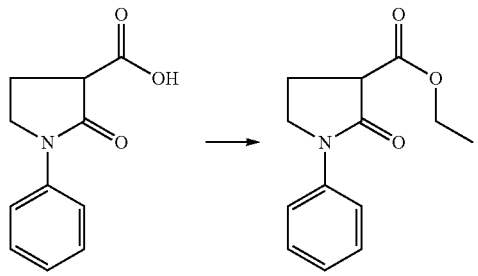
a)

Thionyl chloride (5.8 g) is added dropwise at 0° C. to a solution of 2-oxo-1-phenylpyrrolidine-3-carboxylic acid (5 g) in 5 ml of ethanol, and the mixture is stirred at 80° C. for 4 h.

When the reaction is complete, the solvent is removed in vacuo, and the residue is partitioned between water and ethyl acetate. The organic phase is washed with saturated sodium hydrogencarbonate solution and saturated sodium chloride solution and dried over sodium sulfate. Removal of solvent and drying agent gives ethyl 2-oxo-1-phenylpyrrolidine-3-carboxylate, which is sufficiently pure for further reactions;

$^1$H NMR (400 MHz, DMSO-$d_6$) [ppm] 7.82-7.81 (t, J=2 Hz, 1H), 7.56-7.54 (m, 1H), 7.43-7.39 (t, J=8 Hz, 1H), 7.24-7.21 (m, 1H), 4.17-4.12 (m, 2H), 3.3.92-3.73 (m, 3H), 2.39-2.27 (m, 2H), 1.22-1.14 (t, J=7 Hz, 3H);

LCMS: mass found (M+1, 234);
Method: A—0.1% of TFA in $H_2O$, B—0.1% of TFA in acetonitrile: flow rate—2.0 ml/min;
Column: X Bridge C8 (50×4.6 mm.3.5µ)+ve mode;
Rt (min): 3.360 area % 98.577.

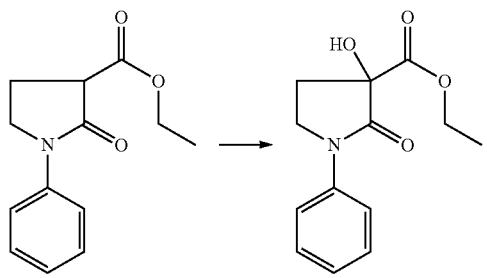
b)

Cerium chloride heptahydrate (1.59 g) is added to a solution of ethyl 2-oxo-1-phenylpyrrolidine-3-carboxylate (5 g) in 10 ml of isopropanol, and $O_2$ gas is passed in for 15 min, the mixture is then left to stir for 14 h.

All volatile constituents are then removed in vacuo, and the batch is purified by chromatography.

The ethyl 3-hydroxy-2-oxo-1-phenylpyrrolidine-3-carboxylate obtained is analysed using chiral HPLC and subsequently separated into the enantiomers.

The 'R' enantiomer elutes after Rt(min) 8.197.
The 'S' enantiomer elutes after Rt(min) 11.240;

(Chiralpak AD-H (250×4.6) mm, 5 µm; n-hexane/IPA=60:40).

$^1$H NMR (400 MHz, DMSO-$d_6$) [ppm] 7.67-7.65 (d, J=8 Hz, 2H), 7.42-7.38 (m, 2H), 7.20-7.17 (m, 1H), 6.53 (s, 1H), 4.13 (m, 2H), 3.91-3.80 (m, 2H), 3.92-3.79 (m, 2H), 2.58-2.51 (m, 1H), 2.17-2.10 (m, 1H), 1.19-1.16 (t, J=8 Hz, 2H);

LCMS: mass found (M+1, 250);
Method: A—0.1% of TFA in $H_2O$, B—0.1% of TFA in acetonitrile: flow rate—2.0 ml/min;
Column: X Bridge C8 (50×4.6 mm.3.5µ)+ve mode;
Rt (min): 2.973 area % 98.698.

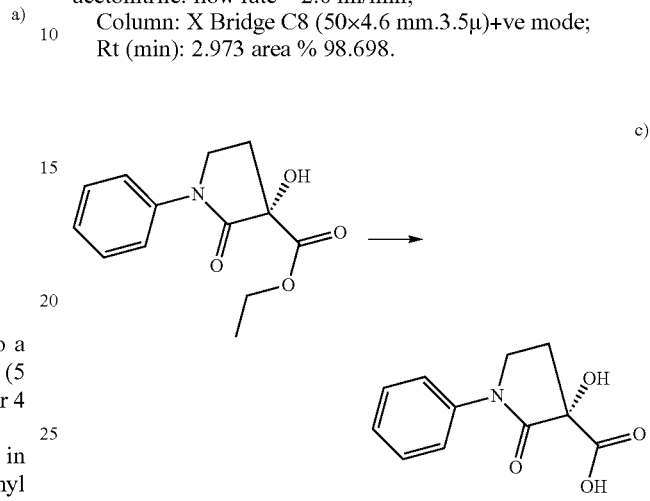
c)

LiOH/$H_2O$ (750 mg) is added to a solution of ethyl (S)-3-hydroxy-2-oxo-1-phenylpyrrolidine-3-carboxylate (1.5 g) in THF/$H_2O$=3:1, and the mixture is stirred for 4 h. The solvent is then removed in vacuo, and the batch is acidified using 1.5N HCl. The aqueous phase is extracted with ethyl acetate, and the combined organic phases are dried over sodium sulfate, giving (S)-3-hydroxy-2-oxo-1-phenylpyrrolidine-3-carboxylic acid;

$^1$H NMR (400 MHz, DMSO-$d_6$) [ppm] 7.68-7.65 (m, 2H), 7.42-7.37 (m, 2H), 7.20-7.15 (m, 1H), 6.53 (s, 1H), 3.87-3.81 (m, 2H), 2.56-2.51 (m, 1H), 2.13-2.07 (m, 1H);

LCMS: mass found (M+1, 222);
Method: A—0.1% of TFA in $H_2O$, B—0.1% of TFA in acetonitrile: flow rate—2.0 ml/min;
Column: X Bridge C8 (50×4.6 mm.3.5µ)+ve mode;
Rt (min): 1.970 area % 98.63;
Chiral HPLC:
Method: n-hexane:IPA: 60:40; flow rate—1.0 ml/min;
Column: Chiralpak AD-H(250×4.6) mm, 5 m;
Rt (min): 9.794 area % 98.698.

Amide Coupling

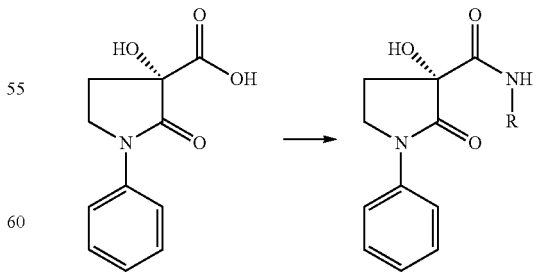

EDCI (3 eq) and HOBT (1.5 eq) are added to a solution of the above-prepared acid (1 eq) and amine (1.2 eq) in dry DMF (3 mml/mmol), and the mixture is warmed in the microwave at 160° C. for 20 min.

When the reaction is complete, the solvent is removed in vacuo and purified by chromatography.

EXAMPLE 3

Preparation of (S)-1-(3-chlorophenyl)-3-hydroxy-2-oxopyrrolidine-3-carboxylic acid (2-thiophen-2-yl-ethyl)amide ("A37")

a)
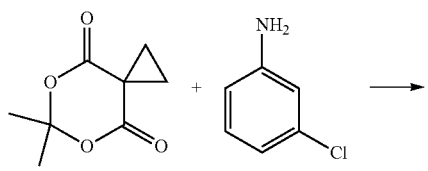

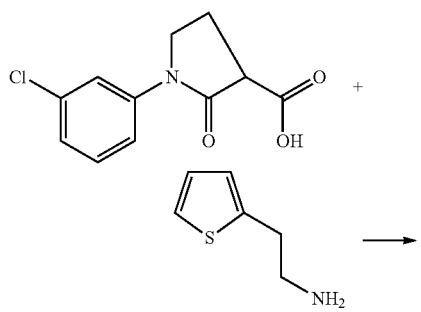

3-Chloroaniline (10.45 g) is added to cyclopropyl-Meldrum's acid (6,6-diemthyl-5,7-dioxaspiro[2.5]octane-4,8-dione; 7 g) in dry dichloromethane, and the mixture is stirred at RT for 14 h.

The batch is then washed with 10% NaOH solution, and the aqueous phase is acidified using 1N HCl until a colourless precipitate forms. This is filtered off and dried in vacuo;

$^1$H NMR (400 MHz, DMSO-d$_6$) [ppm] 12.89 (s, 1H), 7.83-7.82 (t, J=2 Hz, 1H), 7.57-7.54 (m, 1H), 7.43-7.39 (t, J=8 Hz, 1H), 7.23-7.20 (m, 1H), 3.92-3.79 (m, 2H), 3.63-3.59 (m, 1H), 2.36-2.25 (m, 2H);

LCMS: mass found (M+1, 240);

Method: A—0.1% of TFA in H$_2$O, B—0.1% of TFA in acetonitrile: flow rate—2.0 ml/min;

Column: X Bridge C8 (50×4.6 mm.3.5µ)+ve mode;

Rt (min): 3.073 area % 98.91.

b)
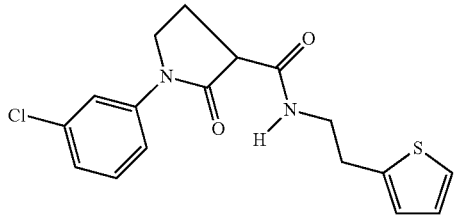

The acid (0.2 g) prepared under a) is dissolved in dry dichloromethane. 2-Thiopenethylamine (127 mg), triethylamine (25 mg) and T3P (399 mg) are subsequently added, and the batch is stirred for 14 h. The mixture is subjected to aqueous work-up and is extracted with dichloromethane.

The organic phase is washed with water, saturated sodium hydrogencarbonate solution and saturated sodium chloride solution, dried over sodium sulfate, evaporated and chromatographed on silica gel;

$^1$H NMR (400 MHz, DMSO-d$_6$) [ppm] 8.36-8.35 (t, J=5.4 Hz, 1H), 7.85-7.84 (d, J=2 Hz, 1H), 7.56-7.54 (dd, J=2, 6.2 Hz, 1H), 7.43-7.39 (t, J=8 Hz, 1H), 7.33-7.32 (dd, J=2, 4 Hz, 1H), 7.22-7.20 (dd, J=2, 6 Hz, 1H), 6.95-6.92 (m, 2H), 3.90-3.79 (m, 2H), 3.54-3.50 (m, 1H), 3.38 (m, 2H), 2.96-2.93 (t, J=6.8 Hz, 1H), 2.29-2.23 (m, 2H);

LCMS: mass found (M+1, 349);

Method: A—0.1% of TFA in H$_2$O, B—0.1% of TFA in acetonitrile: flow rate—2.0 ml/min;

Column: X Bridge C8 (50×4.6 mm.3.5µ)+ve mode;

Rt (min): 4.417 area % 99.65.

c)
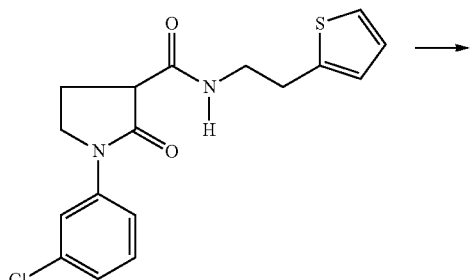

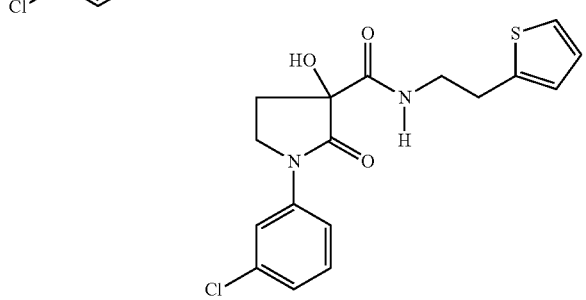

The amide prepared under b) is dissolved in tert-butanol (100 mg). tert-Butyl hydrogen peroxide (70% eq.) solution (0.051 g) and sodium ethoxide (20% in ethanol; 39 mg) are added, and the mixture is stirred at 70° C. for 1 h.

When the reaction is complete, the solvent is removed in vacuo, and water is added until a colourless precipitate forms. This is filtered off and chromatographed.

The enantiomers are obtained by chiral preparative HPLC.

The enantiomer which elutes after Rt(min) 5.419 is the active S-configured compound "A37"; (Chiralpak AD-H (250×4.6) mm, 5 µm; n-hexane/IPA=60:40);

¹H NMR (400 MHz, DMSO-d₆) [ppm] 8.13 (t, J=5.8, 1H), 7.89 (t, J=2.0, 1H), 7.61 (d, J=8.2, 1H), 7.43 (t, J=8.1, 1H), 7.33 (dd, J=5.0, 1.0, 1H), 7.25 (d, J=8.0, 1H), 6.94 (dd, J=5.0, 3.5, 1H), 6.88 (d, J=3.5, 1H), 6.69 (s, 1H), 3.91-3.75 (m, 2H), 3.46-3.33 (m, 2H), 2.95 (t, J=7.4, 2H), 2.08 (dt, J=13.2, 8.2, 1H);

LCMS: mass found (M+1, 365);

Method: A—0.1% of TFA in H₂O, B—0.1% of TFA in acetonitrile: flow rate—2.0 ml/min;

Column: X Bridge C8 (50×4.6 mm.3.5µ)+ve mode;

Rt (min): 4.055 area % 99.02;

HPLC>99.25%:

Method: A—0.1% of TFA in H₂O, B—0.1% of TFA in acetonitrile: flow rate—2.0 ml/min;

Column: X Bridge C8 (50×4.6 mm.3.5µ);

Rt (min): 4.102;

Chiral HPLC:

Method: n-hexane:IPA=60:40; flow rate—1.0 ml/min

Column: Chiralpak AD-H(250×4.6) mm, 5 m;

Rt (min): 5.419 area % 100.

EXAMPLE 4

Preparation of (S)-3-fluoro-2-oxo-1-phenylpyrrolidine-3-carboxylic acid (2-thiophen-2-ylethyl)amide ("A86")

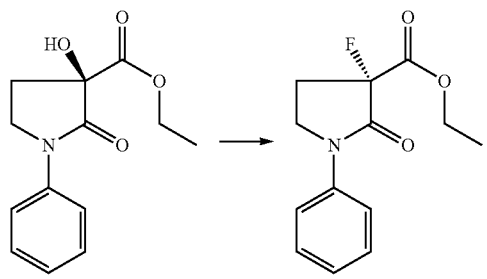

a)

300 mg of ethyl (R)-3-hydroxy-2-oxo-1-phenylpyrrolidine-3-carboxylate are dissolved in dry dichloromethane, 244 mg of DAST are slowly added at −78° C., and the mixture is stirred for a further 4 h.

When the reaction is complete, the batch is poured into saturated sodium hydrogencarbonate solution, the aqueous phase is extracted with dichloromethane, and the combined organic phases are dried over sodium sulfate. Drying agent and solvent are removed, and the residue (180 mg) is reacted further in the subsequent reaction without further purification.

LCMS: mass found (M+1, 252);

Method: A—0.1% of TFA in H₂O, B—0.1% of TFA in acetonitrile: flow rate—2.0 ml/min;

Column: X Bridge C8 (50×4.6 mm.3.5µ)+ve mode;

Rt (min): 3.745 area % 93.764.

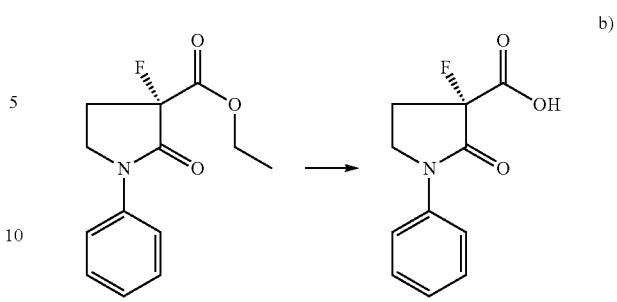

b)

84 mg of LiOH/H₂O are added to a solution of 180 mg of ethyl (S)-3-fluoro-2-oxo-1-phenylpyrrolidine-3-carboxylate in THF/H₂O=3:1, and the mixture is stirred at RT for 4 h. When the reaction is complete, the batch is neutralised using 1.5 N HCl. The aqueous phase is extracted with ethyl acetate, and the organic phase is dried over sodium sulfate. Removal of the solvent in vacuo gives 90 mg of (S)-3-fluoro-2-oxo-1-phenylpyrrolidine-3-carboxylic acid;

LCMS: mass found (M+1, 222);

Method: A—0.1% of HCOOH, B—MeOH: flow rate=1.0 ml/min;

Column: Atlantis DC18 (50×4.6 mm.50µ)+ve mode;

Rt (min): 1.948 area % 90.84.

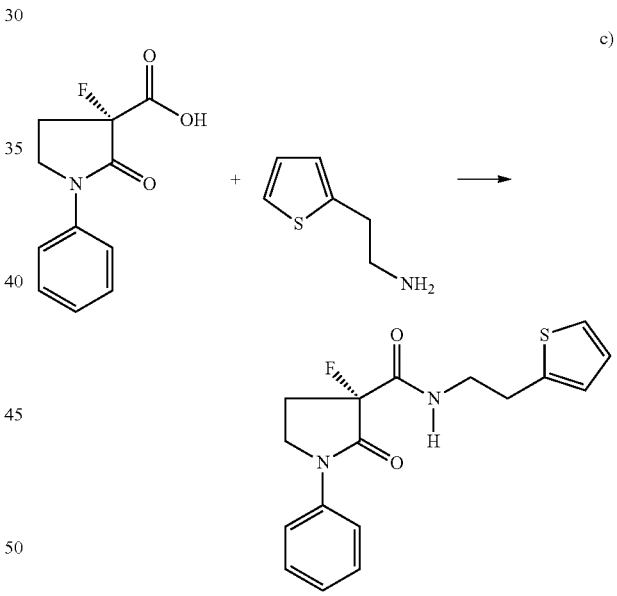

c)

230 mg of EDCI, 65 mg of HOBt are added to a solution of 90 mg of (S)-3-fluoro-2-oxo-1-phenylpyrrolidine-3-carboxylic acid and 61 mg of 2-thiophen-2-ylethylamine in dry DMF, and the mixture is warmed in the microwave at 160° C. for 20 min. When the reaction is complete, all volatile constituents are removed in vacuo, and the residue is purified by chromatography, giving 23 mg of "A86";

¹H NMR (400 MHz, DMSO-d₆) δ [ppm] 8.72 (s, 1H), 7.69 (d, J=7.7, 2H), 7.50-7.40 (m, 2H), 7.33 (dd, J=5.1, 1.2, 1H), 7.23 (t, J=7.4, 1H), 6.94 (dd, J=5.1, 3.4, 1H), 6.89 (d, J=3.4, 1H), 3.97 (dd, J=9.2, 3.3, 1H), 3.92 (dd, J=6.2, 3.4, 1H), 3.48-3.37 (m, 2H), 2.98 (t, J=7.3, 2H), 2.77-2.62 (m, 1H), 2.47-2.35 (m, 2H);

$^{19}$F NMR (377 MHz, DMSO-d$_6$) δ [ppm]-158.16.
LCMS: mass found (M+1, 333);
Method: A—0.1% of TFA in H$_2$O, B—0.1% of TFA in acetonitrile: flow rate—2.0 ml/min;
Column: X Bridge C8 (50×4.6 mm.3.5μ)+ve mode;
Rt (min): 4.147 area % 97.65;
HPLC>97%:
Method: A—0.1% of TFA in H$_2$O, B—0.1% of TFA in acetonitrile: flow—2.0 ml/min;
Column: X Bridge C8 (50×4.6 mm.3.5μ);
Rt (min): 4.209.
EXAMPLE 5
Preparation of (S)-3-amino-2-oxo-1-phenylpyrrolidine-3-carboxylic acid (3-chloro-5-fluorobenzyl) amide ("A91a")
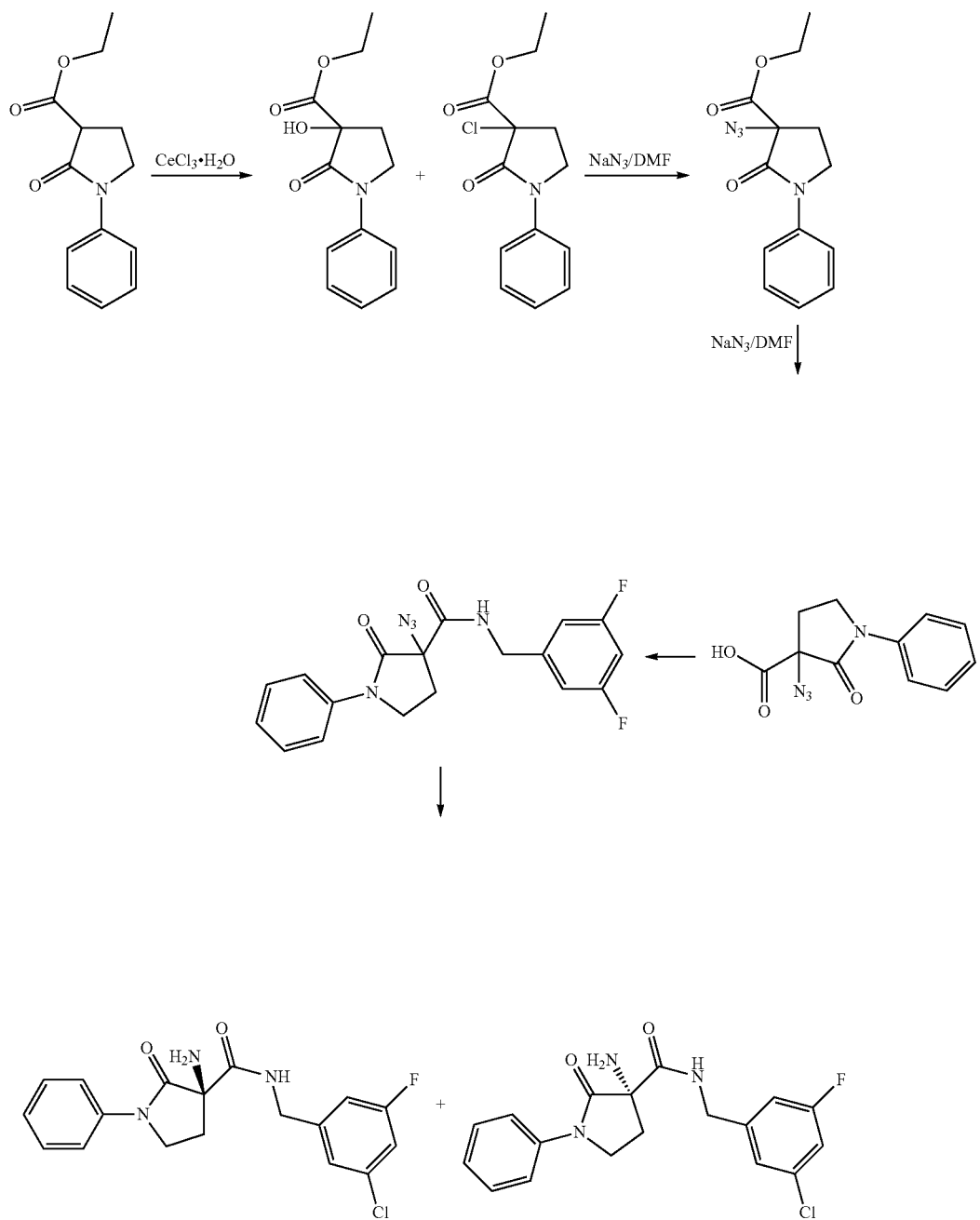

EXAMPLE 6

6.1 Synthesis of ethyl 2-oxo-1-phenylpyrrolidine-3-carboxylate

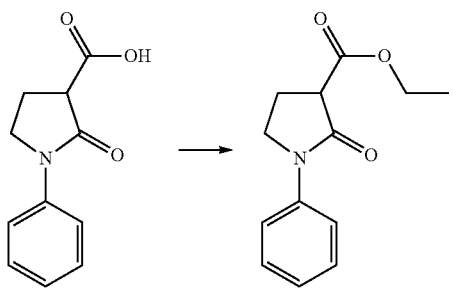 [SMILES: O=C(O)C1CCN(c2ccccc2)C1=O ; CCOC(=O)C1CCN(c2ccccc2)C1=O]

Thionyl chloride is added at 0° C. (5.8 g) to a solution of 2-oxo-1-phenylpyrrolidine-3-carboxylic acid (5 g) in ethanol, and the batch is stirred at 80° C. for 4 h. When the reaction is complete, the batch is concentrated in vacuo, the residue is taken up in water and extracted with ethyl acetate. The organic phase is washed with saturated sodium bicarbonate solution and saturated sodium chloride solution and dried over sodium sulfate, giving ethyl 2-oxo-1-phenylpyrrolidine-3-carboxylate (4.5 g, 79%);

$^1$H NMR (400 MHz, DMSO-$d_6$) δ [ppm] 7.82-7.81 (t, J=2 Hz, 1H), 7.56-7.54 (m, 1H), 7.43-7.39 (t, J=8 Hz, 1H), 7.24-7.21 (m, 1H), 4.17-4.12 (m, 2H), 3.92-3.73 (m, 3H), 2.39-2.27 (m, 2H), 1.22-1.14 (t, J=7 Hz, 3H);

LC/MS: 233.0 (M+H at 1.234 min)

HPLC:

Method: A—0.1% of TFA in H$_2$O, B—0.1% of TFA in ACN: flow—2.0 ml/min.

Column: X Bridge C8 (50×4.6 mm.3.5μ)+ve mode

Rt (min): 3.360 area % 98.577.

6.2 Synthesis of ethyl (S)— and (R)-3-hydroxy-2-oxo-1-phenylpyrrolidine-3-carboxylate and ethyl 3-chloro-2-oxo-1-phenylpyrrolidine-3-carboxylate

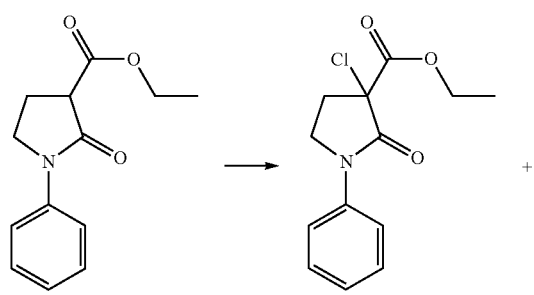

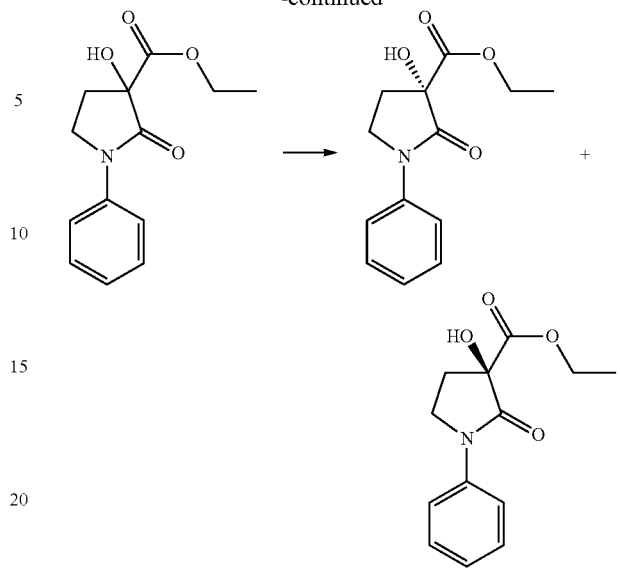

Cerium(III) chloride heptahydrate (1.59 g) is added to a solution of ethyl 2-oxo-1-phenylpyrrolidine-3-carboxylate (5 g) in isopropanol, and O$_2$ is passed in for 15 min. The batch is stirred at RT for 12 h. When the reaction is complete, the solvent is removed in vacuo, and the residue is purified by chromatography on silica gel. Ethyl 3-hydroxy-2-oxo-1-phenylpyrrolidine-3-carboxylate (2.7 g) is analysed by means of chiral HPLC and purified by this method. The substance which elutes at Rt (min) 8.197 is the "R" enantiomer (1.2 g) and the substance which elutes at Rt (min) 11.240 the "S" enantiomer (1.2 g);

(Chiralpak AD-H (250×4.6) mm, 5 μm; n-hexane/isopropanol=60:40).

The S enantiomer necessary is used further for the synthesis of alcohol derivatives.

In this oxidation, ethyl 3-chloro-2-oxo-1-phenylpyrrolidine-3-carboxylate is also formed as racemate in a yield of 20%. Before the enantiomer separation of the alcohols, this is separated off (1 g) by chromatography over silica gel and also employed in racemic form for the next step.

6.3 Synthesis of ethyl 3-azido-2-oxo-1-phenylpyrrolidine-3-carboxylate

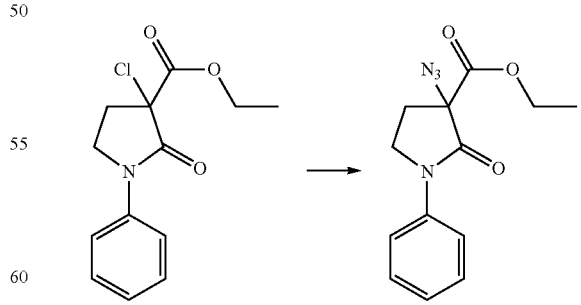

NaN$_3$ (58 mg, 0.89 mmol) is added to a solution of ethyl 3-chloro-2-oxo-1-phenylpyrrolidine-3-carboxylate (0.2 g, 0.74 mmol) in dry DME (5 ml). The reaction solution is stirred at 75° C. under nitrogen for 14 h. After completion, the batch is diluted with ethyl acetate and extracted with water.

The organic phase is dried over sodium sulfate, concentrated, and the residue is employed further directly in the next step (200 mg, 97%);

Thin-layer chromatogram: hexane/ethyl acetate=7:3 $R_f$: 0.4;

LC/MS: 275.0 (M+H at 1.275 min);

$^1$H NMR (DMSO-$d_6$, 400 MHz): δ [ppm] 7.67-7.65 (m, 2H), 7.46-7.42 (m, 2H), 7.26-7.23 (m, 1H), 4.30-4.22 (m, 2H), 3.95-3.92 (m, 2H), 2.68-2.63 (m, 1H), 2.16-2.10 (m, 1H), 1.22 (t, J=7.08 Hz, 3H).

6.4 Synthesis of 3-azido-2-oxo-1-phenylpyrrolidine-3-carboxylic acid

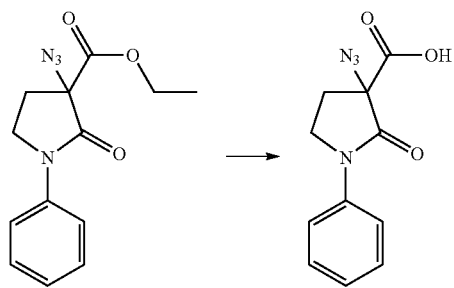 [SMILES: CCOC(=O)C1(N=[N+]=[N-])CCN(c2ccccc2)C1=O ; [N-]=[N+]=NC1(C(=O)O)CCN(c2ccccc2)C1=O]

LiOH (91 mg, 2.1 mmol) is added to a solution of ethyl 3-azido-2-oxo-1-phenylpyrrolidine-3-carboxylate (0.2 g, 0.7 mmol) in THF (2 ml) and H$_2$O (1 ml), and the batch is stirred at RT for 20 hours. When the reaction is complete, all volatile constituents are removed in vacuo, the residue is diluted with water and acidified using 1.5 N HCl solution. The precipitate obtained is filtered off and washed with water.

Drying in vacuo gives a colourless solid as product. (150 mg, 84%);

Thin-layer chromatogram: hexane/ethyl acetate (7/3): $R_f$: 0.4;

LC/MS: 247.0 (M+H at 1.247 min);

$^1$H NMR (DMSO-$d_6$, 400 MHz): δ [ppm] 7.68-7.66 (m, 2H), 7.45-7.41 (m, 2H), 7.25-7.21 (m, 1H), 3.95-3.89 (m, 2H), 2.64-2.59 (m, 1H), 2.13-2.05 (m, 1H).

6.5 Synthesis of 3-azido-2-oxo-1-phenylpyrrolidine-3-carboxylic acid (3-chloro-5-fluorobenzyl)amide ("A150")

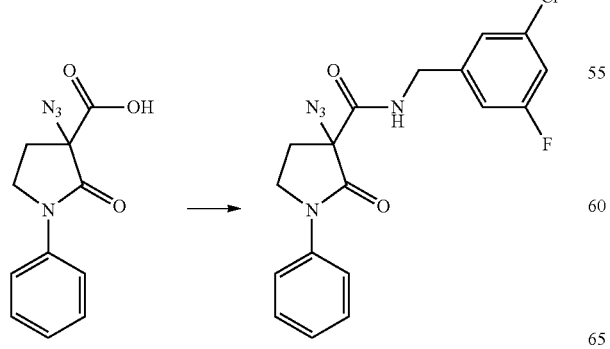

3-Chloro-5-fluorobenzylamine (97 mg, 0.61 mmol) and Et$_3$N (0.24 ml, 1.8 mmol) followed by T3P (0.6 ml, 1.8 mmol) are added at 0° C. to a solution of 3-azido-2-oxo-1-phenylpyrrolidine-3-carboxylic acid (150 mg, 0.61 mmol) in 5 ml of dichloromethane. The reaction mixture is stirred at room temperature under nitrogen for 4 hours. When the reaction is complete, water is added, and the mixture is extracted to exhaustion with dichloromethane. The combined organic phases are subsequently washed with water and saturated sodium chloride solution and dried over sodium sulfate. After filtration and evaporation, the residue is purified by chromatography on silica gel, giving the product as colourless solid (150 mg, 63% yield);

Thin-layer chromatogram: chloroform/methanol=9.5:0.5), $R_f$: 0.3

LC/MS: 388.1 (M+H at 1.388 min);

HPLC: Rt 5.12 min (HPLC purity 95.15%, 95.46%);

$^1$H NMR (DMSO-$d_6$, 400 MHz): δ [ppm] 9.13 (t, J=6.08 Hz, 1H), 7.70-7.68 (m, 2H), 7.43 (t, J=8.64 Hz, 2H), 7.32-7.29 (m, 1H), 7.24-7.20 (m, 2H), 7.09 (d, J=9.80 Hz, 1H), 4.42-4.34 (m, 2H), 3.95-3.89 (m, 2H), 2.61-2.58 (m, 1H), 2.28-2.22 (m, 1H).

6.6 Synthesis of 3-amino-2-oxo-1-phenylpyrrolidine-3-carboxylic acid (3-chloro-5-fluorobenzyl)amide ("A151")

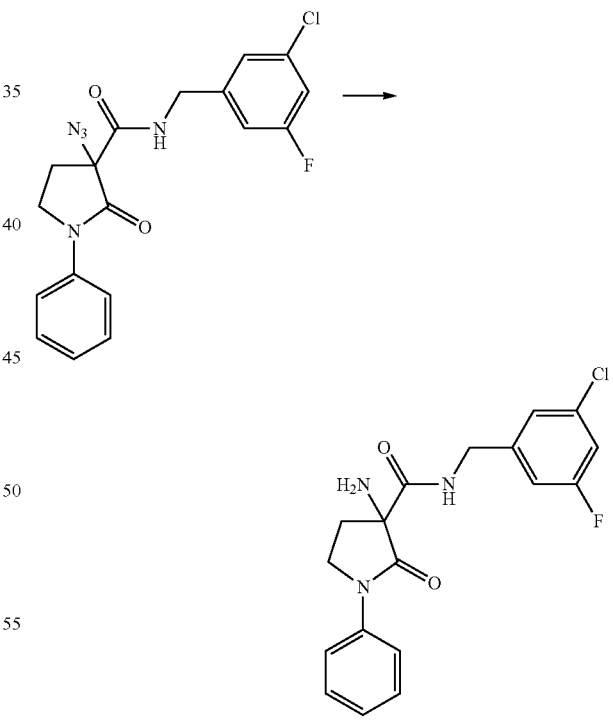

Et$_3$N (0.1 ml, 0.75 mmol) followed by propanedithiol (0.08 ml, 0.75 mmol) are added to a solution of 3-azido-2-oxo-1-phenylpyrrolidine-3-carboxylic acid (3-chloro-5-fluorobenzyl)amide (100 mg, 0.25 mmol) in 2 ml of methanol. The batch is stirred at RT for 12 hours. When the reaction is complete, all volatile constituents are removed in vacuo, and the residue is purified on silica gel.

The following compounds are obtained analogously

| No. | Structure/name | ¹H NMR (400 MHz, DMSO-d₆) δ [ppm] | LC-MS; rt; [M + H⁺]* |
|---|---|---|---|
| "A1" | (S)-3-Hydroxy-2-oxo-1-phenyl-pyrrolidine-3-carboxylic acid 3-bromobenzyl amide | 8.65 (t, J = 6.1, 1H), 7.70 (d, J = 8.3, 2H), 7.47 (s, 1H), 7.40 (t, J = 7.8, 3H), 7.26 (d, J = 4.8, 2H), 7.17 (t, J = 7.3, 1H), 6.73 (s, 1H), 4.34 (dd, J = 15.2, 6.5, 1H), 4.24 (dd, J = 15.3, 6.0, 1H), 3.85 (t, J = 6.8, 2H), 2.62-2.52 (m, 1H), 2.11 (dt, J = 12.9, 7.8, 1H) | 4.005 min [389.0 + 392.0] % |
| "A2" | (S)-3-Hydroxy-2-oxo-1-phenyl-pyrrolidine-3-carboxylic acid [2-(5-tert-butyloxazol-2-yl)ethyl] amide | 8.16-8.11 (m, 1H), 7.68 (d, J = 7.7, 2H), 7.43-7.33 (m, 2H), 7.18 (d, J = 7.5, 1H), 6.68 (s, 1H), 6.66 (s, 1H), 3.83 (m, 2H), 3.56-3.47 (m, 2H), 2.85 (m, 2H), 2.55 (m, 1H), 2.13-2.01 (m, 1H), 1.22 (s, 9H) | 3.513 min [372.3] % |
| "A3" | (S)-3-Hydroxy-2-oxo-1-phenyl-pyrrolidine-3-carboxylic acid [2-(5-ethyltetrazol-2-yl)ethyl] amide | 8.22 (t, J = 6.0, 1H), 7.68 (d, J = 1.1, 1H), 7.66 (d, J = 1.0, 1H), 7.42-7.36 (m, 2H), 7.21-7.12 (m, 1H), 6.65 (s, 1H), 4.78-4.60 (m, 2H), 3.80 (ddd, J = 15.3, 8.7, 5.2, 2H), 3.76-3.65 (m, 1H), 3.56-3.42 (m, 1H), 2.81 (q, J = 7.6, 2H), 2.42 (ddd, J = 12.8, 7.1, 3.8, 1H), 2.05 (dt, J = 12.9, 8.0, 1H), 1.25 (t, J = 7.6, 3H) | 2.679 min [345.3] % |
| "A4" | (S)-3-Hydroxy-2-oxo-1-phenyl-pyrrolidine-3-carboxylic acid 3-chlorobenzyl amide | 8.65 (t, J = 6.2, 1H), 7.69 (dd, J = 8.7, 1.1, 2H), 7.43-7.37 (m, 2H), 7.33 (t, J = 7.6, 2H), 7.27 (dd, J = 6.6, 2.1, 1H), 7.22 (d, J = 7.5, 1H), 7.18 (dd, J = 10.5, 4.2, 1H), 6.73 (s, 1H), 4.35 (dd, J = 15.2, 6.6, 1H), 4.25 (dd, J = 15.4, 6.1, 1H), 3.90-3.80 (m, 2H), 2.61-2.54 (m, 1H), 2.11 (dt, J = 13.0, 7.8, 1H) | 3.886 min [345.0] % |
| "A5" | (S)-3-Hydroxy-2-oxo-1-phenyl-pyrrolidine-3-carboxylic acid benzyl amide | 8.51 (t, J = 6.0, 1H), 7.69-(dd, J = 8.6, 0.9, 2H), 7.45-7.34 (m, 2H), 7.32-7.24 (m, 4H), 7.20 (dt, = 14.8, 4.6, 2H), 6.68 (s, 1H), 4.33 (dd, J = 15.1, 6.5, 1H), 4.27 (dd, J = 15.1, 6.2, 1H), 3.92-3.74 (m, 2H), 2.63-2.52 (m, 2H), 2.11 (dt, J = 12.9, 7.9, 1H) | 3.309 min [311.3] % |

-continued

| No. | Structure/name | ¹H NMR (400 MHz, DMSO-d₆) δ [ppm] | LC-MS; rt; [M + H⁺]* |
|---|---|---|---|
| "A6" | (S)-3-Hydroxy-2-oxo-1-phenyl-pyrrolidine-3-carboxylic acid 3-difluoromethoxybenzyl amide | 8.63 (t, J = 6.3, 1H), 7.77-7.60 (m, 2H), 7.45-7.30 (m, 3H), 7.22-7.10 (m, 3H), 7.07 (s, 1H), 7.02 (d, J = 9.8, 1H), 6.72 (s, 1H), 4.35 (dd, J = 15.4, 6.5, 1H), 4.27 (dd, J = 15.4, 6.2, 1H), 3.85 (dd, J = 8.7, 5.5, 2H), 2.64-2.52 (m, 1H), 2.20-2.05 (m, 1H) | 3.927 min [377.0] % |
| "A7" | (S)-3-Hydroxy-2-oxo-1-phenyl-pyrrolidine-3-carboxylic acid 3-fluorobenzyl amide | 8.64 (t, J = 6.4, 1H), 7.69 (dd, J = 8.7, 1.1, 2H), 7.43-7.37 (m, 2H), 7.33 (td, J = 7.9, 6.1, 1H), 7.21-7.14 (m, 1H), 7.10 (d, J = 7.4, 2H), 7.08-6.99 (m, 2H), 6.73 (s, 1H), 4.37 (dd, J = 15.5, 6.6, 1H), 4.26 (dd, J = 15.4, 6.1, 1H), 3.92-3.75 (m, 2H), 2.63-2.54 (m, 1H), 2.12 (dt, J = 12.9, 7.7, 1H) | 3.522 min [329.0] % |
| "A8" | (S)-3-Hydroxy-2-oxo-1-phenyl-pyrrolidine-3-carboxylic acid 3-trifluoromethoxybenzyl amide | 8.70 (t, J = 6.4, 1H), 7.70 (d, J = 1.1, 1H), 7.68 (d, J = 1.0, 1H), 7.46-7.36 (m, 3H), 7.29 (d, J = 7.9, 1H), 7.25 (s, 1H), 7.22-7.14 (m, 2H), 6.73 (s, 1H), 4.38 (dd, J = 15.5, 6.6, 1H), 4.30 (dd, J = 15.4, 6.1, 1H), 3.90-3.82 (m, 2H), 2.56 (dt, J = 11.5, 5.6, 1H), 2.12 (dt, J = 12.9, 7.7, 1H) | 4.362 min [395.0] % |
| "A9" | (S)-3-Hydroxy-2-oxo-1-phenyl-pyrrolidine-3-carboxylic acid 3-(2-methylidazol-1-yl)benzyl amide | 8.69 (t, J = 6.3, 1H), 7.68 (d, J = 7.9, 2H), 7.43 (dt, J = 22.3, 8.0, 3H), 7.30 (dd, J = 16.9, 8.3, 3H), 7.23 (d, J = 1.0, 1H), 7.17 (t, J = 7.3, 1H), 6.89 (d, J = 1.0, 1H), 6.73 (s, 1H), 4.44 (dd, J = 15.4, 6.7, 1H), 4.31 (dd, J = 15.4, 6.0, 1H), 3.91-3.77 (m, 2H), 2.63-2.54 (m, 1H), 2.25 (s, 3H), 2.11 (dt, J = 13.0, 7.8, 1H) | 2.357 min [391.3] % |
| "A10" | (S)-3-Hydroxy-2-oxo-1-phenyl-pyrrolidine-3-carboxylic acid [2-(5-tert-butyl-1,2,4-oxadiazol-3-yl)-ethyl] amide | (400 MHz, CDCl₃) δ [ppm] 7.66 (dd, J = 8.7, 1.0, 2H), 7.61 (br. s, 1H), 7.45-7.36 (m, 2H), 7.21 (t, J = 7.4, 1H), 4.18 (td, J = 9.2, 7.0, 1H), 3.84 (td, J = 9.2, 1.2, 1H), 3.78-3.60 (m, 2H), 3.07-2.88 (m, 2H), 2.74 (ddd, J = 12.7, 6.9, 1.3, 1H), 2.26 (dt, J = 12.7, 9.3, 1H), 1.45 (s, 9H), 1.33-1.18 (m, 2H), 0.89 (s, 1H) | 3.549 min [373.3] % |

| No. | Structure/name | ¹H NMR (400 MHz, DMSO-d₆) δ [ppm] | LC-MS; rt; [M + H⁺]* |
|---|---|---|---|
| "A11" | (S)-3-Hydroxy-2-oxo-1-phenyl-pyrrolidine-3-carboxylic acid (2-cyclopentylethyl) amide | 7.89 (s, 1H), 7.72-7.66 (m, 2H), 7.39 (t, J = 8.0, 2H), 7.17 (t, J = 7.4, 1H), 6.57 (s, 1H), 5.70 (s, 1H), 3.94-3.74 (m, 2H), 3.08 (m, 2H), 2.11-1.96 (m, 1H), 1.72 (m, 4H), 1.55 (m, 2H), 1.50-1.38 (m, 4H), 1.02 (m, 3H) | HPLC 5.529 min |
| "A12" | (S)-3-Hydroxy-2-oxo-1-phenyl-pyrrolidine-3-carboxylic acid [2-(5-cyclopentyl-1,2,4-oxadiazol-3-yl)-ethyl] amide | (400 MHz, CDCl₃) δ 7.66 (d, J = 7.7, 1H), 7.55 (s, 1H), 7.40 (t, J = 8.0, 1H), 7.21 (t, J = 7.4, 1H), 4.18 (td, J = 9.2, 7.0, 1H), 3.84 (td, J = 9.2, 1.2, 1H), 3.77-3.62 (m, 1H), 3.39-3.27 (m, 1H), 3.04-2.86 (m, 1H), 2.73 (ddd, J = 12.7, 6.9, 1.2, 1H), 2.26 (dt, J = 12.7, 9.3, 1H), 2.14 (m, 1H), 2.01-1.89 (m, 1H), 1.88-1.77 (m, 1H), 1.77-1.68 (m, 1H) | 3.706 min [385.3] % |
| "A13" | (S)-3-Hydroxy-2-oxo-1-phenyl-pyrrolidine-3-carboxylic acid [2-(5-ethyltetrazol-1-yl)ethyl] amide | 8.28 (t, J = 6.1, 1H), 7.67 (d, J = 7.7, 2H), 7.45-7.34 (m, 2H), 7.17 (t, J = 7.4, 1H), 6.66 (s, 1H), 4.52-4.33 (m, 2H), 3.89-3.72 (m, 2H), 3.60 (m, 1H), 3.41 (m, 1H), 2.86 (q, J = 7.5, 2H), 2.41 (ddd, J = 12.7, 7.0, 4.1, 1H), 2.04 (dt, J = 12.9, 8.1, 1H), 1.28 (t, J = 7.5, 3H) | 2.407 min [345.3] % |
| "A14" | (S)-3-Hydroxy-2-oxo-1-phenyl-pyrrolidine-3-carboxylic acid [2-(5-methyl-1,3,4-thiadiazol-2-yl)ethyl] amide | 8.23 (t, J = 6.2, 1H), 7.69 (d, J = 8.0, 2H), 7.40 (t, J = 7.8, 2H), 7.17 (t, J = 7.4, 1H), 6.66 (s, 1H), 3.82 (dd, J = 8.4, 5.2, 2H), 3.55-3.47 (m, 2H), 3.46-3.38 (m, 2H), 3.20 (t, J = 7.0, 2H), 2.66 (s, 3H), 2.08 (dt, J = 12.3, 8.0, 1H) | 2.329 min [347.0] % |
| "A15" | (S)-3-Hydroxy-2-oxo-1-phenyl-pyrrolidine-3-carboxylic acid [2-(5-trifluoromethyl-1,3,4-oxadiazol-2-yl)ethyl] amide | 8.32 (s, 1H), 7.67 (d, J = 7.9, 2H), 7.39 (t, J = 8.0, 2H), 7.17 (t, J = 7.4, 1H), 6.66 (s, 1H), 3.86-3.75 (m, 2H), 3.58 (td, J = 13.4, 6.8, 1H), 3.43 (dt, J = 13.4, 6.6, 2H), 3.23-3.04 (m, 2H), 2.47-2.40 (m, 1H), 2.06 (dt, J = 13.1, 7.7, 1H) | 3.342 min [385.3] % |

-continued

| No. | Structure/name | ¹H NMR (400 MHz, DMSO-$d_6$) δ [ppm] | LC-MS; rt; [M + H⁺]* |
|---|---|---|---|
| "A16" | 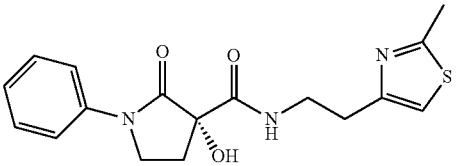<br>(S)-3-Hydroxy-2-oxo-1-phenyl-pyrrolidine-3-carboxylic acid [2-(2-methylthiazol-4-yl)ethyl] amide | 8.10 (t, J = 5.9, 1H), 7.69 (d, J = 7.8, 2H), 7.40 (t, J = 8.0, 2H), 7.17 (t, J = 7.4, 1H), 7.14 (s, 1H), 6.62 (s, 1H), 3.83 (dd, J = 12.2, 5.5, 2H), 3.50-3.35 (m, 2H), 2.82 (t, J = 7.2, 2H), 2.61 (s, 3H), 2.53 (m, 1H), 2.07 (dt, J = 12.9, 8.0, 1H) | HPLC 7.206 min |
| "A17" | 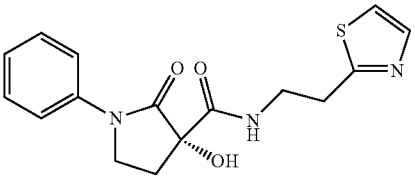<br>(S)-3-Hydroxy-2-oxo-1-phenyl-pyrrolidine-3-carboxylic acid (2-thiazol-2-ylethyl) amide | 8.20 (t, J = 6.0, 1H), 7.71 (d, J = 3.3, 1H), 7.69 (d, J = 7.8, 2H), 7.59 (d, J = 3.3, 1H), 7.45-7.36 (m, 2H), 7.17 (t, J = 7.4, 1H), 6.65 (s, 1H), 3.83 (t, J = 6.3, 2H), 3.52 (dt, J = 13.7, 6.8, 1H), 3.47-3.35 (m, 2H), 3.15 (t, J = 7.1, 2H), 2.56-2.51 (m, 1H), 2.07 (dt, J = 12.9, 7.9, 1H) | 2.143 min [332.0] % |
| "A18" | 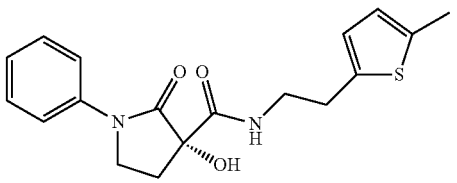<br>(S)-3-Hydroxy-2-oxo-1-phenyl-pyrrolidine-3-carboxylic acid [2-(5-methylthiophen-2-yl)ethyl] amide | 8.07 (t, J = 5.9, 1H), 7.73-7.65 (m, 2H), 7.40 (dd, J = 10.8, 5.3, 2H), 7.17 (t, J = 7.4, 1H), 6.64 (d, J = 3.3, 1H), 6.63 (s, 1H), 6.59 (dd, J = 3.3, 1.1, 1H), 3.91-3.75 (m, 2H), 3.30-3.33 (m, 1H), 3.15 (m, 1H), 2.85 (t, J = 7.4, 2H), 2.53 (m, 1H), 2.34 (s, 3H), 2.07 (dt, J = 12.9, 8.0, 1H) | 3.887 min [345.3] % |
| "A19" | 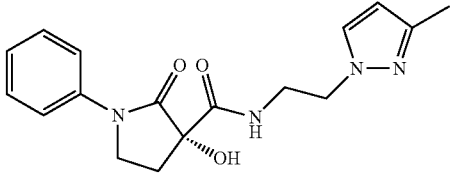<br>(S)-3-Hydroxy-2-oxo-1-phenyl-pyrrolidine-3-carboxylic acid [2-(3-methylpyrazol-1-yl)ethyl] amide | 8.10 (t, J = 5.7, 1H), 7.79-7.65 (m, 2H), 7.53 (d, J = 2.1, 1H), 7.40 (t, J = 8.0, 2H), 7.17 (t, J = 7.4, 1H), 6.65 (s, 1H), 5.97 (d, J = 2.1, 1H), 4.09 (t, J = 6.4, 2H), 3.82 (dd, J = 8.5, 5.4, 2H), 3.48 (m, 1H), 3.40 (m, 1H), 2.52 (m, 1H), 2.14 (s, 3H), 2.06 (dt, J = 12.9, 7.9, 1H) | HPLC: 6.550 min |
| "A20" | 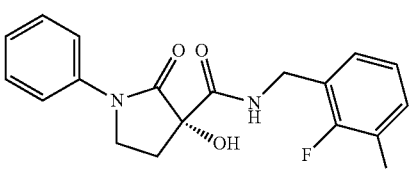<br>(S)-3-Hydroxy-2-oxo-1-phenyl-pyrrolidine-3-carboxylic acid 3-chloro-2-fluorobenzyl amide | 8.64 (t, J = 6.0, 1H), 7.69 (dd, J = 8.7, 1.0, 1H), 7.45 (td, J = 7.9, 1.6, 1H), 7.43-7.37 (m, 1H), 7.31 (td, J = 7.5, 1.5, 1H), 7.18 (td, J = 7.7, 1.8, 1H), 6.75 (s, 1H), 4.41 (dd, J = 15.6, 6.0, 1H), 4.33 (dd, J = 15.5, 6.0, 1H), 3.90-3.80 (m, 1H), 2.62-2.55 (m, 1H), 2.12 (dt, J = 12.9, 8.0, 1H) | 4.002 min [363.0] % |

-continued

| No. | Structure/name | $^1$H NMR (400 MHz, DMSO-$d_6$) δ [ppm] | LC-MS; rt; [M + H$^+$]* |
|---|---|---|---|
| "A21" | (S)-3-Hydroxy-2-oxo-1-phenyl-pyrrolidine-3-carboxylic acid 3-chloro-2,6-difluorobenzyl amide | (400 MHz, CDCl$_3$) δ [ppm] 7.68-7.59 (m, 2H), 7.42-7.36 (m, 2H), 7.36-7.29 (m, 2H), 7.24-7.18 (m, 1H), 6.88 (td, J = 8.8, 1.8, 1H), 4.65 (dd, J = 14.6, 6.5, 1H), 4.50 (dd, J = 14.6, 5.6, 1H), 4.20 (td, J = 9.2, 6.9, 1H), 3.81 (td, J = 9.2, 1.2, 1H), 2.72 (ddd, J = 12.7, 6.9, 1.2, 1H), 2.25 (dt, J = 12.7, 9.3, 1H) | |
| "A22" | (S)-3-Hydroxy-2-oxo-1-phenyl-pyrrolidine-3-carboxylic acid 5-bromo-2-fluorobenzyl amide | 8.66 (t, J = 6.3, 1H), 7.78-7.67 (m, 2H), 7.53-7.44 (m, 2H), 7.40 (t, J = 8.0, 2H), 7.16 (dd, J = 16.7, 8.2, 2H), 6.78 (s, 1H), 4.39 (dd, J = 15.8, 6.6, 1H), 4.26 (dd, J = 15.9, 6.0, 1H), 3.86 (dd, J = 8.0, 5.1, 2H), 2.64-2.54 (m, 1H), 2.13 (dt, J = 13.0, 7.6, 1H) | HPLC 7.301 min |
| "A23" | (S)-3-Hydroxy-2-oxo-1-phenyl-pyrrolidine-3-carboxylic acid 3-bromo-4-fluorobenzyl amide | 8.67 (t, J = 6.3, 1H), 7.69 (d, J = 8.4, 2H), 7.59 (d, J = 6.9, 1H), 7.40 (t, J = 7.8, 2H), 7.31 (d, J = 7.3, 2H), 7.18 (t, J = 7.4, 1H), 6.72 (s, 1H), 4.33 (dd, J = 15.1, 6.7, 1H), 4.22 (dd, J = 15.2, 6.0, 1H), 3.85 (t, J = 6.8, 2H), 2.62-2.52 (m, 1H), 2.11 (dt, J = 13.3, 7.8, 1H) | 4.094 min [409.0 + 410.0] % |
| "A24" | (S)-3-Hydroxy-2-oxo-1-phenyl-pyrrolidine-3-carboxylic acid 3-(pyridin-3-ylmethyl) amide | 8.67 (t, J = 6.3, 1H), 8.48 (d, J = 1.8, 1H), 8.42 (dd, J = 4.7, 1.5, 1H), 7.69 (d, J = 7.9, 2H), 7.65 (dd, J = 12.9, 5.0, 1H), 7.46-7.36 (m, 2H), 7.32 (dd, J = 7.8, 4.8, 1H), 7.17 (t, J = 7.4, 1H), 7.00 (s, 1H), 6.71 (s, 1H), 4.37 (dd, J = 15.2, 6.5, 1H), 4.28 (dd, J = 15.2, 6.1, 1H), 3.94-3.78 (m, 2H), 2.63-2.53 (m, 1H), 2.11 (dt, J = 12.9, 7.8, 1H) | 1.872 min [312.3] % |
| "A25" | (S)-3-Hydroxy-2-oxo-1-phenyl-pyrrolidine-3-carboxylic acid (6-pyrrolidin-1-ylpyridin-2-ylmethyl) amide | 8.44 (t, J = 5.6, 1H), 7.70 (d, J = 8.1, 2H), 7.41 (dd, J = 15.5, 7.4, 3H), 7.17 (t, J = 7.4, 1H), 6.75 (s, 1H), 6.47 (d, J = 7.3, 1H), 6.28 (d, J = 8.4, 1H), 4.31-4.17 (m, 2H), 3.93-3.77 (m, 2H), 3.37 (m, 4H), 3.03-2.95 (m, 1H), 2.64-2.57 (m, 1H), 2.12 (dt, J = 13.0, 8.0, 1H), 2.01-1.83 (m, 4H), 1.09-0.89 (m, 1H) | HPLC 9.533 |

-continued

| No. | Structure/name | ¹H NMR (400 MHz, DMSO-d₆) δ [ppm] | LC-MS; rt; [M + H⁺]* |
|---|---|---|---|
| "A26" | 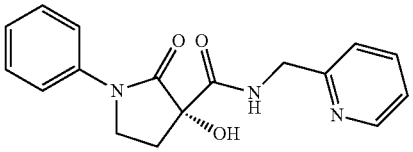<br>(S)-3-Hydroxy-2-oxo-1-phenyl-pyrrolidine-3-carboxylic acid (pyridin-2-ylmethyl) amide | 8.63 (t, J = 5.2, 1H), 8.51 (d, J = 3.8, 1H), 7.77 (t, J = 7.5, 1H), 7.71 (d, J = 8.5, 1H), 7.42 (t, J = 7.6, 2H), 7.33 (d, J = 7.7, 1H), 7.30-7.24 (m, 1H), 7.19 (t, J = 7.2, 1H), 6.79 (s, 1H), 4.46 (dd, J = 16.5, 6.4, 1H), 4.38 (dd,J = 16.1, 6.0, 1H), 3.88 (m, 2H), 2.62 (m, 1H), 2.16 (m, 1H) | 1.959 min [312.3] |
| "A27" | 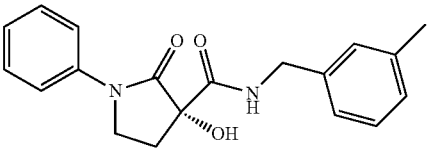<br>(S)-3-Hydroxy-2-oxo-1-phenyl-pyrrolidine-3-carboxylic acid 3-methylbenzyl amide | 8.46 (t, J = 6.2, 1H), 7.70 (d, J = 7.8, 2H), 7.46-7.35 (m, 2H), 7.17 (t, J = 7.3, 2H), 7.07 (d, J = 4.4, 2H), 7.02 (d, J = 7.8, 1H), 6.68 (s, 1H), 4.29 (dd, J = 15.0, 6.5, 1H), 4.23 (dd, J = 15.1, 6.2, 1H), 3.96-3.74 (m, 2H), 2.64-2.52 (m, 1H), 2.26 (s, 3H), 2.11 (dt, J = 12.8, 7.8, 1H) | 3.763 min [325.3] |
| "A28" | 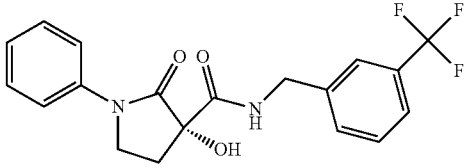<br>(S)-3-Hydroxy-2-oxo-1-phenyl-pyrrolidine-3-carboxylic acid 3-trifluoromethylbenzyl amide | 8.74 (t, J = 6.3, 1H), 7.69 (d, J = 7.8, 2H), 7.63 (s, 1H), 7.54 (dd, J = 13.3, 6.1, 3H), 7.40 (t, J = 8.0, 2H), 7.17 (t, J = 7.4, 1H), 6.74 (s, 1H), 4.43 (dd, J = 15.5, 6.5, 1H), 4.33 (dd, J = 15.4, 6.1, 1H), 3.94-3.76 (m, 2H), 2.57 (dt, J = 11.8, 5.7, 1H), 2.12 (dt, J = 13.0, 7.8, 1H) | 4.260 min [379.0] % |
| "A29" | 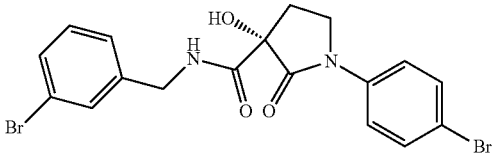<br>(S)-1-(4-Bromophenyl)-3-hydroxy-2-oxopyrrolidine-3-carboxylic acid 3-bromobenzyl amide | (400 MHz, CDCl₃) δ [ppm] 7.58 (d, J = 9.1, 1H), 7.52 (d, J = 9.1, 1H), 7.42 (d, J = 4.6, 1H), 7.22 (dd, J = 4.8, 1.4, 1H), 4.50-4.36 (m, 1H), 4.20 (dd, J = 16.1, 9.2, 1H), 3.83 (t, J = 9.2, 1H), 3.66 (s, 1H), 2.78 (dd, J = 12.8, 6.9, 1H), 2.29 (dt, J = 12.8, 9.4, 1H) | 4.583 min 467.0 + 469.0 + 472.0] % |
| "A30" | 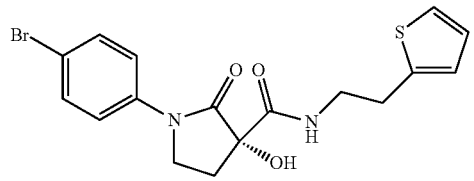<br>(S)-1-(4-Bromophenyl)-3-hydroxy-2-oxopyrrolodine-3-carboxylic acid (2-thiophen-2-ylethyl) amide | 8.11 (s, 1H), 7.68 (d, J = 9.0, 2H), 7.58 (d, J = 9.0, 2H), 7.32 (d, J = 5.1, 1H), 6.98-6.90 (m, 1H), 6.89 (s, 1H), 6.66 (s, 1H), 3.88-3.76 (m, 2H), 3.36 (d, J = 5.9, 2H), 2.95 (t, J = 7.3, 2H), 2.53 (s, 1H), 2.07 (dt, J = 12.4, 7.6, 2H) | 4.127 min [409.0 + 410.0] % |
| "A31" | 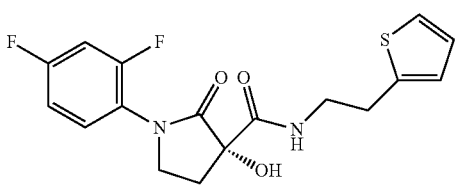<br>(S)-1-(2,4-Difluorophenyl)-3-hydroxy-2-oxopyrrolodine-3-carboxylic acid(2-thiophen-2-yl-ethyl) amide | 8.08 (t, J = 6.0, 1H), 7.50-7.41 (m, 1H), 7.41-7.36 (m, 1H), 7.33 (dd, J = 5.1, 1.2, 1H), 7.20-7.13 (m, 1H), 6.94 (dd, J = 5.1, 3.4, 1H), 6.89 (d, J = 2.4, 1H), 6.66 (s, 1H), 3.81-3.65 (m, 2H), 3.49-3.35 (m, 2H), 2.96 (t, J = 7.4, 2H), 2.57-2.52 (m, 1H), 2.13 (ddd, J = 12.9, 8.4, 7.3, 1H) | 3.539 min [367.0] % |

-continued

| No. | Structure/name | ¹H NMR (400 MHz, DMSO-$d_6$) δ [ppm] | LC-MS; rt; [M + H⁺]* |
|---|---|---|---|
| "A32" | 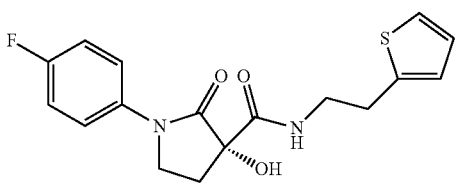<br>(S)-1-(4-Fluorophenyl)-3-hydroxy-2-oxopyrrolodine-3-carboxylic acid (2-thiophen-2-ylethyl) amide | (400 MHz, CDCl₃) δ [ppm] 7.67-7.59 (m, 1H), 7.18 (dd, J = 5.1, 1.1, 1H), 7.10 (dd, J = 11.7, 5.7, 1H), 6.96 (dd, J = 5.1, 3.4, 0H), 6.87 (d, J = 3.4, 1H), 4.17 (td, J = 9.2, 6.9, 1H), 3.80 (t, J = 9.2, 1H), 3.55 (dd, J = 13.1, 6.7, 2H), 3.07 (t, J = 6.7, 1H), 2.71 (dd, J = 13.4, 6.3, 1H), 2.25 (dt, J = 12.7, 9.3, 1H) | 3.623 min [349.0] % |
| "A33" | 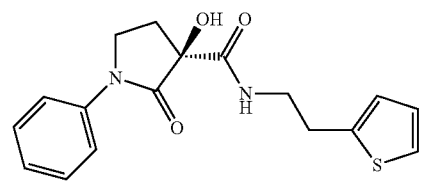<br>(S)-Hydroxy-2-oxo-1-phenyl-pyrrolidine-3-carboxylic acid (2-thiophen-2-ylethyl) amide | | 1) HPLC 7.19 min |
| "A34" | 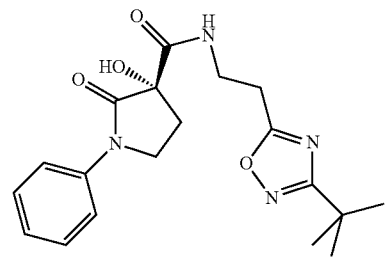<br>(S)-3-Hydroxy-2-oxo-1-phenyl-pyrrolidine-3-carboxylic acid [2-(3-tert-butyl-1,2,4-oxadiazol-5-yl)-ethyl] amide | 8.24 (t, J = 6.1, 1H), 7.68 (d, J = 7.8, 2H), 7.39 (t, J = 8.0, 2H), 7.17 (t, J = 7.4, 1H), 6.66 (s, 1H), 3.82 (dd, J = 7.8, 5.7, 2H), 3.64-3.49 (m, 1H), 3.41 (td, J = 13.0, 6.6, 2H), 3.12-3.01 (m, 2H), 2.06 (dt, J = 12.8, 7.9, 1H), 1.28 (s, 9H) | 3.564 min [373.3] % |
| "A35" | 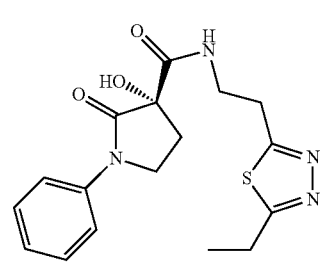<br>(S)-3-Hydroxy-2-oxo-1-phenyl-pyrrolidine-3-carboxylic acid [2-(5-ethyl-1,3,4-thiadiazol-2-yl)ethyl] amide | 8.23 (t, J = 6.0, 1H) 7.70 (d, J = 1.1, 1H), 7.68 (d, J = 0.8, 1H), 7.46-7.35 (m, 2H), 7.17 (t, J = 7.4, 1H), 6.66 (s, 1H), 3.90-3.74 (m, 2H), 3.51 (dt, J = 13.4, 6.7, 1H), 3.46-3.36 (m, 1H), 3.21 (t, J = 6.9, 2H), 3.02 (q, J = 7.5, 2H), 2.07 (dt, J = 12.9, 8.0, 1H), 1.27 (t, J = 7.5, 3H) | 2.631 min [361.0] % |

| No. | Structure/name | ¹H NMR (400 MHz, DMSO-d$_6$) δ [ppm] | LC-MS; rt; [M + H$^+$]* |
|---|---|---|---|
| "A36" | (S)-3-Hydroxy-2-oxo-1-phenyl-pyrrolidine-3-carboxylic acid 3-thiazol-2-ylbenzyl amide | 8.68 (t, J = 6.4, 1H), 7.92 (d, J = 3.2, 1H), 7.85 (s, 1H), 7.81 (dt, J = 7.6, 1.4, 1H), 7.78 (d, J = 3.2, 1H), 7.70 (dd, J = 8.7, 1.0, 2H), 7.47-7.35 (m, 4H), 7.24-7.13 (m, 1H), 6.72 (s, 1H), 4.45-4.29 (m, 2H), 3.95-3.72 (m, 2H), 2.64-2.55 (m, 1H), 2.13 (dt, J = 12.9, 7.8, 1H) | 3.457 min [394.0] % |
| "A37" | (S)-1-(3-Chlorophenyl)-3-hydroxy-2-oxopyrrolidine-3-carboxylic acid (2-thiophen-2-ylethyl) amide | 8.13 (t, J = 5.8, 1H), 7.89 (t, J = 2.0, 1H), 7.61 (d, J = 8.2, 1H), 7.43 (t, J = 8.1, 1H), 7.33 (dd, J = 5.0, 1.0, 1H), 7.25 (d, J = 8.0, 1H), 6.94 (dd, J = 5.0, 3.5, 1H), 6.88 (d, J = 3.5, 1H), 6.69 (s, 1H), 3.91-3.75 (m, 2H), 3.46-3.33 (m, 2H), 2.95 (t, J = 7.4, 2H), 2.08 (dt, J = 13.2, 8.2, 1H) | |
| "A38" | (S)-1-(4-Fluorophenyl)-3-hydroxy-2-oxopyrrolidine-3-carboxylic acid 3-bromobenzyl amide | 8.66 (t, J = 6.4, 1H), 7.77-7.69 (m, 2H), 7.46 (s, 1H), 7.44-7.36 (m, 1H), 7.29-7.21 (m, 4H), 6.73 (s, 1H), 4.34 (dd, J = 15.3, 6.6, 1H), 4.24 (dd, J = 15.4, 6.1, 1H), 3.84 (t, J = 6.9, 2H), 2.61-2.52 (m, 2H), 2.11 (dt, J = 12.8, 7.7, 1H) | 4.130 min [409.0 + 410.0] % |
| "A39" | (S)-3-Chloro-2-oxo-1-phenyl-pyrrolidine-3-carboxylic acid 3-bromobenzyl amide | 9.03 (t, J = 6.0, 1H), 7.68 (s, 1H), 7.66 (s, 1H), 7.49 (s, 1H), 7.46-7.39 (m, 3H), 7.33-7.27 (m, 2H), 7.24 (dd, J = 13.6, 6.2, 1H), 4.41 (dd, J = 15.4, 6.3, 1H), 4.33 (dd, J = 15.4, 6.0, 1H), 4.07-3.87 (m, 2H), 3.04 (dt, J = 14.8, 7.6, 1H), 2.57-2.51 (m, 1H) | 5.006 min [407.0 + 409.0] |

| No. | Structure/name | ¹H NMR (400 MHz, DMSO-d₆) δ [ppm] | LC-MS; rt; [M + H⁺]* |
|---|---|---|---|
| "A40" | 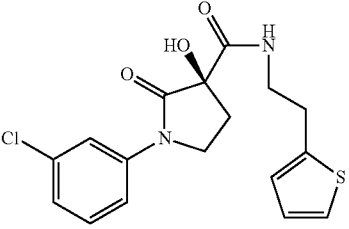<br>(R)-1-(3-Chlorophenyl)-3-hydroxy-2-oxopyrrolidine-3-carboxylic acid (2-thiophen-2-ylethyl) amide | 8.13 (t, J = 5.9, 1H), 7.89 (t, J = 2.0, 1H), 7.61 (ddd, J = 8.3, 2.1, 0.7, 1H), 7.43 (t, J = 8.2, 1H), 7.33 (dd, J = 5.1, 1.2, 1H), 7.27-7.21 (m, 1H), 6.94 (dd, J = 5.1, 3.4, 1H), 6.88 (d, J = 3.4, 1H), 6.69 (s, 1H), 3.89-3.80 (m, 2H), 3.45-3.34 (m, 2H), 2.95 (t, J = 7.2, 2H), 2.08 (dt, J = 13.0, 8.0, 2H) | 4.045 min [365.0] % |
| "A41" | 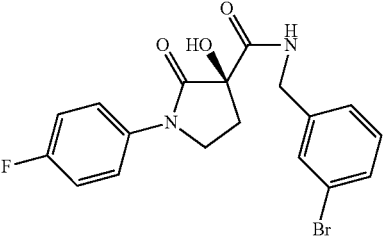<br>(R)-1-(4-Fluorophenyl)-3-hydroxy-2-oxopyrrolidine-3-carboxylic acid 3-bromobenzyl amide | 8.66 (t, J = 6.3, 1H), 7.81-7.65 (m, 2H), 7.46 (s, 1H), 7.41 (td, J = 4.8, 2.0, 1H), 7.31-7.21 (m, 4H), 6.74 (s, 1H), 4.34 (dd, J = 15.3, 6.6, 1H), 4.24 (dd, J = 15.3, 6.1, 1H), 3.84 (dd, J = 8.2, 5.5, 2H), 2.56 (dt, J = 11.6, 5.5, 1H), 2.11 (dt, J = 13.0, 7.7, 1H) | 4.133 min [409.0 + 410.0] % |
| "A42" | 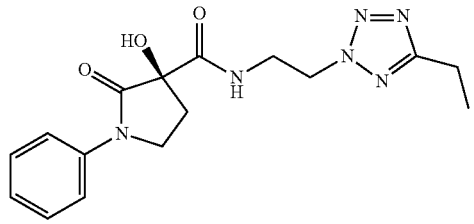<br>(R)-3-Hydroxy-2-oxo-1-phenyl-pyrrolidine-3-carboxylic acid [2-(5-ethyltetrazol-2-yl)ethyl] amide | 8.22 (t, J = 6.0, 1H), 7.67 (dd, J = 8.7, 1.0, 2H), 7.44-7.34 (m, 2H), 7.17 (dd, J = 10.5, 4.2, 1H), 6.65 (s, 1H), 4.78-4.57 (m, 2H), 3.84-3.74 (m, 2H), 3.74-3.66 (m, 1H), 3.54-3.39 (m, 1H), 2.81 (q, J = 7.6, 2H), 2.42 (ddd, J = 12.8, 7.1, 3.7, 1H), 2.05 (dt, J = 12.9, 8.1, 1H), 1.25 (t, J = 7.6, 3H) | |
| "A43" | 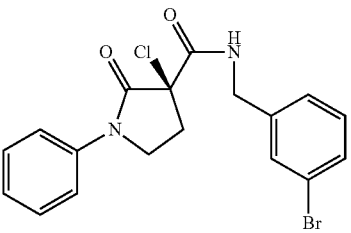<br>(R)-3-Chloro-2-oxo-1-phenyl-pyrrolidine-3-carboxylic acid 3-bromobenzyl amide | 9.03 (t, J = 6.1, 1H), 7.68 (d, J = 1.1, 1H), 7.66 (d, J = 0.8, 1H), 7.49 (s, 1H), 7.48-7.40 (m, 3H), 7.29 (dd, J = 4.1, 1.6, 2H), 7.26-7.19 (m, 1H), 4.41 (dd, J = 15.4, 6.3, 1H), 4.33 (dd, J = 15.4, 6.0, 1H), 4.06-3.90 (m, 2H), 3.04 (dt, J = 14.8, 7.5, 1H), 2.59-2.51 (m, 1H) | 5.002 min [407.0 + 409.0] % |

-continued

| No. | Structure/name | ¹H NMR (400 MHz, DMSO-$d_6$) δ [ppm] | LC-MS; rt; [M + H⁺]* |
|---|---|---|---|
| "A44" | (S)-3-Hydroxy-2-oxo-1-phenyl-pyrrolidine-3-carboxylic acid (2-pyrazol-1-ylethyl) amide | 8.11 (t, J = 5.9, 1H), 7.74-7.63 (m, 3H), 7.44 (d, J = 1.4, 1H), 7.43-7.37 (m, 2H), 7.18 (dd, J = 10.6, 4.2, 1H), 6.65 (s, 1H), 6.21 (t, J = 2.0, 1H), 4.20 (t, J = 6.4, 2H), 3.82 (dd, J = 8.4, 5.4, 2H), 3.52 (m,, 1H), 3.42 (m, 1H), 2.06 (m, 1H) | 2.376 min [315.0] % |
| "A45" | (S)-3-Hydroxy-2-oxo-1-phenyl-pyrrolidine-3-carboxylic acid (2-pyrrolidin-1-ylethyl) amide | 7.85 (s, 1H), 7.68 (dd, J = 8.7, 1.0, 2H), 7.44-7.34 (m, 2H), 7.17 (dd, J = 10.6, 4.2, 1H), 6.65 (s, 1H), 3.93-3.76 (m, 2H), 3.20 (qd, J = 13.1, 6.3, 2H), 2.52 (m, 3H), 2.46 (m, 4H), 2.07 (dt, J = 12.9, 8.0, 1H), 1.67 (m, 4H) | 1.990 min [318.3] % |
| "A46" | (S)-3-Hydroxy-2-oxo-1-phenyl-pyrrolidine-3-carboxylic acid 3-chloro-2,4-difluorobenzyl amide | 8.66 (t, J = 6.2, 1H), 7.69 (dd, J = 8.7, 1.0, 2H), 7.43-7.33 (m, 3H), 7.30 (td, J = 8.8, 1.5, 1H), 7.18 (t, J = 7.4, 1H), 6.74 (s, 1H), 4.38 (dd, J = 15.3, 6.2, 1H), 4.30 (dd, J = 15.6, 6.2, 1H), 3.90-3.80 (m, 2H), 2.63-2.52 (m, 1H), 2.11 (dt, J = 13.0, 7.7, 1H) | 4.169 min [381.0] % |
| "A47" | (S)-3-Hydroxy-2-oxo-1-phenyl-pyrrolidine-3-carboxylic acid 3-chloro-4-fluorobenzyl amide | 8.68 (t, J = 6.4, 1H), 7.69 (dd, J = 8.7, 1.0, 2H), 7.46 (dd, J = 7.3, 2.1, 1H), 7.43-7.36 (m, 2H), 7.34 (d, J = 9.3, 1H), 7.30-7.22 (m, 1H), 7.17 (t, J = 7.4, 1H), 6.73 (s, 1H), 4.33 (dd, J = 15.2, 6.8, 1H), 4.22 (dd, J = 15.3, 6.1, 1H), 3.85 (dd, J = 8.6, 5.6, 2H), 2.63-2.52 (m, 1H), 2.11 (dt, J = 13.0, 7.6, 1H) | 4.128 min [363.0] % |

| No. | Structure/name | ¹H NMR (400 MHz, DMSO-d₆) δ [ppm] | LC-MS; rt; [M + H⁺]* |
|---|---|---|---|
| "A48" | (S)-3-Hydroxy-2-oxo-1-phenyl-pyrrolidine-3-carboxylic acid 3-chloro-5-fluorobenzyl amide | 8.72 (t, J = 6.4, 1H), 7.69 (dd, J = 8.7, 1.0, 2H), 7.45-7.33 (m, 2H), 7.27 (dt, J = 8.8, 2.1, 1H), 7.18 (dd, J = 13.0, 4.5, 2H), 7.10 (d, J = 9.0, 1H), 6.76 (s, 1H), 4.38 (dd, J = 15.7, 6.6, 1H), 4.24 (dd, J = 15.9, 6.0, 1H), 3.89-3.82 (m, 2H), 2.62-2.54 (m, 1H), 2.12 (dt, J = 12.9, 7.6, 1H) | 4.052 min [363.0] % |
| "A49" | (S)-3-Hydroxy-2-oxo-1-phenyl-pyrrolidine-3-carboxylic acid 5-chloro-2-fluorobenzyl amide | 8.67 (t, J = 6.3, 1H), 7.70 (dd, J = 8.7, 1.1, 2H), 7.44-7.31 (m, 4H), 7.26-7.14 (m, 2H), 6.78 (s, 1H), 4.39 (dd, J = 15.7, 6.6, 1H), 4.26 (dd, J = 15.7, 5.8, 1H), 3.91-3.81 (m, 2H), 2.63-2.54 (m, 1H), 2.13 (dt, J = 13.0, 7.7, 1H) | 3.985 min [363.0] % |
| "A50" | (S)-1-(3-Chloro-4-fluorophenyl)-3-hydroxy-2-oxopyrrolidine-3-carboxylic acid 3-bromobenzyl amide | 8.68 (t, J = 6.4, 1H), 8.00 (dd, J = 6.7, 2.7, 1H), 7.68 (ddd, J = 9.1, 4.2, 2.8, 1H), 7.47 (dd, J = 12.1, 6.1, 2H), 7.44-7.39 (m, 1H), 7.32-7.19 (m, 2H), 6.78 (s, 1H), 4.34 (dd, J = 15.4, 6.6, 1H), 4.24 (dd, J = 15.3, 6.1, 1H), 3.92-3.77 (m, 2H), 2.61-2.52 (m, 1H), 2.10 (ddd, J = 19.9, 12.4, 6.8, 1H) | 4.587 min [441.0] % |
| "A51" | (S)-1-(3-Chloro-4-fluorophenyl)-3-hydroxy-2-oxopyrrolidine-3-carboxylic acid (2-thiophen-2-yl-ethyl) amide | 8.13 (t, J = 6.0, 1H), 7.99 (dd, J = 6.7, 2.7, 1H), 7.75-7.63 (m, 1H), 7.48 (d, J = 9.1, 1H), 7.33 (dd, J = 5.1, 1.1, 1H), 6.94 (dd, J = 5.1, 3.4, 1H), 6.88 (d, J = 3.3, 1H), 6.69 (s, 1H), 3.89-3.75 (m, 2H), 3.46-3.35 (m, 1H), 2.95 (t, J = 7.3, 2H), 2.07 (dt, J = 13.0, 7.9, 1H) | 4.148 min [383.0] % |

| No. | Structure/name | $^1$H NMR (400 MHz, DMSO-$d_6$) δ [ppm] | LC-MS; rt; [M + H$^+$]* |
|---|---|---|---|
| "A52" | (S)-1-(2,4-fluorophenyl)-3-hydroxy-2-oxopyrrolidine-3-carboxylic acid 3-bromobenzyl amide | 8.63 (t, J = 6.4, 1H), 7.50-7.44 (m, 2H), 7.44-7.36 (m, 2H), 7.30-7.24 (m, 2H), 7.16 (ddd, J = 8.2, 2.9, 1.5, 1H), 6.75 (s, 1H), 4.35 (dd, J = 15.3, 6.6, 1H), 4.26 (dd, J = 15.4, 6.1, 1H), 3.83-3.66 (m, 2H), 2.64-2.55 (m, 1H), 2.23-2.13 (m, 2H) | 4.207 min [427.0 + 428.0] % |
| "A53" | (R)-3-Hydroxy-1-naphthalen-1-yl-2-oxopyrrolidine-3-carboxylic acid 3-bromobenzyl amide | 8.69 (t, J = 6.3, 1H), 8.00 (d, J = 7.5, 1H), 7.95 (t, J = 7.2, 2H), 7.62-7.49 (m, 4H), 7.43 (dd, J = 12.9, 7.3, 2H), 7.31 (d, J = 1.1, 1H), 7.26 (t, J = 7.7, 1H), 6.84 (s, 1H), 4.40 (dd, J = 15.4, 6.6, 1H), 4.33 (dd, J = 15.4, 6.2, 1H), 3.91-3.75 (m, 2H), 2.69 (ddd, J = 12.7, 7.4, 3.2, 1H), 2.40-2.29 (m, 1H) | 4.364 min [439.0 + 442.0] % |
| "A54" | (S)-3-Hydroxy-1-naphthalen-2-yl-2-oxopyrrolidine-3-carboxylic acid 3-bromobenzyl amide | 8.69 (t, J = 6.4, 1H), 8.10-8.04 (m, 2H), 7.95 (d, J = 9.7, 1H), 7.90 (dd, J = 8.1, 2.9, 2H), 7.54-7.43 (m, 3H), 7.43-7.39 (m, 1H), 7.28 (t, J = 1.9, 1H), 6.78 (s, 1H), 4.36 (dd, J = 15.4, 6.6, 1H), 4.26 (dd, J = 15.4, 6.2, 1H), 3.99 (dd, J = 8.5, 5.6, 2H), 2.70-2.57 (m, 2H), 2.18 (dt, J = 12.9, 7.6, 1H) | 4.622 min [441.0 + 442.0] % |
| "A55" | (S)-3-Hydroxy-naphthalen-2-yl-2-oxopyrrolidine-3-carboxylic acid (2-thiophen-2-ylethyl) amide | 8.14 (t, J = 5.9, 1H), 8.08-8.02 (m, 2H), 7.94 (d, J = 8.7, 1H), 7.93-7.87 (m, 2H), 7.54-7.49 (m, 1H), 7.49-7.44 (m, 1H), 7.33 (dd, J = 5.1, 1.2, 1H), 6.95 (dd, J = 5.1, 3.4, 1H), 6.90 (d, J = 2.6, 1H), 6.69 (s, 1H), 4.01-3.93 (m, 2H), 3.38 (dd, J = 17.0, 10.5, 2H), 3.30-3.22 (m, 1H), 2.97 (t, J = 7.4, 2H), 2.61-2.52 (m, 2H), 2.13 (dt, J = 12.8, 7.8, 1H) | 4.264 min [381.0] % |

| No. | Structure/name | ¹H NMR (400 MHz, DMSO-$d_6$) δ [ppm] | LC-MS; rt; [M + H⁺]* |
|---|---|---|---|
| "A56" | 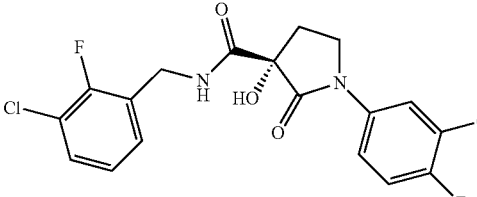<br>(S)-1-(3-Chloro-4-fluorophenyl)-3-hydroxy-2-oxopyrrolidine-3-carboxylic acid 3-chloro-2-fluorobenzyl amide | 8.68 (t, J = 6.2, 1H), 7.99 (dd, J = 6.7, 2.7, 1H), 7.75-7.63 (m, 1H), 7.48 (d, J = 9.1, 1H), 7.46-7.42 (m, 1H), 7.30 (t, J = 6.5, 1H), 7.18 (t, J = 8.0, 1H), 6.83 (s, 1H), 4.40 (dd, J = 15.6, 6.4, 1H), 4.32 (dd, J = 15.6, 6.2, 1H), 3.90-3.81 (m, 2H), 2.63-2.53 (m, 1H), 2.12 (dt, J = 13.0, 7.7, 1H) | 4.602 min [415.0 + 417.0] % |
| "A57" | 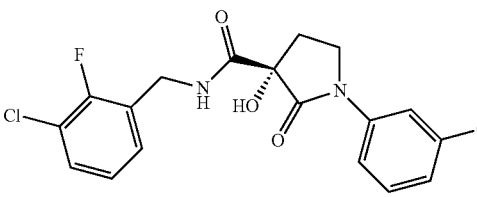<br>(S)-1-(3-Chlorophenyl)-3-hydroxy-2-oxopyrrolidine-3-carboxylic acid 3-chloro-2-fluorobenzyl amide | 8.67 (t, J = 6.2, 1H), 7.88 (t, J = 2.0, 1H), 7.61 (dd, J = 8.3, 1.3, 1H), 7.48-7.41 (m, 1H), 7.32-7.27 (m, 1H), 7.25 (dd, J = 7.9, 1.3, 1H), 7.19 (dt, J = 8.3, 4.2, 1H), 6.80 (s, 1H), 4.40 (dd, J = 15.7, 6.7, 1H), 4.32 (dd, J = 15.6, 5.8, 1H), 3.86 (t, J = 6.8, 2H), 2.63-2.51 (m, 1H), 2.12 (dt, J = 13.0, 7.7, 1H) | 4.525 min [397.0 + 398.0 + 399.0] % |
| "A58" | 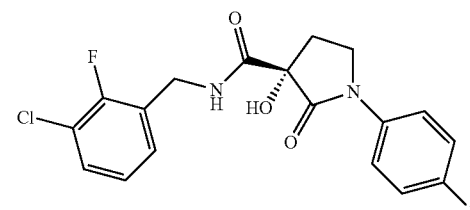<br>(S)-1-(4-Fluorophenyl)-3-hydroxy-2-oxopyrrolidine-3-carboxylic acid 3-chloro-2-fluorobenzyl amide | 8.65 (t, J = 6.2, 1H), 7.76-7.65 (m, 2H), 7.52-7.36 (m, 1H), 7.33-7.28 (m, 1H), 7.27-7.22 (m, 2H), 7.18 (td, J = 7.9, 0.9, 1H), 6.76 (s, 1H), 4.40 (dd, J = 15.7, 6.3, 1H), 4.33 (dd, J = 15.3, 6.2, 1H), 3.84 (dd, J = 8.7, 5.6, 2H), 2.63-2.51 (m, 2H), 2.11 (dt, J = 12.9, 7.7, 1H) | 4.129 min [381.0] % |
| "A59" | 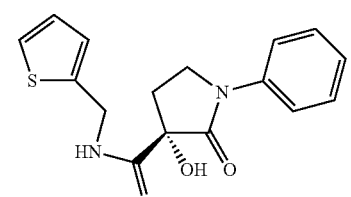<br>(S)-3-Hydroxy-2-oxo-1-phenyl-pyrrolidine-3-carboxylic acid (thiophen-2-ylmethyl) amide | 8.58 (t, J = 6.2, 1H), 7.70 (d, J = 1.1, 1H), 7.68 (d, J = 1.0, 1H), 7.45-7.33 (m, 3H), 7.22-7.14 (m, 1H), 6.99-6.87 (m, 2H), 6.66 (s, 1H), 4.44 (d, J = 6.4, 2H), 3.91-3.78 (m, 2H), 2.59-2.52 (m, 1H), 2.09 (dt, J = 12.9, 8.5, 1H) | 3.373 min [317.0] % |
| "A60" | 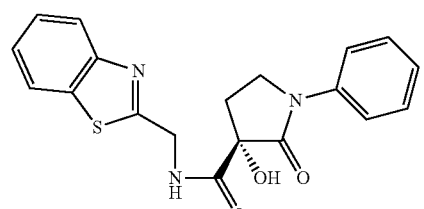<br>(S)-3-Hydroxy-2-oxo-1-phenyl-pyrrolidine-3-carboxylic acid (benzothiazol-2-ylmethyl) amide | 9.03 (t, J = 6.2, 1H), 8.05 (d, J = 8.0, 1H), 7.93 (d, J = 7.9, 1H), 7.70 (d, J = 7.7, 2H), 7.53-7.46 (m, 1H), 7.44-7.35 (m, 3H), 7.18 (t, J = 7.4, 1H), 6.81 (s, 1H), 4.72 (dd, J = 16.2, 6.2, 1H), 4.65 (dd, J = 16.2, 6.1, 1H), 3.86 (dd, J = 9.7, 5.5, 2H), 2.60 (dd, J = 12.1, 7.6, 1H), 2.16 (dt, J = 12.7, 7.8, 1H) | 3.462 min [368.0] % |

-continued

| No. | Structure/name | ¹H NMR (400 MHz, DMSO-d₆) δ [ppm] | LC-MS; rt; [M + H⁺]* |
|---|---|---|---|
| "A61" | (S)-3-Chloro-2-oxo-1-phenyl-pyrrolidine-3-carboxylic acid (2-thiophen-2-ylethyl) amide | 8.51 (s, 1H), 7.67 (d, J = 1.1, 1H), 7.65 (d, J = 0.8, 1H), 7.43 (t, J = 8.0, 2H), 7.32 (dd, J = 5.1, 1.2, 1H), 7.23 (t, J = 7.4, 1H), 6.94 (dd, J = 5.0, 3.4, 1H), 6.89 (d, J = 3.3, 1H), 4.06-3.82 (m, 2H), 3.54-3.35 (m, 3H), 2.97 (dt, J = 20.8, 7.4, 3H) | 4.522 min [349.0] % |
| "A62" | (S)-3-Hydroxy-2-oxo-1-phenyl-pyrrolidine-3-carboxylic acid (furan-2-ylmethyl) amide | 8.37 (s, 1H), 7.70 (d, J = 1.1, 1H), 7.68 (d, J = 0.9, 1H), 7.54 (dd, J = 1.8, 0.8, 1H), 7.44-7.37 (m, 2H), 7.17 (t, J = 7.4, 1H), 6.68 (s, 1H), 6.37 (dd, J = 3.2, 1.8, 1H), 6.21 (d, J = 2.4, 1H), 4.28 (d, J = 6.6, 2H), 3.89-3.82 (m, 2H), 2.60-2.53 (m, 1H), 2.09 (dt, J = 12.9, 8.4, 1H) | 2.863 min [301.0] % |
| "A63" | 3-Hydroxy-2-oxo-1-phenyl-pyrrolidine-3-carboxylic acid (3-methylbutyl) amide | 7.86 (br. t, J = 5.9, 1H), 7.69 (dt, J = 9.0, 1.7, 2H), 7.44-7.37 (m, 2H), 7.22-7.12 (m, 1H), 6.56 (s, 1H), 3.96-3.72 (m, 2H), 3.11 (dd, J = 14.4, 6.2, 2H), 2.57-2.52 (m, 1H), 2.14-1.98 (m, 1H), 1.56 (dp, J = 13.3, 6.7, 1H), 1.33 (dd, J = 14.5, 7.0, 2H), 0.87 (d, J = 2.2, 3H), 0.86 (d, J = 2.2, 3H) | 1.978 min [291.0] |
| "A64" | 3-Hydroxy-2-oxo-1-phenyl-pyrrolidine-3-carboxylic acid (furan-2-ylmethyl) amide | 8.35 (t, J = 6.0, 1H), 7.70 (dd, J = 8.7, 1.0, 2H), 7.55 (dd, J = 1.7, 0.8, 1H), 7.47-7.35 (m, 2H), 7.18 (t, J = 7.4, 1H), 6.67 (s, 1H), 6.38 (dd, J = 3.1, 1.9, 1H), 6.22 (dd, J = 3.1, 0.7, 1H), 4.29 (d, J = 6.2, 2H), 3.93-3.80 (m, 2H), 2.56 (ddd, J = 12.8, 7.3, 4.1, 1H), 2.18-2.04 (m, 1H) | 1.716 min [301.10] |
| "A65" | 3-Hydroxy-2-oxo-1-phenyl-pyrrolidine-3-carboxylic acid (2-thiophen-2-ylethyl) amide | 8.08 (t, J = 5.9, 1H), 7.71 (s, 1H), 7.69 (d, J = 8.8, 1H), 7.48-7.37 (m, 2H), 7.33 (dt, J = 10.3, 5.1, 1H), 7.23-7.13 (m, 1H), 6.96 (dd, J = 5.0, 3.5, 1H), 6.90 (t, J = 7.1, 1H), 6.61 (d, J = 17.5, 1H), 3.91-3.80 (m, 2H), 3.48-3.38 (m, 1H), 3.33-3.22 (m, 3H), 2.98 (t, J = 7.3, 2H), 2.58-2.52 (m, 1H), 2.10 (m, 1H) | |

| No. | Structure/name | $^1$H NMR (400 MHz, DMSO-$d_6$) δ [ppm] | LC-MS; rt; [M + H$^+$]* |
|---|---|---|---|
| "A66" | 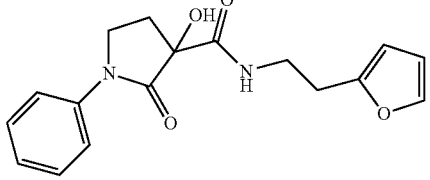<br>3-Hydroxy-2-oxo-1-phenyl-pyrrolidine-3-carboxylic acid (2-furan-2-ylethyl) amide | 8.06 (t, J = 5.9, 1H), 7.70 (t, J = 1.5, 1H), 7.68 (t, J = 1.6, 1H), 7.52 (dd, J = 1.8, 0.7, 1H), 7.44-7.37 (m, 2H), 7.22-7.14 (m, 1H), 6.62 (s, 1H), 6.35 (dd, J = 3.1, 1.9, 1H), 6.16 (dd, J = 3.1, 0.7, 1H), 3.92-3.76 (m, 2H), 3.40 (td, J = 13.7, 7.4, 1H), 2.79 (t, J = 7.3, 2H), 2.53 (dd, J = 6.1, 3.6, 1H), 2.15-2.00 (m, 1H) | 1.814 min [315.10] |
| "A67" | 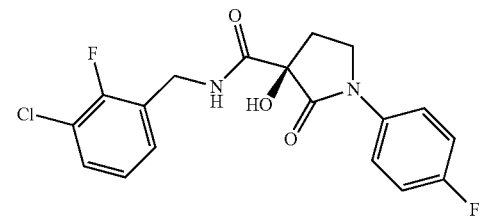<br>(R)-1-(4-Fluorophenyl)-3-hydroxy-2-oxopyrrolidine-3-carboxylic acid 3-chloro-2-fluorobenzyl amide | 8.65 (t, J = 6.3, 1H), 7.78-7.68 (m, 2H), 7.45 (td, J = 8.0, 1.6, 1H), 7.33-7.28 (m, 1H), 7.27-7.22 (m, 2H), 7.18 (td, J = 7.9, 0.8, 1H), 6.75 (d, J = 4.2, 1H), 4.40 (dd, J = 15.6, 6.3, 1H), 4.33 (dd, J = 15.6, 5.9, 1H), 3.89-3.79 (m, 2H), 2.62-2.52 (m, 1H), 2.11 (dt, J = 13.0, 7.7, 1H) | 4.138 min [381.0] % |
| "A68" | 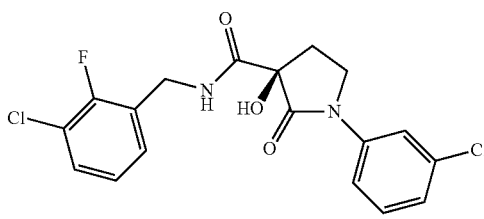<br>(R)-1-(3-Chlorophenyl)-3-hydroxy-2-oxopyrrolidine-3-carboxylic acid 3-chloro-2-fluorobenzyl amide | 8.67 (t, J = 6.3, 1H), 7.88 (t, J = 2.1, 1H), 7.61 (dd, J = 8.3, 1.3, 1H), 7.50-7.40 (m, 2H), 7.32-7.27 (m, 1H), 7.25 (ddd, J = 8.0, 2.0, 0.8, 1H), 7.19 (td, J = 8.0, 0.9, 1H), 6.80 (s, 1H), 4.40 (dd, J = 15.5, 6.4, 1H), 4.32 (dd, J = 15.7, 5.9, 1H), 3.86 (t, J = 6.9, 2H), 2.62-2.53 (m, 1H), 2.12 (dt, J = 13.0, 7.7, 2H) | 4.523 min [397.0] % |
| "A69" | 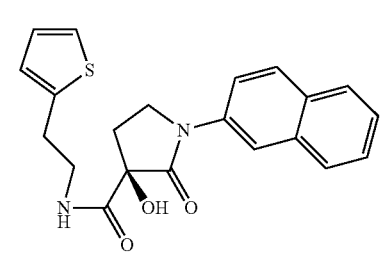<br>(R)-3-Hydroxy-1-naphthalen-2-yl-2-oxopyrrolidine-3-carboxylic acid (2-thiophen-2-ylethyl) amide | 8.14 (t, J = 5.9, 1H), 8.09-8.04 (m, 2H), 7.94 (d, J = 8.7, 1H), 7.92-7.87 (m, 2H), 7.51 (dd, J = 10.9, 4.2, 1H), 7.47 (dd, J = 10.8, 4.2, 1H), 7.33 (dd, J = 5.1, 1.2, 1H), 6.95 (dd, J = 5.1, 3.4, 1H), 6.90 (d, J = 2.5, 1H), 6.69 (s, 1H), 4.04-3.88 (m, 2H), 3.48-3.35 (m, 1H), 3.29 (d, J = 5.9, 1H), 2.97 (t, J = 7.3, 2H), 2.63-2.52 (m, 1H), 2.13 (dt, J = 12.8, 7.9, 1H) | 4.214 min [381.0] % |
| "A70" | 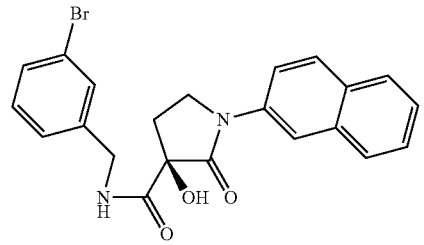<br>(R)-3-Hydroxy-1-naphthalen-2-yl-2-oxopyrrolidine-3-carboxylic acid 3-bromobenzyl amide | 8.69 (t, J = 6.3, 1H), 8.05 (s, 1H), 7.95 (d, J = 9.7, 1H), 7.90 (dd, J = 8.0, 3.1, 2H), 7.55-7.44 (m, 3H), 7.44-7.39 (m, 1H), 7.28 (s, 1H), 6.78 (s, 1H), 4.36 (dd, J = 15.4, 6.6, 1H), 4.26 (dd, J = 15.4, 6.2, 1H), 3.99 (t, J = 7.0, 2H), 2.70-2.56 (m, 1H), 2.18 (dt, J = 13.1, 7.8, 1H) | 4.629 min [441.0] % |

-continued

| No. | Structure/name | ¹H NMR (400 MHz, DMSO-d₆) δ [ppm] | LC-MS; rt; [M + H⁺]* |
|---|---|---|---|
| "A71" | (S)-3-Hydroxy-1-naphthalen-1-yl-2-oxopyrrolidine-3-carboxylic acid 3-bromobenzyl amide | 8.69 (t, J = 6.4, 1H), 8.02-7.98 (m, 1H), 7.95 (t, J = 7.5, 2H), 7.61-7.49 (m, 4H), 7.45 (d, J = 7.3, 1H), 7.41 (dd, J = 5.5, 4.2, 1H), 7.31 (d, J = 7.8, 1H), 7.26 (t, J = 7.7, 1H), 6.82 (s, 1H), 4.40 (dd, J = 15.1, 6.6, 1H), 4.33 (dd, J = 15.3, 6.3, 1H), 3.86 (dd, J = 16.3, 7.4, 1H), 3.79 (td, J = 8.8, 3.3, 1H), 2.69 (ddd, J = 12.9, 7.5, 3.1, 1H), 2.34 (dt, J = 12.9, 8.5, 1H) | 4.394 min [439.0 + 442.0] % |
| "A72" | (R)-1-(2,4-Difluorophenyl)-3-hydroxy-2-oxopyrrolidine-3-carboxylic acid 3-bromobenzyl amide | 8.64 (t, J = 6.5, 1H), 7.50-7.44 (m, 2H), 7.44-7.37 (m, 2H), 7.26 (dd, J = 4.1, 2.2, 2H), 7.17 (t, J = 8.6, 1H), 6.75 (s, 1H), 4.35 (dd, J = 15.4, 6.5, 1H), 4.26 (dd, J = 15.4, 6.1, 1H), 3.81-3.66 (m, 2H), 2.64-2.56 (m, 1H), 2.22-2.13 (m, 1H) | 4.055 min [425.0 + 427.0] % |
| "A73" | (R)-1-(3-Chloro-4-fluorophenyl)-3-hydroxy-2-oxopyrrolidine-3-carboxylic acid 3-bromobenzyl amide | 8.68 (t, J = 6.4, 1H), 8.00 (dd, J = 6.7, 2.7, 1H), 7.68 (ddd, J = 9.1, 4.2, 2.8, 1H), 7.47 (dd, J = 12.2, 6.0, 2H), 7.45-7.35 (m, 1H), 7.33-7.22 (m, 2H), 6.78 (s, 1H), 4.34 (dd, J = 15.3, 6.6, 1H), 4.24 (dd, J = 15.4, 6.1, 1H), 3.93-3.82 (m, 2H), 2.62-2.51 (m, 2H), 2.11 (dt, J = 12.9, 7.7, 1H) | 4.586 min [441.0] % |
| "A74" | (R)-3-Hydroxy-2-oxo-1-phenyl-pyrrolidine-3-carboxylic acid 3-chloro-4-fluorobenzyl amide | 8.68 (t, J = 6.4, 1H), 7.74-7.65 (m, 2H), 7.47 (dd, J = 7.3, 2.1, 1H), 7.40 (dtd, J = 6.3, 4.2, 2.1, 2H), 7.34 (d, J = 9.3, 1H), 7.27 (ddd, J = 8.5, 4.8, 2.1, 1H), 7.17 (t, J = 7.4, 1H), 6.73 (s, 1H), 4.33 (dd, J = 15.1, 6.7, 1H), 4.22 (dd, J = 15.2, 6.3, 1H), 3.85 (dd, J = 8.5, 5.6, 2H), 2.62-2.53 (m, 1H), 2.18-2.04 (m, 1H). | 4.124 min [363.0] % |

| No. | Structure/name | $^1$H NMR (400 MHz, DMSO-$d_6$) δ [ppm] | LC-MS; rt; [M + H$^+$]* |
|---|---|---|---|
| "A75" | (R)-3-Hydroxy-2-oxo-1-phenyl-pyrrolidine-3-carboxylic acid benzyl amide | 8.52 (t, J = 6.2, 1H), 7.75-7.64 (m, 2H), 7.45-7.35 (m, 2H), 7.33-7.14 (m, 6H), 6.68 (s, 1H), 4.33 (dd, J = 15.0, 6.5, 1H), 4.27 (dd, J = 15.0, 6.2, 1H), 3.92-3.79 (m, 2H), 2.62-2.53 (m, 1H), 2.17-2.05 (m, 1H) | |
| "A76" | (R)-1-(4-Bromophenyl)-3-hydroxy-2-oxopyrrolidine-3-carboxylic acid 3-bromobenzyl amide | (400 MHz, CDCl$_3$) δ [ppm] 7.60-7.55 (m, 1H), 7.55-7.47 (m, 1H), 7.42 (t, J = 3.5, 1H), 7.23-7.17 (m, 1H), 4.51-4.33 (m, 1H), 4.19 (td, J = 9.1, 7.0, 1H), 3.82 (t, J = 8.7, 1H), 3.77 (s, 1H), 2.78 (dd, J = 12.8, 5.9, 1H), 2.29 (dt, J = 12.8, 9.3, 1H) | 4.596 min [467.0 + 469.0 + 472.0] % |
| "A77" | (R)-1-(4-Bromophenyl)-3-hydroxy-2-oxopyrrolidine-3-carboxylic acid (2-thiophen-2-ylethyl) amide | (400 MHz, CDCl$_3$) δ [ppm] 7.61-7.54 (m, 2H), 7.54-7.49 (m, 2H), 7.18 (dd, J = 5.1, 1.2, 1H), 7.07 (s, 1H), 6.96 (dd, J = 5.1, 3.4, 1H), 6.87 (dd, J = 3.4, 1.0, 1H), 4.16 (td, J = 9.2, 6.9, 1H), 3.80 (td, J = 9.2, 1.2, 1H), 3.55 (dd, J = 13.0, 6.6, 3H), 3.07 (t, J = 6.9, 2H), 2.71 (ddd, J = 12.8, 6.9, 1.2, 1H), 2.25 (dt, J = 12.7, 9.4, 2H) | 4.133 min [409.0 + 412.0] % |
| "A78" | (R)-1-(4-Fluorophenyl)-3-hydroxy-2-oxopyrrolidine-3-carboxylic acid (2-thiophen-2-ylethyl) amide | (400 MHz, CDCl$_3$) δ [ppm] 7.69-7.58 (m, 2H), 7.18 (dd, J = 5.1, 1.1, 1H), 7.15-7.04 (m, 2H), 6.96 (dd, J = 5.1, 3.4, 1H), 6.87 (d, J = 2.6, 1H), 4.17 (td, J = 9.2, 7.0, 1H), 3.79 (dd, J = 9.2, 8.1, 1H), 3.58 (s, 1H), 3.55 (q, J = 6.6, 2H), 3.07 (t, J = 6.8, 2H), 2.80-2.64 (m, 1H), 2.25 (dt, J = 12.8, 9.3, 1H) | 3.624 min [349.0] % |
| "A79" | (R)-3-Hydroxy-2-oxo-1-phenyl-pyrrolidine-3-carboxylic acid 3-bromobenzyl amide | 8.65 (s, 1H), 7.70 (d, J = 8.2, 2H), 7.45 (d, J = 12.1, 1H), 7.43 (s, 3H), 7.26 (d, J = 3.8, 2H), 7.17 (t, J = 7.1, 1H), 6.73 (s, 1H), 4.34 (dd, J = 15.1, 6.5, 1H), 4.24 (dd, J = 15.5, 6.1, 1H), 3.85 (t, J = 6.7, 2H), 2.56 (dd, J = 13.0, 6.4, 1H), 2.19-2.05 (m, 1H) | |

| No. | Structure/name | $^1$H NMR (400 MHz, DMSO-$d_6$) δ [ppm] | LC-MS; rt; [M + H$^+$]* |
|---|---|---|---|
| "A80" | (S)-1-(3-Chlorophenyl)-3-hydroxy-2-oxopyrrolidine-3-carboxylic acid 3-bromobenzyl amide | 8.68 (t, J = 6.4, 1H), 7.90 (t, J = 2.1, 1H), 7.62 (dd, J = 8.0, 1.7, 1H), 7.42 (ddd, J = 7.9, 7.2, 2.1, 3H), 7.30-7.22 (m, 3H), 6.77 (s, 1H), 4.34 (dd, J = 15.4, 6.6, 1H), 4.24 (dd, J = 15.4, 6.1, 1H), 3.92-3.79 (m, 2H), 2.63-2.52 (m, 1H), 2.12 (dt, J = 13.0, 7.8, 1H) | 4.547 min [423.0 + 424.0] % |
| "A81" | (S)-1-(4-Bromophenyl)-3-hydroxy-2-oxopyrrolidine-3-carboxylic acid 3-chloro-2-fluorobenzyl amide | 8.66 (t, J = 6.2, 1H), 7.74-7.64 (m, 2H), 7.64-7.56 (m, 2H), 7.52-7.41 (m, 1H), 7.30 (t, J = 7.3, 1H), 7.18 (t, J = 7.9, 1H), 6.78 (s, 1H), 4.40 (dd, J = 15.4, 6.5, 1H), 4.32 (dd, J = 15.5, 6.2, 1H), 3.91-3.76 (m, 2H), 2.63-2.52 (m, 1H), 2.12 (dt, J = 12.9, 7.7, 1H) | 5.804 min [438.7 + 440.0] % |
| "A82" | (S)-1-(2,4-Difluorophenyl)-3-hydroxy-2-oxopyrrolidine-3-carboxylic acid 3-chloro-2-fluoro-benzyl amide | 8.63 (t, J = 6.3, 1H), 7.51-7.36 (m, 3H), 7.30 (t, J = 6.6, 1H), 7.16 (dd, J = 13.5, 5.4, 2H), 6.77 (s, 1H), 4.42 (dd, J = 15.6, 6.4, 1H), 4.34 (dd, J = 15.5, 6.0, 1H), 3.84-3.67 (m, 2H), 2.72-2.56 (m, 1H), 2.17 (dt, J = 13.0, 7.6, 1H) | 4.073 min [399.0] % |
| "A83" | (S)-3-Hydroxy-2-oxo-1-phenyl-pyrrolidine-3-carboxylic acid (5-methyl-1,3,4-oxadiazol-2-ylmethyl) amide | 8.69 (t, J = 6.0, 1H), 7.73-7.63 (m, 2H), 7.40 (dd, J = 10.8, 5.3, 2H), 7.17 (t, J = 7.4, 1H), 6.75 (s, 1H), 4.51 (dd, J = 16.1, 6.1, 1H), 4.42 (dd, J = 16.1, 5.8, 1H), 3.92-3.76 (m, 2H), 2.59-2.52 (m, 1H), 2.45 (s, 3H), 2.12 (dt, J = 13.0, 7.9, 1H) | 2.188 min [317.0] % |
| "A84" | (S)-3-Hydroxy-2-oxo-1-phenyl-pyrrolidine-3-carboxylic acid (3-methylthiophen-2-ylmethyl) amide | 8.45 (t, J = 6.1, 1H), 7.74-7.66 (m, 2H), 7.46-7.37 (m, 2H), 7.25 (d, J = 5.1, 1H), 7.22-7.14 (m, 1H), 6.79 (d, J = 5.1, 1H), 6.64 (s, 1H), 4.39 (dd, J = 15.2, 6.4, 1H), 4.33 (dd, J = 15.4, 6.4, 1H), 3.84 (ddd, J = 14.2, 9.2, 3.7, 2H), 2.60-2.52 (m, 1H), 2.16 (s, 3H), 2.09 (dt, J = 12.9, 8.5, 1H) | 3.541 min [331.0] % |

| No. | Structure/name | ¹H NMR (400 MHz, DMSO-d₆) δ [ppm] | LC-MS; rt; [M + H⁺]* |
|---|---|---|---|
| "A85" | (S)-3-Hydroxy-2-oxo-1-phenyl-pyrrolidine-3-carboxylic acid (thiazol-2-ylmethyl) amide | 8.89 (t, J = 6.2, 1H), 7.70 (td, J = 3.2, 1.0, 3H), 7.60 (d, J = 3.3, 1H), 7.40 (dd, J = 10.7, 5.3, 2H), 7.18 (t, J = 7.4, 1H), 6.76 (s, 1H), 4.59 (dd, J = 16.0, 6.4, 1H), 4.54 (dd, J = 16.0, 6.3, 1H), 3.92-3.80 (m, 2H), 2.61-2.52 (m, 1H), 2.13 (dt, J = 12.9, 8.0, 1H) | 2.356 min [318.0] |
| "A86" | (S)-3-Fluoro-2-oxo-1-phenyl-pyrrolidine-3-carboxylic acid (2-thiophen-2-ylethyl) amide | ¹⁹F NMR (377 MHz, DMSO) δ [ppm] −158.16; ¹H NMR 400 MHz, DMSO-d6) δ [ppm] 8.72 (s, 1H), 7.69 (d, J = 7.7, 2H), 7.50-7.40 (m, 2H), 7.33 (dd, J = 5.1, 1.2, 1H), 7.23 (t, J = 7.4, 1H), 6.94 (dd, J = 5.1, 3.4, 1H), 6.89 (d, J = 3.4, 1H), 3.97 (dd, J = 9.2, 3.3, 1H), 3.92 (dd, J = 6.2, 3.4, 1H), 3.48-3.37 (m, 2H), 2.98 (t, J = 7.3, 2H), 2.77-2.62 (m, 1H), 2.47-2.35 (m, 2H) | |
| "A87" | (R)-1-(3-Chlorophenyl)-3-hydroxy-2-oxopyrrolidine-3-carboxylic acid 3-bromobenzyl amide | 8.68 (t, J = 6.3, 1H), 7.90 (t, J = 2.1, 1H), 7.62 (ddd, J = 8.3, 2.1, 0.8, 1H), 7.48-7.44 (m, 1H), 7.44-7.38 (m, 2H), 7.31-7.20 (m, 3H), 6.78 (s, 1H), 4.34 (dd, J = 15.3, 6.6, 1H), 4.24 (dd, J = 15.3, 6.1, 1H), 3.92-3.77 (m, 2H), 2.64-2.53 (m, 1H), 2.12 (dt, J = 13.0, 7.8, 1H) | 4.487 min [422.8 + 424.8] % |
| "A88" | (R)-1-(2,4-Difluorophenyl)-3-hydroxy-2-oxopyrrolidine-3-carboxylic acid 3-chloro-2-fluoro-benzyl amide | 8.63 (t, J = 6.3, 1H), 7.51-7.36 (m, 3H), 7.30 (dd, J = 10.7, 3.9, 1H), 7.20-7.13 (m, 2H), 6.78 (s, 1H), 4.41 (dd, J = 15.6, 6.4, 1H), 4.34 (dd, J = 15.6, 6.1, 1H), 3.84-3.66 (m, 2H), 2.61 (ddd, J = 12.8, 7.4, 4.2, 1H), 2.17 (ddd, J = 13.0, 8.2, 7.0, 1H) | 4.075 min [399.0] % |
| "A89" | (R)-1-(4-Bromophenyl)-3-hydroxy-2-oxopyrrolidine-3-carboxy acid 3-chloro-2-fluorobenzyl amide | 8.66 (t, J = 6.3, 1H), 7.73-7.63 (m, 2H), 7.63-7.56 (m, 2H), 7.45 (t, J = 6.8, 1H), 7.30 (t, J = 6.5, 1H), 7.18 (t, J = 7.9, 1H), 6.78 (s, 1H), 4.40 (dd, J = 15.5, 6.3, 1H), 4.32 (dd, J = 15.6, 5.8, 1H), 3.87-3.80 (m, 2H), 2.62-2.53 (m, 2H), 2.12 (dt, J = 13.0, 7.7, 1H) | 5.804 min [438.7 + 440.0] % |

| No. | Structure/name | $^1$H NMR (400 MHz, DMSO-$d_6$) δ [ppm] | LC-MS; rt; [M + H$^+$]* |
|---|---|---|---|
| "A90" | 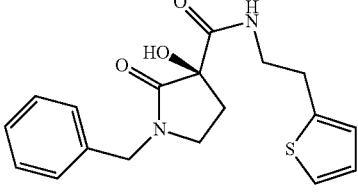<br>(R)-1-Benzyl-3-hydroxy-2-oxo-pyrrolidine-3-carboxylic acid (2-thiophen-2-ylethyl) amide | 8.02 (t, J = 6.0, 1H), 7.38-7.31 (m, 3H), 7.26 (t, J = 6.8, 3H), 6.94 (dd, J = 5.1, 3.4, 1H), 6.90 (dd, J = 3.4, 1.0, 1H), 6.45 (s, 1H), 4.48 (d, J = 15.2, 1H), 4.36 (d, J = 15.2, 1H), 3.40 (ddd, J = 14.0, 10.2, 4.9, 1H), 3.30-3.16 (m, 3H), 2.95 (t, J = 7.4, 2H), 2.37 (ddd, J = 12.9, 7.7, 3.5, 1H), 1.93 (ddd, J = 13.0, 8.7, 7.0, 1H) | |
| "A91" | 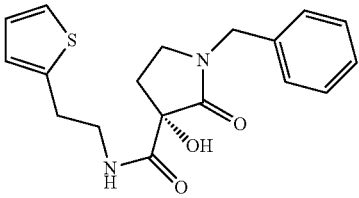<br>(S)-1-Benzyl-3-hydroxy-2-oxo-pyrrolidine-3-carboxylic acid (2-thiophen-2-ylethyl) amide | 8.02 (t, J = 6.0, 1H), 7.37-7.31 (m, 3H), 7.27 (dd, J = 10.2, 4.6, 3H), 6.94 (dd, J = 5.1, 3.4, 1H), 6.89 (dd, J = 3.3, 1.0, 1H), 6.45 (s, 1H), 4.48 (d, J = 15.3, 1H), 4.36 (d, J = 15.2, 1H), 3.46-3.38 (m, 2H), 3.30-3.18 (m, 4H), 2.95 (t, J = 7.4, 2H), 2.37 (ddd, J = 12.8, 7.6, 3.4, 1H), 1.93 (ddd, J = 12.9, 8.7, 7.0, 1H) | |
| "A91a" | (S)-3-Amino-2-oxo-1-phenyl-pyrrolidine-3-carboxylic acid (3-chloro-5-fluorobenzyl) amide | | 1) HPLC 2) LC-MS; rt; [M + H+] |
| "A92" | 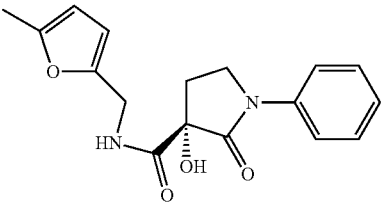<br>(S)-3-Hydroxy-2-oxo-1-phenyl-pyrrolidine-3-carboxylic acid (5-methylfuran-2-ylethyl) amide | 8.27 (t, J = 6.1, 1H), 7.69 (dd, J = 8.7, 1.0, 2H), 7.47-7.33 (m, 2H), 7.17 (t, J = 7.4, 1H), 6.67 (s, 1H), 6.07 (d, J = 3.0, 1H), 5.96 (dd, J = 3.0, 1.0, 1H), 4.22 (d, J = 6.0, 3H), 3.94-3.73 (m, 2H), 2.60-2.55 (m, 1H), 2.21 (s, 3H), 2.15-2.03 (m, 1H) | 1) 3.342 min 2) [313.1] |
| "A93" | 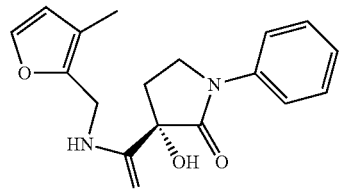<br>(S)-3-Hydroxy-2-oxo-1-phenyl-pyrrolidine-3-carboxylic acid (3-methylfuran-2-ylethyl) amide | 8.23 (d, J = 5.4, 1H), 7.69 (dd, J = 8.7, 1.0, 2H), 7.45 (d, J = 1.8, 1H), 7.44-7.37 (m, 2H), 7.17 (t, J = 7.4, 1H), 6.63 (s, 1H), 6.24 (d, J = 1.8, 1H), 4.24 (dd, J = 5.9, 2.6, 2H), 3.90-3.78 (m, 2H), 2.56-2.53 (m, 1H), 2.13-2.03 (m, 1H), 1.97 (s, 3H) | 1) 3.326 min 2) [313] |
| "A94" | 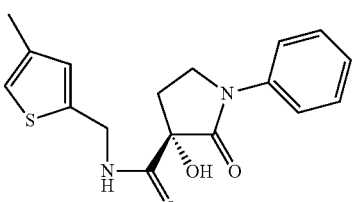<br>(S)-3-Hydroxy-2-oxo-1-phenyl-pyrrolidine-3-carboxylic acid (4-methylthiophen-2-ylethyl) amide | 8.52 (t, J = 6.2, 1H), 7.70 (dd, J = 5.4, 3.4, 2H), 7.44-7.37 (m, 2H), 7.22-7.14 (m, 1H), 6.94-6.90 (m, 1H), 6.76 (s, 1H), 6.66 (s, 1H), 4.45-4.30 (m, 2H), 3.93-3.78 (m, 2H), 2.56-2.51 (m, 1H), 2.13 (s, 3H), 2.12-2.05 (m, 1H) | 1) 3.666 min 2) 3.762 min [331.0] |

| No. | Structure/name | ¹H NMR (400 MHz, DMSO-d₆) δ [ppm] | LC-MS; rt; [M + H⁺]* |
|---|---|---|---|
| "A95" | (S)-3-Hydroxy-2-oxo-1-phenyl-pyrrolidine-3-carboxylic acid (5-methylthiophen-2-ylmethyl) amide | 8.48 (t, J = 6.2, 1H), 7.69 (dd, J = 8.7, 1.1, 2H), 7.44-7.36 (m, 2H), 7.23-7.09 (m, 1H), 6.71 (d, J = 3.3, 1H), 6.65 (s, 1H), 6.63-6.54 (m, 1H), 4.44-4.28 (m, 2H), 3.92-3.76 (m, 2H), 2.57-2.51 (m, 1H), 2.36 (d, J = 0.8, 3H), 2.15-2.04 (m, 1H) | 1) 3.653 min 2) 2.553 [331.2] |
| "A96" | (S)-1-(3-Chlorophenyl)-3-hydroxy-2-oxopyrrolidine-3-carboxylic acid 3,5-difluorobenzyl amide | 8.75 (t, J = 6.3, 1H), 7.88 (t, J = 2.1, 1H), 7.62 (ddd, J = 8.4, 2.1, 0.8, 1H), 7.44 (t, J = 8.2, 1H), 7.25 (ddd, J = 8.1, 2.0, 0.8, 1H), 7.07 (tt, J = 9.4, 2.4, 1H), 6.97 (dd, J = 8.6, 2.1, 2H), 6.82 (s, 1H), 4.38 (dd, J = 15.8, 6.7, 1H), 4.24 (dd, J = 15.8, 6.1, 1H), 3.92-3.80 (m, 2H), 2.63-2.54 (m, 1H), 2.13 (dt, J = 13.0, 7.6, 1H) | 1) 4.352 min 2) 4.344 min [381.0] |
| "A97" | (S)-1-(3-Chlorophenyl)-3-hydroxy-2-oxopyrrolidine-3-carboxylic acid 3,5-dichlorobenzyl amide | 8.77 (t, J = 6.3, 1H), 7.90 (t, J = 2.1, 1H), 7.62 (ddd, J = 8.3, 2.1, 0.8, 1H), 7.45 (d, J = 2.0, 1H), 7.43 (t, J = 6.1, 1H), 7.31 (d, J = 1.9, 2H), 7.25 (ddd, J = 8.0, 2.0, 0.8, 1H), 6.82 (s, 1H), 4.36 (dd, J = 15.7, 6.7, 1H), 4.23 (dd, J = 15.7, 6.0, 1H), 3.94-3.79 (m, 2H), 2.62-2.54 (m, 1H), 2.21-2.08 (m, 1H) | 1) 4.888 min 2) 3.373 min [415.0 + 416.0] |
| "A98" | (S)-1-(4-Fluorophenyl)-3-hydroxy-2-oxopyrrolidine-3-carboxylic acid 3,5-difluorobenzyl amide | 8.73 (t, J = 6.4, 1H), 7.76-7.67 (m, 2H), 7.30-7.19 (m, 2H), 7.06 (tt, J = 9.4, 2.3, 1H), 7.02-6.93 (m, 2H), 6.78 (s, 1H), 4.39 (dd, J = 15.8, 6.7, 1H), 4.24 (dd, J = 15.9, 6.0, 1H), 3.84 (dd, J = 8.0, 5.7, 2H), 2.59 (dt, J = 11.9, 5.7, 1H), 2.12 (dt, J = 13.0, 7.6, 1H) | 1) 3.930 min 2) 3.935 min [365.0] |
| "A99" | (S)-1-(4-Fluorophenyl)-3-hydroxy-2-oxopyrrolidine-3-carboxylic acid 3,5-dichlorobenzyl amide | 8.74 (t, J = 6.4, 1H), 7.77-7.68 (m, 2H), 7.45 (t, J = 1.9, 1H), 7.32 (d, J = 1.9, 2H), 7.28-7.22 (m, 2H), 6.78 (s, 1H), 4.36 (dd, J = 15.7, 6.7, 1H), 4.23 (dd, J = 15.7, 6.0, 1H), 3.90-3.79 (m, 2H), 2.61-2.52 (m, 1H), 2.11 (dt, J = 13.0, 7.6, 1H) | 1) 4.566 min 2) 4.563 min [397.0 + 399.0] |

| No. | Structure/name | ¹H NMR (400 MHz, DMSO-d₆) δ [ppm] | LC-MS; rt; [M + H⁺]* |
|---|---|---|---|
| "A100" | (S)-3-Hydroxy-2-oxo-1-phenyl-pyrrolidine-3-carboxylic acid 3,5-difluorobenzyl amide | 8.72 (t, J = 6.4, 1H), 7.73-7.67 (m, 2H), 7.43-7.37 (m, 2H), 7.18 (dd, J = 10.5, 4.2, 1H), 7.06 (tt, J = 9.4, 2.4, 1H), 7.00-6.95 (m, 2H), 6.77 (s, 1H), 4.39 (dd, J = 15.9, 6.8, 1H), 4.24 (dd, J = 15.8, 6.0, 1H), 3.86 (dd, J = 8.0, 5.7, 2H), 2.63-2.55 (m, 1H), 2.18-2.07 (m, 1H). | 1) 3.829 min 2) 3.472 min [347.2] |
| "A101" | (S)-3-Hydroxy-2-oxo-1-phenyl-pyrrolidine-3-carboxylic acid 3,5-dichlorobenzyl amide | 8.74 (t, J = 6.4, 1H), 7.70 (dd, J = 8.7, 1.0, 2H), 7.45 (t, J = 1.9, 1H), 7.44-7.36 (m, 2H), 7.32 (d, J = 1.9, 2H), 7.18 (t, J = 7.4, 1H), 6.77 (s, 1H), 4.37 (dd, J = 15.6, 6.7, 1H), 4.23 (dd, J = 15.7, 6.0, 1H), 3.90-3.78 (m, 2H), 2.63-2.53 (m, 1H), 2.12 (dt, J = 13.0, 7.7, 1H) | 1) 4.431 min 2) 4.451 min [379.0 + 381.3] |
| "A102" | (S)-1-(3-Chlorophenyl)-3-hydroxy-2-oxopyrrolidine-3-carboxylic acid 3-chloro-5-fluorobenzyl amide | 8.76 (t, J = 6.3, 1H), 7.89 (t, J = 2.1, 1H), 7.62 (ddd, J = 8.3, 2.1, 0.7, 1H), 7.44 (t, J = 8.2, 1H), 7.30-7.22 (m, 2H), 7.20 (s, 1H), 7.09 (d, J = 9.6, 1H), 6.82 (s, 1H), 4.37 (dd, J = 15.8, 6.7, 1H), 4.24 (dd, J = 15.8, 6.0, 1H), 3.93-3.81 (m, 2H), 2.63-2.54 (m, 1H), 2.18-2.08 (m, 1H) | 1) 4.630 min 2) 4.624 min [397.0 + 399.0] |
| "A103" | (S)-1-(4-Fluorophenyl)-3-hydroxy-2-oxopyrrolidine-3-carboxylic acid 3-chloro-5-fluorobenzyl amide | 8.73 (t, J = 6.4, 1H), 7.79-7.64 (m, 2H), 7.26 (ddd, J = 12.3, 7.1, 2.1, 3H), 7.20 (s, 1H), 7.10 (d, J = 9.3, 1H), 6.77 (s, 1H), 4.38 (dd, J = 15.8, 6.7, 1H), 4.24 (dd, J = 15.8, 6.1, 1H), 3.94-3.73 (m, 2H), 2.64-2.53 (m, 1H), 2.12 (dt, J = 13.1, 7.7, 1H) | 1) 4.245 min 2) 4.354 min [381.0] |

| No. | Structure/name | $^1$H NMR (400 MHz, DMSO-$d_6$) δ [ppm] | LC-MS; rt; [M + H$^+$]* |
|---|---|---|---|
| "A104" | (S)-1-(2,3-Dihydrobenzo-1,4-dioxin-6-yl)-3-hydroxy-2-oxo-pyrrolidine-3-carboxylic acid 3-chloro-5-fluorobenzyl amide | 8.70 (t, J = 6.4, 1H), 7.27 (dt, J = 6.2, 2.9, 2H), 7.20 (s, 1H), 7.11 (d, J = 2.5, 1H), 7.09 (d, J = 2.6, 1H), 6.87 (d, J = 8.8, 1H), 6.72 (s, 1H), 4.37 (dd, J = 15.9, 6.7, 1H), 4.27-4.19 (m, 5H), 3.82 -3.74 (m, 2H), 2.59-2.51 (m, 1H), 2.07 (dt, J = 12.9, 7.6, 1H) | 1) 4.066 min 2) 4.019 min [421.0] |
| "A105" | (S)-1-Benzo-1,3-dioxol-5-yl-3-hydroxy-2-oxopyrrolidine-3-carboxylic acid 3-chloro-5-fluoro-benzyl amide | 8.71 (t, J = 6.4, 1H), 7.40 (d, J = 2.2, 1H), 7.27 (dt, J = 8.7, 2.1, 1H), 7.20 (s, 1H), 7.09 (d, J = 8.9, 1H), 7.04 (dd, J = 8.5, 2.2, 1H), 6.94 (d, J = 8.5, 1H), 6.73 (s, 1H), 6.02 (s, 2H), 4.37 (dd, J = 15.8, 6.8, 1H), 4.23 (dd, J = 15.8, 5.9, 1H), 3.79 (dd, J = 7.5, 6.1, 2H), 2.61-2.52 (m, 1H), 2.08 (dt, J = 12.9, 7.6, 1H) | 1) 4.062 min 2) 4.044 min [407.0] |
| "A106" | (S)-3-Hydroxy-2-oxo-1-quinolin-6-ylpyrrolidine-3-carboxylic acid 3-chloro-5-fluorobenzyl amide | 8.85 (dd, J = 4.2, 1.7, 1H), 8.79 (t, J = 6.4, 1H), 8.36 (d, J = 7.6, 1H), 8.32 (dd, J = 9.2, 2.5, 1H), 8.12 (d, J = 2.5, 1H), 8.05 (d, J = 9.2, 1H), 7.53 (dd, J = 8.3, 4.2, 1H), 7.28 (dt, J = 8.8, 2.1, 1H), 7.22 (s, 1H), 7.11 (d, J = 9.7, 1H), 6.87 (s, 1H), 4.39 (dd, J = 15.8, 6.6, 1H), 4.26 (dd, J = 15.8, 6.1, 1H), 4.05-3.96 (m, 2H), 2.64 (dt, J = 6.9, 5.8, 1H), 2.20 (dt, J = 13.0, 7.6, 1H) | 1) 3.027 min 2) 3.099 min [414.0] |
| "A107" | (S)-3-Hydroxy-1-methyl-2-oxo-pyrrolidine-3-carboxylic acid 3-chloro-5-fluorobenzyl amide | 8.59 (t, J = 6.4, 1H), 7.31-7.23 (m, 1H), 7.19 (s, 1H), 7.09 (d, J = 9.8, 1H), 6.46 (s, 1H), 4.36 (dd, J = 15.7, 6.8, 1H), 4.21 (dd, J = 15.8, 5.8, 1H), 2.76 (s, 3H), 2.45-2.40 (m, 1H), 2.00-1.88 (m, 1H) | 1) 2.869 min 2) 2.950 min [301.0] |

| No. | Structure/name | ¹H NMR (400 MHz, DMSO-d$_6$) δ [ppm] | LC-MS; rt; [M + H⁺]* |
|---|---|---|---|
| "A108" | 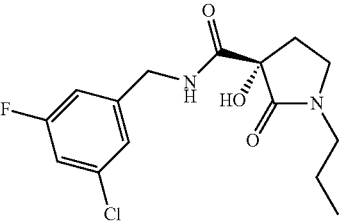<br>(S)-3-Hydroxy-2-oxo-1-propyl pyrrolidine-3-carboxylic acid 3-chloro-5-fluorobenzyl amide | 8.57 (t, J = 6.4, 1H), 7.26 (dt, J = 8.8, 2.2, 1H), 7.18 (s, 1H), 7.13-7.01 (m, 1H), 6.44 (s, 1H), 4.36 (dd, J = 15.8, 6.8, 1H), 4.21 (dd, J = 15.8, 6.0, 1H), 3.27-3.16 (m, 1H), 3.11 (dt, J = 13.5, 6.8, 1H), 2.47-2.39 (m, 1H), 1.94 (ddd, J = 13.0, 8.3, 6.9, 1H), 1.47 (h, J = 7.3, 2H), 0.80 (t, J = 7.4, 3H) | 1) 3.482 min<br>2) 3.504 min<br>[329.0] |
| "A109" | 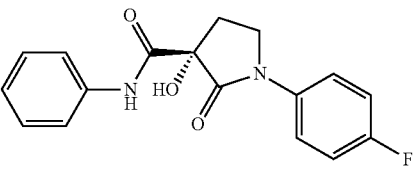<br>(S)-1-(4-Fluorophenyl)-3-hydroxy-2-oxopyrrolidine-3-carboxylic acid phenyl amide | 9.79 (s, 1H), 7.80-7.69 (m, 4H), 7.34-7.24 (m, 4H), 7.08 (dd, J = 10.6, 4.2, 1H), 7.02 (s, 1H), 3.89 (dd, J = 8.2, 5.5, 2H), 2.76-2.61 (m, 1H), 2.19 (dt, J = 13.1, 7.7, 1H) | 1) 3.689 min<br>2) 3.653 min<br>[315.0] |
| "A110" | 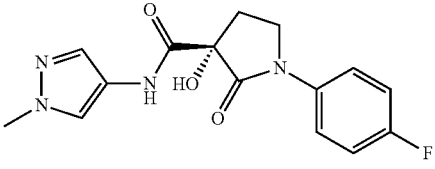<br>(S)-1-(4-Fluorophenyl)-3-hydroxy-2-oxopyrrolidine-3-carboxylic acid (1-methyl-1H-pyrazol-4-yl) amide | 10.11 (s, 1H), 7.90 (s, 1H), 7.73 (dd, J = 9.1, 4.9, 2H), 7.59 (s, 1H), 7.25 (t, J = 8.9, 2H), 6.87 (s, 1H), 3.88 (dd, J = 12.2, 5.5, 2H), 3.76 (s, 3H), 2.72-2.58 (m, 2H), 2.23-2.07 (m, 1H) | 1) 2.516 min<br>2) 2.576 min<br>[319.2] |
| "A111" | 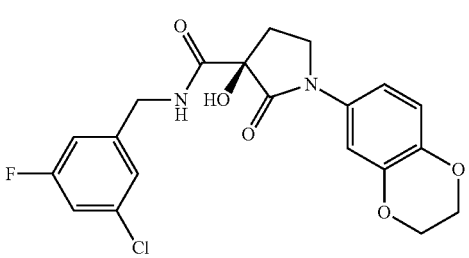<br>(R)-1-(2,3-Dihydrobenzo-1,4-dioxin-6-yl)-3-hydroxy-2-oxopyrrolidine-3-carboxylic acid 3-chloro-5-fluorobenzyl amide | 8.70 (t, J = 6.4, 1H), 7.28 (dd, J = 4.6, 2.4, 1H), 7.26 (d, J = 3.5, 1H), 7.20 (s, 1H), 7.11 (d, J = 2.5, 1H), 7.09 (d, J = 2.6, 1H), 6.86 (d, J = 8.8, 1H), 6.72 (s, 1H), 4.37 (dd, J = 15.8, 6.8, 1H), 4.27-4.18 (m, 5H), 3.84-3.72 (m, 2H), 2.55 (dd, J = 13.1, 6.1, 1H), 2.07 (dt, J = 13.0, 7.6, 1H) | 1) 4.069 min<br>2) 4.025 min<br>[421.0] |
| "A112" | 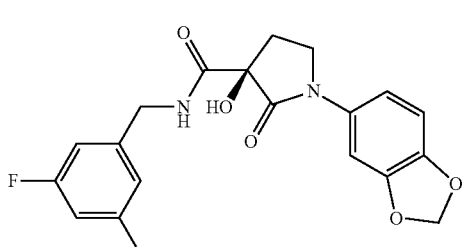<br>(R)-1-Benzo-1,3-dioxol-5-yl-3-hydroxy-2-oxopyrrolidine-3-carboxylic acid 3-chloro-5-fluoro-benzyl amide | 8.71 (t, J = 6.3, 1H), 7.40 (d, J = 2.1, 1H), 7.27 (d, J = 8.7, 1H), 7.20 (s, 1H), 7.09 (d, J = 9.4, 1H), 7.04 (dd, J = 8.5, 2.1, 1H), 6.94 (d, J = 8.5, 1H), 6.74 (s, 1H), 6.02 (s, 2H), 4.37 (dd, J = 15.7, 6.7, 1H), 4.23 (dd, J = 15.7, 6.0, 1H), 3.79 (t, J = 6.8, 2H), 2.63-2.52 (m, 1H), 2.15-2.02 (m, 1H) | 1) 4.060 min<br>2) 4.199 min<br>[407.0] |

| No. | Structure/name | $^1$H NMR (400 MHz, DMSO-$d_6$) δ [ppm] | LC-MS; rt; [M + H$^+$]* |
|---|---|---|---|
| "A113" | (S)-3-Hydroxy-1-methyl-2-oxo-pyrrolidine-3-carboxylic acid 3-chloro-5-fluorobenzyl amide | 8.59 (t, J = 6.3, 1H), 7.26 (dt, J = 8.8, 2.2, 1H), 7.19 (s, 1H), 7.09 (d, J = 9.7, 1H), 6.46 (s, 1H), 4.36 (dd, J = 15.8, 6.8, 1H), 4.21 (dd, J = 15.8, 6.0, 1H), 3.37-3.28 (m, 5H), 2.47-2.41 (m, 1H), 2.01-1.85 (m, 1H) | 1) 2.867 min 2) 2.950 min [301.0] |
| "A114" | (R)-3-Hydroxy-2-oxo-1-propyl-pyrrolidine-3-carboxylic acid 3-chloro-5-fluorobenzyl amide | 8.57 (t, J = 6.4, 1H), 7.26 (dt, J = 8.8, 2.2, 1H), 7.18 (s, 1H), 7.08 (d, J = 9.7, 1H), 6.44 (s, 1H), 4.36 (dd, J = 15.8, 6.8, 1H), 4.21 (dd, J = 15.8, 6.0, 1H), 3.26-3.17 (m, 1H), 3.11 (dt, J = 13.4, 6.8, 1H), 2.47-2.39 (m, 1H), 2.02-1.86 (m, 1H), 1.47 (h, J = 7.3, 2H), 0.80 (t, J = 7.4, 3H) | 1) 3.482 min 2) 3.505 min [329.0] |
| "A115" | 3-Fluoro-2-oxo-1-phenyl-pyrrolidine-3-carboxylic acid 3-chloro-5-fluorobenzyl amide | 9.26 (t, J = 5.6, 1H), 7.70 (dd, J = 8.7, 1.0, 2H), 7.49-7.41 (m, 2H), 7.30 (dt, J = 8.8, 2.1, 1H), 7.28-7.23 (m, 1H), 7.21 (d, J = 4.1, 1H), 7.10 (d, J = 9.6, 1H), 4.44 (dd, J = 15.8, 6.5, 1H), 4.29 (dd, J = 15.8, 5.9, 1H), 4.05-3.89 (m, 2H), 2.79 (tdd, J = 14.1, 7.5, 3.8, 1H), 2.57-2.39 (m, 7H) | 1) 4.729 min 2) 4.799 min [365.0] |
| "A116" | (3)-Hydroxy-1-(2-methylpyridin-4-yl)-2-oxopyrrolidine-3-carboxylic acid 3-chloro-5-fluorobenzyl amide | | 1) 2.958 min 2) 2.911 min [378.0] |
| "A117" | (S)-1-Ethyl-3-hydroxy-2-oxo-pyrrolidine-3-carboxylic acid 3-chloro-5-fluorobenzyl amide | | 1) 3.123 min 2) 3.218 min [315.0] |

| No. | Structure/name | ¹H NMR (400 MHz, DMSO-d₆) δ [ppm] | LC-MS; rt; [M + H⁺]* |
|---|---|---|---|
| "A118" | 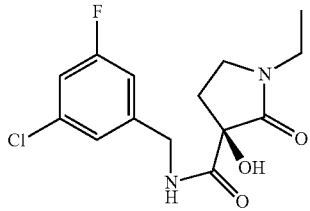<br>(R)-1-Ethyl-3-hydroxy-2-oxo-pyrrolidine-3-carboxylic acid 3-chloro-5-fluorobenzyl amide | | 1) 3.122 min<br>2) 3.218 min<br>[315.0] |
| "A119" | 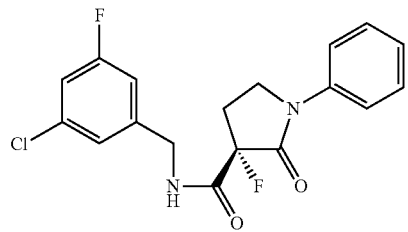<br>(S)-3-Fluoro-2-oxo-1-phenyl-pyrrolidine-3-carboxylic acid 3-chloro-5-fluorobenzyl amide | | 1) 4.729 min<br>2) 4.819 min<br>[365.0] |
| "A120" | 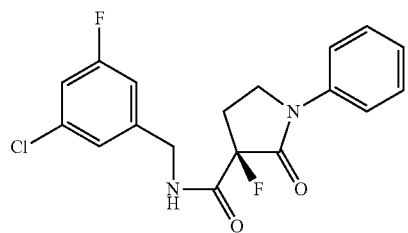<br>(R)-3-Fluoro-2-oxo-1-phenyl-pyrrolidine-3-carboxylic acid 3-chloro-5-fluorobenzyl amide | | 1) 4.718 min<br>2) 4.799 min<br>[365.0] |

The following compounds are prepared analogously:
(S)-3-hydroxy-1-isobutyl-2-oxopyrrolidine-3-carboxylic acid 3-chloro-5-fluorobenzyl amide ("A121")

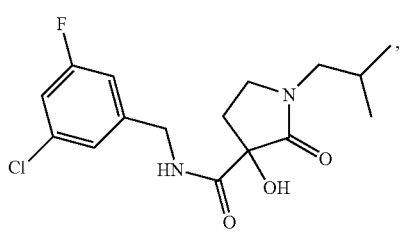 [SMILES: CC(C)CN1CCC(O)(C(=O)NCc2cc(F)cc(Cl)c2)C1=O]

(S)-1-(2-amino-1-methylethyl)-3-hydroxy-2-oxopyrrolidine-3-carboxylic acid 3-chloro-5-fluorobenzyl amide ("A122")

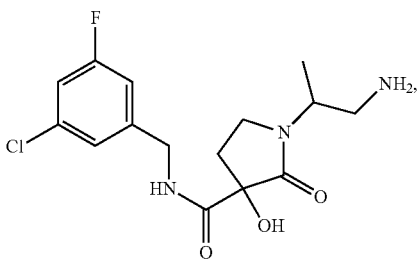 [SMILES: CC(CN)N1CCC(O)(C(=O)NCc2cc(F)cc(Cl)c2)C1=O]

(S)-1-(2-dimethylamino-1-methylethyl)-3-hydroxy-2-oxopyrrolidine-3-carboxylic acid 3-chloro-5-fluorobenzyl amide ("A123")

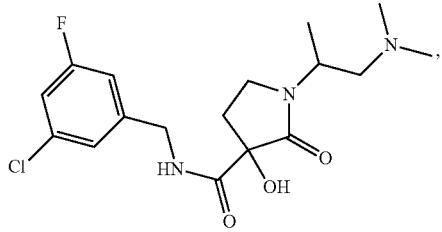 [SMILES: CC(CN(C)C)N1CCC(O)(C(=O)NCc2cc(F)cc(Cl)c2)C1=O]

(S)-1-(2-aminoethyl)-3-hydroxy-2-oxopyrrolidine-3-carboxylic acid 3-chloro-5-fluorobenzyl amide ("A124")

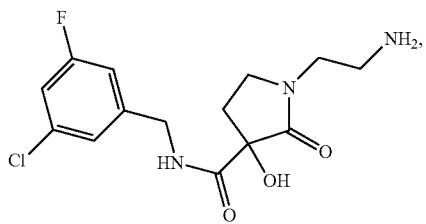 [SMILES: NCCN1CCC(O)(C(=O)NCc2cc(F)cc(Cl)c2)C1=O]

(S)-1-(2-dimethylaminoethyl)-3-hydroxy-2-oxopyrrolidine-3-carboxylic acid 3-chloro-5-fluorobenzyl amide ("A125")

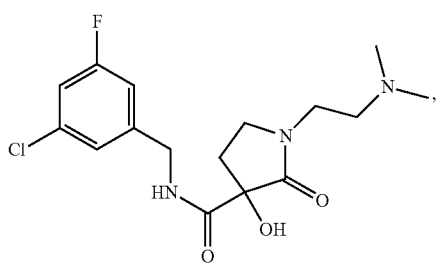 [SMILES: CN(C)CCN1CCC(O)(C(=O)NCc2cc(F)cc(Cl)c2)C1=O]

(S)-1-(3-dimethylaminopropyl)-3-hydroxy-2-oxopyrrolidine-3-carboxylic acid 3-chloro-5-fluorobenzyl amide ("A126")

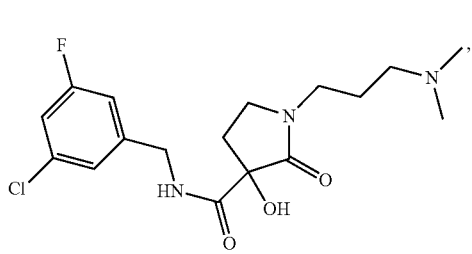 [SMILES: CN(C)CCCN1CCC(O)(C(=O)NCc2cc(F)cc(Cl)c2)C1=O]

(S)-3-hydroxy-1-(3-hydroxypropyl)-2-oxopyrrolidine-3-carboxylic acid 3-chloro-5-fluorobenzyl amide ("A127")

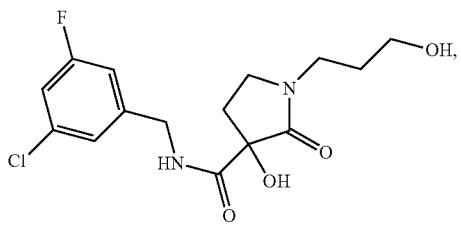 [SMILES: O=C(NCc1cc(F)cc(Cl)c1)C1(O)CCN(CCCO)C1=O]

(S)-3-hydroxy-1-(3-methoxypropyl)-2-oxopyrrolidine-3-carboxylic acid 3-chloro-5-fluorobenzyl amide ("A128")

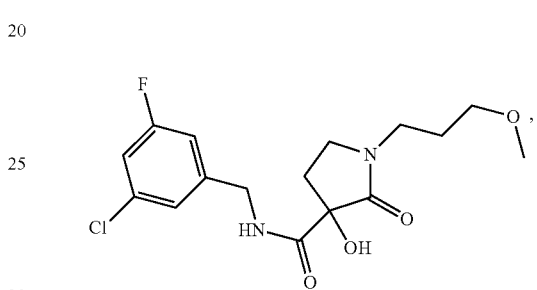

(S)-3-hydroxy-1-(2-methoxyethyl)-2-oxopyrrolidine-3-carboxylic acid 3-chloro-5-fluorobenzyl amide ("A129")

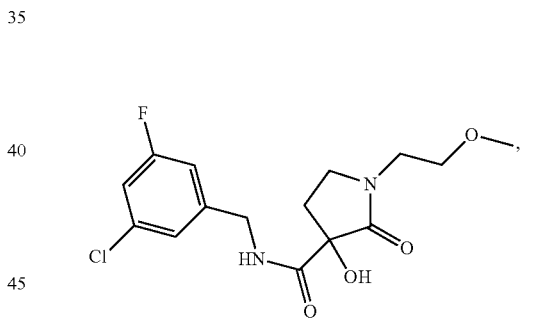

(S)-1-(2-formylaminoethyl)-3-hydroxy-2-oxopyrrolidine-3-carboxylic acid 3-chloro-5-fluorobenzyl amide ("A130")

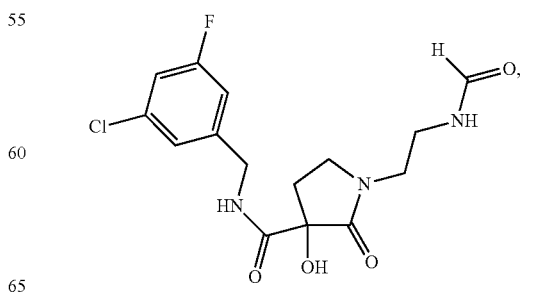

101

(S)-1-(2-acetylaminoethyl)-3-hydroxy-2-oxopyrrolidine-3-carboxylic acid 3-chloro-5-fluorobenzyl amide ("A131")

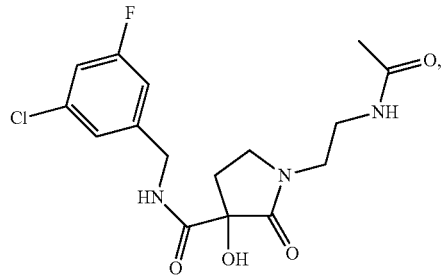 [SMILES: CC(=O)NCCN1CCC(O)(C(=O)NCc2cc(F)cc(Cl)c2)C1=O]

(S)-1-[1-(acetylaminomethyl)-cyclopropyl]-3-hydroxy-2-oxopyrrolidine-3-carboxylic acid 3-chloro-5-fluorobenzyl amide ("A132")

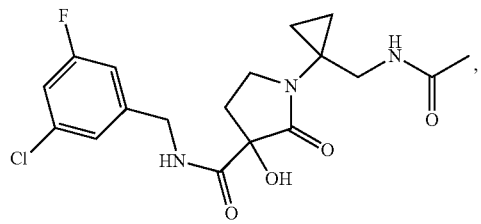 [SMILES: CC(=O)NCC1(N2CCC(O)(C(=O)NCc3cc(F)cc(Cl)c3)C2=O)CC1]

(S)-3-hydroxy-2-oxo-1-(2-ureidoethyl)pyrrolidine-3-carboxylic acid 3-chloro-5-fluorobenzyl amide ("A133")

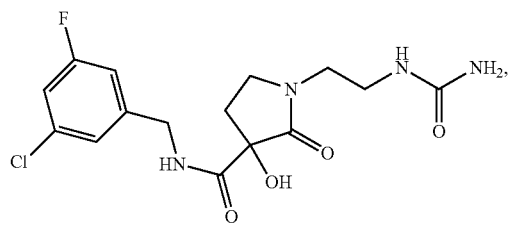 [SMILES: NC(=O)NCCN1CCC(O)(C(=O)NCc2cc(F)cc(Cl)c2)C1=O]

(S)-1-(1H-benzimidazol-5-yl)-3-hydroxy-2-oxopyrrolidine-3-carboxylic acid 3-chloro-5-fluorobenzyl amide ("A134")

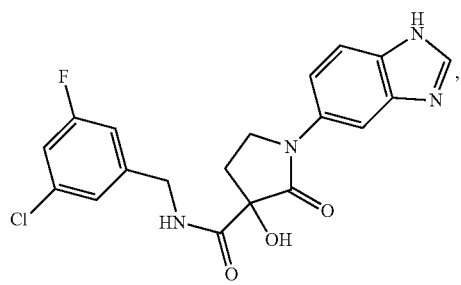 [SMILES: O=C(NCc1cc(F)cc(Cl)c1)C1(O)CCN(c2ccc3[nH]cnc3c2)C1=O]

102

(S)-3-hydroxy-2-oxo-1-(2-oxo-2,3-dihydro-1H-indol-5-yl)pyrrolidine-3-carboxylic acid 3-chloro-5-fluorobenzyl amide ("A135")

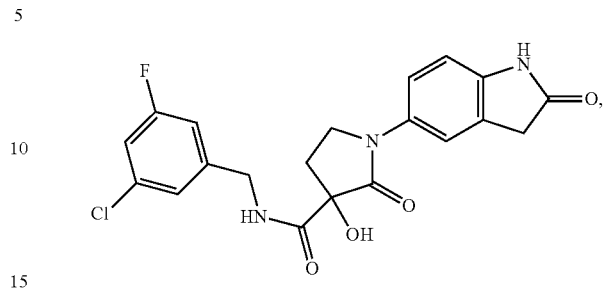

(S)-3-hydroxy-2-oxo-1-((S)-2,2,2-trifluoro-1-formylaminomethylethyl)pyrrolidine-3-carboxylic acid 3-chloro-5-fluorobenzyl amide ("A136")

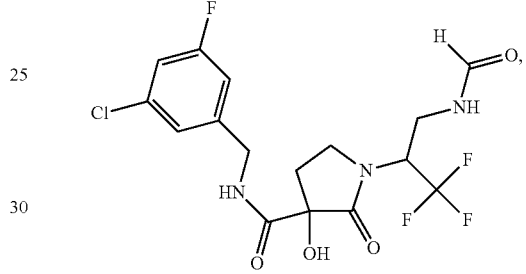

1-(3-carbamoylphenyl)-3-hydroxy-2-oxopyrrolidine-3-carboxylic acid 3-chloro-5-fluorobenzyl amide ("A137")

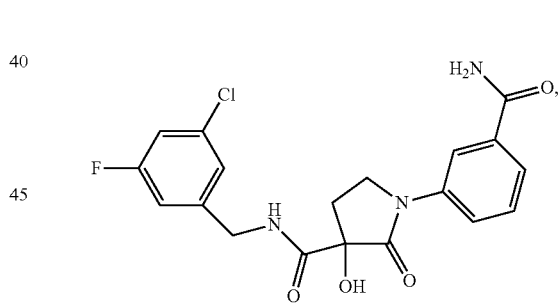

1-(2-carbamoylphenyl)-3-hydroxy-2-oxopyrrolidine-3-carboxylic acid 3-chloro-5-fluorobenzyl amide ("A138")

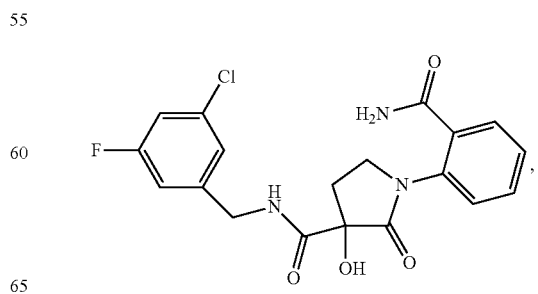

tert-butyl {2-[(S)-3-(3-chloro-5-fluorobenzylcarbamoyl)-3-hydroxy-2-oxopyrrolidin-1-yl]-ethyl}carbamate ("A140")

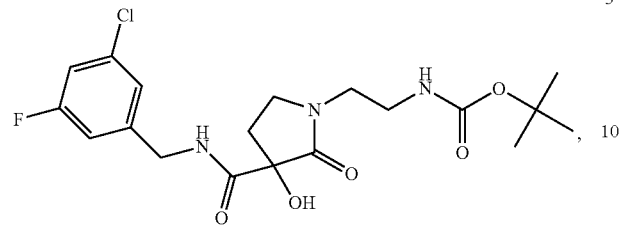

1-(3-cyanophenyl)-3-hydroxy-2-oxopyrrolidine-3-carboxylic acid 3-chloro-5-fluorobenzyl amide ("A141")

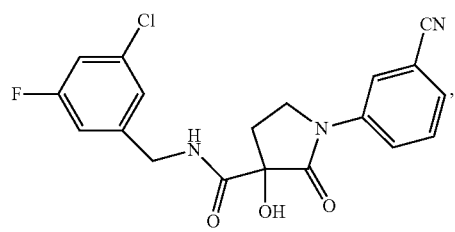 [SMILES: N#Cc1cccc(N2CCC(O)(C(=O)NCc3cc(F)cc(Cl)c3)C2=O)c1]

1-(2-cyanophenyl)-3-hydroxy-2-oxopyrrolidine-3-carboxylic acid 3-chloro-5-fluorobenzyl amide ("A142"),
1-(4-cyanophenyl)-3-hydroxy-2-oxopyrrolidine-3-carboxylic acid 3-chloro-5-fluorobenzyl amide ("A143"),
1-(3-amino-3-oxopropyl)-N-[(3-chloro-5-fluorophenyl)methyl]-3-hydroxy-2-oxopyrrolidine-3-carboxamide ("A144")

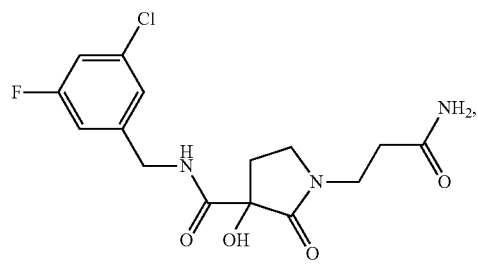 [SMILES: NC(=O)CCN1CCC(O)(C(=O)NCc2cc(F)cc(Cl)c2)C1=O]

N-[(3-chloro-5-fluorophenyl)methyl]-3-hydroxy-1-[3-(methylamino)-3-oxopropyl]-2-oxopyrrolidine-3-carboxamide ("A145")

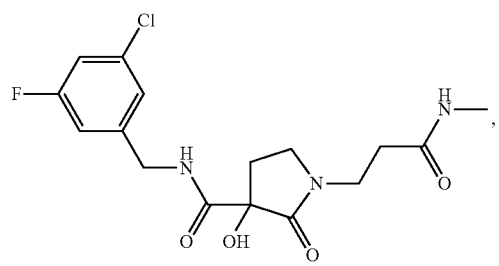 [SMILES: CNC(=O)CCN1CCC(O)(C(=O)NCc2cc(F)cc(Cl)c2)C1=O]

1-(4-amino-4-oxobutyl)-N-[(3-chloro-5-fluorophenyl)methyl]-3-hydroxy-2-oxopyrrolidine-3-carboxamide ("A146"), N-[(3-chloro-5-fluorophenyl)methyl]-3-hydroxy-1-[4-(methylamino)-4-oxobutyl]-2-oxopyrrolidine-3-carboxamide ("A147"),
1-(2-cyanoethyl)-3-hydroxy-2-oxopyrrolidine-3-carboxylic acid 3-chloro-5-fluorobenzyl amide ("A148")

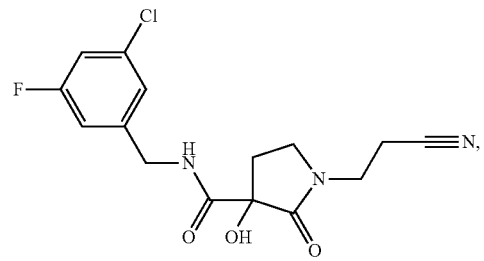 [SMILES: N#CCCN1CCC(O)(C(=O)NCc2cc(F)cc(Cl)c2)C1=O]

1-(3-cyanopropyl)-3-hydroxy-2-oxopyrrolidine-3-carboxylic acid 3-chloro-5-fluorobenzyl amide ("A149")
3-hydroxy-1-(6-methylpyridin-3-yl)-2-oxopyrrolidine-3-carboxylic acid 3-chloro-5-fluorobenzyl amide ("A152")

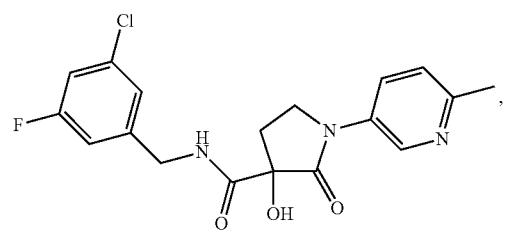 [SMILES: Cc1ccc(N2CCC(O)(C(=O)NCc3cc(F)cc(Cl)c3)C2=O)cc1]

3-hydroxy-2-oxopyrrolidine-1,3-dicarboxylic acid 3-(3-chloro-5-fluorobenzyl amide)-1-ethyl amide ("A153")

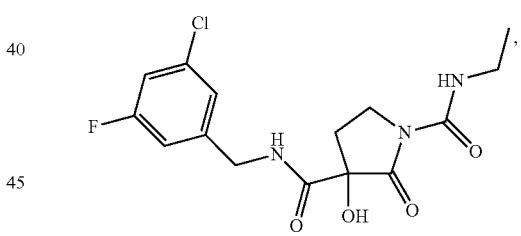

3-hydroxy-2-oxopyrrolidine-1,3-dicarboxylic acid 3-(3-chloro-5-fluorobenzyl amide)-1-phenyl amide ("A154")

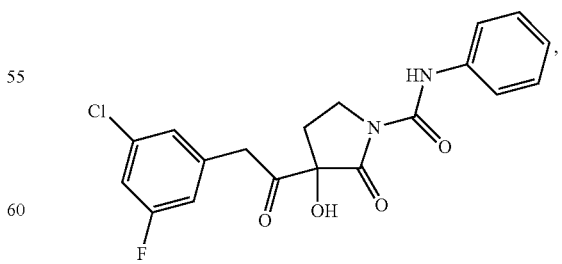

3-azido-N-[(3-chloro-5-fluorophenyl)-methyl]-2-oxo-1-phenylpyrrolidine-3-carboxamide ("A155"),
3-hydroxy-2-oxo-1-p-tolylpyrrolidine-3-carboxylic acid 3-chloro-5-fluorobenzyl amide ("A156")

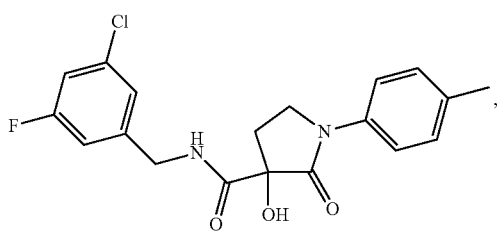

1-carbamoylmethyl-3-hydroxy-2-oxopyrrollidine-3-carboxylic acid 3-chloro-5-fluorobenzyl amide ("A157")

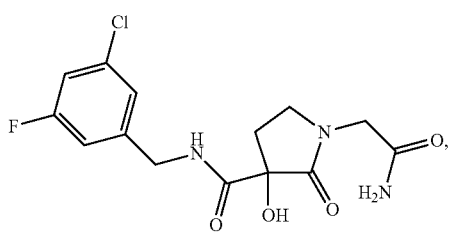 [SMILES: NC(=O)CN1CCC(O)(C(=O)NCc2cc(F)cc(Cl)c2)C1=O]

(3S)-1-[(1S)-2-amino-1-methyl-2-oxoethyl]-N-[(3-chloro-5-fluorophenyl)methyl]-3-hydroxy-2-oxopyrrolidine-3-carboxamide ("A158")

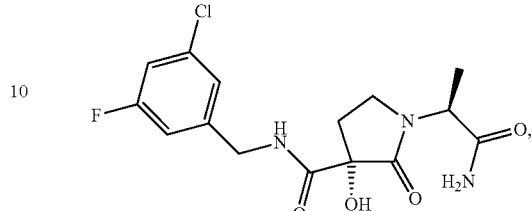

(3S)-1-[(1R)-2-amino-1-methyl-2-oxoethyl]-N-[(3-chloro-5-fluorophenyl)methyl]-3-hydroxy-2-oxopyrrolidine-3-carboxamide ("A159"), 3-hydroxy-2-oxo-1-(4-fluorophenyl)pyrrolidine-3-carboxylic acid 3-trifluoromethyl-5-fluorobenzyl amide ("A160"), 3-hydroxy-2-oxo-1-phenylpyrrolidine-3-carboxylic acid 3,5-(bistrifluoromethyl)benzyl amide ("A161").

The following compounds are obtained analogously

| No. | Structure/name | $^1$H NMR (400 MHz, DMSO-d$_6$) δ [ppm] | LC-MS; rt; [M + H$^+$] * |
|---|---|---|---|
| "A162" | (S)-1-(4-Fluorophenyl)-3-hydroxy-2-oxopyrrolidine-3-carboxylic acid 3-fluoro-5-trifluoromethylbenzyl amide | 8.82 (t, J = 6.3, 1H), 7.76-7.70 (m, 2H), 7.53 (s, 1H), 7.51 (s, 2H), 7.43 (d, J = 9.5, 1H), 7.28-7.22 (m, 2H), 6.79 (s, 1H), 4.46 (dd, J = 15.8, 6.7, 1H), 4.32 (dd, J = 15.9, 6.0, 1H), 3.84 (t, J = 6.8, 2H), 2.63-2.54 (m, 1H), 2.12 (dt, J = 13.1, 7.6, 1H). | 4.57 min [415] |
| "A163" | (S)-1-(4-Fluorophenyl)-3-hydroxy-2-oxopyrrolidine-3-carboxylic acid 3,5-bistrifluoromethylbenzyl amide | 8.90 (t, J = 6.3, 1H), 7.96 (d, J = 4.1, 3H), 7.76-7.70 (m, 2H), 7.30-7.20 (m, 2H), 6.81 (s, 1H), 4.55 (dd, J = 15.9, 6.7, 1H), 4.40 (dd, J = 16.0, 6.0, 1H), 3.90-3.79 (m, 2H), 2.64-2.54 (m, 1H), 2.12 (dt, J = 13.0, 7.5, 1H). | 5.09 min [465] |

| No. | Structure/name | ¹H NMR (400 MHz, DMSO-d₆) δ [ppm] | LC-MS; rt; [M + H⁺] * |
|---|---|---|---|
| "A164" | (S)-3-Hydroxy-2-oxo-1-phenyl-pyrrolidine-3-carboxylic acid 3-fluoro-5-trifluoromethylbenzyl amide | 8.81 (t, J = 6.3, 1H), 7.70 (t, J = 1.6, 1H), 7.68 (d, J = 1.0, 1H), 7.52 (d, J = 7.8, 2H), 7.43 (d, J = 8.8, 2H), 7.21-7.12 (m, 1H), 6.78 (s, 1H), 4.47 (dd, J = 16.0, 6.8, 1H), 4.32 (dd, J = 15.8, 6.0, 1H), 3.86 (dd, J = 8.3, 5.7, 2H), 2.58 (dt, J = 6.7, 5.8, 1H), 2.12 (dt, J = 13.1, 7.6, 1H). | 4.48 min; [397] |
| "A165" | (S)-3-Hydroxy-2-oxo-1-phenyl-pyrrolidine-3-carboxylic acid 3,5-bistrifluoromethylbenzyl amide | 8.90 (t, J = 6.4, 1H), 7.96 (d, J = 6.2, 3H), 7.69 (dd, J = 8.7, 1.0, 2H), 7.40 (dd, J = 10.7, 5.3, 2H), 7.17 (t, J = 7.4, 1H), 6.80 (s, 1H), 4.55 (dd, J = 15.9, 6.6, 1H), 4.40 (dd, J = 15.9, 5.9, 1H), 3.92-3.77 (m, 2H), 2.58 (ddd, J = 12.0, 7.4, 4.4, 1H), 2.12 (dt, J = 13.0, 7.6, 1H). | 5.02 min [447] |
| "A166" | (S)-3-Amino-2-oxo-1-phenyl-pyrrolidine-3-carboxylic acid 3-chloro-5-fluorobenzyl amide | 8.74 (s, 1H), 7.69 (d, J = 8.0, 2H), 7.39 (t, J = 7.9, 2H), 7.28 (d, J = 8.7, 1H), 7.17 (dd, J = 14.5, 7.2, 2H), 7.09 (d, J = 9.3, 1H), 4.35 (dd, J = 15.7, 6.2, 1H), 4.26 (dd, J = 15.7, 5.8, 1H), 3.89-3.78 (m, 2H), 2.57 (br. s, 2H), 2.06 (dt, J = 12.7, 7.8, 1H). | 3.53 min [362] |
| "A167" | (R)-3-Hydroxy-2-oxo-1-phenyl-pyrrolidine-3-carboxylic acid 3-chloro-5-fluorobenzyl amide | 8.73 (t, J = 6.3, 1H), 7.69 (dd, J = 8.7, 1.0, 2H), 7.43-7.38 (m, 2H), 7.27 (dt, J = 8.8, 2.1, 1H), 7.21-7.15 (m, 2H), 7.12-7.08 (m, 1H), 6.77 (s, 1H), 4.38 (dd, J = 15.7, 6.7, 1H), 4.24 (dd, J = 15.7, 6.1, 1H), 3.89-3.83 (m, 2H), 2.63-2.54 (m, 1H), 2.12 (dt, J = 13.1, 7.7, 1H). | 4.15 min [363] |

| No. | Structure/name | ¹H NMR (400 MHz, DMSO-d₆) δ [ppm] | LC-MS; rt; [M + H⁺] * |
|---|---|---|---|
| "A168" | (R)-3-Amino-2-oxo-1-phenyl-pyrrolidine-3-carboxylic acid 3-chloro-5-fluorobenzyl amide | 8.77 (s, 1H), 7.69 (d, J = 7.8, 2H), 7.40 (t, J = 8.0, 2H), 7.30-7.25 (m, 1H), 7.22-7.13 (m, 2H), 7.09 (d, J = 9.3, 1H), 4.35 (dd, J = 15.6, 6.0, 1H), 4.27 (dd, J = 15.9, 5.9, 1H), 3.89-3.81 (m, 2H), 2.14-2.03 (m, 1H). | 3.53 min [362] |
| "A169" | (S)-3-Azido-2-oxo-1-phenyl-pyrrolidine-3-carboxylic acid 3-chloro-5-fluorobenzyl amide | 9.13 (s, 1H), 7.69 (d, J = 7.7, 2H), 7.46-7.40 (m, 2H), 7.31 (d, J = 9.1, 1H), 7.26-7.18 (m, 2H), 7.09 (d, J = 8.6, 1H), 4.36 (dd, J = 11.5, 6.2, 2H), 3.92 (d, J = 7.5, 3H), 1.23 (s, 3H). | 5.11 min [388] |
| "A170" | (S)-3-Hydroxy-1-(1-methyl-1H-pyrazol-4-yl)-2-oxopyrrolidine-3-carboxylic acid 3-chloro-2-fluoro-benzyl amide | 8.62 (t, J = 6.0, 1H), 8.01 (s, 0H), 7.63 (s, 1H), 7.45 (t, J = 7.0, 1H), 7.30 (t, J = 6.7, 1H), 7.18 (t, J = 7.9, 1H), 6.69 (s, 1H), 4.39 (dd, J = 15.2, 6.1, 1H), 4.31 (dd, J = 15.6, 6.2, 1H), 3.68 (dd, J = 14.7, 5.9, 2H), 2.59 (dd, J = 8.9, 4.3, 1H), 2.17-2.07 (m, 1H). | 3.12 min [367] |
| "A171" | (S)-3-Hydroxy-1-(2-methoxyethyl)-2-oxopyrrolidine-3-carboxylic acid 3,5-difluorobenzyl amide | 8.57 (t, J = 6.3, 1H), 7.09-7.02 (m, 1H), 6.97 (d, J = 6.7, 1H), 6.47 (s, 1H), 4.37 (dd, J = 15.9, 6.8, 1H), 4.21 (dd, J = 15.9, 5.9, 1H), 3.39 (ddd, J = 13.4, 10.5, 5.4, 4H), 3.23 (s, 3H), 2.48-2.38 (m, 1H), 1.98-1.89 (m, 1H). | 2.70 min [329] |

| No. | Structure/name | $^1$H NMR (400 MHz, DMSO-d$_6$) δ [ppm] | LC-MS; rt; [M + H$^+$] * |
|---|---|---|---|
| "A172" | (S)-3-Hydroxy-2-oxo-1-p-tolyl-pyrrolidine-3-carboxylic acid 3-chloro-5-fluorobenzyl amide | 8.72 (t, J = 6.4, 1H), 7.60-7.55 (m, 2H), 7.27 (dt, J = 8.8, 2.2, 1H), 7.20 (dd, J = 4.9, 3.3, 3H), 7.10 (d, J = 9.7, 1H), 6.73 (s, 1H), 4.37 (dd, J = 15.8, 6.7, 1H), 4.23 (dd, J = 15.8, 6.0, 1H), 3.82 (dd, J = 7.5, 6.1, 2H), 2.63-2.54 (m, 1H), 2.28 (s, 3H), 2.10 (dt, J = 13.0, 7.6, 1H). | 4.42 min [377.3] |
| "A173" | (S)-1-Cyclohexyl-3-hydroxy-2-oxo-pyrrolidine-3-carboxylic acid 3-chloro-5-fluorobenzyl amide | 8.55 (t, J = 6.4, 1H), 7.26 (dt, J = 8.8, 2.2, 1H), 7.18 (s, 1H), 7.09 (d, J = 9.7, 1H), 6.42 (s, 1H), 4.35 (dd, J = 15.8, 6.7, 1H), 4.20 (dd, J = 15.8, 6.0, 1H), 3.68 (ddd, J = 11.8, 8.0, 3.8, 1H), 3.32-3.21 (m, 3H), 2.46-2.36 (m, 1H), 1.98-1.83 (m, 1H), 1.80-1.67 (m, 2H), 1.66-1.50 (m, 3H), 1.50-1.21 (m, 4H), 1.19-0.99 (m, 2H). | 4.19 min [369.3] |
| "A174" | (S)-3-Hydroxy-1-(1-methyl-1H-pyrazol-4-yl)-2-oxopyrrolidine-3-carboxylic acid 3-chloro-5-fluoro-benzyl amide | 8.71 (t, J = 6.4, 1H), 8.01 (s, 1H), 7.63 (d, J = 0.6, 1H), 7.27 (dt, J = 8.8, 2.2, 1H), 7.19 (s, 1H), 7.09 (d, J = 9.6, 1H), 6.70 (s, 1H), 4.36 (dd, J = 15.8, 6.7, 1H), 4.23 (dd, J = 15.7, 6.1, 1H), 3.75-3.62 (m, 2H), 2.60 (ddd, J = 12.2, 7.7, 4.3, 1H), 2.18-2.05 (m, 1H). | 3.17 min [367] |
| "A175" | (S)-3-Hydroxy-2-oxo-1-m-tolyl-pyrrolidine-3-carboxylic acid 3-chloro-5-fluorobenzyl amide | 8.72 (t, J = 6.3, 1H), 7.50 (d, J = 6.5, 2H), 7.31-7.24 (m, 2H), 7.20 (s, 1H), 7.10 (d, J = 9.7, 1H), 7.00 (d, J = 7.3, 1H), 6.74 (s, 1H), 4.38 (dd, J = 15.8, 6.7, 1H), 4.23 (dd, J = 15.7, 6.0, 1H), 3.83 (dd, J = 8.0, 5.6, 2H), 2.63-2.53 (m, 1H), 2.11 (dt, J = 13.0, 7.6, 1H). | 4.45 min [377] |

| No. | Structure/name | ¹H NMR (400 MHz, DMSO-d₆) δ [ppm] | LC-MS; rt; [M + H⁺] * |
|---|---|---|---|
| "A176" | (R)-3-Hydroxy-1-(1-methyl-1H-pyrazol-4-yl)-2-oxopyrrolidine-3-carboxylic acid 3-chloro-2-fluoro-benzyl amide | 8.62 (t, J = 6.1, 1H), 8.01 (s, 1H), 7.63 (s, 1H), 7.45 (t, J = 7.4, 1H), 7.30 (t, J = 6.9, 1H), 7.18 (t, J = 7.9, 1H), 6.69 (s, 1H), 4.39 (dd, J = 15.6, 6.8, 1H), 4.31 (dd, J = 15.6, 6.2, 1H), 3.82 (s, 3H), 3.74-3.60 (m, 2H), 2.64-2.57 (m, 1H), 2.13 (dt, J = 13.0, 7.5, 1H). | 3.11 min [367] |
| "A177" | (R)-1-Cyclohexyl-3-hydroxy-2-oxopyrrolidine-3-carboxylic acid 3-chloro-5-fluorobenzyl amide | 8.55 (t, J = 6.3, 1H), 7.26 (dt, J = 8.8, 2.1, 1H), 7.18 (s, 1H), 7.09 (d, J = 9.6, 1H), 6.42 (s, 1H), 4.35 (dd, J = 15.7, 6.7, 1H), 4.20 (dd, J = 15.7, 5.9, 1H), 3.68 (tt, J = 11.8, 3.7, 1H), 3.31-3.21 (m, 2H), 2.45-2.36 (m, 1H), 1.98-1.84 (m, 1H), 1.80-1.68 (m, 2H), 1.66-1.50 (m, 3H), 1.50-1.20 (m, 5H), 1.15-1.01 (m, 1H). | 4.19 min [369] |
| "A178" | (R)-3-Hydroxy-2-oxo-1-m-tolyl-pyrrolidine-3-carboxylic acid 3-chloro-5-fluorobenzyl amide | 8.72 (t, J = 6.4, 1H), 7.50 (d, J = 6.4, 2H), 7.31-7.24 (m, 2H), 7.20 (s, 1H), 7.10 (d, J = 9.7, 1H), 7.00 (d, J = 7.6, 1H), 6.74 (s, 1H), 4.38 (dd, J = 15.8, 6.8, 1H), 4.23 (dd, J = 15.7, 6.0, 1H), 3.83 (t, J = 6.8, 2H), 2.62-2.52 (m, 1H), 2.31 (s, 3H), 2.11 (dt, J = 13.0, 7.6, 1H). | 4.45 min [377] |
| "A179" | (S)-1-(2-Cyanophenyl)-3-hydroxy-2-oxopyrrolidine-3-carboxylic acid 3-chloro-5-fluorobenzyl amide | 8.74 (t, J = 6.5, 1H), 7.92 (dd, J = 8.0, 1.5, 1H), 7.84-7.74 (m, 1H), 7.51 (ddd, J = 6.3, 3.7, 1.1, 2H), 7.27 (dd, J = 8.8, 2.2, 1H), 7.21 (s, 1H), 7.11 (d, J = 8.8, 1H), 6.87 (s, 1H), 4.39 (dd, J = 15.7, 7.0, 1H), 4.26 (dd, J = 15.8, 6.2, 1H), 3.97-3.76 (m, 3H), 2.69-2.56 (m, 2H), 2.28-2.14 (m, 1H). | 3.87 min [388] |

| No. | Structure/name | $^1$H NMR (400 MHz, DMSO-d$_6$) δ [ppm] | LC-MS; rt; [M + H$^+$] * |
|---|---|---|---|
| "A180" | 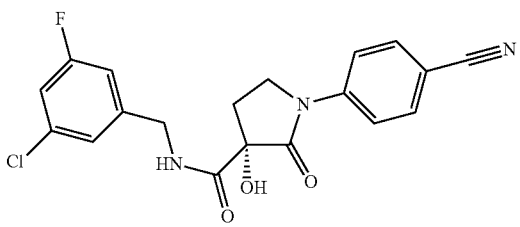<br>(S)-1-(4-Cyanophenyl)-3-hydroxy-2-oxopyrrolidine-3-carboxylic acid 3-chloro-5-fluorobenzyl amide | 8.79 (s, 1H), 7.91 (q, J = 9.1, 4H), 7.27 (d, J = 8.7, 1H), 7.19 (s, 1H), 7.08 (s, 1H), 6.88 (s, 1H), 4.37 (dd, J = 15.6, 6.2, 2H), 4.23 (dd, J = 15.7, 5.8, 2H), 3.90 (dd, J = 11.5, 5.7, 2H), 2.63-2.57 (m, 2H), 2.15 (dt, J = 11.6, 7.4, 2H). | 4.15 min [386.3] |
| "A181" | 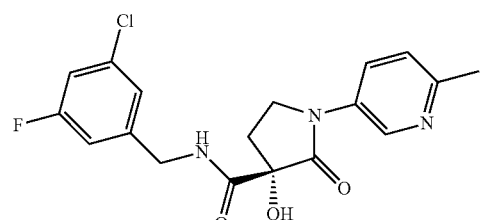<br>(S)-3-Hydroxy-1-(6-methylpyridin-3-yl)-2-oxopyrrolidine-3-carboxylic acid 3-chloro-5-fluorobenzyl amide | 8.76 (q, J = 5.2, 1H), 8.01 (dd, J = 8.5, 2.7, 1H), 7.32-7.24 (m, 1H), 7.20 (s, 1H), 7.09 (d, J = 8.7, 1H), 6.81 (s, 1H), 4.37 (dd, J = 15.8, 6.7, 1H), 4.24 (dd, J = 15.7, 6.0, 1H), 3.86 (dd, J = 8.5, 5.7, 1H), 2.60 (dt, J = 6.8, 5.8, 1H), 2.45 (s, 3H), 2.14 (dt, J = 12.9, 7.4, 1H). | 2.88 min [378] |
| "A182" | 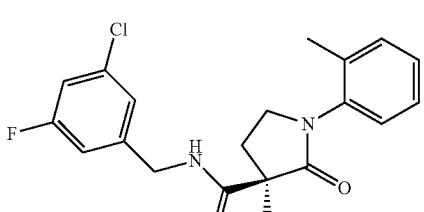<br>(S)-3-Hydroxy-2-oxo-1-o-tolyl-pyrrolidine-3-carboxylic acid 3-chloro-5-fluorobenzyl amide | 8.69 (t, J = 6.4, 1H), 7.32-7.17 (m, 6H), 7.11 (d, J = 9.7, 1H), 6.70 (s, 1H), 4.41 (dd, J = 15.9, 6.7, 1H), 4.24 (dd, J = 15.8, 6.0, 1H), 3.68 (dd, J = 8.3, 5.3, 2H), 2.65-2.57 (m, 1H), 2.19 (dt, J = 13.0, 7.6, 1H), 2.11 (s, 3H). | 4.17 min [377] |
| "A183" | 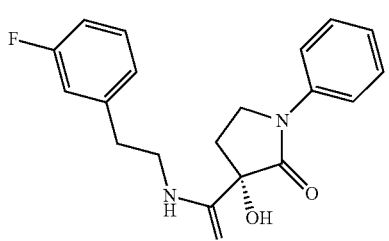<br>(S)-3-Hydroxy-2-oxo-1-phenyl-pyrrolidine-3-carboxylic acid [2-(3-fluorophenyl)ethyl] amide | 8.02 (t, J = 5.9, 1H), 7.69 (dd, J = 8.7, 1.0, 2H), 7.44-7.37 (m, 2H), 7.35-7.28 (m, 1H), 7.17 (t, J = 7.4, 1H), 7.09-6.97 (m, 3H), 6.62 (s, 1H), 3.86-3.79 (m, 2H), 3.42-3.34 (m, 1H), 2.77 (t, J = 7.3, 2H), 2.47-2.37 (m, 2H), 2.05 (dt, J = 12.8, 7.9, 1H). | 3.79 min [343.3] |

| No. | Structure/name | ¹H NMR (400 MHz, DMSO-d₆) δ [ppm] | LC-MS; rt; [M + H⁺] * |
|---|---|---|---|
| "A184" | (S)-3-Hydroxy-2-oxo-1-phenyl-pyrrolidine-3-carboxylic acid [2-(4-fluorophenyl)ethyl] amide | 8.00 (t, J = 5.8, 1H), 7.72-7.66 (m, 2H), 7.43-7.37 (m, 2H), 7.23 (dd, J = 8.6, 5.7, 2H), 7.17 (t, J = 7.4, 1H), 7.08 (t, J = 8.9, 2H), 6.61 (s, 1H), 3.86-3.67 (m, 2H), 3.31-3.13 (m, 2H), 2.73 (t, J = 7.4, 2H), 2.47-2.41 (m, 1H), 2.05 (dt, J = 12.8, 7.9, 1H). | 3.78 min [343] |
| "A185" | (S)-3-Hydroxy-2-oxo-1-phenyl-pyrrolidine-3-carboxylic acid phenethyl amide | 8.00 (t, J = 6.0, 1H), 7.69 (dd, J = 8.7, 1.0, 2H), 7.44-7.37 (m, 2H), 7.33-7.24 (m, 2H), 7.18 (ddd, J = 13.8, 7.8, 1.7, 4H), 6.62 (s, 1H), 3.89-3.77 (m, 2H), 3.40-3.34 (m, 2H), 2.74 (t, J = 7.5, 2H), 2.47-2.40 (m, 1H), 2.06 (dt, J = 12.9, 7.9, 1H). | 3.64 min [325.3] |
| "A186" | (R)-1-(2-Cyanophenyl)-3-hydroxy-2-oxopyrrolidine-3-carboxylic acid 3-chloro-5-fluorobenzyl amide | 8.74 (t, J = 6.3, 1H), 7.92 (dd, J = 8.0, 1.5, 1H), 7.82-7.76 (m, 1H), 7.55-7.48 (m, 2H), 7.27 (d, J = 8.8, 1H), 7.21 (s, 1H), 7.11 (d, J = 9.7, 1H), 6.87 (s, 1H), 4.39 (dd, J = 15.8, 6.8, 1H), 4.26 (dd, J = 15.7, 5.9, 1H), 3.96-3.83 (m, 2H), 2.62 (m, 1H), 2.27-2.17 (m, 1H). | 3.87 min [388] |
| "A187" | (R)-1-(4-Cyanophenyl)-3-hydroxy-2-oxopyrrolidine-3-carboxylic acid 3-chloro-5-fluorobenzyl amide | 8.79 (t, J = 6.5, 1H), 7.91 (q, J = 9.1, 4H), 7.27 (d, J = 8.7, 1H), 7.19 (s, 1H), 7.09 (d, J = 8.8, 1H), 6.89 (s, 1H), 4.37 (dd, J = 15.8, 6.7, 1H), 4.24 (dd, J = 15.9, 6.0, 1H), 3.90 (t, J = 6.5, 2H), 2.64-2.56 (m, 1H), 2.20-2.10 (m, 1H). | 4.14 min [386.3] |

| No. | Structure/name | ¹H NMR (400 MHz, DMSO-d₆) δ [ppm] | LC-MS; rt; [M + H⁺] * |
|---|---|---|---|
| "A188" | (R)-3-Hydroxy-1-(6-methylpyridin-3-yl)-2-oxopyrrolidine-3-carboxylic acid 3-chloro-5-fluorobenzyl amide | 8.76 (q, J = 5.2, 1H), 8.01 (dd, J = 8.5, 2.7, 1H), 7.32-7.24 (m, 1H), 7.20 (s, 0H), 7.09 (d, J = 8.9, 1H), 6.81 (s, 1H), 4.37 (dd, J = 15.8, 6.7, 1H), 4.24 (dd, J = 15.7, 6.1, 1H), 3.86 (dd, J = 8.5, 5.7, 1H), 2.60 (dt, J = 6.8, 5.7, 1H), 2.45 (s, 3H), 2.14 (dt, J = 12.9, 7.4, 1H). | 2.88 min [378] |
| "A189" | (R)-3-Hydroxy-2-oxo-1-p-tolyl-pyrrolidine-3-carboxylic acid 3-chloro-5-fluorobenzyl amide | 8.72 (t, J = 6.3, 1H), 7.57 (d, J = 8.5, 2H), 7.27 (dt, J = 8.8, 2.1, 1H), 7.23-7.18 (m, 3H), 7.10 (d, J = 9.8, 1H), 6.73 (s, 1H), 4.38 (dd, J = 15.8, 6.8, 1H), 4.23 (dd, J = 15.7, 6.1, 1H), 3.86-3.79 (m, 2H), 2.62-2.53 (m, 1H), 2.28 (s, 3H), 2.10 (dt, J = 13.0, 7.6, 1H). | 4.44 min [377] |
| "A190" | (R)-3-Hydroxy-1-(1-methyl-1H-pyrazol-4-yl)-2-oxopyrrolidine-3-carboxylic acid 3-chloro-5-fluoro-benzyl amide | 8.71 (t, J = 6.4, 1H), 8.01 (s, 1H), 7.63 (d, J = 0.5, 1H), 7.31-7.23 (m, 1H), 7.19 (s, 1H), 7.09 (d, J = 9.7, 1H), 6.70 (s, 1H), 4.37 (dd, J = 15.8, 6.6, 1H), 4.23 (dd, J = 15.9, 5.9, 1H), 3.82 (s, 3H), 3.74-3.62 (m, 2H), 2.60 (ddd, J = 12.1, 7.6, 4.2, 1H), 2.13 (ddd, J = 13.1, 8.5, 6.7, 1H). | 3.19 min [367] |
| "A191" | (R)-3-Hydroxy-2-oxo-1-o-tolyl-pyrrolidine-3-carboxylic acid 3-chloro-5-fluorobenzyl amide | 8.69 (t, J = 6.4, 1H), 7.31-7.17 (m, 6H), 7.11 (d, J = 9.7, 1H), 6.70 (s, 1H), 4.41 (dd, J = 15.9, 6.7, 1H), 4.24 (dd, J = 15.8, 6.0, 1H), 3.68 (dd, J = 8.3, 5.3, 2H), 2.66-2.55 (m, 1H), 2.19 (dt, J = 13.0, 7.6, 1H), 2.11 (s, 3H). | 4.17 min [377] |

| No. | Structure/name | ¹H NMR (400 MHz, DMSO-d₆) δ [ppm] | LC-MS; rt; [M + H⁺] * |
|---|---|---|---|
| "A192" | 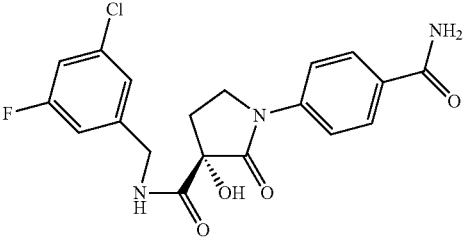<br>(S)-1-(4-Carbamoylphenyl)-3-hydroxy-2-oxopyrrolidine-3-carboxylic acid 3-chloro-5-fluoro-benzyl amide | 8.76 (t, J = 6.4, 1H), 7.95 (br. s, 1H), 7.91 (d, J = 8.8, 2H), 7.79 (d, J = 8.9, 2H), 7.33 (br. s, 1H), 7.27 (d, J = 8.7, 1H), 7.20 (s, 1H), 7.10 (d, J = 9.2, 1H), 6.82 (s, 1H), 4.38 (dd, J = 15.8, 6.9, 1H), 4.24 (dd, J = 15.8, 6.0, 1H), 3.89 (dd, J = 9.3, 5.1, 2H), 3.37 (m, 1H), 2.64-2.55 (m, 2H), 2.19-2.08 (m, 1H). | 3.2 min [406] |
| "A193" | 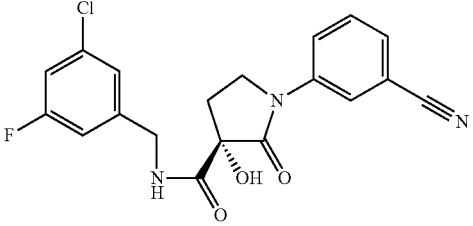<br>(S)-1-(3-Cyanophenyl)-3-hydroxy-2-oxopyrrolidine-3-carboxylic acid 3-chloro-5-fluorobenzyl amide | 8.78 (t, J = 6.3, 1H), 8.16 (s. 1H), 8.08 (dt, J = 7.4, 2.0, 1H), 7.68-7.59 (m, 2H), 7.27 (dd, J = 8.8, 2.0, 1H), 7.19 (s, 1H), 7.09 (d, J = 9.5, 1H), 6.86 (s, 1H), 4.38 (dd, J = 15.6, 6.7, 1H), 4.24 (dd, J = 15.7, 6.0. 1H), 3.96-3.84 (m, 2H), 2.59 (ddd, J = 11.8, 7.1, 4.5, 1H), 2.14 (dt, J = 13.1, 7.9, 1H). | 4.16 min [388.3] |
| "A194" | 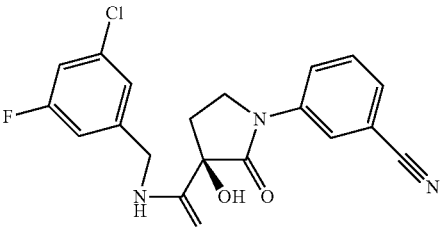<br>(R)-1-(3-Cyanophenyl)-3-hydroxy-2-oxopyrrolidine-3-carboxylic acid 3-chloro-5-fluorobenzyl amide | 8.78 (t, J = 6.4, 1H), 8.16 (d, J = 1.5, 1H), 8.08 (dt, J = 7.5, 2.1, 1H), 7.68-7.59 (m, 2H), 7.27 (dt, J = 8.8, 2.1, 1H), 7.19 (s, 1H), 7.09 (d, J = 9.6, 1H), 6.86 (s, 1H), 4.38 (dd, J = 15.8, 6.7, 1H), 4.24 (dd, J = 15.7, 6.0, 1H), 3.96-3.83 (m, 2H), 2.59 (ddd, J = 11.8, 7.1, 4.6, 1H), 2.14 (dt, J = 13.0, 7.7, 1H). | 4.14 min [388.1] |
| "A195" | 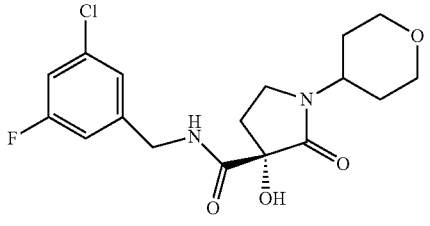<br>(S)-3-Hydroxy-2-oxo-1-(tetrahydro-pyran-4-yl)pyrrolidine-3-carboxylic acid 3-chloro-5-fluorobenzyl amide | 8.58 (t, J = 6.3, 1H), 7.26 (dt, J = 8.7, 2.1, 1H), 7.18 (s, 1H), 7.09 (d, J = 9.7, 1H), 6.47 (s, 1H), 4.35 (dd, J = 15.8, 6.7, 1H), 4.21 (dd, J = 15.8, 6.0, 1H), 4.02-3.83 (m, 3H), 3.38 (dd, J = 11.9, 9.7, 2H), 2.46-2.38 (m, 1H), 1.92 (dt, J = 13.0, 7.4, 1H), 1.69 (m, 2H), 1.57-1.40 (m, 2H). | 3.1 min [371] |

-continued

| No. | Structure/name | ¹H NMR (400 MHz, DMSO-d₆) δ [ppm] | LC-MS; rt; [M + H⁺]* |
|---|---|---|---|
| "A196" | (S)-3-Hydroxy-2-oxo-1-phenyl-pyrrolidine-3-carboxylic acid [2-(2-fluorophenyl)ethyl] amide | 8.08 (t, J = 5.9, 1H), 7.68 (d, J = 7.7, 2H), 7.43-7.36 (m, 2H), 7.25 (dt, J = 7.3, 4.6, 2H), 7.13 (ddd, J = 15.4, 11.1, 4.2, 3H), 6.60 (s, 1H), 3.86-3.76 (m, 2H), 3.45-3.19 (m, 2H), 2.85-2.71 (m, 2H), 2.48-2.39 (m, 1H), 2.05 (dt, J = 12.9, 8.0, 1H). | 3.74 min [343] |
| "A197" | 5-[(S)-3-(3-Chloro-5-fluorobenzyl-carbamoyl)-3-hydroxy-2-oxo-pyrrolidin-1-yl]pyridine-2-carboxylic acid amide | 9.00 (d, J = 2.4, 1H), 8.80 (t, J = 6.3, 1H), 8.28 (dd, J = 8.7, 2.5, 1H), 8.07 (d, J = 8.6, 2H), 7.60 (s, 1H), 7.28 (d, J = 8.8, 1H), 7.20 (s, 1H), 7.10 (d, J = 9.2, 1H), 6.91 (s, 1H), 4.38 (dd, J = 15.8, 6.7, 1H), 4.25 (dd, J = 15.7, 6.0, 1H), 4.03-3.88 (m, 2H), 2.69-2.58 (m, 1H), 2.24-2.12 (m, 1H). | 3.18 min [407] |
| "A198" | (S)-1-(1-Ethyl-1H-pyrazol-4-yl)-3-hydroxy-2-oxopyrrolidine-3-carboxylic acid 3-chloro-2-fluoro-benzyl amide | 8.62 (t, J = 6.3, 1H), 8.04 (s, 1H), 7.65 (d, J = 0.4, 1H), 7.50-7.42 (m, 1H), 7.30 (t, J = 6.5, 1H), 7.18 (t, J = 7.9, 1H), 6.68 (s, 1H), 4.39 (dd, J = 15.6, 6.3, 1H), 4.31 (dd, J = 15.6, 5.9, 1H), 4.11 (q, J = 7.3, 2H), 3.75-3.62 (m, 2H), 2.60 (ddd, J = 12.0, 7.6, 4.2, 1H), 2.18-2.06 (m, 1H), 1.33 (t, J = 7.3, 3H). | 3.36 min [381.3] |
| "A199" | (S)-3-Hydroxy-2-oxo-1-phenyl-pyrrolidine-3-carboxylic acid (1-phenylcyclopropyl) amide | 8.64 (s, 1H), 7.69 (dd, J = 8.7, 1.0, 2H), 7.44-7.36 (m, 2H), 7.26-7.18 (m, 2H), 7.18-7.09 (m, 3H), 6.67 (s, 1H), 3.88-3.76 (m, 2H), 2.61-2.51 (m, 1H), 2.10 (dt, J = 13.0, 7.8, 1H), 1.29-1.18 (m, 4H). | 3.61 min [337] |

| No. | Structure/name | ¹H NMR (400 MHz, DMSO-d₆) δ [ppm] | LC-MS; rt; [M + H⁺] * |
|---|---|---|---|
| "A200" | 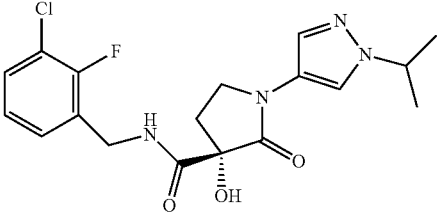<br>(S)-3-Hydroxy-1-(1-isopropyl-1H-pyrazol-4-yl)-2-oxopyrrolidine-3-carboxylic acid 3-chloro-2-fluoro-benzyl amide | 8.63 (t, J = 6.2, 1H), 8.03 (s, 1H), 7.66 (s, 1H), 7.49-7.42 (m, 1H), 7.30 (dd, J = 10.4, 4.1, 1H), 7.19 (dt, J = 8.6, 4.3, 1H), 6.69 (s, 1H), 4.49 (dq, J = 13.3, 6.6, 1H), 4.39 (dd, J = 15.6, 6.4, 1H), 4.31 (dd, J = 15.5, 6.1, 1H), 3.76-3.62 (m, 2H), 2.59 (ddd, J = 12.0, 7.6, 4.2, 1H), 2.12 (ddd, J = 18.7, 11.3, 6.3, 1H), 1.38 (d, J = 6.7, 6H). | 3.61 min [395.3] |
| "A201" | 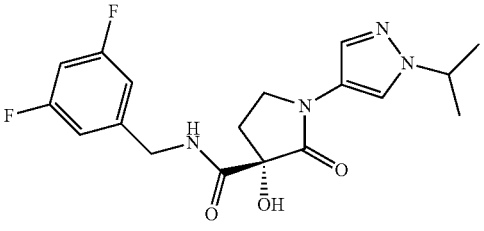<br>(S)-3-Hydroxy-1-(1-isopropyl-1H-pyrazol-4-yl)-2-oxopyrrolidine-3-carboxylic acid 3,5-difluorobenzyl amide | 8.71 (t, J = 6.4, 1H), 8.03 (d, J = 0.5, 1H), 7.66 (d, J = 0.5, 1H), 7.07 (tt, J = 9.4, 2.4, 1H), 7.01-6.93 (m, 2H), 6.69 (s, 1H), 4.55-4.43 (m, 1H), 4.38 (dd, J = 15.9, 6.8, 1H), 4.23 (dd, J = 15.8, 6.0, 1H), 3.76-3.61 (m, 2H), 2.61 (ddd, J = 12.2, 7.6, 4.3, 1H), 2.13 (ddd, J = 13.1, 8.5, 6.8, 1H), 1.38 (d, J = 6.7, 6H). | 3.37 min [379.2] |
| "A202" | 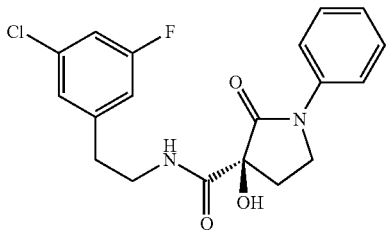<br>(S)-3-Hydroxy-2-oxo-1-phenyl-pyrrolidine-3-carboxylic acid [2-(3-chloro-5-fluorophenyl)ethyl] amide | 8.06 (t, J = 6.0, 1H), 7.68 (dd, J = 8.7, 1.0, 2H), 7.44-7.35 (m, 2H), 7.24 (dt, J = 8.9, 2.2, 1H), 7.20-7.13 (m, 2H), 7.08 (dd, J = 9.7, 1.4, 1H), 6.63 (s, 1H), 3.81 (dd, J = 7.8, 5.8, 2H), 3.45-3.35 (m, 2H), 2.78 (t, J = 6.9, 2H), 2.43 (dt, J = 12.8, 5.6, 1H), 2.05 (dt, J = 12.9, 7.8, 1H). | 4.31 min [377] |
| "A203" | 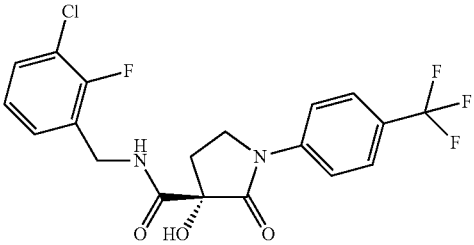<br>(S)-3-Hydroxy-2-oxo-1-(4-trifluoromethylphenyl)pyrrolidine-3-carboxylic acid 3-chloro-2-fluorobenzyl amide | 8.70 (t, J = 6.2, 1H), 7.94 (d, J = 8.6, 2H), 7.77 (d, J = 8.7, 2H), 7.49-7.42 (m, 1H), 7.30 (t, J = 6.5, 1H), 7.18 (dd, J = 8.2, 7.5, 1H), 6.85 (s, 1H), 4.40 (dd, J = 15.6, 6.5, 1H), 4.33 (dd, J = 15.6, 6.0, 1H), 3.91 (dd, J = 8.6, 5.6, 2H), 2.60 (dt, J = 6.7, 5.6. 1H), 2.15 (dt, J= 13.1, 7.8, 1H). | 4.89 min [431] |

| No. | Structure/name | ¹H NMR (400 MHz, DMSO-d₆) δ [ppm] | LC-MS; rt; [M + H⁺] * |
|---|---|---|---|
| "A204" | (S)-3-Hydroxy-2-oxo-1-phenyl-pyrrolidine-3-carboxylic acid ((1S,2R)-2-phenylcyclopropyl) amide | 8.25 (d, J = 5.2, 1H), 7.69 (dd, J = 8.7, 1.0, 2H), 7.44-7.37 (m, 2H), 7.24 (dd, J = 10.3, 4.6, 2H), 7.20-7.06 (m, 4H), 6.62 (s, 1H), 3.87-3.81 (m, 2H), 2.88 (td, J = 8.3, 4.9, 1H), 2.61-2.51 (m, 1H), 2.13-2.00 (m, 2H), 1.40-1.32 (m, 1H), 1.13 (dt, J = 7.9, 5.8, 1H). | 3.85 min [337.3] |
| "A205" | 5-[(R)-3-(3-Chloro-5-fluorobenzyl-carbamoyl)-3-hydroxy-2-oxo-pyrrolidin-1-yl]pyridine-2-carboxylic acid amide | 9.00 (d, J = 2.1, 1H), 8.80 (t, J = 6.3, 1H), 8.28 (dd, J = 8.7, 2.6, 1H), 8.07 (d, J = 8.6, 2H), 7.60 (s, 1H), 7.28 (dt, J = 8.8, 2.1, 1H), 7.20 (s, 1H), 7.10 (d, J = 9.6, 1H), 6.90 (s, 1H), 4.38 (dd, J = 15.8, 6.7, 1H), 4.25 (dd, J = 15.6, 6.0, 1H), 4.01-3.90 (m, 2H), 2.68-2.58 (m, 1H), 2.23-2.13 (m, 1H). | 3.18 min [407] |
| "A206" | (R)-3-Hydroxy-1-(1-isopropyl-1H-pyrazol-4-yl)-2-oxopyrrolidine-3-carboxylic acid 3-chloro-2-fluoro-benzyl amide | 8.63 (t, J = 6.3, 1H), 8.03 (d, J = 0.5, 1H), 7.66 (d, J = 0.5, 1H), 7.49-7.42 (m, 1H), 7.34-7.26 (m, 1H), 7.18 (td, J = 7.9, 0.8, 1H), 6.68 (s, 1H), 4.54-4.43 (m, 1H), 4.39 (dd, J = 15.6, 6.4, 1H), 4.31 (dd, J = 15.6, 6.0, 1H), 3.75-3.62 (m, 2H), 2.60 (ddd, J = 11.9, 7.5, 4.2, 1H), 2.20-2.07 (m, 1H), 1.38 (d, J = 6.7, 6H). | 3.62 min [395.3] |
| "A207" | (R)-3-Hydroxy-1-(1-isopropyl-1H-pyrazol-4-yl)-2-oxopyrrolidine-3-carboxylic acid 3,5-difluorobenzyl amide | 8.71 (t, J = 6.4, 1H), 8.03 (s, 1H), 7.66 (s, 1H), 7.29-6.83 (m, 3H), 6.67 (d, J = 14.3, 1H), 4.55-4.43 (m, 1H), 4.38 (dd, J = 15.8, 6.7, 1H), 4.23 (dd, J = 15.8, 6.0, 1H), 3.77-3.62 (m, 2H), 2.61 (ddd, J = 12.2, 7.6, 4.4, 1H), 2.12 (ddd, J = 19.8, 11.8, 6.7, 1H), 1.38 (d, J = 6.7, 6H). | 3.38 min [379.2] |

| No. | Structure/name | ¹H NMR (400 MHz, DMSO-d₆) δ [ppm] | LC-MS; rt; [M + H⁺] * |
|---|---|---|---|
| "A208" | (R)-3-Hydroxy-2-oxo-1-(tetrahydropyran-4-yl)pyrrolidine-3-carboxylic acid 3-chloro-5-fluoro-benzyl amide | 8.58 (t, J = 6.5, 1H), 7.26 (dt, J = 8.7, 2.1, 1H), 7.18 (s, 1H), 7.09 (d, J = 9.7, 1H), 6.47 (s, 1H), 4.35 (dd, J = 15.9, 6.9, 1H), 4.21 (dd, J = 15.7, 6.0, 1H), 4.00-3.84 (m, 3H), 3.44-3.34 (m, 3H), 2.47-2.38 (m, 1H), 1.96-1.87 (m, 1H), 1.78-1.61 (m, 2H), 1.53-1.41 (m, 2H). | 3.1 min [371] |
| "A209" | (R)-1-(1-Ethyl-1H-pyrazol-4-yl)-3-hydroxy-2-oxopyrrolidine-3-carboxylic acid 3-chloro-2-fluoro-benzyl amide | 8.62 (t, J = 6.3, 1H), 8.04 (s, 1H), 7.65 (d, J = 0.4, 1H), 7.50-7.41 (m, 1H), 7.30 (t, J = 6.5, 1H), 7.18 (t, J = 7.9, 1H), 6.68 (s, 1H), 4.39 (dd, J = 15.6, 6.3, 1H), 4.31 (dd, J = 15.6, 5.9, 1H), 4.11 (q, J = 7.3, 2H), 3.76-3.62 (m, 2H), 2.60 (ddd, J = 12.0, 7.6, 4.2, 1H), 2.20-2.06 (m, 1H), 1.33 (t, J = 7.3, 3H). | 3.35 min [381] |
| "A210" | 1-(1-Acetyl-2,3-dihydro-1H-indol-5-yl)-3-hydroxy-2-oxopyrrolidine-3-carboxylic acid 3-chloro-5-fluorobenzyl amide | 8.71 (t, J = 6.4, 1H), 8.01 (d, J = 8.8, 1H), 7.62 (s, 1H), 7.39 (d, J = 8.7, 1H), 7.30-7.24 (m, 1H), 7.20 (s, 1H), 7.10 (d, J = 10.0, 1H), 6.72 (s, 1H), 4.38 (dd, J = 15.8, 6.7, 1H), 4.23 (dd, J = 15.8, 6.0, 1H), 4.09 (t, J = 8.6, 2H), 3.81 (t, J = 6.9, 2H), 3.15 (t, J = 8.4, 2H), 2.63-2.52 (m, 1H), 2.14 (s, 3H), 2.09 (dd, J = 13.8, 6.2, 1H). | 3.66 min [446] |
| "A211" | (S)-1-(1-Ethyl-1H-pyrazol-4-yl)-3-hydroxy-2-oxopyrrolidine-3-carboxylic acid 3,5-difluorobenzyl amide | 8.70 (t, J = 6.2, 1H), 8.04 (s, 1H), 7.65 (s, 1H), 7.06 (t, J = 9.4, 1H), 6.97 (d, J = 6.5, 2H), 6.69 (s, 1H), 4.38 (dd, J = 15.8, 6.8, 1H), 4.23 (dd, J = 15.8, 5.9, 1H), 4.11 (q, J = 7.2, 2H), 3.77-3.60 (m, 2H), 2.61 (ddd, J = 12.3, 7.6, 4.4, 1H), 2.21-2.07 (m, 1H), 1.33 (t, J = 7.3, 3H). | 3.06 min [365] |

| No. | Structure/name | ¹H NMR (400 MHz, DMSO-d₆) δ [ppm] | LC-MS; rt; [M + H⁺] * |
|---|---|---|---|
| "A212" | 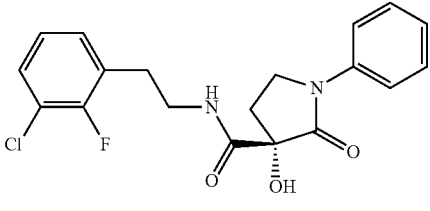<br>(S)-3-Hydroxy-2-oxo-1-phenyl-pyrrolidine-3-carboxylic acid [2-(3-chloro-2-fluorophenyl)ethyl] amide | 8.12 (t, J = 6.0, 1H), 7.68 (dd, J = 8.7, 1.0, 2H), 7.45-7.36 (m, 3H), 7.28-7.22 (m, 1H), 7.15 (dt, J = 16.5, 7.6, 2H), 6.60 (s, 1H), 3.80 (dd, J = 7.9, 5.7, 2H), 3.39 (td, J = 13.8, 7.2, 1H), 3.31-3.20 (m, 1H), 2.82 (dd, J = 10.6, 6.7, 2H), 2.47-2.37 (m, 1H), 2.04 (dt, J = 12.9, 7.9, 1H). | 4.18 min [3773.] |
| "A213" | 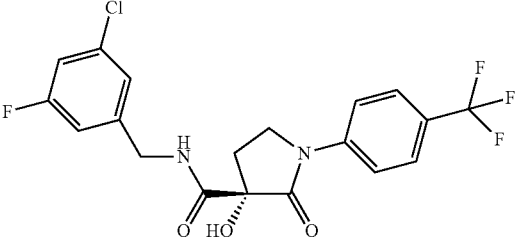<br>(S)-3-Hydroxy-2-oxo-1-(4-trifluoromethylphenyl)pyrrolidine-3-carboxylic acid 3-chloro-5-fluorobenzyl amide | 8.78 (t, J = 6.3, 1H), 7.94 (d, J = 8.6, 2H), 7.78 (d, J = 8.7, 2H), 7.27 (dt, J = 8.8, 2.2, 1H), 7.20 (s, 1H), 7.09 (d, J = 8.9, 1H), 6.86 (s, 1H), 4.38 (dd, J = 15.8, 6.7, 1H), 4.24 (dd, J = 15.8, 6.1, 1H), 3.97-3.86 (m, 2H), 2.64-2.55 (m, 1H), 2.15 (dt, J = 13.1, 7.7, 1H). | $$ 6.299 min [429.0] |
| "A214" | 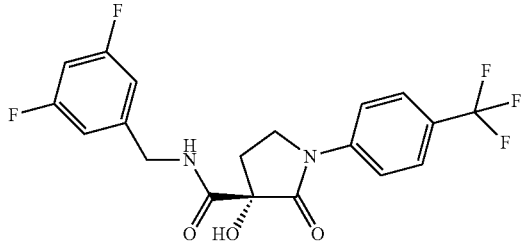<br>(S)-3-Hydroxy-2-oxo-1-(4-trifluoromethylphenyl)pyrrolidine-3-carboxylic acid 3,5-difluoro-benzyl amide | 8.77 (t, J = 6.4, 1H), 7.94 (d, J = 8.6, 2H), 7.78 (d, J = 8.8, 2H), 7.12-7.02 (m, 1H), 6.98 (d, J = 6.6, 2H), 6.86 (s, 1H), 4.39 (dd, J = 15.7, 6.8, 1H), 4.25 (dd, J = 15.9, 6.1, 1H), 3.92 (dd, J = 8.7, 5.7, 2H), 2.61 (dt, J = 6.7, 5.7, 1H), 2.16 (dt, J = 13.0, 7.6, 1H). | $$ 6.055 min [413.0] |
| "A215" | 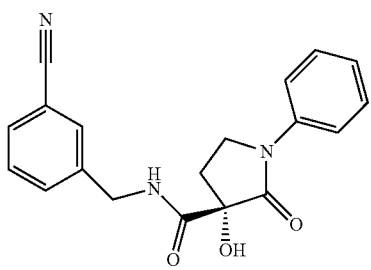<br>(S)-3-Hydroxy-2-oxo-1-phenyl-pyrrolidine-3-carboxylic acid 3-cyanobenzyl amide | 8.73 (t, J = 6.4, 1H), 7.75-7.66 (m, 4H), 7.61 (d, J = 7.9, 1H), 7.56-7.48 (m, 1H), 7.45-7.36 (m, 2H), 7.18 (t, J = 7.4, 1H), 6.76 (s, 1H), 4.41 (dd, J = 15.5, 6.7, 1H), 4.29 (dd, J = 15.6, 6.1, 1H), 3.85 (dd, J = 7.6, 6.0, 2H), 2.64-2.54 (m, 1H), 2.12 (dt, J = 13.0, 7.7, 1H). | 3.352 min [336.2] |

| No. | Structure/name | ¹H NMR (400 MHz, DMSO-d₆) δ [ppm] | LC-MS; rt; [M + H⁺] * |
|---|---|---|---|
| "A216" | (R)-3-Hydroxy-2-oxo-1-(4-trifluoromethylphenyl)pyrrolidine-3-carboxylic acid 3-chloro-2-fluorobenzyl amide | 8.70 (t, J = 6.2, 1H), 7.94 (d, J = 8.6, 2H), 7.77 (d, J = 8.8, 2H), 7.51-7.42 (m, 1H), 7.30 (t, J = 6.5, 1H), 7.18 (t, J = 7.9, 1H), 6.85 (s, 1H), 4.40 (dd, J = 15.6, 6.3, 1H), 4.33 (dd, J = 15.5, 6.1, 1H), 3.91 (dd, J = 8.6, 5.6, 2H), 2.60 (dt, J = 6.6, 5.7, 1H), 2.15 (dt, J = 13.0, 7.8, 1H). | 4.879 min [431.0] |
| "A217" | (R)-3-Hydroxy-2-oxo-1-(4-trifluoromethylphenyl)pyrrolidine-3-carboxylic acid 3-chloro-5-fluorobenzyl amide | 8.78 (t, J = 6.3, 1H), 7.94 (d, J = 8.6, 2H), 7.78 (d, J = 8.7, 2H), 7.27 (dt, J = 8.8, 2.1, 1H), 7.20 (s, 1H), 7.09 (d, J = 9.6, 1H), 6.86 (s, 1H), 4.38 (dd, J = 15.7, 6.7, 1H), 4.24 (dd, J = 15.8, 6.1, 1H), 3.97-3.84 (m, 2H), 2.65-2.56 (m, 1H), 2.15 (dt, J = 13.1, 7.7, 1H). | $$ 6.301 min [429.0] |
| "A218" | (R)-3-Hydroxy-2-oxo-1-(4-trifluoromethylphenyl)pyrrolidine-3-carboxylic acid 3,5-difluoro-benzyl amide | 8.77 (t, J = 6.4, 1H), 7.94 (d, J = 8.7, 2H), 7.78 (d, J = 8.8, 2H), 7.11-7.03 (m, 1H), 6.98 (d, J = 6.6, 2H), 6.86 (s, 1H), 4.39 (dd, J = 15.8, 6.7, 1H), 4.24 (dd, J = 15.8, 6.0, 1H), 3.91 (dd, J = 8.7, 5.7, 2H), 2.61 (dt, J = 6.8, 5.8, 1H), 2.16 (dt, J = 13.0, 7.6, 1H). | 4.69 min [415] |
| "A219" | (S)-1-(4-Fluorophenyl)-3-hydroxy-2-oxopyrrolidine-3-carboxylic acid [2-(3,5-difluorophenyl)ethyl] amide | 8.05 (t, J = 6.0, 1H), 7.75-7.68 (m, 2H), 7.28-7.20 (m, 2H), 7.03 (tt, J = 9.5, 2.3, 1H), 6.98-6.92 (m, 2H), 6.63 (s, 1H), 3.80 (dd, J = 7.8, 5.7, 2H), 3.42-3.25 (m, 2H), 2.78 (t, J = 7.0, 2H), 2.44 (dt, J = 12.8, 5.6, 1H), 2.04 (dt, J = 12.9, 7.8, 1H). | 4.22 min [379.3] |

-continued

| No. | Structure/name | ¹H NMR (400 MHz, DMSO-d₆) δ [ppm] | LC-MS; rt; [M + H⁺] * |
|---|---|---|---|
| "A220" | (R)-3-Hydroxy-2-oxo-1-(3-trifluoromethylphenyl)pyrrolidine-3-carboxylic acid [2-(3-chloro-5-fluorophenyl)ethyl] amide | 8.21 (s, 1H), 8.11 (t, J = 6.0, 1H), 7.87 (d, J = 8.1, 1H), 7.65 (t, J = 8.0, 1H), 7.54 (d, J = 7.8, 1H), 7.23 (dt, J = 8.9, 2.2, 1H), 7.15 (s, 1H), 7.07 (d, J = 9.5, 1H), 6.70 (s, 1H), 3.94-3.82 (m, 2H), 3.43-3.34 (m, 2H), 3.30 (s, 1H), 2.78 (t, J = 6.9, 2H), 2.47-2.41 (m, 1H), 2.08 (dt, J = 13.2, 8.5, 1H). | 5.09 min [445] |
| "A221" | (R)-3-Hydroxy-2-oxo-1-(4-trifluoromethylphenyl)pyrrolidine-3-carboxylic acid [2-(3-chloro-5-fluorophenyl)ethyl] amide | 8.10 (t, J = 6.0, 1H), 7.93 (d, J = 8.6, 2H), 7.77 (d, J = 8.8, 2H), 7.24 (dt, J = 8.9, 2.1, 1H), 7.15 (s, 1H), 7.07 (d, J = 9.0, 1H), 6.72 (s, 1H), 3.93-3.81 (m, 2H), 3.43-3.33 (m, 2H), 2.78 (t, J = 6.9, 2H), 2.48-2.41 (m, 1H), 2.08 (dt, J = 12.8, 8.0, 1H). | HPLC: 5.066 Min 99.06% purity |
| "A222" | (R)-1-(3-Fluorophenyl)-3-hydroxy-2-oxopyrrolidine-3-carboxylic acid [2-(3-chloro-5-fluorophenyl)ethyl] amide | 8.08 (t, J = 6.0, 1H), 7.69 (dt, J = 12.0, 2.2, 1H), 7.51-7.39 (m, 2H), 7.23 (dt, J = 8.9, 2.2, 1H), 7.15 (d, J = 1.5, 1H), 7.10-7.05 (m, 1H), 7.04-6.98 (m, 1H), 6.68 (s, 1H), 3.87-3.76 (m, 2H), 3.45-3.34 (m, 1H), 2.78 (t, J = 6.9, 2H), 2.43 (ddd, J = 12.8, 7.2, 4.1, 1H), 2.05 (dt, J = 12.9, 7.9, 1H). | 4.58 min [395] |
| "A223" | (S)-1-(4-Fluorophenyl)-3-hydroxy-2-oxopyrrolidine-3-carboxylic acid [2-(3-chloro-5-fluorophenyl)ethyl] amide | 8.06 (t, J = 6.0, 1H), 7.75-7.68 (m, 2H), 7.28-7.21 (m, 3H), 7.16 (s, 1H), 7.08 (dd, J = 9.7, 1.4, 1H), 6.63 (s, 1H), 3.80 (dd, J = 7.6, 6.0, 2H), 3.44-3.34 (m, 1H), 2.78 (t, J = 7.0, 2H), 2.43 (dt, J = 12.7, 5.5, 1H), 2.04 (dt, J = 12.9, 7.8, 1H). | 4.4 min [395] |

| No. | Structure/name | ¹H NMR (400 MHz, DMSO-$d_6$) δ [ppm] | LC-MS; rt; [M + H]⁺ * |
|---|---|---|---|
| "A224" | (S)-1-(3-Carbamoylphenyl)-3-hydroxy-2-oxopyrrolidine-3-carboxylic acid [2-(3-chloro-5-fluorophenyl)ethyl] amide | 8.08 (t, J = 6.0, 1H), 8.05-7.99 (m, 2H), 7.94 (dd, J = 8.2, 1.4, 1H), 7.67 (d, J = 7.8, 1H), 7.47 (t, J = 8.0, 1H), 7.42 (s, 1H), 7.24 (dt, J = 8.9, 2.1, 1H), 7.16 (s, 1H), 7.08 (dd, J = 9.7, 1.4, 1H), 6.66 (s, 1H), 3.89-3.83 (m, 2H), 3.42-3.34 (m, 1H), 2.78 (t, J = 7.0, 2H), 2.44 (dd, J = 12.3, 6.0, 1H), 2.07 (dt, J = 12.9, 7.8, 1H). | 3.44 min [420] |
| "A225" | (R)-3-Hydroxy-2-oxo-1-(3-trifluoromethylphenyl)pyrrolidine-3-carboxylic acid 3-chloro-5-fluorobenzyl amide | 8.80 (t, J = 6.4, 1H), 8.21 (s, 1H), 7.89 (d, J = 8.3, 1H), 7.66 (t, J = 8.0, 1H), 7.54 (d, J = 7.8, 1H), 7.27 (dt, J = 8.7, 2.1, 1H), 7.20 (s, 1H), 7.09 (d, J = 9.6, 1H), 6.89 (s, 1H), 4.38 (dd, J = 15.8, 6.7, 1H), 4.24 (dd, J = 15.8, 6.0, 1H), 4.00-3.84 (m, 2H), 2.60 (ddd, J = 11.8, 7.2, 4.4, 1H), 2.15 (dt, J = 13.1, 7.7, 1H). | 4.89 min [431] |
| "A226" | (R)-1-(3-Fluorophenyl)-3-hydroxy-2-oxopyrrolidine-3-carboxylic acid 3-chloro-5-fluorobenzyl amide | 8.75 (t, J = 6.5, 1H), 7.69 (dt, J = 11.9, 2.2, 1H), 7.46 (dt, J = 15.0, 8.6, 2H), 7.27 (dd, J = 8.8, 2.1, 1H), 7.20 (s, 1H), 7.09 (d, J = 8.8, 1H), 7.03 (t, J = 7.9, 1H), 6.82 (s, 1H), 4.37 (dd, J = 15.4, 6.6, 1H), 4.24 (dd, J = 15.8, 5.7, 1H), 3.92-3.79 (m, 2H), 2.58 (dt, J = 6.8, 5.7, 1H), 2.13 (dt, J = 13.1, 7.7, 1H). | 4.39 min [381] |
| "A227" | (S)-3-Hydroxy-2-oxo-1-phenyl-pyrrolidine-3-carboxylic acid [2-(3,5-difluorophenyl)ethyl] amide | 8.05 (t, J = 6.0, 1H), 7.68 (dt, J = 9.0, 1.7, 2H), 7.43-7.36 (m, 2H), 7.21-7.13 (m, 1H), 7.03 (tt, J = 9.5, 2.3, 1H), 6.99-6.92 (m, 2H), 6.63 (s, 1H), 3.82 (dd, J = 7.7, 5.9, 2H), 3.41-3.34 (m, 2H), 2.78 (t, J = 7.0, 2H), 2.44 (dt, J = 12.8, 5.5, 1H), 2.05 (dt, J = 12.9, 7.8, 1H). | 3.97 min [361.3] |
| "A228" | (S)-1-(4-Fluorophenyl)-3-hydroxy-2-oxopyrrolidine-3-carboxylic acid 2-chloro-3,6-difluorobenzyl amide | 8.22 (t, J = 5.5, 1H), 7.70 (ddd, J = 10.7, 5.4, 3.0, 2H), 7.43 (td, J = 9.0, 4.7, 1H), 7.33-7.20 (m, 3H), 6.65 (s, 1H), 4.50 (dd, J = 15.0, 5.1, 1H), 4.43 (dd, J = 14.5, 4.5, 1H), 3.89-3.76 (m, 2H), 2.52 (m, 1H), 2.07 (dt, J = 12.9, 8.4, 1H). | 4.01 min [399] |

| No. | Structure/name | $^1$H NMR (400 MHz, DMSO-$d_6$) δ [ppm] | LC-MS; rt; [M + H$^+$]* |
|---|---|---|---|
| "A229" | (S)-1-(1-Carbamoylmethyl-1H-pyrazol-4-yl)-3-hydroxy-2-oxo-pyrrolidine-3-carboxylic acid 3-chloro-2-fluorobenzyl amide | 8.62 (t, J = 6.2, 1H), 8.04 (s, 1H), 7.66 (s, 1H), 7.51-7.43 (m, 2H), 7.31 (t, J = 6.5, 1H), 7.23 (s, 1H), 7.18 (t, J = 7.9, 1H), 6.70 (s, 1H), 4.74 (s, 2H), 4.40 (dd, J = 15.7, 6.2, 1H), 4.36-4.29 (m, 1H), 3.77-3.64 (m, 2H), 3.49-3.39 (m, 1H), 3.16 (d, J = 5.2, 1H), 2.61 (ddd, J = 12.1, 7.5, 4.3, 1H), 2.20-2.09 (m, 1H). | HPLC 2.866 min 96.09% purity |
| "A230" | Tert-Butyl 4-[(R)-3-(3,5-difluoro-benzylcarbamoyl)-3-hydroxy-2-oxopyrrolidin-1-yl]piperidine-1-carboxylate | | 4.17 min [354.3] |
| "A231" | (R)-1-(3-Carbamoylphenyl)-3-hydroxy-2-oxopyrrolidine-3-carboxylic acid 3-chloro-5-fluoro-benzyl amide | 8.75 (t, J = 6.4, 1H), 8.07-8.00 (m, 2H), 7.99-7.92 (m, 1H), 7.67 (d, J = 7.9, 1H), 7.48 (t, J = 8.0, 1H), 7.42 (s, 1H), 7.27 (dt, J = 8.8, 2.2, 1H), 7.20 (s, 1H), 7.10 (d, J = 9.7, 1H), 6.80 (s, 1H), 4.38 (dd, J = 15.8, 6.7, 1H), 4.25 (dd, J = 15.7, 6.0, 1H), 3.94-3.84 (m, 2H), 2.65-2.54 (m, 1H), 2.14 (dt, J = 13.0, 7.6, 1H). | 3.32 min [406] |
| "A232" | (S)-3-Hydroxy-2-oxo-1-(3-trifluoromethylphenyl)pyrrolidine-3-carboxylic acid [2-(3-chloro-5-fluorophenyl)ethyl] amide | 11.12 (s, 1H), 8.69 (d, J = 6.7, 1H), 7.70 (s, 1H), 7.41-7.38 (m, 2H), 7.38-7.35 (m, 1H), 7.27 (d, J = 8.8, 1H), 7.22 (s, 1H), 7.12 (d, J = 9.5, 1H), 6.69 (s, 1H), 6.42 (s, 1H), 4.40 (dd, J = 15.8, 7.1, 2H), 4.25 (dd, J = 15.8, 5.8, 2H), 3.91-3.84 (m, 2H), 2.64-2.55 (m, 2H), 2.14 (t, J = 6.6, 1H), 2.12-2.08 (m, 1H). | 5.09 min [445] |

-continued

| No. | Structure/name | ¹H NMR (400 MHz, DMSO-d₆) δ [ppm] | LC-MS; rt; [M + H⁺] * |
|---|---|---|---|
| "A233" | (S)-3-Hydroxy-2-oxo-1-(4-trifluoromethylphenyl)pyrrolidine-3-carboxylic acid [2-(3-chloro-5-fluorophenyl)ethyl] amide | 8.11 (t, J = 6.0, 1H), 7.93 (d, J = 8.6, 2H), 7.77 (d, J = 8.7, 2H), 7.24 (dt, J = 8.9, 2.1, 1H), 7.15 (s, 1H), 7.08 (dd, J = 9.3, 1.8, 1H), 6.75 (s, 1H), 3.94-3.81 (m, 2H), 3.44-3.34 (m, 2H), 2.78 (t, J = 6.9, 2H), 2.47-2.41 (m, 1H), 2.08 (dt, J = 12.8, 7.9, 1H). | HPLC 5.068 min 99.04% purity |
| "A234" | (S)-1-(3-Fluorophenyl)-3-hydroxy-2-oxopyrrolidine-3-carboxylic acid [2-(3-chloro-5-fluorophenyl)ethyl] amide | 8.08 (t, J = 6.0, 1H), 7.69 (dt, J = 12.0, 2.2, 1H), 7.46 (tdd, J = 16.3, 11.0, 5.1, 2H), 7.23 (dt, J = 8.9, 2.1, 1H), 7.15 (s, 1H), 7.08 (dd, J = 9.3, 1.8, 1H), 7.05-6.98 (m, 1H), 6.68 (s, 1H), 3.89-3.70 (m, 2H), 3.44-3.33 (m, 2H), 2.78 (t, J = 6.9, 2H), 2.46-2.38 (m, 1H), 2.05 (dt, J = 13.0, 8.0, 1H). | 4.59 min [395] |
| "A235" | (S)-3-Hydroxy-2-oxo-1-(3-trifluoromethylphenyl)pyrrolidine-3-carboxylic acid 3-chloro-5-fluorobenzyl amide | 8.80 (t, J = 6.1, 1H), 8.21 (s, 1H), 7.89 (d, J = 8.2, 1H), 7.66 (t, J = 8.0, 1H), 7.55 (d, J = 7.7, 1H), 7.27 (d, J = 8.7, 1H), 7.20 (s, 1H), 7.09 (d, J = 9.6, 1H), 6.90 (s, 1H), 4.38 (dd, J = 15.7, 6.7, 1H), 4.24 (dd, J = 15.8, 5.8, 1H), 3.98-3.86 (m, 2H), 2.64-2.55 (m, 1H), 2.22-2.07 (m, 1H). | 4.89 min [431] |
| "A236" | Tert-Butyl 4-[(S)-3-(3,5-difluoro-benzylcarbamoyl)-3-hydroxy-2-oxopyrrolidin-1-yl]piperidine-1-carboxylate | 8.57 (d, J = 6.6, 1H), 7.07 (d, J = 9.2, 1H), 6.97 (d, J = 6.6, 2H), 6.47 (s, 1H), 4.36 (dd, J = 15.9, 6.7, 2H), 4.21 (dd, J = 16.0, 6.0, 1H), 4.00 (dd, J = 17.8, 12.9, 3H), 3.94-3.84 (m, 2H), 1.97-1.86 (m, 2H), 1.59-1.48 (m, 4H), 1.39 (s, 9H), 1.23 (s, 1H), 1.14 (t, J = 7.5, 2H). | 4.17 min [354.3] |

| No. | Structure/name | $^1$H NMR (400 MHz, DMSO-d$_6$) δ [ppm] | LC-MS; rt; [M + H$^+$] * |
|---|---|---|---|
| "A237" | (S)-1-(3-Carbamoylphenyl)-3-hydroxy-2-oxopyrrolidine-3-carboxylic acid 3-chloro-5-fluoro-benzyl amide | 8.75 (t, J = 6.4, 1H), 8.07-8.00 (m, 2H), 7.99-7.93 (m, 1H), 7.67 (d, J = 7.9, 1H), 7.48 (t, J = 8.0, 1H), 7.42 (s, 1H), 7.27 (dt, J = 8.8, 2.2, 1H), 7.20 (s, 1H), 7.10 (d, J = 9.7, 1H), 6.80 (s, 1H), 4.38 (dd, J = 15.8, 6.7, 1H), 4.25 (dd, J = 15.7, 6.0, 1H), 3.94-3.86 (m, 2H), 2.64-2.56 (m, 1H), 2.14 (dt, J = 13.0, 7.6, 1H). | 3.25 min [406] |
| "A238" | (S)-1-(3-Fluorophenyl)-3-hydroxy-2-oxopyrrolidine-3-carboxylic acid 3-chloro-5-fluorobenzyl amide | 8.77 (t, J = 6.3, 1H), 7.70 (dt, J = 11.9, 2.2, 1H), 7.55-7.42 (m, 2H), 7.29 (dt, J = 8.8, 2.1, 1H), 7.21 (s, 1H), 7.11 (d, J = 9.6, 1H), 7.04 (td, J = 8.1, 1.6, 1H), 6.83 (s, 1H), 4.39 (dd, J = 15.7, 6.7, 1H), 4.25 (dd, J = 15.7, 6.0, 1H), 3.93-3.83 (m, 2H), 2.64-2.55 (m, 1H), 2.14 (dt, J = 13.1, 7.7, 1H). | 4.4 min [381] |
| "A239" | (S)-3-Hydroxy-1-(6-methylpyridin-3-yl)-2-oxopyrrolidine-3-carboxylic acid [2-(3-chloro-5-fluorophenyl)-ethyl] amide | 8.75 (d, J = 2.6, 1H), 8.08 (t, J = 5.9, 1H), 8.00 (dd, J = 8.5, 2.7, 1H), 7.29 (d, J = 8.5, 1H), 7.23 (dt, J = 8.9, 2.2, 1H), 7.15 (s, 1H), 7.08 (dd, J = 9.3, 1.8, 1H), 6.67 (s, 1H), 3.88-3.77 (m, 2H), 3.42-3.33 (m, 2H), 2.78 (t, J = 7.0, 2H), 2.44 (s, 3H), 2.07 (dt, J = 12.9, 7.8, 1H). | 3.09 min [392.3] |
| "A240" | (S)-3-Hydroxy-1-(1-isopropyl-1H-pyrazol-4-yl)-2-oxopyrrolidine-3-carboxylic acid [2-(3-chloro-5-fluorophenyl)ethyl] amide | 8.06-7.97 (m, 2H), 7.65 (s, 1H), 7.24 (dt, J = 8.9, 2.1, 1H), 7.15 (s, 1H), 7.07 (d, J = 9.2, 1H), 6.54 (d, J = 8.0, 1H), 4.48 (dt, J = 13.3, 6.7, 1H), 3.71-3.59 (m, 2H), 3.42-3.33 (m, 2H), 2.77 (t, J = 7.0, 2H), 2.44 (dd, J = 7.8, 3.9, 1H), 2.12-1.99 (m, 1H), 1.38 (d, J = 6.7, 6H). | 3.94 min [409.3] |

| No. | Structure/name | ¹H NMR (400 MHz, DMSO-d₆) δ [ppm] | LC-MS; rt; [M + H⁺] * |
|---|---|---|---|
| "A241" | 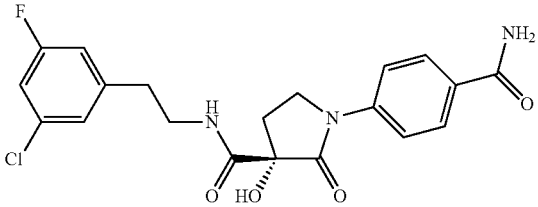<br>(S)-1-(4-Carbamoylphenyl)-3-hydroxy-2-oxopyrrolidine-3-carboxylic acid [2-(3-chloro-5-fluorophenyl)ethyl] amide | 8.09 (t, J = 6.0, 1H), 7.95 (s, 1H), 7.91 (d, J = 8.9, 2H), 7.77 (d, J = 8.9, 2H), 7.33 (s, 1H), 7.24 (dt, J = 8.8, 2.1, 1H), 7.16 (s, 1H), 7.08 (d, J = 9.0, 1H), 6.68 (s, 1H), 3.90-3.80 (m, 2H), 3.44-3.34 (m, 2H), 2.78 (t, J = 6.9, 2H), 2.47-2.38 (m, 1H), 2.06 (dt, J = 12.8, 7.9, 1H). | 3.42 min [420] |
| "A242" | 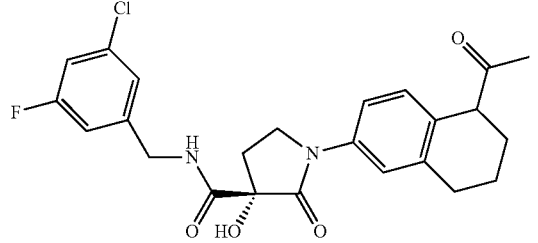<br>(S)-1-(1-Acetyl-1,2,3,4-tetrahydro-quinolin-6-yl)-3-hydroxy-2-oxo-pyrrolidine-3-carboxylic acid 3-chloro-5-fluorobenzyl amide | 8.72 (t, J = 6.3, 1H), 7.49 (s, 1H), 7.27 (dd, J = 8.8, 2.2, 1H), 7.20 (s, 1H), 7.09 (d, J = 9.2, 1H), 6.75 (s, 1H), 4.38 (dd, J = 15.7, 6.7, 1H), 4.23 (dd, J = 15.7, 5.8, 1H), 3.83 (t, J = 6.8, 1H), 3.65 (t, J = 6.3, 2H), 2.70 (t, J = 6.6, 1H), 2.56 (dd, J = 12.7, 6.0, 1H), 2.19-2.05 (m, 3H), 1.91-1.81 (m, 2H). | 3.89 min [460.3] |
| "A243" | 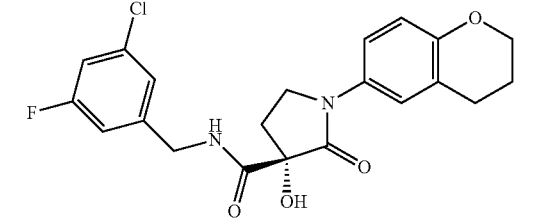<br>(S)-1-Chroman-6-yl-3-hydroxy-2-oxopyrrolidine-3-carboxylic acid 3-chloro-5-fluorobenzyl amide | 8.69 (t, J = 6.4, 1H), 7.36 (dd, J = 8.8, 2.7, 1H), 7.31 (d, J = 2.6, 1H), 7.27 (dt, J = 8.8, 2.1, 1H), 7.20 (s, 1H), 7.09 (d, J = 9.0, 1H), 6.74 (d, J = 8.8, 1H), 6.68 (s, 1H), 4.37 (dd, J = 15.8, 6.7, 1H), 4.23 (dd, J = 15.8, 6.0, 1H), 4.14-4.08 (m, 2H), 3.81-3.74 (m, 2H), 2.73 (t, J = 6.4, 2H), 2.60-2.51 (m, 1H), 2.08 (dt, J = 13.0, 7.6, 1H), 1.95-1.86 (m, 2H). | 4.41 min [419.3] |

| No. | Structure/name | $^1$H NMR (400 MHz, DMSO-$d_6$) δ [ppm] | LC-MS; rt; [M + H$^+$] * |
|---|---|---|---|
| "A244" | 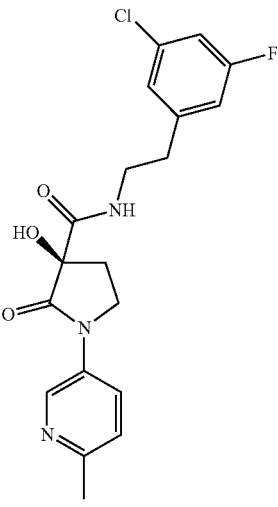<br>(R)-3-Hydroxy-1-(6-methylpyridin-3-yl)-2-oxopyrrolidine-3-carboxylic acid [2-(3-chloro-5-fluorophenyl)-ethyl] amide | 8.75 (d, J = 2.6, 1H), 8.08 (t, J = 5.9, 1H), 8.00 (dd, J = 8.5, 2.7, 1H), 7.29 (d, J = 8.5, 1H), 7.23 (dt, J = 8.9, 2.1, 1H), 7.15 (s, 1H), 7.08 (dd, J = 9.7, 1.4, 1H), 6.67 (s, 1H), 3.88-3.77 (m, 2H), 3.44-3.35 (m, 1H), 2.78 (t, J = 6.9, 2H), 2.44 (s, 3H), 2.43 (m, 1H), 2.07 (dt, J = 12.9, 7.8, 1H). | 3.09 min [392.3] |
| "A245" | 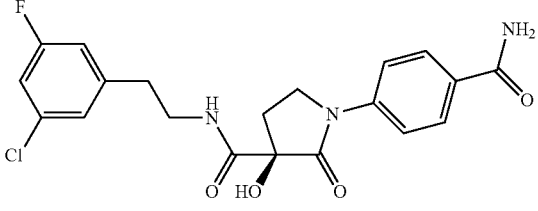<br>(R)-1-(4-Carbamoylphenyl)-3-hydroxy-2-oxopyrrolidine-3-carboxylic acid [2-(3-chloro-5-fluorophenyl)ethyl] amide | 8.09 (t, J = 6.0, 1H), 7.95 (s, 1H), 7.91 (d, J = 8.9, 2H), 7.77 (d, J = 8.9, 2H), 7.33 (s, 1H), 7.24 (dt, J = 8.8, 2.1, 1H), 7.16 (s, 1H), 7.08 (d, J = 9.0, 1H), 6.68 (s, 1H), 3.91-3.79 (m, 2H), 3.43-3.35 (m, 2H), 2.78 (t, J = 6.9, 2H), 2.47-2.38 (m, 1H), 2.06 (dt, J = 12.8, 7.9, 1H). | 3.42 min [420] |
| "A246" | 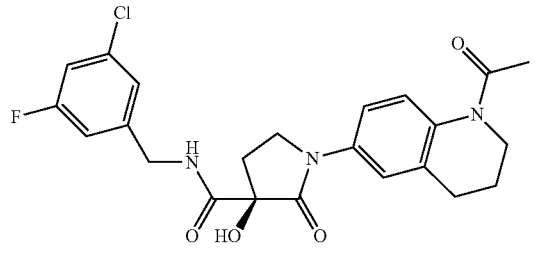<br>(R)-1-(1-Acetyl-1,2,3,4-tetrahydroquinolin-6-yl)-3-hydroxy-2-oxopyrrolidine-3-carboxylic acid 3-chloro-5-fluorobenzyl amide | 8.72 (t, J = 6.2, 1H), 7.49 (s, 2H), 7.30-7.24 (m, 1H), 7.20 (s, 1H), 7.09 (d, J = 9.4, 1H), 6.75 (s, 1H), 4.38 (dd, J = 15.9, 6.7, 1H), 4.23 (dd, J = 15.7, 6.3, 1H), 3.83 (t, J = 6.7, 2H), 3.65 (t, J = 6.4, 2H), 2.70 (t, J = 6.5, 2H), 2.56 (dd, J = 12.7, 5.9, 1H), 2.14 (s, 3H), 2.10 (dd, J = 12.9, 7.8, 2H), 1.90-1.81 (m, 2H). | 3.89 min [460.3] |

| No. | Structure/name | $^1$H NMR (400 MHz, DMSO-$d_6$) δ [ppm] | LC-MS; rt; [M + H$^+$] * |
|---|---|---|---|
| "A247" | 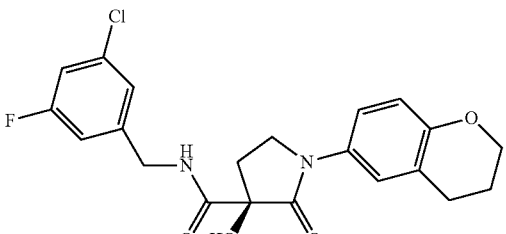<br>(R)-1-Chroman-6-yl-3-hydroxy-2-oxopyrrolidine-3-carboxylic acid 3-chloro-5-fluorobenzyl amide | 8.69 (t, J = 6.4, 1H), 7.36 (dd, J = 8.8, 2.7, 1H), 7.31 (d, J = 2.6, 1H), 7.27 (dt, J = 8.8, 2.1, 1H), 7.20 (s, 1H), 7.09 (d, J = 9.6, 1H), 6.74 (d, J = 8.8, 1H), 6.68 (s, 1H), 4.37 (dd, J = 16.0, 6.9, 1H), 4.23 (dd, J = 15.8, 6.0, 1H), 4.14-4.07 (m, 2H), 3.81-3.74 (m, 2H), 2.73 (t, J = 6.4, 2H), 2.60-2.51 (m, 1H), 2.08 (dt, J = 13.0, 7.6, 1H), 1.95-1.86 (m, 2H). | 4.41 min [419.3] |
| "A248" | 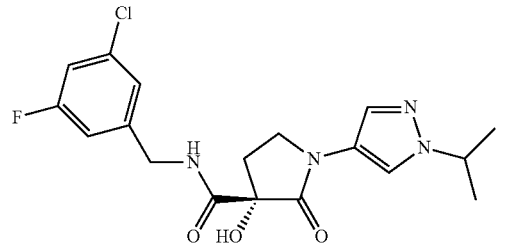<br>(S)-3-Hydroxy-1-(1-isopropyl-1H-pyrazol-4-yl)-2-oxopyrrolidine-3-carboxylic acid 3-chloro-5-fluoro-benzyl amide | 8.70 (t, J = 6.4, 1H), 8.03 (s, 1H), 7.66 (s, 1H), 7.27 (dt, J = 8.8, 2.1, 1H), 7.19 (s, 1H), 7.09 (d, J = 9.6, 1H), 6.69 (s, 1H), 4.48 (dt, J = 13.3, 6.7, 1H), 4.36 (dd, J = 15.7, 6.7, 1H), 4.23 (dd, J = 15.7, 6.0, 1H), 3.74-3.63 (m, 2H), 2.60 (ddd, J = 12.1, 7.6, 4.2, 1H), 2.17-2.09 (m, 1H), 1.38 (d, J = 6.7, 6H). | 3.78 min [395] |
| "A249" | 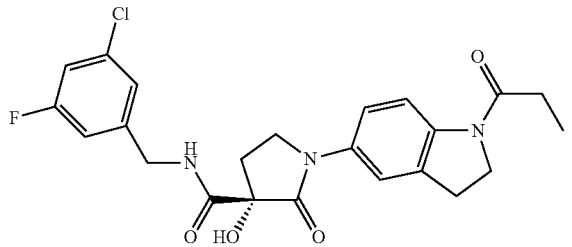<br>(S)-3-Hydroxy-2-oxo-1-(1-propionyl-2,3-dihydro-1H-indol-5-yl)pyrrolidine-3-carboxylic acid 3-chloro-5-fluorobenzyl amide | 8.71 (t, J = 6.4, 1H), 8.05 (d, J = 8.7, 1H), 7.62 (s, 1H), 7.40 (d, J = 8.4, 1H), 7.27 (dd, J = 8.7, 2.2, 1H), 7.20 (s, 1H), 7.10 (d, J = 8.8, 1H), 6.72 (s, 1H), 4.38 (dd, J = 15.5, 6.7, 1H), 4.23 (dd, J = 15.8, 5.9, 1H), 4.08 (t, J = 8.5, 2H), 3.84-3.79 (m, 2H), 3.15 (t, J = 8.5, 2H), 2.61-2.52 (m, 2H), 2.46-2.41 (m, 2H), 2.10 (dt, J = 13.0, 7.4, 1H), 1.07-1.02 (m, 3H). | 4.07 min [460] |
| "A250" | 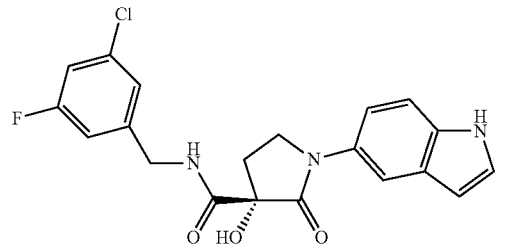<br>(S)-3-Hydroxy-1-(1H-indol-5-yl)-2-oxopyrrolidine-3-carboxylic acid 3-chloro-5-fluorobenzyl amide | 11.12 (s, 1H), 8.69 (d, J = 6.7, 1H), 7.70 (s, 1H), 7.44-7.34 (m, 3H), 7.27 (d, J = 8.8, 1H), 7.22 (s, 1H), 7.12 (d, J = 9.5, 1H), 6.69 (s, 1H), 6.42 (s, 1H), 4.40 (dd, J = 15.8, 7.1, 1H), 4.25 (dd, J = 15.8, 5.8, 1H), 3.90-3.84 (m, 2H), 2.64-2.55 (m, 2H), 2.12 (dt, J = 12.9, 7.6, 1H). | 3.94 min [402] |

-continued

| No. | Structure/name | ¹H NMR (400 MHz, DMSO-d₆) δ [ppm] | LC-MS; rt; [M + H⁺]* |
|---|---|---|---|
| "A251" | 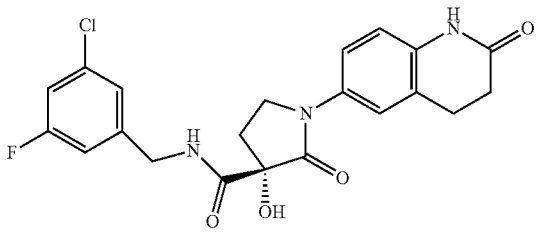<br>(S)-3-Hydroxy-2-oxo-1-(2-oxo-1,2,3,4-tetrahydroquinolin-6-yl)-pyrrolidine-3-carboxylic acid 3-chloro-5-fluorobenzyl amide | 12.06 (s, 1H), 10.10 (s, 1H), 8.70 (t, J = 6.3, 1H), 7.65 (s, 1H), 7.47 (s, 1H), 7.43 (dd, J = 8.6, 2.4, 1H), 7.27 (dt, J = 8.7, 2.1, 1H), 7.20 (s, 1H), 7.09 (d, J = 8.9, 1H), 7.03 (s, 2H), 6.85 (d, J = 8.6, 1H), 6.72 (s, 1H), 4.37 (dd, J = 15.7, 6.8, 1H), 4.23 (dd, J = 15.7, 6.1, 1H), 3.79 (t, J = 6.8, 1H), 2.87 (t, J = 7.6, 1H), 2.61-2.52 (m, 1H), 2.43 (dd, J = 8.3, 6.7, 2H), 2.09 (dt, J = 12.9, 7.6, 1H). | 3.38 min [432] |
| "A252" | 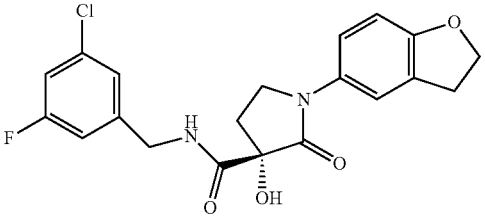<br>(S)-1-(2,3-Dihydrobenzofuran-5-yl)-3-hydroxy-2-oxopyrrolidine-3-carboxylic acid 3-chloro-5-fluoro-benzyl amide | 8.69 (t, J = 6.3, 1H), 7.53 (s, 1H), 7.32 (dd, J = 8.6, 2.2, 1H), 7.27 (d, J = 8.7, 1H), 7.20 (s, 1H), 7.10 (d, J = 9.2, 1H), 6.77 (d, J = 8.6, 1H), 6.69 (s, 1H), 4.52 (t, J = 8.7, 2H), 4.38 (dd, J = 15.7, 6.7, 1H), 4.23 (dd, J = 15.7, 6.1, 1H), 3.82-3.76 (m, 2H), 3.18 (t, J = 8.7, 2H), 2.62-2.52 (m, 1H), 2.09 (dt, J = 12.9, 7.6, 1H). | 4.06 min [405] |
| "A253" | 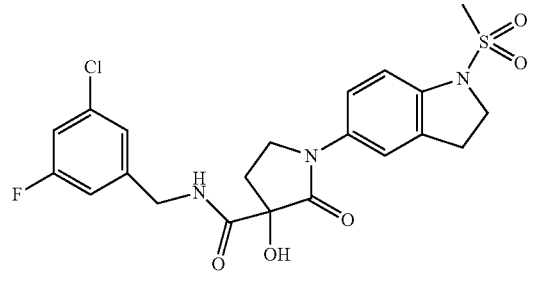<br>3-Hydroxy-1-(1-methanesulfonyl-2,3-dihydro-1H-indol-5-yl)-2-oxo-pyrrolidine-3-carboxylic acid 3-chloro-5-fluorobenzyl amide | 8.71 (t, J = 6.3, 1H), 7.64 (d, J = 2.0, 1H), 7.46 (dd, J = 8.6, 2.1, 1H), 7.29-7.23 (m, 2H), 7.20 (s, 1H), 7.09 (d, J = 9.6, 1H), 6.74 (s, 1H), 4.38 (dd, J =15.7, 6.6, 1H), 4.23 (dd, J = 15.8, 6.0, 1H), 3.94 (t, J = 8.5, 2H), 3.85-3.78 (m, 2H), 3.13 (t, J = 8.4, 2H), 2.96 (s, 2H), 2.61-2.53 (m, 1H), 2.11 (dt, J = 13.0, 7.7, 1H). | 3.99 min [482] |
| "A254" | 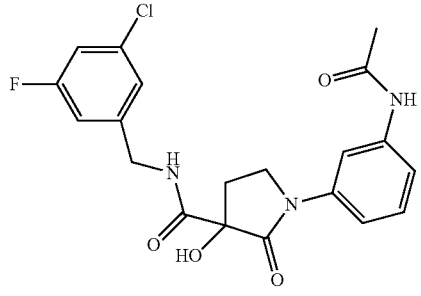<br>1-(3-Acetylaminophenyl)-3-hydroxy-2-oxopyrrolidine-3-carboxylic acid 3-chloro-5-fluoro-benzyl amide | 10.02 (s, 1H), 8.73 (s, 1H), 7.93 (s, 1H), 7.48-7.43 (m, 1H), 7.34-7.24 (m, 3H), 7.20 (s, 1H), 7.09 (d, J = 9.7, 1H), 6.78 (s, 1H), 4.38 (dd, J = 15.7, 6.2, 1H), 4.24 (dd, J = 15.7, 5.3, 1H), 3.81 (dd, J = 8.3, 5.6, 2H), 2.62-2.53 (m, 1H), 2.12 (m, 1H), 2.03 (s, 3H). | 3.53 min [420] |

| No. | Structure/name | ¹H NMR (400 MHz, DMSO-d$_6$) δ [ppm] | LC-MS; rt; [M + H⁺] * |
|---|---|---|---|
| "A255" | 3-Hydroxy-1-[4-(5-methyl-1,3,4-oxadiazol-2-yl)-phenyl]-2-oxo-pyrrolidine-3-carboxylic acid 3-chloro-5-fluorobenzyl amide | 8.78 (t, J = 6.4, 1H), 8.03-7.98 (m, 2H), 7.97-7.92 (m, 2H), 7.27 (dt, J = 8.8, 2.1, 1H), 7.20 (s, 1H), 7.10 (d, J = 9.6, 1H), 6.86 (s, 1H), 4.38 (dd, J = 15.7, 6.7, 1H), 4.24 (dd, J = 15.7, 6.0, 1H), 3.97-3.87 (m, 2H), 2.65-2.58 (m, 1H), 2.16 (m, 1H). | 3.76 min [445] |
| "A256" | (R)-3-Hydroxy-1-(1-isopropyl-1H-pyrazol-4-yl)-2-oxopyrrolidine-3-carboxylic acid 3-chloro-5-fluoro-benzyl amide | | 3.71 min [395] |
| "A257" | (R)-3-Hydroxy-2-oxo-1-(1-propionyl-2,3-dihydro-1H-indol-5-yl)pyrrolidine-3-carboxylic acid 3-chloro-5-fluorobenzyl amide | 8.71 (t, J = 6.4, 1H), 8.05 (d, J = 8.6, 1H), 7.62 (s, 1H), 7.40 (d, J = 8.5, 1H), 7.27 (dt, J = 8.9, 2.2, 1H), 7.20 (s, 1H), 7.10 (d, J = 9.5, 1H), 6.72 (s, 1H), 4.38 (dd, J = 15.7, 6.7, 1H), 4.23 (dd, J = 15.6, 6.0, 1H), 4.08 (t, J = 8.6, 2H), 3.84-3.79 (m, 2H), 3.15 (t, J = 8.5, 2H), 2.61-2.52 (m, 2H), 2.45 (d, J = 7.4, 2H), 2.15-2.06 (m, 1H), 1.07-1.02 (m, 3H). | 4.00 min [460] |
| "A258" | (R)-3-Hydroxy-1-(1H-indol-5-yl)-2-oxopyrrolidine-3-carboxylic acid 3-chloro-5-fluorobenzyl amide | 11.12 (s, 1H), 8.70 (t, J = 6.4, 1H), 7.70 (s, 1H), 7.45-7.34 (m, 3H), 7.27 (d, J = 8.6, 1H), 7.22 (s, 1H), 7.12 (d, J = 9.6, 1H), 6.69 (s, 1H), 6.42 (s, 1H), 4.40 (dd, J = 15.4, 6.6, 1H), 4.30-4.23 (m, 1H), 3.87 (t, J = 6.7, 2H), 2.63-2.56 (m, 1H), 2.12 (dt, J = 12.9, 7.6, 1H). | 3.94 min [402] |

| No. | Structure/name | ¹H NMR (400 MHz, DMSO-d$_6$) δ [ppm] | LC-MS; rt; [M + H⁺] * |
|---|---|---|---|
| "A259" | 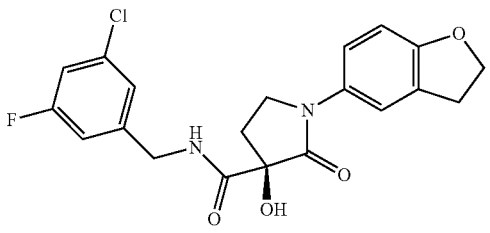<br>(R)-1-(2,3-Dihydrobenzofuran-5-yl)-3-hydroxy-2-oxopyrrolidine-3-carboxylic acid 3-chloro-5-fluoro-benzyl amide | 8.69 (t, J = 6.4, 1H), 7.55-7.52 (m, 1H), 7.32 (dd, J = 8.6, 2.4, 1H), 7.27 (dt, J = 8.8, 2.2, 1H), 7.20 (s, 1H), 7.10 (d, J = 9.7, 1H), 6.77 (d, J = 8.6, 1H), 6.69 (s, 1H), 4.52 (t, J = 8.7, 2H), 4.38 (dd, J = 15.7, 6.7, 1H), 4.23 (dd, J = 15.8, 6.0, 1H), 3.78 (dd, J = 7.5, 6.1, 2H), 3.18 (t, J = 8.7, 2H), 2.60-2.52 (m, 1H), 2.09 (dt, J = 12.9, 7.6, 1H). | 4.05 min [405] |
| "A260" | 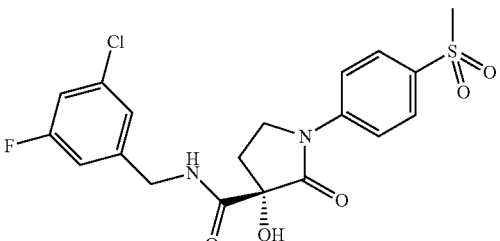<br>(S)-3-Hydroxy-1-(4-methane-sulfonylphenyl)-2-oxopyrrolidine-3-carboxylic acid 3-chloro-5-fluorobenzyl amide | 8.78 (t, J = 6.3, 1H), 8.00-7.93 (m, 3H), 7.27 (dt, J = 8.8, 2.1, 1H), 7.20 (s, 1H), 7.09 (d, J = 9.8, 1H), 6.88 (s, 1H), 4.38 (dd, J = 15.4, 6.6, 1H), 4.24 (dd, J = 15.8, 5.9, 1H), 3.92 (t, J = 6.1, 2H), 2.60 (dt, J = 7.1, 5.8, 1H), 2.21-2.12 (m, 1H). | 4.98 min [439] |
| "A261" | 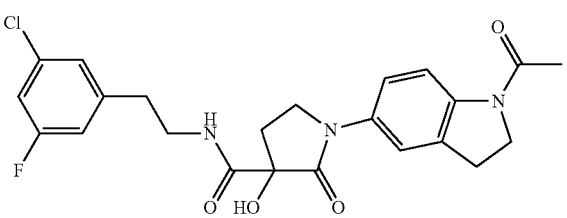<br>1-(1-Acetyl-2,3-dihydro-1H-indol-5-yl)-3-hydroxy-2-oxopyrrolidine-3-carboxylic acid [2-(3-chloro-5-fluorophenyl)ethyl] amide | 8.05 (t, J = 6.0, 1H), 8.00 (d, J = 8.8, 1H), 7.61 (s, 1H), 7.42-7.34 (m, 1H), 7.24 (dt, J = 8.8, 2.1, 1H), 7.16 (s, 1H), 7.08 (d, J = 9.1, 1H), 4.09 (t, J = 8.6, 2H), 3.81-3.74 (m, 2H), 3.43-3.23 (m, 4H), 3.15 (t, J = 8.5, 2H), 2.77 (t, J = 7.0, 2H), 2.46-2.37 (m, 1H), 2.14 (s, 3H), 2.03 (dt, J = 12.7, 7.8, 1H). | 3.83 min [460.3] |
| "A262" | 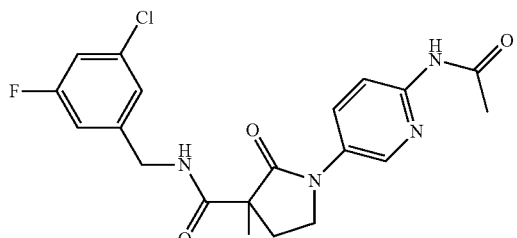<br>1-(6-Acetylaminopyridin-3-yl)-3-hydroxy-2-oxopyrrolidine-3-carboxylic acid 3-chloro-5-fluoro-benzyl amide | 10.54 (s, 1H), 8.76 (t, J = 6.4, 1H), 8.66-8.63 (m, 1H), 8.13-8.05 (m, 2H), 7.27 (dt, J = 8.8, 2.1, 1H), 7.20 (s, 1H), 7.10 (d, J = 9.6, 1H), 6.80 (s, 1H), 4.38 (dd, J = 15.7, 6.8, 1H), 4.24 (dd, J = 15.8, 6.1, 1H), 3.92-3.81 (m, 2H), 2.60 (ddd, J = 12.0, 7.1, 4.8, 1H), 2.14 (dt, J = 13.0, 7.6, 1H), 2.07 (s, 3H). | 3.03 min [421] |

| No. | Structure/name | ¹H NMR (400 MHz, DMSO-d₆) δ [ppm] | LC-MS; rt; [M + H⁺] * |
|---|---|---|---|
| "A263" | (R)-3-Hydroxy-1-(4-methane-sulfonylphenyl)-2-oxopyrrolidine-3-carboxylic acid 3-chloro-5-fluorobenzyl amide | 8.78 (t, J = 6.4, 1H), 8.00-7.92 (m, 3H), 7.27 (dt, J = 8.8, 2.1, 1H), 7.20 (s, 1H), 7.09 (d, J = 8.8, 1H), 6.88 (s, 1H), 4.38 (dd, J = 16.1, 6.7, 1H), 4.24 (dd, J = 15.8, 6.0, 1H), 3.92 (t, J = 6.1, 2H), 3.19 (s, 3H), 2.65-2.57 (m, 1H), 2.16 (dt, J = 13.1, 7.7, 1H). | 5.01 min [439] |
| "A264" | (R)-3-Hydroxy-1-(1-methane-sulfonyl-2,3-dihydro-1H-indol-5-yl)-2-oxopyrrolidine-3-carboxylic acid 3-chloro-5-fluorobenzyl amide | 8.70 (t, J = 6.3, 1H), 7.64 (d, J = 2.0, 1H), 7.46 (dd, J = 8.6, 2.1, 1H), 7.29-7.23 (m, 2H), 7.20 (s, 1H), 7.09 (d, J = 9.6, 1H), 6.74 (s, 1H), 4.38 (dd, J = 15.8, 6.6, 1H), 4.23 (dd, J = 15.8, 6.0, 1H), 3.94 (t, J = 8.5, 2H), 3.85-3.78 (m, 2H), 3.13 (t, J = 8.4, 2H), 2.96 (s, 2H), 2.61-2.53 (m, 1H), 2.11 (dt, J = 13.0, 7.7, 1H). | $$$ 10.55 min 100% purity |
| "A265" | (S)-3-Hydroxy-1-(1-methane-sulfonyl-2,3-dihydro-1H-indol-5-yl)-2-oxopyrrolidine-3-carboxylic acid 3-chloro-5-fluorobenzyl amide | 8.72 (t, J = 6.3, 1H), 7.64 (d, J = 2.0, 1H), 7.46 (dd, J = 8.6, 2.1, 1H), 7.29-7.23 (m, 2H), 7.21 (s, 1H), 7.09 (d, J = 9.6, 1H), 6.74 (s, 1H), 4.38 (dd, J = 15.7, 6.6, 1H), 4.23 (dd, J = 15.7, 6.0, 1H), 3.94 (t, J = 8.5, 2H), 3.85-3.78 (m, 2H), 3.13 (t, J = 8.4, 2H), 2.96 (s, 2H), 2.61-2.53 (m, 1H), 2.11 (dt, J = 13.0, 7.7, 1H). | $$$ 6.50 min 100% purity |
| "A266" | (R)-3-Hydroxy-1-[4-(5-methyl-1,3,4-oxadiazol-2-yl)-phenyl]-2-oxopyrrolidine-3-carboxylic acid 3-chloro-5-fluorobenzyl amide | 8.78 (t, J = 6.4, 1H), 8.04-7.98 (m, 2H), 7.97-7.91 (m, 2H), 7.27 (dt, J = 8.8, 2.1, 1H), 7.20 (s, 1H), 7.10 (d, J = 9.6, 1H), 6.86 (s, 1H), 4.38 (dd, J = 15.7, 6.7, 1H), 4.24 (dd, J = 15.7, 6.0, 1H), 3.97-3.87 (m, 2H), 2.65-2.58 (m, 1H), 2.17-2.15 (m, 1H). | $$$ 14.31 min 100% purity |

| No. | Structure/name | ¹H NMR (400 MHz, DMSO-d$_6$) δ [ppm] | LC-MS; rt; [M + H⁺] * |
|---|---|---|---|
| "A267" | (S)-3-Hydroxy-1-(1-methane-sulfonyl-2,3-dihydro-1H-indol-5-yl)-2-oxopyrrolidine-3-carboxylic acid 3-chloro-5-fluorobenzyl amide | 8.79 (t, J = 6.4, 1H), 8.00 (m, 2H), 7.97-7.92 (m, 2H), 7.27 (dt, J = 8.8, 2.1, 1H), 7.20 (s, 1H), 7.10 (d, J = 9.6, 1H), 6.86 (s, 1H), 4.38 (dd, J = 15.7, 6.7, 1H), 4.24 (dd, J = 15.7, 6.0, 1H), 3.97-3.87 (m, 2H), 2.65-2.58 (m, 1H), 2.16 (m, 1H). | $$$ 5.54 min 89% purity |
| "A268" | (S)-3-Hydroxy-1-(3-methane-sulfonylphenyl)-2-oxopyrrolidine-3-carboxylic acid 3-chloro-5-fluorobenzyl amide | 8.79 (t, J = 6.4, 1H), 8.32 (s, 1H), 7.99 (d, J = 7.7, 1H), 7.71 (dt, J = 15.6, 7.8, 2H), 7.27 (d, J = 8.9, 1H), 7.20 (s, 1H), 7.10 (d, J = 9.6, 1H), 6.87 (s, 1H), 4.37 (dd, J = 16.1, 6.7, 1H), 4.25 (dd, J = 15.7, 6.1, 1H), 3.93 (t, J = 6.9, 2H), 3.23 (s, 3H), 2.64-2.57 (m, 2H), 2.45-2.38 (m, 1H), 2.16 (dt, J = 13.3, 7.9, 1H). | 4.99 min [441] |
| "A269" | (S)-3-Hydroxy-1-(6-methylpyridin-3-yl)-2-oxopyrrolidine-3-carboxylic acid 3,5-difluorobenzyl amide | 8.74 (dd, J = 7.5, 4.6, 2H), 8.01 (dd, J = 8.5, 2.7, 1H), 7.30 (d, J = 8.5, 1H), 7.07 (tt, J = 9.4, 2.4, 1H), 6.99 (t, J = 6.4, 2H), 6.81 (s, 1H), 4.38 (dd, J = 15.8, 6.8, 1H), 4.25 (dd, J = 15.9, 6.1, 1H), 3.87 (t, J = 6.8, 2H), 2.64-2.55 (m, 1H), 2.45 (s, 3H), 2.14 (dt, J = 13.0, 7.5, 1H). | 2.49 min [362] |
| "A270" | (S)-1-(4-Acetylaminophenyl)-3-hydroxy-2-oxopyrrolidine-3-carboxylic acid 3-chloro-5-fluoro-benzyl amide | 9.96 (s, 1H), 8.71 (t, J = 6.5, 1H), 7.66-7.55 (m, 4H), 7.27 (d, J = 8.5, 1H), 7.20 (s, 1H), 7.09 (d, J = 9.2, 1H), 6.73 (s, 1H), 4.38 (dd, J = 15.4, 6.6, 1H), 4.23 (dd, J = 15.7, 5.9, 1H), 3.81 (t, J = 6.8, 2H), 2.62-2.53 (m, 2H), 2.16-2.05 (m, 2H), 2.02 (s, 3H). | 3.37 min [420] |

| No. | Structure/name | $^1$H NMR (400 MHz, DMSO-$d_6$) δ [ppm] | LC-MS; rt; [M + H$^+$]* |
|---|---|---|---|
| "A271" | (S)-3-Hydroxy-1-(3-methane-sulfonylaminophenyl)-2-oxo-pyrrolidine-3-carboxylic acid 3-chloro-5-fluorobenzyl amide | 9.84 (s, 1H), 8.73 (t, J = 6.4, 1H), 7.67 (s, 1H), 7.35 (dd, J = 3.9, 2.1, 2H), 7.27 (dt, J = 8.8, 2.2, 1H), 7.20 (s, 1H), 7.09 (d, J = 8.9, 1H), 7.05-7.00 (m, 1H), 6.79 (s, 1H), 4.37 (dd, J = 15.7, 6.7, 1H), 4.24 (dd, J = 15.7, 6.0, 1H), 3.87-3.77 (m, 2H), 2.99 (s, 3H), 2.63-2.53 (m, 1H), 2.12 (dt, J = 13.0, 7.8, 1H). | 3.72 min [456] |
| "A272" | 3-Hydroxy-1-[3-(5-methyl-1,3,4-oxadiazol-2-yl)-phenyl]-2-oxo-pyrrolidine-3-carboxylic acid 3-chloro-5-fluorobenzyl amide | 8.79 (t, J = 6.4, 1H), 8.44 (t, J = 1.8, 1H), 7.84-7.76 (m, 2H), 7.63 (t, J = 8.0, 1H), 7.27 (dt, J = 8.7, 2.1, 1H), 7.21 (s, 1H), 7.10 (d, J = 9.5, 1H), 6.86 (s, 1H), 4.38 (dd, J = 15.8, 6.7, 1H), 4.25 (dd, J = 15.7, 6.0, 1H), 3.99-3.84 (m, 2H), 2.65-2.60 (m, 1H), 2.59 (s, 3H), 2.22-2.10 (m, 1H). | 3.80 min [445] |
| "A273" | (R)-3-Hydroxy-1-(6-methylpyridin-3-yl)-2-oxopyrrolidine-3-carboxylic acid 3,5-difluorobenzyl amide | 8.74 (dd, J = 7.6, 4.7, 2H), 8.01 (dd, J = 8.5, 2.7, 1H), 7.30 (d, J = 8.5, 1H), 7.07 (tt, J = 9.3, 2.3, 1H), 6.99 (t, J = 6.4, 2H), 6.81 (s, 1H), 4.38 (dd, J = 15.9, 6.7, 1H), 4.25 (dd, J = 15.8, 6.0, 1H), 3.87 (t, J = 6.8, 2H), 2.65-2.56 (m, 1H), 2.45 (s, 3H), 2.14 (dt, J = 13.1, 7.5, 1H). | 2.48 min [362] |
| "A274" | (S)-1-(1-Acetyl-1H-indol-5-yl)-3-hydroxy-2-oxopyrrolidine-3-carboxylic acid 3-chloro-5-fluoro-benzyl amide | 8.73 (t, J = 6.4, 1H), 8.31 (d, J = 9.0, 1H), 7.92 (d, J = 2.1, 1H), 7.88 (d, J = 3.8, 1H), 7.65 (dd, J = 9.0, 2.2, 1H), 7.27 (dt, J = 8.8, 2.1, 1H), 7.21 (s, 1H), 7.11 (d, J = 9.6, 1H), 6.76 (d, J = 4.0, 2H), 4.39 (dd, J = 15.7, 6.7, 1H), 4.25 (dd, J = 15.7, 6.1, 1H), 3.91 (t, J = 6.8, 2H), 2.64 (s, 3H), 2.62-2.55 (m, 1H), 2.14 (dt, J = 12.9, 7.5, 1H). | 4.10 min [444] |

| No. | Structure/name | $^1$H NMR (400 MHz, DMSO-d$_6$) δ [ppm] | LC-MS; rt; [M + H$^+$]* |
|---|---|---|---|
| "A275" | 3-Hydroxy-2-oxo-1-(1-propionyl-1H-indol-5-yl)pyrrolidine-3-carboxylic acid 3-chloro-5-fluoro-benzyl amide | 8.72 (t, J = 6.4, 1H), 8.34 (d, J = 9.0, 1H), 7.94-7.90 (m, 2H), 7.66 (dd, J = 9.0, 2.2, 1H), 7.27 (dt, J = 8.8, 2.1, 1H), 7.21 (s, 1H), 7.11 (d, J = 9.7, 1H), 6.76 (d, J = 4.3, 2H), 4.39 (dd, J = 15.7, 6.7, 1H), 4.25 (dd, J = 15.7, 6.0, 1H), 3.91 (t, J = 6.8, 2H), 3.06 (q, J = 7.3, 2H), 2.61 (dt, J = 11.9, 5.7, 1H), 2.14 (dt, J = 13.0, 7.6, 1H), 1.17 (t, J = 7.3, 3H). | 4.42 min [458] |
| "A276" | 3-Hydroxy-1-(1-methanesulfonyl-1H-indol-5-yl)-2-oxopyrrolidine-3-carboxylic acid 3-chloro-5-fluoro-benzyl amide | 8.72 (t, J = 6.4, 1H), 7.94 (d, J = 2.0, 1H), 7.84 (d, J = 9.0, 1H), 7.71 (dd, J = 9.1, 2.1, 1H), 7.59 (d, J = 3.6, 1H), 7.30-7.25 (m, 1H), 7.21 (s, 1H), 7.11 (d, J = 8.9, 1H), 6.86 (d, J = 3.6, 1H), 6.76 (s, 1H), 4.39 (dd, J = 15.7, 6.6, 1H), 4.25 (dd, J = 15.7, 5.9, 1H), 3.95-3.85 (m, 2H), 3.41 (s, 3H), 2.65-2.57 (m, 1H), 2.15 (dt, J = 13.1, 7.6, 1H). | 4.24 min [480.0] |
| "A277" | 3-Hydroxy-1-(6-methanesulfonyl-aminopyridin-3-yl)-2-oxo-pyrrolidine-3-carboxylic acid 3-chloro-5-fluorobenzyl amide | 10.56 (s, 1H), 8.74 (t, J = 6.5, 1H), 8.57 (s, 1H), 8.11 (dd, J = 9.0, 2.7, 1H), 7.27 (d, J = 8.7, 1H), 7.20 (s, 1H), 7.10 (d, J = 9.8, 1H), 7.02 (d, J = 8.9, 1H), 6.80 (s, 1H), 4.38 (dd, J = 15.9, 6.7, 2H), 4.24 (dd, J = 15.7, 5.8, 1H), 3.88-3.82 (m, 2H), 3.28 (s, 3H), 2.60 (dd, J = 13.0, 6.2, 2H), 2.15 (dd, J = 14.3, 6.5, 2H). | 3.26 min [457] |
| "A278" | (R)-1-(1-Acetyl-1H-indol-5-yl)-3-hydroxy-2-oxopyrrolidine-3-carboxylic acid 3-chloro-5-fluoro-benzyl amide | 8.72 (t, J = 6.3, 1H), 8.31 (d, J = 9.0, 1H), 7.92 (d, J = 2.0, 1H), 7.88 (d, J = 3.8, 1H), 7.65 (dd, J = 9.0, 2.1, 1H), 7.30-7.24 (m, 1H), 7.21 (s, 1H), 7.11 (d, J = 9.7, 1H), 6.76 (d, J = 5.1, 2H), 4.39 (dd, J = 15.8, 6.7, 1H), 4.25 (dd, J = 15.7, 6.0, 1H), 3.91 (t, J = 6.8, 2H), 2.64 (s, 3H), 2.60 (dd, J = 12.6, 6.2, 1H), 2.14 (dt, J = 13.1, 7.6, 1H). | 4.09 min [444] |

| No. | Structure/name | ¹H NMR (400 MHz, DMSO-d₆) δ [ppm] | LC-MS; rt; [M + H⁺]* |
|---|---|---|---|
| "A279" | 3-Hydroxy-2-oxo-1-[1-(tetrahydro-pyran-2-yl)-1H-indazol-5-yl]-pyrrolidine-3-carboxylic acid 3-chloro-5-fluorobenzyl amide | 8.73 (t, J = 6.4, 1H), 8.12 (s, 1H), 7.94 (dd, J = 10.1, 1.4, 1H), 7.82 (ddd, J = 12.4, 9.1, 2.0, 1H), 7.75 (d, J = 9.2, 1H), 7.27 (dt, J = 8.8, 2.1, 1H), 7.21 (s, 1H), 7.11 (d, J = 9.6, 1H), 6.76 (d, J = 0.7, 1H), 5.84 (dd, J = 9.6, 2.4, 1H), 4.39 (dd, J = 15.8, 6.7, 1H), 4.25 (dd, J = 15.7, 6.0, 1H), 3.90 (dd, J = 17.8, 11.2, 3H), 3.74 (ddd, J = 11.5, 9.3, 5.3, 1H), 2.68-2.56 (m, 1H), 2.47-2.33 (m, 1H), 2.15 (dt, J = 13.0, 7.5, 1H), 2.09-1.92 (m, 2H), 1.86-1.67 (m, 1H), 1.57 (dd, J = 8.0, 4.6, 2H). | 4.34 min [486.1] |
| "A280" | (S)-1-(6-Acetylaminopyridin-3-yl)-3-hydroxy-2-oxopyrrolidine-3-carboxylic acid 3-chloro-5-fluoro-benzyl amide | 10.54 (s, 1H), 8.76 (t, J = 6.4, 1H), 8.66-8.63 (m, 1H), 8.13-8.05 (m, 2H), 7.27 (dt, J = 8.8, 2.1, 1H), 7.20 (s, 1H), 7.10 (d, J = 9.6, 1H), 6.80 (s, 1H), 4.38 (dd, J = 15.7, 6.8, 1H), 4.24 (dd, J = 15.8, 6.1, 1H), 3.92-3.81 (m, 2H), 2.60 (ddd, J = 12.0, 7.1, 4.8, 1H), 2.14 (dt, J = 13.0, 7.6, 1H), 2.07 (s, 3H). | 1.873 min [421.1] $ |
| "A281" | (R)-1-(6-Acetylaminopyridin-3-yl)-3-hydroxy-2-oxopyrrolidine-3-carboxylic acid 3-chloro-5-fluoro-benzyl amide | 10.55 (s, 1H), 8.77 (t, J = 6.4, 1H), 8.66-8.63 (m, 1H), 8.13-8.05 (m, 2H), 7.27 (dt, J = 8.8, 2.1, 1H), 7.21 (s, 1H), 7.10 (d, J = 9.6, 1H), 6.80 (s, 1H), 4.38 (dd, J = 15.7, 6.8, 1H), 4.24 (dd, J = 15.8, 6.1, 1H), 3.92-3.81 (m, 2H), 2.60 (ddd, J = 12.0, 7.1, 4.8, 1H), 2.14 (dt, J = 13.0, 7.6, 1H), 2.08 (s, 3H). | 1.874 min [421.0] $ |
| "A282" | (S)-1-(1-Formyl-2,3-dihydro-1H-indol-5-yl)-3-hydroxy-2-oxo-pyrrolidine-3-carboxylic acid 3-chloro-5-fluorobenzyl amide | 9.00 (s, 1H), 8.71 (t, J = 6.4, 1H), 7.63 (d, J = 13.1, 1H), 7.45 (s, 1H), 7.31-7.24 (m, 1H), 7.20 (s, 1H), 7.10 (d, J = 9.6, 1H), 6.73 (s, 1H), 4.38 (dd, J = 15.8, 6.7, 1H), 4.24 (dd, J = 15.7, 6.0, 1H), 3.82 (t, J = 6.8, 2H), 3.13 (dt, J = 17.1, 8.6, 2H), 2.62-2.53 (m, 1H), 2.11 (dt, J = 12.9, 7.5, 1H). | 3.51 min [432.0] |

| No. | Structure/name | $^1$H NMR (400 MHz, DMSO-$d_6$) δ [ppm] | LC-MS; rt; [M + H$^+$]* |
|---|---|---|---|
| "A283" | 3-Hydroxy-1-(1H-indazol-5-yl)-2-oxopyrrolidine-3-carboxylic acid 3-chloro-5-fluorobenzyl amide | 13.09 (s, 1H), 8.72 (t, J = 6.4, 1H), 8.08 (s, 1H), 7.91 (d, J = 1.5, 1H), 7.76 (dd, J = 9.0, 1.9, 1H), 7.56 (d, J = 9.0, 1H), 7.27 (dt, J = 8.8, 2.1, 1H), 7.21 (s, 1H), 7.11 (d, J = 9.7, 1H), 6.74 (s, 1H), 4.39 (dd, J = 15.7, 6.8, 1H), 4.25 (dd, J = 15.8, 6.0, 1H), 3.91 (t, J = 6.8, 2H), 2.65-2.57 (m, 1H), 2.14 (dt, J = 12.9, 7.5, 1H). | 3.41 min [403.0] |
| "A284" | 3-Hydroxy-1-(1-methyl-2-oxo-1,2,3,4-tetrahydroquinolin-6-yl)-2-oxopyrrolidine-3-carboxylic acid 3-chloro-5-fluorobenzyl amide | 8.71 (t, J = 6.3, 1H), 7.57 (dd, J = 8.8, 2.4, 1H), 7.54 (s, 1H), 7.30-7.24 (m, 1H), 7.20 (s, 1H), 7.11 (d, J = 8.7, 2H), 6.73 (s, 1H), 4.38 (dd, J = 15.8, 6.7, 1H), 4.24 (dd, J = 15.7, 6.0, 1H), 3.83 (t, J = 6.8, 2H), 3.24 (s, 3H), 2.87 (t, J = 7.3, 2H), 2.63-2.51 (m, 3H), 2.12 (dt, J = 13.0, 7.6, 1H). | 3.67 min [446.0] |
| "A285" | (R)-1-(1-Formyl-2,3-dihydro-1H-indol-5-yl)-3-hydroxy-2-oxo-pyrrolidine-3-carboxylic acid 3-chloro-5-fluorobenzyl amide | 9.00 (s, 1H), 8.71 (t, J = 6.4, 1H), 7.63 (d, J = 12.9, 1H), 7.45 (t, J = 4.7, 1H), 7.27 (dt, J = 8.8, 2.1, 1H), 7.20 (s, 1H), 7.10 (d, J = 9.1, 1H), 6.73 (s, 1H), 4.38 (dd, J = 15.7, 6.7, 1H), 4.24 (dd, J = 15.7, 6.0, 1H), 3.82 (dd, J = 8.2, 5.6, 2H), 3.14 (dt, J = 17.1, 5.1, 2H), 2.57 (dt, J = 6.6, 5.6, 1H), 2.11 (dt, J = 13.0, 7.6, 1H). | 3.52 min [432.0] |
| "A286" | Methyl 5-[3-(3-chloro-5-fluoro-benzylcarbamoyl)-3-hydroxy-2-oxopyrrolidin-1-yl]-2,3-dihydro-indole-1-carboxylate | 8.71 (t, J = 6.4, 1H), 7.68 (br. s, 1H), 7.59 (s, 1H), 7.45-7.40 (m, 1H), 7.27 (dt, J = 8.8, 2.2, 1H), 7.20 (s, 1H), 7.10 (d, J = 9.6, 1H), 6.73 (s, 1H), 4.38 (dd, J = 15.7, 6.7, 1H), 4.24 (dd, J = 15.8, 6.0, 1H), 3.96 (t, J = 8.7, 2H), 3.81 (t, J = 6.9, 2H), 3.73 (s, 3H), 3.11 (t, J = 8.6, 2H), 2.56 (dt, J = 17.8, 5.5, 1H), 2.10 (dt, J = 12.9, 7.6, 1H). | 4.198 min [462] |

| No. | Structure/name | ¹H NMR (400 MHz, DMSO-d₆) δ [ppm] | LC-MS; rt; [M + H⁺] * |
|---|---|---|---|
| "A287" | (S)-3-Hydroxy-1-(1-methyl-carbamoylmethyl-1H-indol-5-yl)-2-oxopyrrolidine-3-carboxylic acid 3-chloro-5-fluorobenzyl amide | δ 8.70 (t, J = 6.4, 1H), 8.02 (d, J = 4.6, 1H), 7.72 (d, J = 1.8, 1H), 7.43 (dd, J = 8.9, 2.0, 1H), 7.36 (d, J = 8.9, 1H), 7.34 (d, J = 3.1, 1H), 7.27 (dt, J = 8.7, 2.1, 1H), 7.22 (s, 1H), 7.11 (d, J = 9.7, 1H), 6.74 (s, 1H), 6.44 (dd, J = 3.1, 0.6, 1H), 4.79 (s, 2H), 4.39 (dd, J = 15.8, 6.8, 1H), 4.25 (dd, J = 15.7, 6.0, 1H), 3.87 (t, J = 6.8, 2H), 2.64-2.55 (m, 4H), 2.13 (dt, J = 12.9, 7.5, 1H). | 3.56 min [473] |
| "A288" | (S)-3-Hydroxy-2-oxo-1-phenyl-pyrrolidine-3-carboxylic acid (1-phenylprop-2-ynyl) amide | 8.64 (d, J = 8.7, 1H), 7.70 (dd, J = 8.7, 1.0, 2H), 7.47 (d, J = 7.2, 2H), 7.44-7.33 (m, 5H), 7.33-7.27 (m, 1H), 7.22-7.14 (m, 1H), 6.71 (s, 1H), 6.02-5.63 (m, 1H), 3.85 (td, J = 8.8, 5.2, 2H), 3.50 (d, J = 2.5, 1H), 2.55-2.50 (m, 1H), 2.09 (dt, J = 13.0, 7.8, 1H). | 3.91 min [335] |
| "A289" | (R)-3-Hydroxy-1-(1-methyl-carbamoylmethyl-1H-indol-5-yl)-2-oxopyrrolidine-3-carboxylic acid 3-chloro-5-fluorobenzyl amide | 8.69 (t, J = 6.3, 1H), 8.00 (d, J = 4.5, 1H), 7.72 (d, J = 2.0, 1H), 7.43 (dd, J = 8.9, 2.0, 1H), 7.36 (d, J = 9.0, 1H), 7.34 (d, J = 3.1, 1H), 7.27 (dt, J = 8.7, 2.1, 1H), 7.22 (s, 1H), 7.11 (d, J = 9.0, 1H), 6.71 (s, 1H), 6.44 (d, J = 3.1, 1H), 4.79 (s, 2H), 4.39 (dd, J = 15.8, 6.8, 1H), 4.25 (dd, J = 15.6, 5.9, 1H), 3.87 (t, J = 6.7, 2H), 2.65-2.55 (m, 4H), 2.13 (dt, J = 12.9, 7.5, 1H). | 3.56 min [473] |
| "A290" | 5-[(S)-3-(3-Chloro-5-fluorobenzyl-carbamoyl)-3-hydroxy-2-oxo-pyrrolidin-1-yl]-2,3-dihydroindole-1-carboxylic acid ethyl amide | 8.69 (t, J = 6.3, 1H), 7.80 (d, J = 8.8, 1H), 7.51 (d, J = 2.1, 1H), 7.32-7.24 (m, 2H), 7.20 (s, 1H), 7.10 (d, J = 8.8, 1H), 6.68 (s, 1H), 6.61 (t, J = 5.5, 1H), 4.38 (dd, J = 15.7, 6.7, 1H), 4.23 (dd, J = 16.0, 6.1, 1H), 3.86 (t, J = 8.7, 2H), 3.79 (dd, J = 8.6, 5.7, 2H), 3.18-3.08 (m, 4H), 2.60-2.51 (m, 2H), 2.09 (dt, J = 13.0, 7.6, 1H), 1.07 (t, J = 7.1, 3H). | 3.78 min [475] |

| No. | Structure/name | ¹H NMR (400 MHz, DMSO-d₆) δ [ppm] | LC-MS; rt; [M + H⁺] * |
|---|---|---|---|
| "A291" | 5-[(R)-3-(3-Chloro-5-fluorobenzyl-carbamoyl)-3-hydroxy-2-oxo-pyrrolidin-1-yl]-2,3-dihydroindole-1-carboxylic acid ethyl amide | δ 8.69 (t, J = 6.4, 1H), 7.80 (d, J = 8.8, 1H), 7.51 (d, J = 2.0, 1H), 7.32-7.23 (m, 2H), 7.20 (s, 1H), 7.10 (d, J = 9.1, 1H), 6.68 (s, 1H), 6.61 (t, J = 5.5, 1H), 4.38 (dd, J = 15.8, 6.8, 1H), 4.23 (dd, J = 15.8, 6.0, 1H), 3.86 (t, J = 8.7, 2H), 3.79 (dd, J = 8.6, 5.7, 2H), 3.20-3.06 (m, 4H), 2.55 (dt, J = 6.8, 5.7, 1H), 2.09 (dt, J = 12.9, 7.6, 1H), 1.07 (t, J = 7.1, 3H). | 3.78 min [475] |
| "A292" | (S)-3-Hydroxy-2-oxo-1-phenyl-pyrrolidine-3-carboxylic acid (3-morpholin-4-ylpropyl) amide | 8.17 (t, J = 5.7, 1H), 7.68 (dt, J = 9.0, 1.7, 2H), 7.44-7.35 (m, 2H), 7.22-7.13 (m, 1H), 6.60 (s, 1H), 3.89-3.77 (m, 2H), 3.63-3.51 (m, 4H), 3.14 (dd, J = 12.8, 6.8, 2H), 2.58-2.51 (m, 1H), 2.40-2.20 (m, 6H), 2.07 (m, 1H), 1.58 (p, 7 = 6.8, 2H). | 1.94 min [348] |
| "A293" | (S)-3-Hydroxy-2-oxo-1-phenyl-pyrrolidine-3-carboxylic acid (2,3-dihydrobenzo-1,4-dioxin-5-yl-methyl) amide | | 3.47 min [369] |
| "A294" | (S)-3-Hydroxy-2-oxo-1-phenyl-pyrrolidine-3-carboxylic acid 2-chlorobenzyl amide | 8.59 (t, J = 6.3, 1H), 7.70 (dt, J = 9.0, 1.7, 2H), 7.44-7.24 (m, 6H), 7.21-7.14 (m, 1H), 6.79 (s, 1H), 4.41 (dd, J = 16.2, 6.5, 1H), 4.31 (dd, J = 16.1, 6.1, 1H), 3.86 (dd, J = 8.5, 5.6, 2H), 2.65-2.57 (m, 1H), 2.14 (dt, J = 12.9, 7.7, 1H). | 3.82 min [345] |

| No. | Structure/name | ¹H NMR (400 MHz, DMSO-d₆) δ [ppm] | LC-MS; rt; [M + H⁺] * |
|---|---|---|---|
| "A295" | (S)-3-Hydroxy-2-oxo-1-phenyl-pyrrolidine-3-carboxylic acid (benzo-1,3-dioxol-5-ylmethyl) amide | | 3.36 min [355] |
| "A296" | (S)-3-Hydroxy-2-oxo-1-phenyl-pyrrolidine-3-carboxylic acid [3-(2-oxopyrrolidin-1-yl)-propyl] amide | 8.01 (t, J = 6.1, 1H), 7.69 (dd, J = 8.7, 1.0, 2H), 7.40 (dd, J = 10.8, 5.3, 2H), 7.17 (t, J = 7.4, 1H), 6.61 (s, 1H), 3.90-3.77 (m, 2H), 3.32-3.29 (m, 2H), 3.16 (m, 2H), 3.05 (m, 2H), 2.53 (ddd, J = 11.8, 6.6, 3.5, 2H), 2.20 (t, J = 8.1, 2H), 2.07 (m, 1H), 1.95-1.85 (m, 2H), 1.59 (p, J = 6.9, 2H). | 2.35 min [346] |
| "A297" | (S)-3-Hydroxy-2-oxo-1-phenyl-pyrrolidine-3-carboxylic acid 4-tert-butylbenzyl amide | 8.44 (t, J = 6.3, 1H), 7.69 (dd, J = 8.7, 1.1, 2H), 7.44-7.36 (m, 2H), 7.34-7.28 (m, 2H), 7.18 (d, J = 7.7, 3H), 6.66 (s, 1H), 4.27 (d, J = 6.4, 1H), 4.24 (d, J = 6.3, 1H), 3.86 (m, 3H), 2.61-2.52 (m, 1H), 2.10 (dt, J = 12.9, 7.8, 1H), 1.25 (s, 9H). | 4.76 min [367] |
| "A298" | (S)-3-Hydroxy-2-oxo-1-phenyl-pyrrolidine-3-carboxylic acid (1-methylbutyl) amide | 7.69 (dt, J = 9.0, 1.7, 2H), 7.52 (d, J = 8.7, 1H), 7.44-7.36 (m, 2H), 7.19-7.14 (m, 1H), 6.59 (d, J = 1.0, 1H), 3.92-3.70 (m, 3H), 2.58-2.50 (m, 1H). 2.07 (m, 1H), 1.54-1.14 (m, 5H), 1.06 (dd, J = 6.6, 4.2, 3H), 0.84 (dt, J = 11.5, 7.2, 3H). | 3.43 min [291] |
| "A299" | (S)-3-Hydroxy-2-oxo-1-phenyl-pyrrolidine-3-carboxylic acid 2-fluorobenzyl amide | 8.53 (t, J = 6.3, 1H), 7.73-7.66 (m, 2H), 7.43-7.37 (m, 2H), 7.34 (t, J = 7.8, 1H), 7.31-7.25 (m, 1H), 7.20-7.11 (m, 3H), 6.73 (s, 1H), 4.38 (dd, J = 15.6, 6.4, 1H), 4.31 (dd, J = 15.5, 5.9, 1H), 3.91-3.80 (m, 2H), 2.58 (ddd, J = 12.9, 7.0, 4.5, 1H), 2.12 (dt, J = 13.0, 7.7, 1H). | 3.51 min [329] |

-continued

| No. | Structure/name | ¹H NMR (400 MHz, DMSO-d₆) δ [ppm] | LC-MS; rt; [M + H⁺]* |
|---|---|---|---|
| "A300" | (S)-3-Hydroxy-3-(morpholin-4-carbonyl)-1-phenylpyrrolidin-2-one | 7.71-7.65 (m, 2H), 7.40 (dd, J = 10.8, 5.3, 2H), 7.17 (t, J = 7.4, 1H), 6.77 (s, 1H), 4.09 (m, 1H), 3.78 (m, 2H), 3.73-3.62 (m, 2H), 3.59 (m, 5H), 2.72-2.63 (m, 1H), 2.11 (dt, J = 12.6, 8.9, 1H). | 2.38 min [291] |
| "A301" | (S)-3-Hydroxy-2-oxo-1-phenyl-pyrrolidine-3-carboxylic acid (3-isopropoxypropyl) amide | 7.94 (t, J = 5.8, 1H), 7.68 (dt, J = 9.0, 1.7, 2H), 7.43-7.34 (m, 2H), 7.22-7.12 (m, 1H), 6.59 (s, 1H), 3.89-3.76 (m, 2H), 3.49 (hept, J = 6.1, 1H), 3.36 (t, J = 6.2, 2H), 3.14 (p, J = 6.6, 2H), 2.56-2.50 (m, 1H), 2.12-1.98 (m, 1H), 1.63 (p, J = 6.5, 2H), 1.06 (dd, J = 6.1, 3.0, 6H). | 3.05 min [321] |
| "A302" | (S)-3-Hydroxy-2-oxo-1-phenyl-pyrrolidine-3-carboxylic acid 2-trifluoromethylbenzyl amide | | 4.20 min [379] |
| "A303" | (S)-3-Hydroxy-2-oxo-1-phenyl-pyrrolidine-3-carboxylic acid benzyl ethyl amide | 7.70 (d, J = 8.0, 2H), 7.43-7.37 (m, 2H), 7.37-7.26 (m, 3H), 7.25-7.14 (m, 3H), 6.75 (s, 1H), 4.98 (dd, J = 78.2, 15.8, 1H), 4.49 (dd, J = 48.6, 15.3, 1H), 3.83 (dd, J = 19.3, 9.9, 1H), 3.75-3.56 (m, 2H), 3.10 (ddd, J = 23.0, 13.8, 6.1, 1H), 2.77-2.61 (m, 1H), 2.24-2.09 (m, 1H), 1.15 (t, J = 6.8, 2H), 0.90 (t, J = 6.9, 1H). | 4.22 min [339] |
| "A304" | (S)-3-Hydroxy-2-oxo-1-phenyl-pyrrolidine-3-carboxylic acid cyclopentyl amide | 7.72-7.66 (m, 2H), 7.63 (d, J = 7.8, 1H), 7.43-7.36 (m, 2H), 7.20-7.13 (m, 1H), 6.59 (s, 1H), 4.06-3.95 (m, 1H), 3.89-3.77 (m, 2H), 2.56-2.51 (m, 1H), 2.11-2.01 (m, 1H), 1.79 (m, 2H), 1.70-1.58 (m, 2H), 1.54-1.37 (m, 4H). | 3.07 min [289] |

-continued

| No. | Structure/name | $^1$H NMR (400 MHz, DMSO-d$_6$) δ [ppm] | LC-MS; rt; [M + H$^+$]* |
|---|---|---|---|
| "A305" | (S)-3-Hydroxy-2-oxo-1-phenyl-pyrrolidine-3-carboxylic acid isobutyl amide | 7.87 (t, J = 6.1, 1H), 7.68 (dt, J = 9.0, 1.8, 2H), 7.43-7.36 (m, 2H), 7.20-7.14 (m, 1H), 6.61 (s, 1H), 3.94-3.74 (m, 2H), 2.98-2.85 (m, 2H), 2.53 (ddd, J = 12.3, 7.1, 3.7, 1H), 2.15-2.03 (m, 1H), 1.75 (dp, J = 13.5, 6.8, 1H), 0.82 (dd, J = 6.7, 3.2, 6H). | 3.00 min [277] |
| "A306" | (S)-3-Hydroxy-2-oxo-1-phenyl-pyrrolidine-3-carboxylic acid [1-(4-chlorophenyl)ethyl] amide | 8.28 (t, J = 7.6, 1H), 7.72-7.64 (m, 2H), 7.43-7.31 (m, 6H), 7.17 (td, J = 7.4, 4.4, 1H), 6.69 (d, J = 9.2, 1H), 4.98-4.86 (m, 1H), 3.87-3.75 (m, 2H), 2.58 (ddd, J = 22.2, 11.9, 7.8, 1H), 2.47-2.37 (m, 1H), 2.09 (ddd, J = 15.9, 13.8, 8.0, 1H), 1.40 (dd, J = 7.0, 2.2, 3H). | 4.18 min [359] |
| "A307" | (S)-3-Hydroxy-2-oxo-1-phenyl-pyrrolidine-3-carboxylic acid butyl methyl amide | 7.68 (dd, J = 8.7, 1.0, 2H), 7.43-7.35 (m, 2H), 7.20-7.12 (m, 1H), 6.57 (s, 1H), 3.79 (t, J = 8.6, 1H), 3.71-3.45 (m, 2H), 3.22 (m, 1H), 3.18 (m, 2H), 2.77 (m, 1H), 2.60 (m, 1H), 2.11 (m, 1H), 1.52 (m, 1H), 1.49-1.38 (m, 1H), 1.23 (m, 2H), 0.87 (m, 3H). | 3.64 min [291] |
| "A308" | (S)-3-Hydroxy-1-phenyl-3-(piperidine-1-carbonyl)pyrrolidin-2-one | 7.71-7.64 (m, 2H), 7.39 (dd, J = 10.8, 5.3, 2H), 7.16 (t, J = 7.4, 1H), 6.64 (s, 1H), 3.88 (s, 1H), 3.81-3.74 (m, 1H), 3.64 (m, 2H), 3.52 (m, 1H), 3.26 (m, 1H), 2.60 (m, 1H), 2.11 (m, 1H), 1.53 (m, 6H). | 3.18 min [289] |
| "A309" | (S)-3-Hydroxy-2-oxo-1-phenyl-pyrrolidine-3-carboxylic acid tert-butyl amide | 7.72-7.65 (m, 2H), 7.43-7.36 (m, 2H), 7.21-7.14 (m, 1H), 7.03 (s, 1H), 6.70 (s, 1H), 3.90-3.75 (m, 2H), 2.55-2.50 (m, 1H), 2.05 (ddd, J = 12.9, 8.7, 7.6, 1H), 1.28 (s, 9H). | 3.10 min [277] |

-continued

| No. | Structure/name | $^1$H NMR (400 MHz, DMSO-d$_6$) δ [ppm] | LC-MS; rt; [M + H$^+$]* |
|---|---|---|---|
| "A310" | (S)-3-Hydroxy-2-oxo-1-phenyl-pyrrolidine-3-carboxylic acid butyl amide | 7.89 (t, J = 5.9, 1H), 7.68 (dt, J = 9.0, 1.7, 2H), 7.44-7.36 (m, 2H), 7.20-7.13 (m, 1H), 6.58 (s, 1H), 3.92-3.77 (m, 2H), 3.08 (dd, J = 13.2, 6.9, 2H), 2.57-2.50 (m, 1H), 2.12-2.01 (m, 1H), 1.45-1.34 (m, 2H), 1.25 (dq, J = 14.1, 7.2, 3H), 0.85 (t, J = 7.3, 3H). | 3.07 min [277] |
| "A311" | (S)-3-(4-Acetylpiperazine-1-carbonyl)-3-hydroxy-1-phenyl-pyrrolidin-2-one | 7.68 (dd, J = 8.7, 1.0, 2H), 7.43-7.36 (m, 2H), 7.21-7.13 (m, 1H), 7.02 (d, J = 15.9, 1H), 6.82 (s, 1H), 4.09 (m, 1H), 3.79 (m, 1H), 3.72-3.53 (m, 4H), 3.44 (m, 2H), 3.24 (m, 1H), 3.16 (d, J = 5.2, 1H), 2.69 (dd, J= 12.5, 5.9, 1H), 2.13 (dt, J = 12.6, 9.0, 1H), 2.01 (s, 3H). | 2.30 min [332] |
| "A312" | (S)-3-Hydroxy-2-oxo-1-phenyl-pyrrolidine-3-carboxylic acid ethyl amide | 7.94 (t, J = 5.7, 1H), 7.72-7.65 (m, 2H), 7.43-7.34 (m, 2H), 7.21-7.13 (m, 1H), 6.58 (s, 1H), 3.90-3.75 (m, 2H), 3.17-3.05 (m, 2H), 2.57-2.51 (m, 1H), 2.07 (ddd, J = 12.9, 8.5, 7.4, 1H), 1.02 (t, J = 7.2, 3H). | 2.15 min [249] |
| "A313" | (S)-3-Hydroxy-2-oxo-1-phenyl-pyrrolidine-3-carboxylic acid dipropyl amide | 7.68 (dt, J = 9.0, 1.7, 2H), 7.42-7.34 (m, 2H), 7.19-7.13 (m, 1H), 6.55 (s, 1H), 3.79 (td, J = 9.2, 1.9, 1H), 3.62 (dt, J = 9.3, 6.8, 1H), 3.51 (t, J = 7.9, 2H), 3.21-3.05 (m, 2H), 2.58 (ddd, J = 12.6, 6.6, 1.9, 1H), 2.13 (dt, J = 12.7, 8.8, 1H), 1.61 (pd, J = 13.2, 7.4, 2H), 1.51-1.38 (m, 2H), 0.81 (dt, J = 12.3, 7.4, 6H). | 4.04 min [305] |
| "A314" | (S)-3-Hydroxy-2-oxo-1-phenyl-pyrrolidine-3-carboxylic acid (2-pyridin-3-ylethyl) amide | 8.42 (d, J = 1.7, 1H), 8.40 (dd, J = 4.8, 1.6, 1H), 8.07 (t, J = 6.0, 1H), 7.68 (dd, J = 8.7, 1.0, 2H), 7.65-7.57 (m, 2H), 7.43-7.35 (m, 2H), 7.29 (ddd, J = 7.8, 4.8, 0.7, 1H), 7.22-7.13 (m, 1H), 6.62 (s, 1H), 3.87-3.75 (m, 2H), 3.44-3.20 (m, 2H), 2.77 (t, J = 7.1, 2H), 2.44 (m, 1H), 2.10-1.99 (m, 1H). | 1.88 min [326] |

-continued

| No. | Structure/name | ¹H NMR (400 MHz, DMSO-d₆) δ [ppm] | LC-MS; rt; [M + H⁺] * |
|---|---|---|---|
| "A315" | (S)-3-Hydroxy-3-(4-isopropyl-piperazine-1-carbonyl)-1-phenyl-pyrrolidin-2-one | 7.70-7.64 (m, 2H), 7.42-7.36 (m, 2H), 7.19-7.12 (m, 1H), 6.67 (s, 1H), 3.98 (m, 1H), 3.77 (m, 1H), 3.65 (m, 2H), 3.59-3.37 (m, 2H), 2.63 (m, 2H), 2.46-2.30 (m, 4H), 2.11 (dt, J = 12.7, 8.9, 1H), 0.96 (d, J = 6.5, 6H). | 2.18 min [332] |
| "A316" | (S)-3-Hydroxy-3-(4-methyl-piperidine-1-carbonyl)-1-phenyl pyrrolidin-2-one | 7.67 (dt, J = 12.0, 6.1, 2H), 7.43-7.35 (m, 2H), 7.19-7.12 (m, 1H), 6.64 (s, 1H), 4.61 (m, 1H), 4.26 (m, 1H), 3.84-3.72 (m, 1H), 3.65 (m, 1H), 2.92 (m, 1H), 2.60 (m, 2H), 2.11 (dt, J = 12.6, 8.8, 1H), 1.62 (m, 3H), 1.19 (m, 2H), 0.89 (d, J = 6.1, 3H). | 3.69 min [303] |
| "A317" | (S)-3-Hydroxy-2-oxo-1-phenyl-pyrrolidine-3-carboxylic acid isobutyl methyl amide | 7.71-7.64 (m, 2H), 7.42-7.35 (m, 2H), 7.19-7.12 (m, 1H), 6.58 (s, 1H), 3.81 (m, 1H), 3.62 (m, 1H), 3.17 (s, 3H), 3.10 (m, 1H), 2.77 (s, 1H), 2.67-2.57 (m, 1H), 2.12 (dt, J = 12.8, 8.7, 1H), 2.03-1.80 (m, 1H), 0.81 (d, J = 6.0, 6H). | 3.55 min [291] |
| "A318" | (S)-3-Hydroxy-2-oxo-1-phenyl-pyrrolidine-3-carboxylic acid [2-(2-chlorophenyl)ethyl] amide | 8.09 (t, J = 6.0, 1H), 7.72-7.66 (m, 2H), 7.43-7.37 (m, 3H), 7.34-7.30 (m, 1H), 7.28-7.21 (m, 2H), 7.20-7.14 (m, 1H), 6.60 (s, 1H), 3.85-3.77 (m, 2H), 3.46-3.34 (m, 1H), 3.28 (m, 1H), 2.93-2.78 (m, 2H), 2.47-2.41 (m, 1H), 2.06 (dt, J = 12.9, 7.9, 1H) | 4.00 min [359] |
| "A319" | (S)-3-Hydroxy-2-oxo-1-phenyl-pyrrolidine-3-carboxylic acid methyl phenethyl amide | 7.72-7.66 (m, 2H), 7.39 (t, J = 7.9, 2H), 7.34-7.12 (m, 6H), 6.68 (s, 1H), 3.88 (m, 1H), 3.77 (m, 1H), 3.69-3.47 (m, 1H), 3.40-3.33 (m, 1H), 3.16 (m, 1H), 3.03-2.88 (m, 1H), 2.89 (s, 3H), 2.80-2.72 (m, 1H), 2.51 (m, 1H), 2.09 (dt, J = 12.7, 8.8, 1H). | 4.10 min [339] |

| No. | Structure/name | $^1$H NMR (400 MHz, DMSO-d$_6$) δ [ppm] | LC-MS; rt; [M + H$^+$]* |
|---|---|---|---|
| "A320" | (S)-3-Hydroxy-2-oxo-1-phenyl-pyrrolidine-3-carboxylic acid chroman-3-yl amide | 7.88 (dd, J = 17.7, 8.2, 1H), 7.73-7.66 (m, 2H), 7.44-7.36 (m, 2H), 7.18 (td, J = 7.3, 1.1, 1H), 7.13-7.05 (m, 2H), 6.86 (t, J = 7.4, 1H), 6.81-6.77 (m, 1H), 6.75 (d, J = 1.6, 1H), 4.24-4.11 (m, 1H), 4.11-4.01 (m, 1H), 3.97-3.79 (m, 3H), 3.00-2.78 (m, 2H), 2.57 (m, 1H), 2.09 (m, 1H). | 3.74 min [353] |
| "A321" | (S)-3-Hydroxy-2-oxo-1-phenyl-pyrrolidine-3-carboxylic acid methyl thiophen-3-ylmethyl amide | 7.73-7.67 (m, 2H), 7.50 (s, 1H), 7.40 (dd, J = 10.8, 5.3, 2H), 7.33 (s, 1H), 7.17 (t, J = 7.4, 1H), 6.98 (d, J = 4.4,, 1H), 6.75 (m, 1H), 4.95 (m, 1H), 4.45 (m, 1H), 3.81 (m, 1H), 3.67 (m, 1H), 3.23-3.11 (m, 2H), 2.69 (s, 3H), 2.15 (dt, J = 12.7, 8.8, 1H). | 3.71 min [331] |
| "A322" | (S)-3-Hydroxy-2-oxo-1-phenyl-pyrrolidine-3-carboxylic acid cyclobutyl amide | 8.08 (d, J = 8.4, 1H), 7.68 (dd, J = 8.7, 1.0, 2H), 7.43-7.36 (m, 2H), 7.17 (t, J = 7.4, 1H), 6.59 (s, 1H), 4.29-4.13 (m, 1H), 3.89-3.75 (m, 2H), 2.57-2.50 (m, 1H), 2.16-1.99 (m, 5H), 1.65-1.52 (m, 2H). | 2.73 min [275] |
| "A323" | (S)-3-Hydroxy-2-oxo-1-phenyl-pyrrolidine-3-carboxylic acid cyclopentyl methyl amide | 7.67 (d, J = 7.9, 2H), 7.39 (dd, J = 10.7, 5.3, 2H), 7.16 (t, J = 7.4, 1H), 6.61 (m, 1H), 3.78 (m, 1H), 3.65 (m, 1H), 3.05 (m, 1H), 2.65 (s, 3H), 2.59 (dd, J = 12.8, 4.9, 1H), 2.14 (m, 1H), 1.80 (m, 1H), 1.61 (m, 3H), 1.50 (m, 4H). | 3.62 min [303] |
| "A324" | (S)-3-Hydroxy-2-oxo-1-phenyl-pyrrolidine-3-carboxylic acid cyclohexylmethyl amide | 7.84 (t, J = 6.2, 1H), 7.68 (dt, J = 3.1, 1.7, 2H), 7.43-7.35 (m, 2H), 7.16 (dd, J = 10.6, 4.2, 1H), 6.60 (s, 1H), 3.90-3.75 (m, 2H), 3.01-2.86 (m, 2H), 2.58-2.50 (m, 1H), 2.06 (ddd, J = 23.3, 17.6, 11.7, 1H), 1.64 (m, 5H), 1.44 (ddd, J = 10.9, 9.2, 5.5, 1H), 1.21-0.99 (m, 3H), 0.93-0.75 (m, 2H). | 3.97 min [317] |

-continued

| No. | Structure/name | ¹H NMR (400 MHz, DMSO-d₆) δ [ppm] | LC-MS; rt; [M + H⁺]* |
|---|---|---|---|
| "A325" | (S)-3-Hydroxy-2-oxo-1-phenyl-pyrrolidine-3-carboxylic acid 2-methoxybenzyl amide | 8.25 (t, J = 6.2, 1H), 7.72-7.66 (m, 2H), 7.44-7.35 (m, 2H), 7.25-7.14 (m, 3H), 6.96 (d, J = 7.8, 1H), 6.88 (t, J = 7.4, 1H), 6.73 (s, 1H), 4.30 (dd, J = 15.8, 6.4, 1H), 4.24 (dd, J = 15.8, 6.1, 1H), 3.86 (m, 2H), 3.79 (s, 3H), 2.59 (ddd, J = 12.7, 7.1, 4.3, 1H), 2.12 (dt, J = 12.9, 7.8, 1H). | 3.58 min [341] |
| "A326" | (S)-3-Hydroxy-2-oxo-1-phenyl-pyrrolidine-3-carboxylic acid (1,2-dimethylpropyl) amide | | 3.33 min [291] |
| "A327" | (S)-3-Hydroxy-2-oxo-1-phenyl-pyrrolidine-3-carboxylic acid (3-methylbutyl) amide | 7.87 (t, J = 5.9, 1H), 7.68 (dt, J = 8.9, 1.7, 2H), 7.43-7.36 (m, 2H), 7.20-7.14 (m, 1H), 6.57 (s, 1H), 3.86 (dt, J = 8.9, 0.7, 1H), 3.83-3.77 (m, 1H), 3.10 (dd, J = 14.4, 6.3, 2H), 2.56-2.50 (m, 1H), 2.07 (ddd, J = 12.9, 8.5, 7.6, 1H), 1.54 (dp, J = 13.3, 6.7, 1H), 1.32 (dd, J = 14.5, 7.0, 2H), 0.85 (dd, J = 6.6, 2.2, 6H). | 3.53 min [291] |
| "A328" | (S)-3-Hydroxy-2-oxo-1-phenyl-pyrrolidine-3-carboxylic acid 4-methoxybenzyl amide | 8.41 (t, J = 6.3, 1H), 7.69 (dt, J = 9.0, 1.7, 2H), 7.44-7.34 (m, 2H), 7.23-7.16 (m, 3H), 6.89-6.82 (m, 2H), 6.65 (s, 1H), 4.25 (dd, J = 14.8, 6.5, 1H), 4.20 (dd, J = 14.8, 6.3, 1H), 3.91-3.79 (m, 2H), 3.71 (s, 3H), 2.55 (ddd, J = 12.8, 7.4, 3.9, 1H), 2.14-2.05 (m, 1H). | 3.41 min [341] |
| "A329" | (S)-3-Hydroxy-2-oxo-1-phenyl-pyrrolidine-3-carboxylic acid (2-propoxyethyl) amide | 7.82 (t, J = 5.7, 1H), 7.71-7.66 (m, 2H), 7.43-7.36 (m, 2H), 7.21-7.14 (m, 1H), 6.67 (s, 1H), 3.90-3.76 (m, 2H), 3.40 (t, J = 6.2, 2H), 3.34 (d, J = 6.6, 2H), 3.29 (dd, J = 9.7, 3.8, 1H), 3.26-3.16 (m, 1H), 2.56-2.51 (m, 1H), 2.14-2.01 (m, 1H), 1.54-1.45 (m, 2H), 0.85 (t, J = 7.4, 3H). | 3.01 min [307] |

| No. | Structure/name | ¹H NMR (400 MHz, DMSO-d$_6$) δ [ppm] | LC-MS; rt; [M + H⁺]* |
|---|---|---|---|
| "A330" | (S)-3-Hydroxy-2-oxo-1-phenyl-pyrrolidine-3-carboxylic acid (3-phenylpropyl) amide | 8.00 (t, J = 5.9, 1H), 7.69 (dd, J = 8.7, 1.0, 2H), 7.44-7.36 (m, 2H), 7.29-7.23 (m, 2H), 7.22-7.11 (m, 4H), 6.60 (s, 1H), 3.93-3.76 (m, 2H), 3.18-3.03 (m, 2H), 2.59-2.51 (m, 3H), 2.08 (dt, J = 12.9, 7.9, 1H), 1.73 (dt, J = 14.7, 7.2, 2H). | 4.01 min [339] |
| "A331" | (S)-3-Hydroxy-3-(4-phenethyl-piperazine-1-carbonyl)-1-phenyl-pyrrolidin-2-one | 7.68 (dd, J = 8.7, 1.0, 2H), 7.43-7.36 (m, 2H), 7.29-7.14 (m, 6H), 6.70 (s, 1H), 4.01 (m, 1H), 3.78 (t, J = 8.4, 2H), 3.66 (td, J = 9.4, 6.7, 2H), 3.54 (m, 1H), 3.37 (m, 1H), 2.78-2.69 (m, 2H), 2.69-2.60 (m, 1H), 2.57-2.50 (m, 2H), 2.47-2.27 (m, 3H), 2.11 (dt, J = 12.5, 8.9, 1H). | 3.07 min [394] |
| "A332" | (S)-3-Hydroxy-2-oxo-1-phenyl-pyrrolidine-3-carboxylic acid [2-(3,4-dimethoxyphenyl)ethyl] amide | 7.92 (t, J = 6.0, 1H), 7.72-7.66 (m, 2H), 7.44-7.36 (m, 2H), 7.21-7.14 (m, 1H), 6.84 (d, J = 8.2, 1H), 6.80 (d, J = 1.9, 1H), 6.71 (dd, J = 8.1, 1.9, 1H), 6.61 (s, 1H), 3.89-3.78 (m, 2H), 3.73 (s, 3H), 3.70 (s, 3H), 3.30-3.20 (m, 2H), 2.67 (t, J = 7.3, 2H), 2.53-2.46 (m, 1H), 2.06 (dt, J = 12.9, 7.9, 1H). | 3.28 min [385] |
| "A333" | (S)-3-Hydroxy-2-oxo-1-phenyl-pyrrolidine-3-carboxylic acid 4-trifluoromethylbenzyl amide | 8.71 (t, J = 6.4, 1H), 7.72-7.64 (m, 4H), 7.48 (d, J = 8.0, 2H), 7.44-7.37 (m, 2H), 7.17 (t, J = 7.4, 1H), 6.73 (s, 1H), 4.42 (dd, J = 15.6, 6.6, 1H), 4.34 (dd, J = 15.6, 6.1, 1H), 3.88-3.82 (m, 2H), 2.58 (ddd, J = 12.8, 6.9, 4.7, 1H), 2.12 (dt, J = 12.9, 7.7, 1H). | 4.29 min [379] |

| No. | Structure/name | ¹H NMR (400 MHz, DMSO-d₆) δ [ppm] | LC-MS; rt; [M + H⁺] * |
|---|---|---|---|
| "A334" | 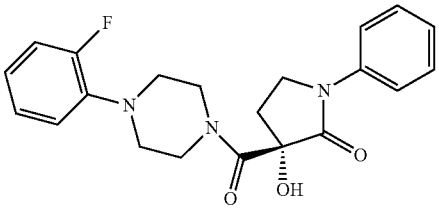<br>(S)-3-[4-(2-Fluorophenyl)-piperazine-1-carbonyl]-3-hydroxy-1-phenylpyrrolidin-2-one | 7.72-7.66 (m, 2H), 7.43-7.36 (m, 2H), 7.20-6.93 (m, 5H), 6.81 (s, 1H), 4.21 (s, 1H), 3.92 (s, 1H), 3.83-3.74 (m, 1H), 3.68 (td, J = 9.4, 6.6, 2H), 3.51 (br. m,, 1H), 2.99 (br. m, 4H), 2.75-2.67 (m, 1H), 2.15 (dt, J = 12.6, 9.0, 1H). | 4.08 min [384 + 385] |
| "A335" | 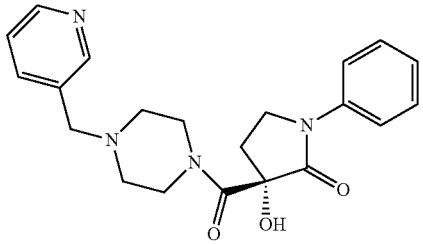<br>(S)-3-Hydroxy-1-phenyl-3-(4-pyridin-3-ylmethylpiperazine-1-carbonyl)pyrrolidin-2-one | 8.50 (d, J = 1.6, 1H), 8.46 (dd, J = 4.8, 1.7, 1H), 7.71 (dt, J = 7.8, 1.9, 1H), 7.68 (d, J = 1.1, 1H), 7.66 (d, J = 1.0, 1H), 7.42-7.33 (m, 3H), 7.20-7.13 (m, 1H), 7.00 (s, 1H), 6.70 (s, 1H), 4.08 (m, 1H), 3.77 (m, 2H), 3.65 (m, 2H), 3.52 (s, 2H), 3.16 (d, J = 5.3, 1H), 2.68-2.60 (m, 1H), 2.39 (s, 3H), 2.30 (m, 1H), 2.15-2.04 (m, 1H). | 1.99 min [381] |
| "A336" | 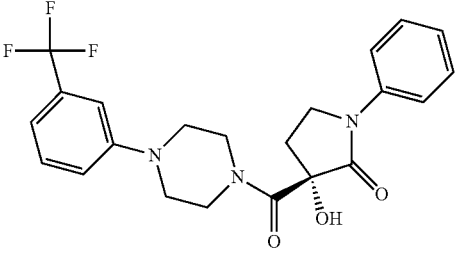<br>(S)-3-Hydroxy-1-phenyl-3-[4-(3-trifluoromethylphenyl)piperazine-1-carbonyl]pyrrolidin-2-one | δ 7.71-7.67 (m, 2H), 7.46-7.36 (m, 3H), 7.27-7.22 (m, 1H), 7.21-7.13 (m, 2H), 7.09 (d, J = 7.6, 1H), 6.81 (s, 1H), 4.22 (m, 1H), 3.93 (m, 1H), 3.80 (t, J = 8.4, 1H), 3.68 (td, J = 9.4, 6.6, 2H), 3.50 (m, 1H), 3.35 (m, 1H), 3.27 (m, 3H), 2.77-2.67 (m, 1H), 2.15 (dt, J = 12.6, 8.9, 1H). | 4.81 min [434.0] |
| "A337" | 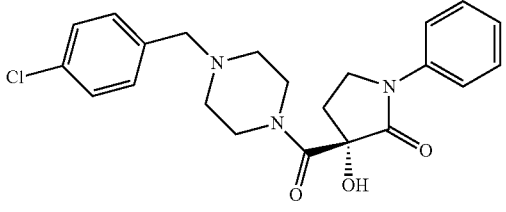<br>(S)-3-[4-(4-Chlorobenzyl)-piperazine-1-carbonyl]-3-hydroxy-1-phenylpyrrolidin-2-one | 7.67 (dd, J = 8.7, 1.0, 2H), 7.38 (dt, J = 10.6, 2.0, 4H), 7.35-7.30 (m, 2H), 7.19-7.11 (m, 1H), 6.69 (s, 1H), 4.03 (m, 1H), 3.77 (m, 2H), 3.65 (m, 2H), 3.54 (m, 1H), 3.47 (s, 2H), 2.68-2.60 (m, 1H), 2.38 (m, 3H), 2.29-2.18 (m, 1H), 2.10 (dt, J = 12.6, 8.9, 1H). | 3.20 min [414.0] |

-continued

| No. | Structure/name | ¹H NMR (400 MHz, DMSO-d₆) δ [ppm] | LC-MS; rt; [M + H⁺]* |
|---|---|---|---|
| "A338" | (S)-3-(4-Benzyloxypiperidine-1-carbonyl)-3-hydroxy-1-phenyl-pyrrolidin-2-one | 7.71-7.66 (m, 2H), 7.42-7.35 (m, 2H), 7.35 (s, 4H), 7.30-7.24 (m, 1H), 7.16 (t, J = 7.4, 1H), 6.71 (s, 1H), 4.52 (s, 2H), 4.34 (m, 1H), 4.08 (m, 1H), 3.86 (m, 1H), 3.82-3.72 (m, 1H), 3.64 (m 3H), 3.33-3.18 (m, 1H), 3.02 (m, 1H), 2.63 (dd, J = 12.6, 5.8, 1H), 2.12 (dt, J = 12.6, 8.9, 1H), 1.88 (m, 2H), 1.47 (m, 2H). | 4.28 min [395] |
| "A339" | (S)-3-[4-(2-Chlorobenzyl)-piperazine-1-carbonyl]-3-hydroxy-1-phenylpyrrolidin-2-one | 7.68 (dd, J = 8.7, 1.0, 2H) 7.50 (dd, J = 7.4, 1.9, 1H), 7.43 (dd, J = 7.7, 1.5, 1H), 7.41-7.36 (m, 2H), 7.34 (dd, J = 7.4, 1.5, 1H), 7.31 (dd, J = 2.9, 2.0, 1H), 7.28 (dd, J = 7.5, 1.9, 1H), 7.16 (t, J = 7.4, 1H), 6.71 (s, 1H), 4.04 (m, 1H), 3.78 (t, J = 8.4, 2H), 3.65 (m, 1H), 3.58 (s, 2H), 3.35 (m, 2H), 2.69-2.59 (m, 1H), 2.47-2.27 (m, 4H), 2.11 (dt, J = 12.6, 8.9, 1H). | 2.98 min [414] |
| "A340" | (S)-3-Hydroxy-3-[4-(4-methoxy-benzyl)piperazine-1-carbonyl]-1-phenylpyrrolidin-2-one | 7.69-7.64 (m, 2H), 7.42-7.35 (m, 2H), 7.21 (dd, J = 6.7, 4.8, 2H), 7.16 (qd, J = 2.3, 1.3, 1H), 6.90-6.85 (m, 2H), 6.68 (s, 1H), 4.01 (m, 1H), 3.77 (m, 1H), 3.72 (s, 3H), 3.65 (m, 2H), 3.54 (m, 1H), 3.40 (s, 2H), 2.68-2.59 (m, 1H), 2.30 (m, 4H), 2.10 (dt, J = 12.6, 8.8, 1H). | 2.92 min [410] |
| "A341" | (S)-3-Hydroxy-3-(4-methane-sulfonylpiperazine-1-carbonyl)-1-phenylpyrrolidin-2-one | 7.71-7.66 (m, 2H), 7.42-7.36 (m, 2H), 7.19-7.14 (m, 1H), 6.84 (s, 1H), 4.20 (m, 1H), 3.79 (t, J = 8.5, 3H), 3.66 (td, J = 9.4, 6.6, 1H), 3.36 (m, 1H), 3.10 (m, 4H), 2.88 (s, 3H), 2.74-2.65 (m, 1H), 2.14 (dt, J = 12.7, 9.0, 1H). | 2.68 min [368] |

| No. | Structure/name | ¹H NMR (400 MHz, DMSO-d$_6$) δ [ppm] | LC-MS; rt; [M + H⁺] * |
|---|---|---|---|
| "A342" | (S)-3-Hydroxy-2-oxo-1-phenyl-pyrrolidine-3-carboxylic acid (1-methoxymethylpropyl) amide | 7.69 (dd, J = 8.7, 1.0, 2H), 7.51 (t, J = 8.5, 1H), 7.40 (t, J = 7.7, 2H), 7.17 (t, J = 7.4, 1H), 6.67 (d, J = 2.6, 1H), 3.91-3.68 (m, 3H), 3.38-3.32 (m, 1H), 3.30-3.25 (m, 1H), 3.24 (d, J = 2.2, 3H), 2.60-2.50 (m, 2H), 2.09 (dq, J = 12.9, 7.8, 1H), 1.58-1.33 (m, 2H), 0.81 (q, J = 7.5, 3H). | 2.77 min + 2.83 min [307] |
| "A343" | (S)-3-Hydroxy-2-oxo-1-phenyl-pyrrolidine-3-carboxylic acid 4-chlorobenzyl amide | 8.60 (t, J = 6.3, 1H), 7.69 (dt, J = 8.9, 1.7, 2H), 7.43-7.33 (m, 4H), 7.31-7.25 (m, 2H), 7.21-7.13 (m, 1H), 6.70 (s, 1H), 4.31 (dd, J = 15.2, 6.5, 1H), 4.24 (dd, J = 15.2, 6.2, 1H), 3.91-3.76 (m, 2H), 2.56 (ddd, J = 12.8, 7.1, 4.4, 1H), 2.17-2.04 (m, 1H). | 3.93 min [345.0] |
| "A344" | [1-[[(3S)-3-hydroxy-2-oxo-1-phenylpyrrolidine-3-carbonyl]amino]-2-(3-thienyl)ethyl]boronic acid | | HPLC 3.53 min |
| "A345" | (S)-3-Hydroxy-1-(1-methyl-2-oxo-1,2,3,4-tetrahydroquinolin-6-yl)-2-oxopyrrolidine-3-carboxylic acid 3-chloro-5-fluorobenzyl amide | 8.72 (t, J = 6.3, 1H), 7.58 (dd, J = 8.8, 2.4, 1H), 7.54 (s, 1H), 7.30-7.24 (m, 1H), 7.20 (s, 1H), 7.11 (d, J = 8.7, 2H), 6.73 (s, 1H), 4.38 (dd, J = 15.8, 6.7, 1H), 4.24 (dd, J = 15.8, 6.0, 1H), 3.83 (t, J = 6.8, 2H), 3.24 (s, 3H), 2.87 (t, J = 7.3, 2H), 2.63-2.51 (m, 3H), 2.13 (dt, J = 13.0, 7.6, 1H). | 3.67 min [446] |

| No. | Structure/name | ¹H NMR (400 MHz, DMSO-d₆) δ [ppm] | LC-MS; rt; [M + H⁺] * |
|---|---|---|---|
| "A346" | (R)-3-Hydroxy-1-(1-methyl-2-oxo-1,2,3,4-tetrahydroquinolin-6-yl)-2-oxopyrrolidine-3-carboxylic acid 3-chloro-5-fluorobenzyl amide | | 3.67 min [446] |

LCMS:
Method: A—0.1% of TFA in H₂O, B—0.1% of TFA in ACN: flow—2.0 ml/min.
Column: X Bridge C8 (50×4.6 mm.3.5µ)+ve mode

| Time | % B |
|---|---|
| 0 | 05 |
| 8.0 | 100 |
| 8.1 | 100 |
| 8.5 | 05 |
| 10 | 05 |

$

LC-MS method: (instrument: Agilent 1100 series)
Column: Chromolith Speed Rod RP18e-50-4.6
Flow rate: 2.4 ml/min
Solvent A: water+0.05% of HCOOH
Solvent B: acetonitrile+0.04% of HCOOH
WL: 220 nm
Gradient: 0-2.8 min: 4% of B to 100% of B, 2.8-3.3 min: 100% of B.
$$
Method: A—10 mM NH₄HCO₃, B—ACN: flow—1.0 ml/min.
Column: X Bridge C8 (50×4.6 mm.3.5µ)–ve mode

| Time | % B |
|---|---|
| 0 | 05 |
| 8.0 | 100 |
| 8.1 | 100 |
| 8.5 | 05 |
| 10 | 05 |

HPLC:
Method: A—0.1% of TFA in H₂O, B—0.1% of TFA in ACN: flow—2.0 ml/min.
Column: X Bridge C8 (50×4.6 mm.3.5µ)+ve mode

| Time | % B |
|---|---|
| 0 | 5 |
| 8.0 | 100 |
| 8.1 | 100 |
| 8.5 | 5 |
| 10 | 5 |

$$$
Method: isopropanol: flow—0.8 ml/min.
Run time: 20 min
Column: Chiralpak AD

TABLE 1

Inhibition of MetAP-2
IC₅₀ of compounds of the formula I according to the invention

| Compound No. | IC₅₀ enzyme |
|---|---|
| "A1" | A |
| "A2" | C |
| "A3" | B |
| "A4" | A |
| "A5" | A |
| "A6" | B |
| "A7" | A |
| "A8" | B |
| "A9" | B |
| "A10" | C |
| "A11" | A |
| "A12" | C |
| "A13" | C |
| "A14" | C |
| "A15" | C |
| "A16" | B |
| "A17" | A |
| "A18" | A |
| "A19" | B |
| "A20" | A |
| "A21" | A |
| "A22" | A |
| "A23" | A |
| "A24" | B |
| "A25" | C |
| "A26" | C |
| "A27" | A |
| "A28" | A |
| "A29" | A |
| "A30" | A |
| "A31" | A |
| "A32" | A |
| "A33" | A |
| "A34" | C |

TABLE 1-continued

Inhibition of MetAP-2
$IC_{50}$ of compounds of the formula I according to the invention

| Compound No. | $IC_{50}$ enzyme |
|---|---|
| "A35" | C |
| "A36" | B |
| "A37" | A |
| "A38" | A |
| "A39" | C |
| "A40" | A |
| "A41" | B |
| "A42" | C |
| "A43" | C |
| "A44" | B |
| "A45" | C |
| "A46" | A |
| "A47" | A |
| "A48" | A |
| "A49" | A |
| "A50" | A |
| "A51" | A |
| "A52" | A |
| "A53" | C |
| "A54" | A |
| "A55" | A |
| "A56" | A |
| "A57" | A |
| "A58" | A |
| "A59" | A |
| "A60" | C |
| "A61" | C |
| "A62" | A |
| "A63" | A |
| "A64" | B |
| "A65" | A |
| "A66" | A |
| "A67" | B |
| "A68" | B |
| "A69" | A |
| "A70" | C |
| "A71" | A |
| "A72" | C |
| "A73" | B |
| "A74" | C |
| "A75" | C |
| "A76" | C |
| "A77" | B |
| "A78" | B |
| "A79" | C |
| "A80" | |
| "A81" | |
| "A82" | |
| "A83" | |
| "A84" | |
| "A162" | A |
| "A163" | C |
| "A164" | A |
| "A165" | C |
| "A170" | A |
| "A171" | B |
| "A172" | A |
| "A173" | A |
| "A180" | A |
| "A181" | A |
| "A192" | A |
| "A193" | A |
| "A200" | A |
| "A211" | A |
| "A215" | A |
| "A220" | B |
| "A231" | B |
| "A233" | A |
| "A240" | A |
| "A250" | A |
| "A253" | A |
| "A254" | A |
| "A260" | A |
| "A261" | A |
| "A267" | A |
| "A270" | A |
| "A279" | A |
| "A282" | A |
| "A283" | A |
| "A284" | A |
| "A285" | C |
| "A286" | A |
| "A287" | A |
| "A288" | A |
| "A290" | A |
| "A292" | C |
| "A295" | B |
| "A298" | B |
| "A300" | C |
| "A301" | B |
| "A302" | A |
| "A303" | C |
| "A305" | B |
| "A307" | 10 |
| "A308" | C |
| "A310" | A |
| "A316" | B |
| "A320" | A |
| "A321" | C |
| "A323" | B |
| "A324" | A |
| "A326" | B |
| "A329" | B |
| "A333" | C |

$IC_{50}$: 10 nM-1M = A
1M-10M = B
>10M = C

The following examples relate to medicaments:

EXAMPLE A

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

EXAMPLE B

Suppositories

A mixture of 20 g of an active compound of the formula I with 100 g of soya lecithin and 1400 g of cocoa butter is melted, poured into moulds and allowed to cool. Each suppository contains 20 mg of active compound.

EXAMPLE C

Solution

A solution is prepared from 1 g of an active compound of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active compound of the formula I are mixed with 99.5 g of Vaseline under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of active compound.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active compound of the formula I are introduced into hard gelatine capsules in a conventional manner in such a way that each capsule contains 20 mg of the active compound.

EXAMPLE H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

The invention claimed is:
1. A compound of formula I

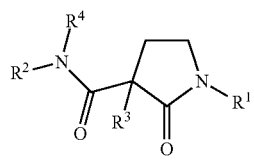

I in which
$R^1$ denotes $[C(R^4)_2]_n Ar^1$, $(CH_2)_n Het$, $(CH_2)_n Cyc$,

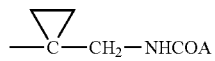

or A,
$R^2$ denotes $[C(R^4)_2]_n Ar^2$, $CH[B(OH)_2]CH_2 Het$, $$—\overset{\triangledown}{C}—Ar^2,$$

$(CH_2)_n Het$, $(CH_2)_n Cyc$, $CH(C\equiv CH)phenyl$ or A,
$R^3$ denotes OH, Hal, $NH_2$, CN, $CF_3$, $CHF_2$ or $N_3$,
$R^4$ denotes H or alkyl having 1, 2, 3 or 4 C atoms, or
$R^2$ and $R^4$ together denote alkylene having 2, 3, 4 or 5 C atoms, where one $CH_2$ group is optionally replaced by NH, NA, N—COA, N—$(CH_2)_n Ar^3$, N—$(CH_2)_n Het^2$, CH-A, CH—O—$(CH_2)_n Ar^3$, N—$SO_2A$ or O and/or is optionally substituted by A,
$Ar^1$ denotes phenyl, naphthyl or biphenyl, each of which is unsubstituted or mono-, di-, tri-, tetra- or pentasubstituted by Hal, A, OH, OA, $NH_2$, NHA, $NA_2$, $NO_2$, CN, COOH, COOA, $CONH_2$, CONHA, $CONA_2$, NHCOA, $NHSO_2A$, COA, CHO, $Het^1$, $SO_2NH_2$ and/or $SO_2A$,
$Ar^2$ denotes phenyl, naphthyl or biphenyl, each of which is unsubstituted or mono-, di-, tri-, tetra- or pentasubstituted by Hal, A, OH, OA, $NH_2$, NHA, $NA_2$, $NO_2$, CN, COOH, COOA, $CONH_2$, CONHA, $CONA_2$, NHCOA, $NHSO_2A$, COA, CHO, $Het^1$, $SO_2NH_2$ and/or $SO_2A$,
$Ar^3$ denotes phenyl, which is unsubstituted or mono-, di- or trisubstituted by Hal, OH, OA and/or A,
Het denotes a mono- or bicyclic saturated, unsaturated or aromatic heterocycle having 1 to 4 N, and/or O and/or S atoms which is unsubstituted or mono-, di- or trisubstituted by Hal, A, OH, OA, $NH_2$, NHA, $NA_2$, $NO_2$, CN, COOH, COOA, $(CH_2)_n CONH_2$, $(CH_2)_n CONHA$, $(CH_2)_n CONA_2$, NHCOA, $NHSO_2A$, COA, CHO, $Het^1$, $SO_2NH_2$, $SO_2A$ and/or =O,
$Het^1$ denotes a monocyclic saturated, unsaturated or aromatic heterocycle having 1 to 4 N, and/or O and/or S atoms which is unsubstituted or mono-, di- or trisubstituted by Hal, A, OH, OA, $NH_2$, NHA, $NA_2$, $NO_2$, CN, COOH and/or COOA,
$Het^2$ denotes pyridyl, pyrimidinyl, furyl, thienyl, imidazolyl, pyrrolyl, oxazolyl, oxadiazolyl, isoxazolyl, thiazolyl, triazolyl, tetrazolyl or thiadiazole,
A denotes unbranched or branched alkyl having 1-10 C atoms, in which 1-7 H atoms are optionally replaced by F, Cl, Br, OH, CHO, COA, COOA, CN, $CONA_2$, CONHA and/or $CONH_2$, and/or in which one or two non-adjacent CH and/or $CH_2$ groups are optionally replaced by O, N and/or $NR^4$, or Cyc,
Cyc denotes cyclic alkyl having 3-7 C atoms,
Hal denotes F, Cl, Br or I,
n denotes 0, 1, 2, 3 or 4,
or a pharmaceutically acceptable salt, tautomer or stereoisomer thereof.
2. A compound according to claim 1, in which
$R^1$ denotes phenyl, benzyl, naphthyl or biphenyl, each of which is unsubstituted or mono-, di-, tri-, tetra- or pentasubstituted by Hal, CN, NHCOA, $NHSO_2A$, $SO_2A$ and/or $CONH_2$; A or $(CH_2)_n Het$,
or a pharmaceutically acceptable salt, tautomer or stereoisomer thereof.
3. A compound according to claim 1, in which
$R^2$ denotes $[C(R^4)_2]_n Ar^2$, $CH[B(OH)_2]CH_2 Het$, $(CH_2)_n Cyc$, $$—\overset{\triangledown}{C}—Ar^2,$$

$CH(C\equiv CH)phenyl$, A or $(CH_2)_n Het$, or a pharmaceutically acceptable salt, tautomer or stereoisomer thereof.

4. A compound according to claim 1, in which
$R^3$ denotes OH, $N_3$, $NH_2$ or F,
or a pharmaceutically acceptable salt, tautomer or stereoisomer thereof.

5. A compound according to claim 1, in which
Het denotes pyridazinyl, pyrazolyl, benzimidazolyl, pyridyl, dibenzofuranyl, carbazolyl, indolyl, dihydroindolyl, benzofuranyl, dihydrobenzofuranyl, 2,3-dihydrobenzo-1,4-dioxinyl, chromanyl, piperazinyl, morpholinyl, tetrahydropyranyl, quinolinyl, isoquinolinyl, isoindolyl, dihydroquinolinyl, dihydroisoquinolinyl, tetrahydroquinolinyl, tetrahydroisoquinolinyl, quinazolinyl, quinoxalinyl, phthalazinyl, purinyl, naphthyridinyl, pyrimidinyl, indazolyl, furyl, thienyl, imidazolyl, pyrrolyl, oxazolyl, oxadiazolyl, isoxazolyl, thiazolyl, triazolyl, tetrazolyl, thiadiazolyl, benzothiazolyl, imidazo[1,2-a]pyridinyl, 1,3-benzodioxolyl, benzoxazolyl, piperidin-1-yl, pyrrolidin-1-yl, 1,2-oxazinan-2-yl, 1,2,5-oxadiazinan-2-yl, 1,3-oxazinan-3-yl or hexahydropyrimidinyl, each of which is unsubstituted or mono-, di- or tri-substituted by A, OA, COOA, COA, CHO, $(CH_2)_nCONH_2$, $(CH_2)_nCONHA$, $(CH_2)_nCONA_2$, $SO_2A$, $NHSO_2A$, =O and/or $Het^1$,
or a pharmaceutically acceptable salt, tautomer or stereoisomer thereof.

6. A compound according to claim 1, in which
$Het^1$ denotes pyridazinyl, pyrazolyl, pyridyl, piperazinyl, morpholinyl, pyrimidinyl, furyl, thienyl, imidazolyl, pyrrolyl, oxazolyl, isoxazolyl, thiazolyl, triazolyl, tetrazolyl, thiadiazole, piperidin-1-yl, pyrrolidin-1-yl, tetrahydropyranyl, 1,2-oxazinan-2-yl, 1,2,5-oxadiazinan-2-yl, 1,3-oxazinan-3-yl or hexahydro-pyrimidinyl, each of which is unsubstituted or mono-, di- or trisubstituted by A and/or OA,
or a pharmaceutically acceptable salt, tautomer or stereoisomer thereof.

7. A compound according to claim 1, in which
$R^1$ denotes phenyl, benzyl, naphthyl or biphenyl, each of which is unsubstituted or mono-, di-, tri-, tetra- or pentasubstituted by Hal, CN, NHCOA, $NHSO_2A$, $SO_2A$ and/or $CONH_2$; A or $(CH_2)_n$Het,
$R^2$ denotes $[C(R^4)_2]_nAr^2$, $(CH_2)_n$Cyc, $CH[B(OH)_2]CH_2$Het,

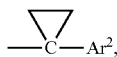

$CH(C\equiv CH)$phenyl, A or $(CH_2)_n$Het, $R^3$ denotes OH, $N_3$, $NH_2$ or F,
$R^4$ denotes H or alkyl having 1, 2, 3 or 4 C atoms, or
$R^2$ and $R^4$ together denote alkylene having 2, 3, 4 or 5 C atoms, in which one $CH_2$ group is optionally replaced by NH, NA, N—COA, N—$(CH_2)_nAr^3$, N—$(CH_2)_nHet^2$, CH-A, CH—O—$(CH_2)_nAr^3$, N—$SO_2A$ or O and/or may be substituted by A,
Het denotes pyridazinyl, pyrazolyl, benzimidazolyl, pyridyl, dibenzofuranyl, carbazolyl, indolyl, dihydroindolyl, benzofuranyl, dihydrobenzofuranyl, 2,3-dihydrobenzo-1,4-dioxinyl, chromanyl, piperazinyl, morpholinyl, tetrahydropyranyl, quinolinyl, isoquinolinyl, isoindolyl, dihydroquinolinyl, dihydroisoquinolinyl, tetrahydroquinolinyl, tetrahydroisoquinolinyl, quinazolinyl, quinoxalinyl, phthalazinyl, purinyl, naphthyridinyl, pyrimidinyl, indazolyl, furyl, thienyl, imidazolyl, pyrrolyl, oxazolyl, oxadiazolyl, isoxazolyl, thiazolyl, triazolyl, tetrazolyl, thiadiazole, benzothiazolyl, imidazo-[1,2-a]pyridinyl, 1,3-benzodioxolyl, benzoxazolyl, piperidin-1-yl, pyrrolidin-1-yl, 1,2-oxazinan-2-yl, 1,2,5-oxadiazinan-2-yl, 1,3-oxazinan-3-yl or hexahydropyrimidinyl, each of which is unsubstituted or mono-, di- or trisubstituted by A, OA, COOA, COA, CHO, $(CH_2)_nCONH_2$, $(CH_2)_nCONHA$, $(CH_2)_nCONA_2$, $SO_2A$, $NHSO_2A$, =O and/or $Het^1$,
$Het^1$ denotes pyridazinyl, pyrazolyl, pyridyl, piperazinyl, morpholinyl, pyrimidinyl, furyl, thienyl, imidazolyl, pyrrolyl, oxazolyl, isoxazolyl, thiazolyl, triazolyl, tetrazolyl, thiadiazole, piperidin-1-yl, pyrrolidin-1-yl, tetrahydropyranyl, 1,2-oxazinan-2-yl, 1,2,5-oxadiazinan-2-yl, 1,3-oxazinan-3-yl or hexahydro-pyrimidinyl, each of which is unsubstituted or mono-, di- or trisubstituted by A and/or OA,
$Het^2$ denotes pyridyl, pyrimidinyl, furyl, thienyl, imidazolyl, pyrrolyl, oxazolyl, oxadiazolyl, isoxazolyl, thiazolyl, triazolyl, tetrazolyl or thiadiazole,
A denotes unbranched or branched alkyl having 1-10 C atoms, in which 1-7 H atoms are optionally replaced by F, Cl, Br, OH, CHO, COA, COOA, CN, $CONA_2$, CONHA and/or $CONH_2$, and/or in which one or two non-adjacent CH and/or $CH_2$ groups are optionally replaced by O, N and/or $NR^4$, or Cyc,
$Ar^2$ denotes phenyl, which is unsubstituted or mono-, di-, tri-, tetra- or pentasubstituted by A, Hal, CN, OH and/or OA,
$Ar^3$ denotes phenyl, which is unsubstituted or mono-, di- or trisubstituted by Hal, OH, OA and/or A,
Cyc denotes cyclic alkyl having 3-7 C atoms,
Hal denotes F, Cl, Br or I,
n denotes 0, 1, 2, 3 or 4,
or a pharmaceutically acceptable salt, tautomer or stereoisomer thereof.

8. A compound, which is one of the following compounds

| Compound No. | Structure/name |
|---|---|
| "A1" | -3-Hydroxy-2-oxo-1-phenylpyrrolidine-3-carboxylic acid 3-bromobenzyl amide |

-continued

| Compound No. | Structure/name |
|---|---|
| "A2" | 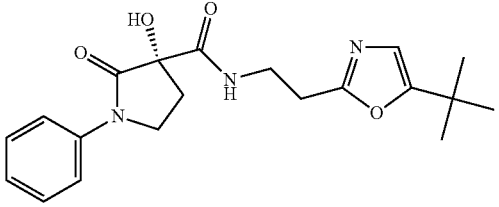<br>(S)-3-Hydroxy-2-oxo-1-phenylpyrrolidine-3-carboxylic acid [2-(5-tert-butyloxazol-2-yl)ethyl] amide |
| "A3" | 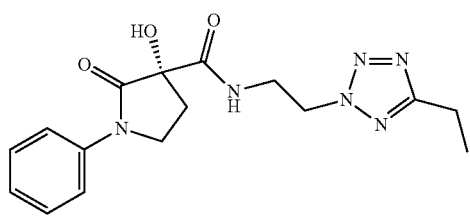<br>(S)-3-Hydroxy-2-oxo-1-phenylpyrrolidine-3-carboxylic acid [2-(5-ethyltetrazol-2-yl)ethyl] amide |
| "A4" | 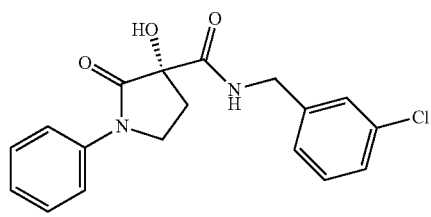<br>(S)-3-Hydroxy-2-oxo-1-phenylpyrrolidine-3-carboxylic acid 3-chlorobenzyl amide |
| "A5" | 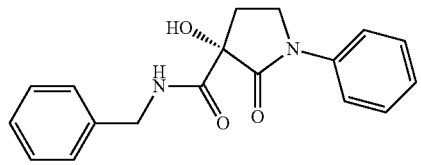<br>(S)-3-Hydroxy-2-oxo-1-phenylpyrrolidine-3-carboxylic acid benzyl amide |
| "A6" | 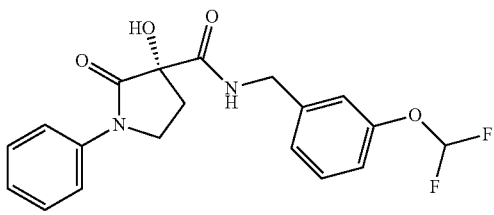<br>(S)-3-Hydroxy-2-oxo-1-phenylpyrrolidine-3-carboxylic acid 3-difluoromethoxybenzyl amide |

| Compound No. | Structure/name |
|---|---|
| "A7" | 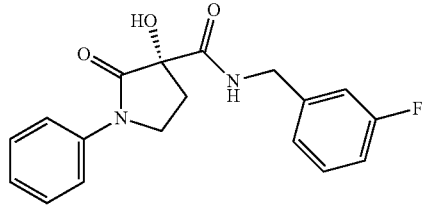<br>(S)-3-Hydroxy-2-oxo-1-phenylpyrrolidine-3-carboxylic acid 3-fluorobenzyl amide |
| "A8" | 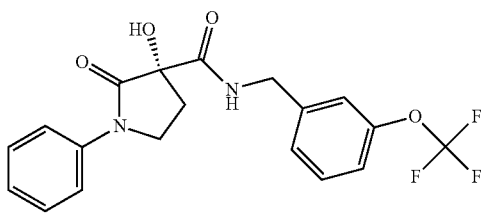<br>(S)-3-Hydroxy-2-oxo-1-phenylpyrrolidine-3-carboxylic acid 3-trifluoromethoxybenzyl amide |
| "A9" | 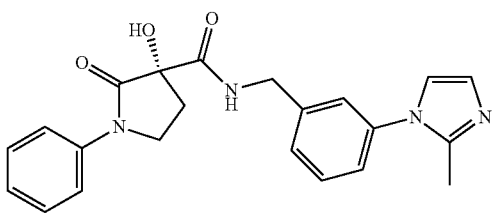<br>(S)-3-Hydroxy-2-oxo-1-phenylpyrrolidine-3-carboxylic acid 3-(2-methylimidazol-1-yl)benzyl amide |
| "A10" | 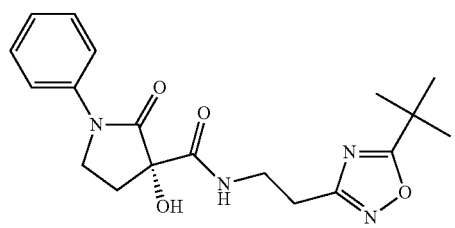<br>(S)-3-Hydroxy-2-oxo-1-phenylpyrrolidine-3-carboxylic acid [2-(5-tert-butyl-1,2,4-oxadiazol-3-yl)ethyl] amide |
| "A11" | 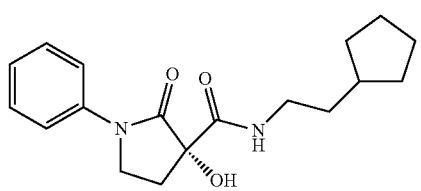<br>(S)-3-Hydroxy-2-oxo-1-phenylpyrrolidine-3-carboxylic acid (2-cyclopentylethyl) amide |

| Compound No. | Structure/name |
|---|---|
| "A12" | 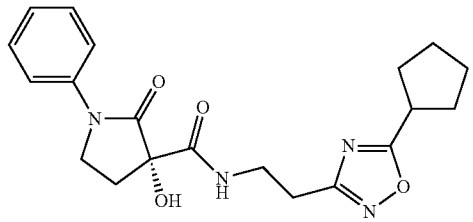<br>(S)-3-Hydroxy-2-oxo-1-phenylpyrrolidine-3-carboxylic acid [2-(5-cyclopentyl-1,2,4-oxadiazol-3-yl)ethyl] amide |
| "A13" | 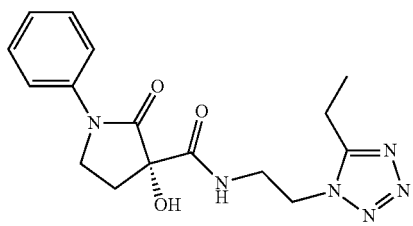<br>(S)-3-Hydroxy-2-oxo-1-phenylpyrrolidine-3-carboxylic acid [2-(5-ethyltetrazol-1-yl)ethyl] amide |
| "A14" | 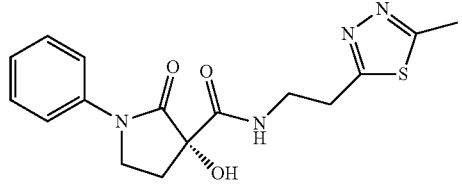<br>(S)-3-Hydroxy-2-oxo-1-phenylpyrrolidine-3-carboxylic acid [2-(5-methyl-1,3,4-thiadiazol-2-yl)ethyl] amide |
| "A15" | 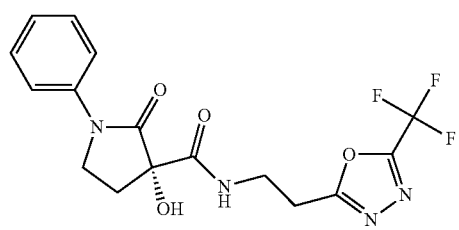<br>(S)-3-Hydroxy-2-oxo-1-phenylpyrrolidine-3-carboxylic acid [2-(5-trifluoromethyl-1,3,4-oxadiazol-2-yl)ethyl] amide |
| "A16" | 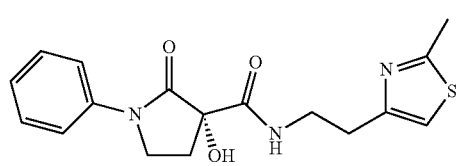<br>(S)-3-Hydroxy-2-oxo-1-phenylpyrrolidine-3-carboxylic acid [2-(2-methylthiazol-4-yl)ethyl] amide |

| Compound No. | Structure/name |
|---|---|
| "A17" | 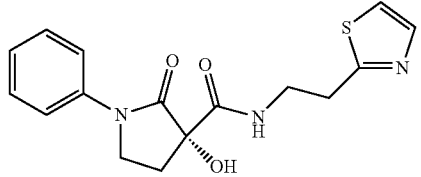<br>(S)-3-Hydroxy-2-oxo-1-phenylpyrrolidine-3-carboxylic acid (2-thiazol-2-ylethyl) amide |
| "A18" | 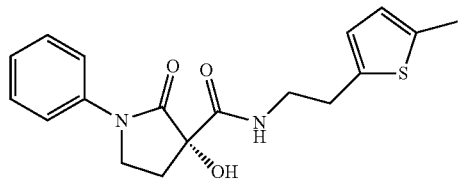<br>(S)-3-Hydroxy-2-oxo-1-phenylpyrrolidine-3-carboxylic acid [2-(5-methylthiophen-2-yl)ethyl] amide |
| "A19" | 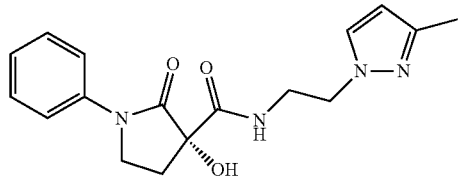<br>(S)-3-Hydroxy-2-oxo-1-phenylpyrrolidine-3-carboxylic acid [2-(3-methylpyrazol-1-yl)ethyl] amide |
| "A20" | 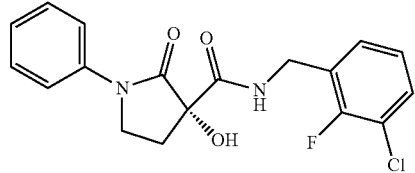<br>(S)-3-Hydroxy-2-oxo-1-phenylpyrrolidine-3-carboxylic acid 3-chloro-2-fluorobenzyl amide |
| "A21" | 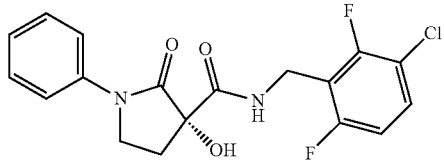<br>(S)-3-Hydroxy-2-oxo-1-phenylpyrrolidine-3-carboxylic acid 3-chloro-2,6-difluorobenzyl amide |
| "A22" | 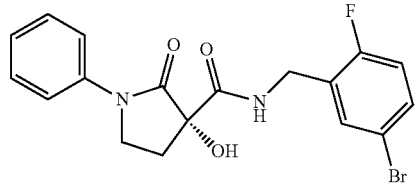<br>(S)-3-Hydroxy-2-oxo-1-phenylpyrrolidine-3-carboxylic acid 5-bromo-2-fluorobenzyl amide |

-continued

| Compound No. | Structure/name |
|---|---|
| "A23" | 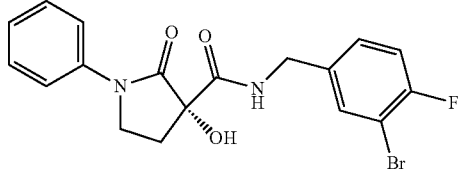<br>(S)-3-Hydroxy-2-oxo-1-phenylpyrrolidine-3-carboxylic acid 3-bromo-4-fluorobenzyl amide |
| "A24" | 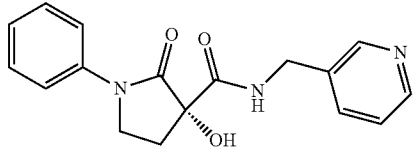<br>(S)-3-Hydroxy-2-oxo-1-phenylpyrrolidine-3-carboxylic acid (pyridin-3-ylmethyl) amide |
| "A25" | 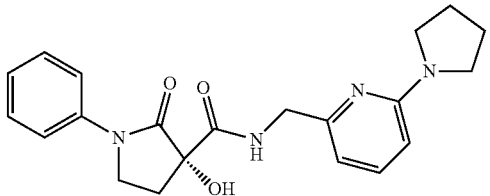<br>(S)-3-Hydroxy-2-oxo-1-phenylpyrrolidine-3-carboxylic acid (6-pyrrolidin-1-ylpyridin-2-ylmethyl) amide |
| "A26" | 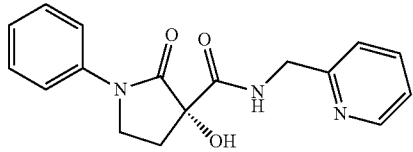<br>(S)-3-Hydroxy-2-oxo-1-phenylpyrrolidine-3-carboxylic acid (pyridin-2-ylmethyl) amide |
| "A27" | 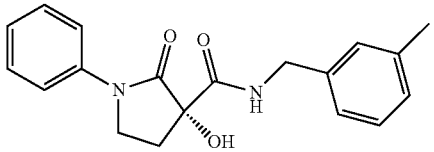<br>(S)-3-Hydroxy-2-oxo-1-phenylpyrrolidine-3-carboxylic acid 3-methylbenzyl amide |
| "A28" | 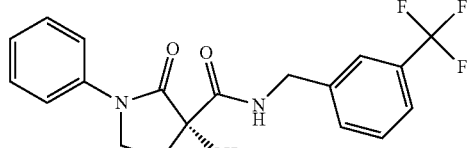<br>(S)-3-Hydroxy-2-oxo-1-phenylpyrrolidine-3-carboxylic acid 3-trifluoromethylbenzyl amide |

| Compound No. | Structure/name |
|---|---|
| "A29" | 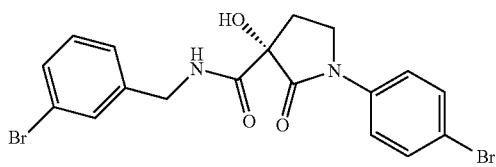<br>(S)-1-(4-Bromophenyl)-3-hydroxy-2-oxopyrrolidine-3-carboxylic acid 3-bromobenzyl amide |
| "A30" | 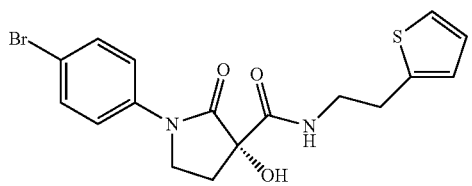<br>(S)-1-(4-Bromophenyl)-3-hydroxy-2-oxopyrrolidine-3-carboxylic acid (2-thiophen-2-ylethyl) amide |
| "A31" | 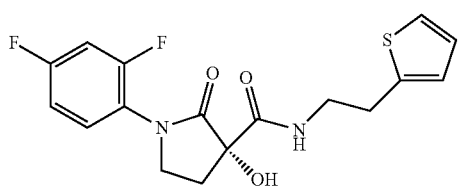<br>(S)-1-(2,4-Difluorophenyl)-3-hydroxy-2-oxopyrrolidine-3-carboxylic acid (2-thiophen-2-ylethyl) amide |
| "A32" | 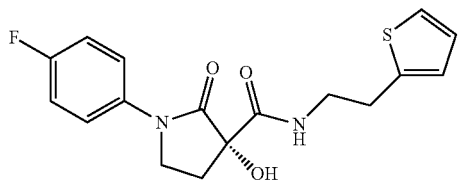<br>(S)-1-(4-Fluorophenyl)-3-hydroxy-2-oxopyrrolidine-3-carboxylic acid (2-thiophen-2-ylethyl) amide |
| "A33" | 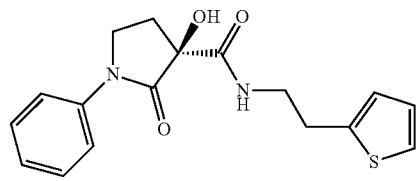<br>(S)-3-Hydroxy-2-oxo-1-phenylpyrrolidine-3-carboxylic acid (2-thiophen-2-ylethyl) amide |

| Compound No. | Structure/name |
|---|---|
| "A34" | 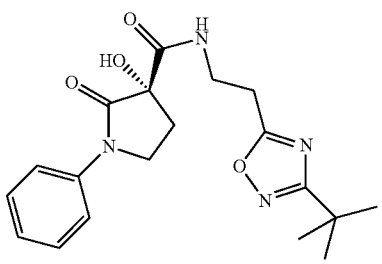<br>(S)-3-Hydroxy-2-oxo-1-phenylpyrrolidine-3-carboxylic acid [2-(3-tert-butyl-1,2,4-oxadiazol-5-yl)ethyl] amide |
| "A35" | 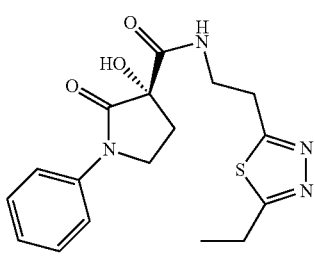<br>(S)-3-Hydroxy-2-oxo-1-phenylpyrrolidine-3-carboxylic acid [2-(5-ethyl-1,3,4-thiadiazol-2-yl)ethyl] amide |
| "A36" | 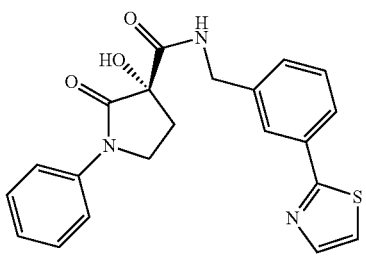<br>(S)-3-Hydroxy-2-oxo-1-phenylpyrrolidine-3-carboxylic acid 3-thiazol-2-ylbenzyl amide |
| "A37" | 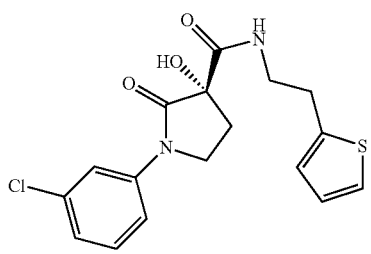<br>(S)-1-(3-Chlorophenyl)-3-hydroxy-2-oxopyrrolidine-3-carboxylic acid (2-thiophen-2-ylethyl) amide |

| Compound No. | Structure/name |
|---|---|
| "A38" | 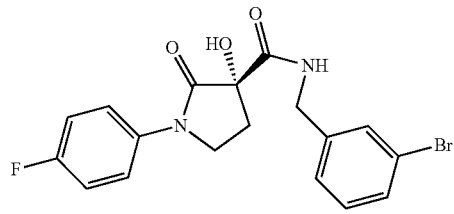<br>(S)-1-(4-Fluorophenyl)-3-hydroxy-2-oxopyrrolidine-3-carboxylic acid 3-bromobenzyl amide |
| "A39" | 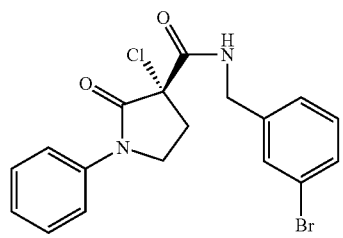<br>(S)-3-Chloro-2-oxo-1-phenylpyrrolidine-3-carboxylic acid 3-bromobenzyl amide |
| "A40" | 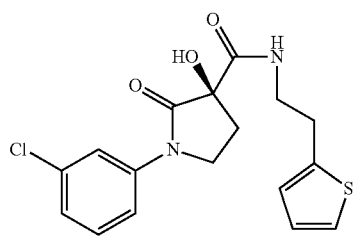<br>(R)-1-(3-Chlorophenyl)-3-hydroxy-2-oxopyrrolidine-3-carboxylic acid (2-thiophen-2-ylethyl) amide |
| "A41" | 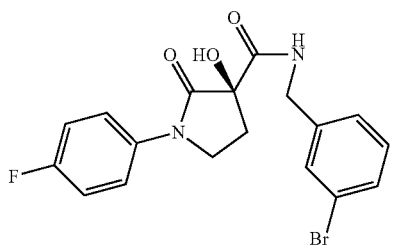<br>(R)-1-(4-Fluorophenyl)-3-hydroxy-2-oxopyrrolidine-3-carboxylic acid 3-bromobenzyl amide |
| "A42" | 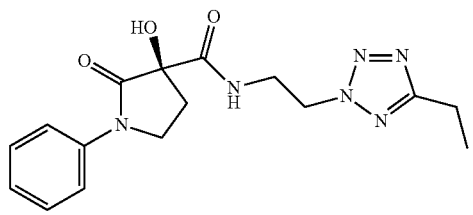<br>(R)-3-Hydroxy-2-oxo-1-phenylpyrrolidine-3-carboxylic acid [2-(5-ethyltetrazol-2-yl)ethyl] amide |

| Compound No. | Structure/name |
|---|---|
| "A43" | 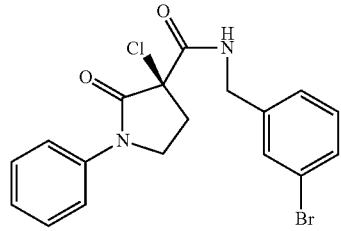<br>(R)-3-Chloro-2-oxo-1-phenylpyrrolidine-3-carboxylic acid 3-bromobenzyl amide |
| "A44" | 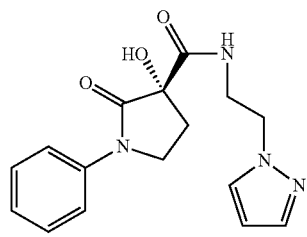<br>(S)-3-Hydroxy-2-oxo-1-phenylpyrrolidine-3-carboxylic acid (2-pyrazol-1-ylethyl) amide |
| "A45" | 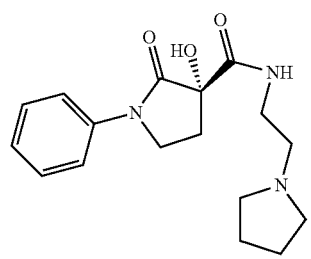<br>(S)-3-Hydroxy-2-oxo-1-phenylpyrrolidine-3-carboxylic acid (2-pyrrolidin-1-ylethyl) amide |
| "A46" | 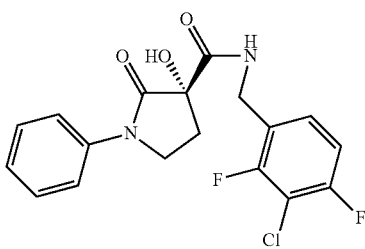<br>(S)-3-Hydroxy-2-oxo-1-phenylpyrrolidine-3-carboxylic acid 3-chloro-2,4-difluorobenzyl amide |

| Compound No. | Structure/name |
|---|---|
| "A47" | 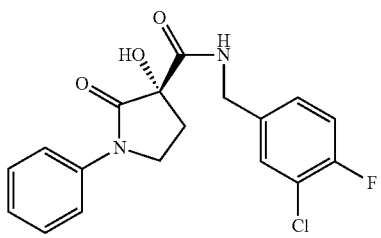<br>(S)-3-Hydroxy-2-oxo-1-phenylpyrrolidine-3-carboxylic acid 3-chloro-4-fluorobenzyl amide |
| "A48" | 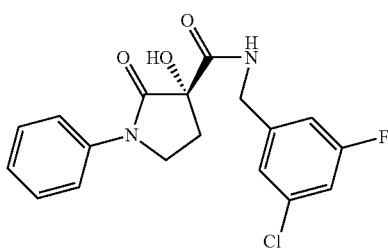<br>(S)-3-Hydroxy-2-oxo-1-phenylpyrrolidine-3-carboxylic acid 3-chloro-5-fluorobenzyl amide |
| "A49" | 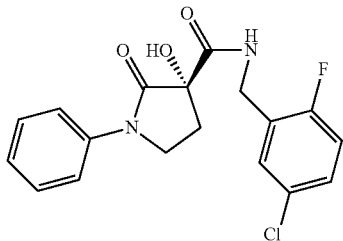<br>(S)-3-Hydroxy-2-oxo-1-phenylpyrrolidine-3-carboxylic acid 5-chloro-2-fluorobenzyl amide |
| "A50" | 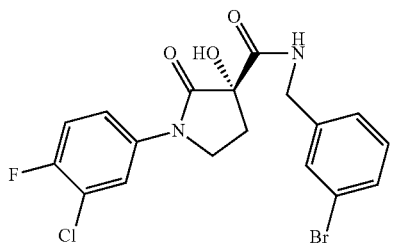<br>(S)-1-(3-Chloro-4-fluorophenyl)-3-hydroxy-2-oxopyrrolidine-3-carboxylic acid 3-bromobenzyl amide |

| Compound No. | Structure/name |
|---|---|
| "A51" | 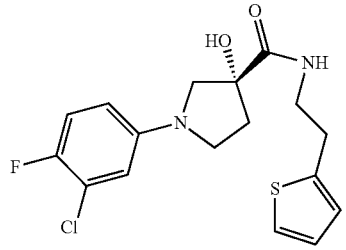<br>(S)-1-(3-Chloro-4-fluorophenyl)-3-hydroxy-2-oxopyrrolidine-3-carboxylic acid (2-thiophen-2-ylethyl) amide |
| "A52" | 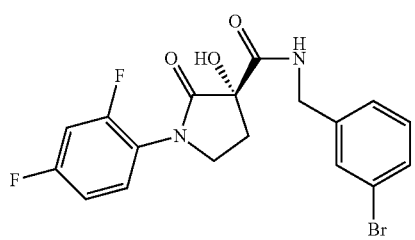<br>(S)-1-(2,4-Difluorophenyl)-3-hydroxy-2-oxopyrrolidine-3-carboxylic acid 3-bromobenzyl amide |
| "A53" | 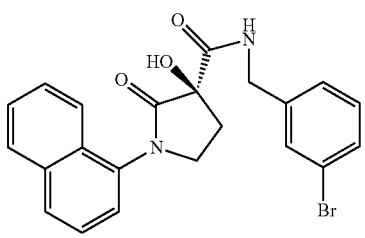<br>(R)-3-Hydroxy-1-naphthalen-1-yl-2-oxopyrrolidine-3-carboxylic acid 3-bromobenzyl amide |
| "A54" | 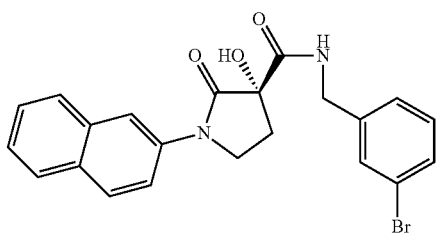<br>(S)-3-Hydroxy-1-naphthalen-2-yl-2-oxopyrrolidine-3-carboxylic acid 3-bromobenzyl amide |

-continued

| Compound No. | Structure/name |
|---|---|
| "A55" | 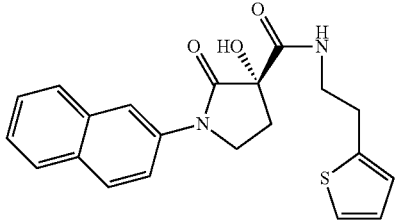<br>(S)-3-Hydroxy-1-naphthalen-2-yl-2-oxopyrrolidine-3-carboxylic acid (2-thiophen-2-ylethyl) amide |
| "A56" | 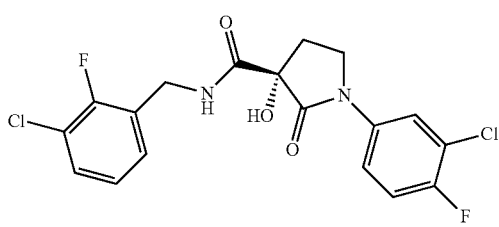<br>(S)-1-(3-Chloro-4-fluorophenyl)-3-hydroxy-2-oxopyrrolidine-3-carboxylic acid 3-chloro-2-fluorobenzyl amide |
| "A57" | 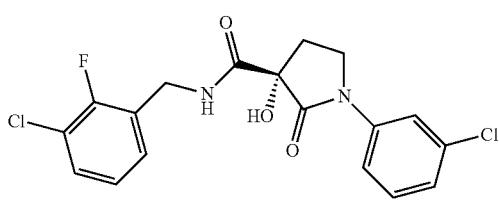<br>(S)-1-(3-Chlorophenyl)-3-hydroxy-2-oxopyrrolidine-3-carboxylic acid 3-chloro-2-fluorobenzyl amide |
| "A58" | 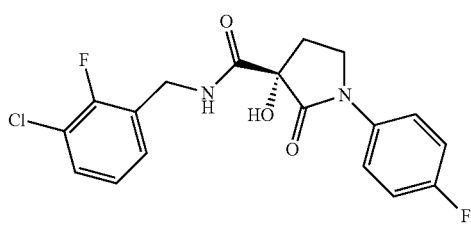<br>(S)-1-(4-Fluorophenyl)-3-hydroxy-2-oxopyrrolidine-3-carboxylic acid 3-chloro-2-fluorobenzyl amide |
| "A59" | 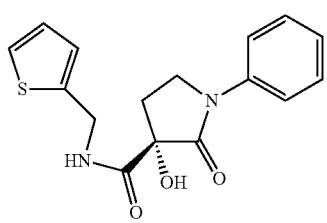<br>(S)-3-Hydroxy-2-oxo-1-phenylpyrrolidine-3-carboxylic acid (thiophen-2-ylmethyl) amide |

| Compound No. | Structure/name |
|---|---|
| "A60" | 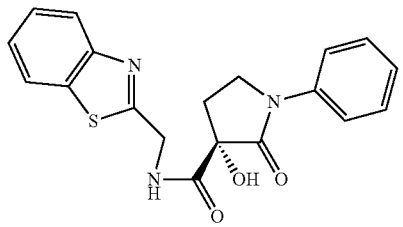<br>(S)-3-Hydroxy-2-oxo-1-phenylpyrrolidine-3-carboxylic acid (benzothiazol-2-ylmethyl) amide |
| "A61" | 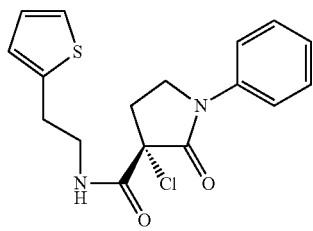<br>(S)-3-Chloro-2-oxo-1-phenylpyrrolidine-3-carboxylic acid (2-thiophen-2-ylethyl) amide |
| "A62" | 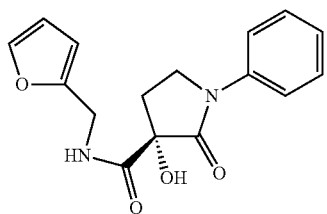<br>(S)-3-Hydroxy-2-oxo-1-phenylpyrrolidine-3-carboxylic acid (furan-2-ylmethyl) amide |
| "A63" | 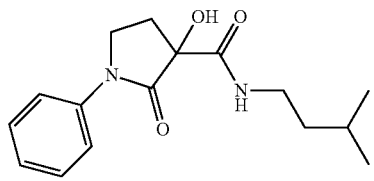<br>3-Hydroxy-2-oxo-1-phenylpyrrolidine-3-carboxylic acid (3-methylbutyl) amide |
| "A64" | 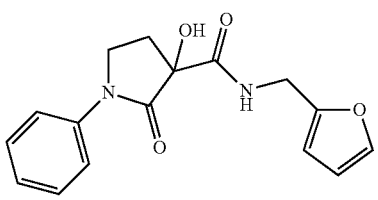<br>3-Hydroxy-2-oxo-1-phenylpyrrolidine-3-carboxylic acid (furan-2-ylmethyl) amide |

| Compound No. | Structure/name |
|---|---|
| "A65" | 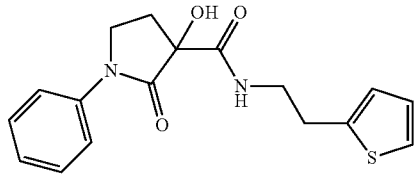<br>3-Hydroxy-2-oxo-1-phenylpyrrolidine-3-carboxylic acid (2-thiophen-2-ylethyl) amide |
| "A66" | 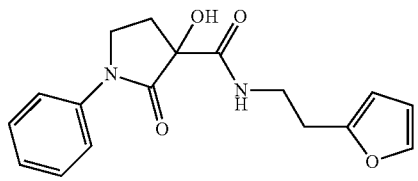<br>3-Hydroxy-2-oxo-1-phenylpyrrolidine-3-carboxylic acid (2-furan-2-ylethyl) amide |
| "A67" | 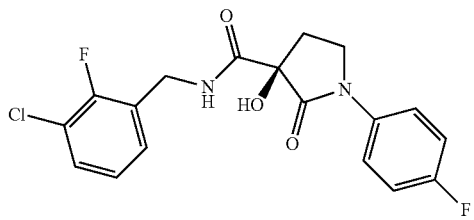<br>(R)-1-(4-Fluorophenyl)-3-hydroxy-2-oxopyrrolidine-3-carboxylic acid 3-chloro-2-fluorobenzyl amide |
| "A68" | 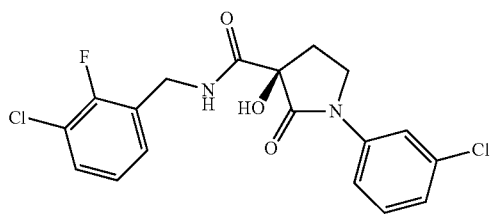<br>(R)-1-(3-Chlorophenyl)-3-hydroxy-2-oxopyrrolidine-3-carboxylic acid 3-chloro-2-fluorobenzyl amide |
| "A69" | 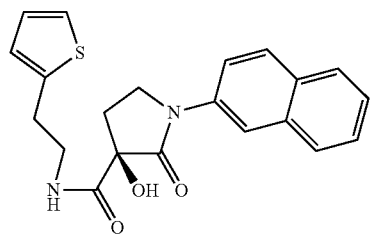<br>(R)-3-Hydroxy-1-naphthalen-2-yl-2-oxopyrrolidine-3-carboxylic acid (2-thiophen-2-ylethyl) amide |

| Compound No. | Structure/name |
|---|---|
| "A70" | 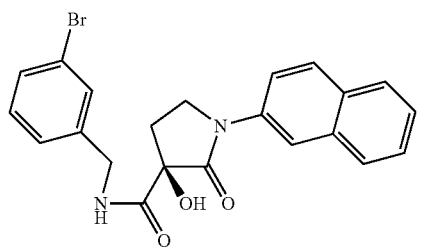<br>(R)-3-Hydroxy-1-naphthalen-2-yl-2-oxopyrrolidine-3-carboxylic acid 3-bromobenzyl amide |
| "A71" | 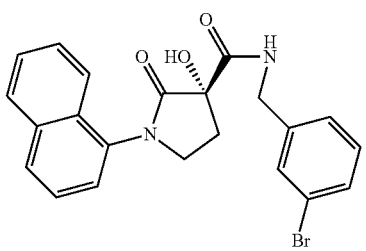<br>(S)-3-Hydroxy-1-naphthalen-1-yl-2-oxopyrrolidine-3-carboxylic acid 3-bromobenzyl amide |
| "A72" | 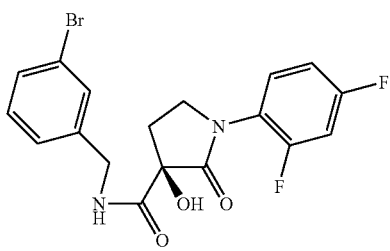<br>(R)-1-(2,4-Difluorophenyl)-3-hydroxy-2-oxopyrrolidine-3-carboxylic acid 3-bromobenzyl amide |
| "A73" | 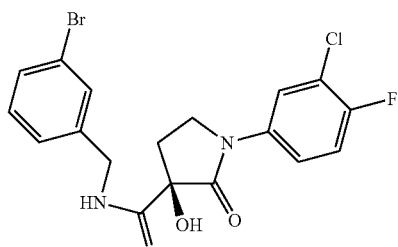<br>(R)-1-(3-Chloro-4-fluorophenyl)-3-hydroxy-2-oxopyrrolidine-3-carboxylic acid 3-bromobenzyl amide |

-continued

| Compound No. | Structure/name |
|---|---|
| "A74" | 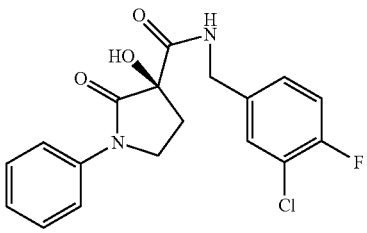<br>(R)-3-Hydroxy-2-oxo-1-phenylpyrrolidine-3-carboxylic acid 3-chloro-4-fluorobenzyl amide |
| "A75" | 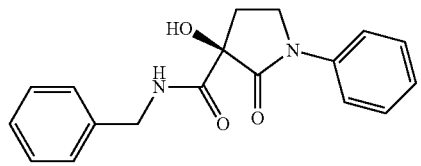<br>(R)-3-Hydroxy-2-oxo-2-phenylpyrrolidine-3-carboxylic acid benzyl amide |
| "A76" | 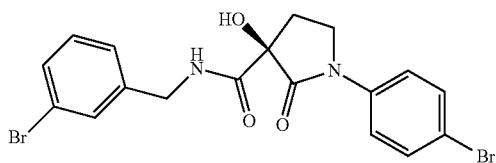<br>(R)-1-(4-Bromophenyl)-3-hydroxy-2-oxopyrrolidine-3-carboxylic acid 3-bromobenzyl amide |
| "A77" | 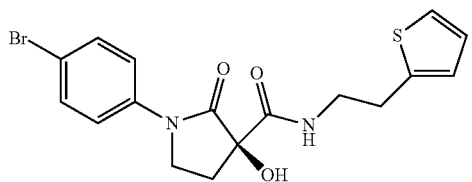<br>(R)-1-(4-Bromophenyl)-3-hydroxy-2-oxopyrrolidine-3-carboxylic acid (2-thiophen-2-ylethyl) amide |
| "A78" | 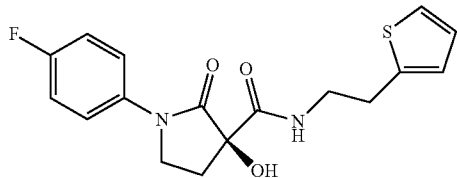<br>(R)-1-(4-Fluorophenyl)-3-hydroxy-2-oxopyrrolidine-3-carboxylic acid (2-thiophen-2-ylethyl) amide |
| "A79" | 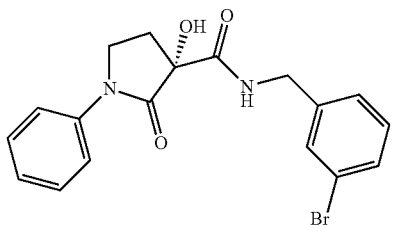<br>(R)-3-Hydroxy-2-oxo-1-phenylpyrrolidine-3-carboxylic acid 3-bromobenzyl amide |

| Compound No. | Structure/name |
|---|---|
| "A80" | 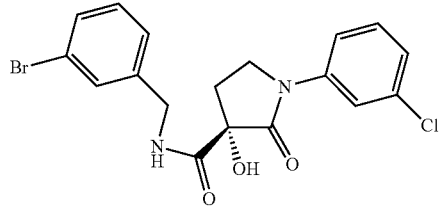<br>(S)-1-(3-Chlorophenyl)-3-hydroxy-2-oxopyrrolidine-3-carboxyl acid 3-bromobenzy] amide |
| "A81" | 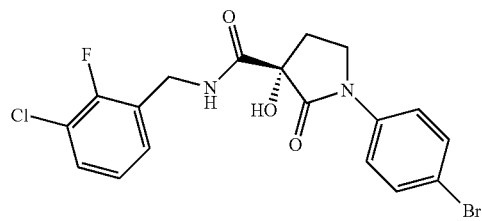<br>(S)-1-(4-Bromophenyl)-3-hydroxy-2-oxopyrrolidine-3-carboxylic acid 3-chloro-2-fluorobenzyl amide |
| "A82" | 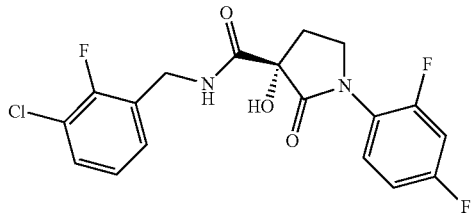<br>(S)-1-(2,4-Difluorophenyl)-3-hydroxy-2-oxopyrrolidine-3-carboxylic acid 3-chloro-2-fluorobenzyl amide |
| "A83" | 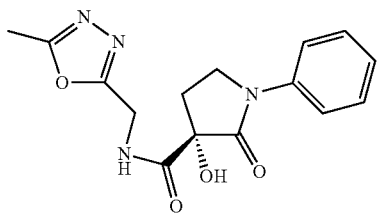<br>(S)-3-Hydroxy-2-oxo-1-phenylpyrrolidine-3-carboxylic acid (5-methyl-1,3,4-oxadiazol-2-ylmethyl) amide |
| "A84" | 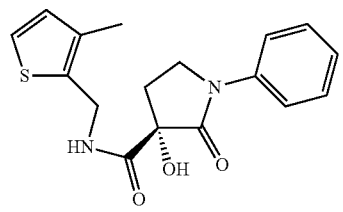<br>(S)-3-Hydroxy-2-oxo-1-phenylpyrrolidine-3-carboxylic acid (3-methylthiophen-2-ylmethyl) amide |

-continued

| Compound No. | Structure/name |
|---|---|
| "A85" | 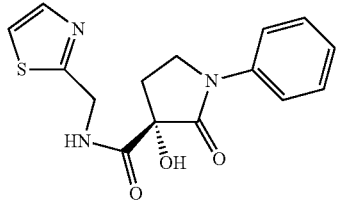<br>(S)-3-Hydroxy-2-oxo-1-phenylpyrrolidine-3-carboxylic acid (thiazol-2-ylmethyl) amide |
| "A86" | 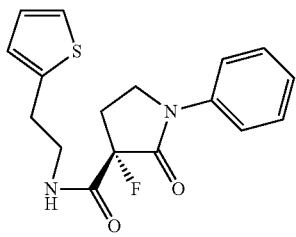<br>(S)-3-Fluoro-2-oxo-1-phenylpyrrolidine-3-carboxylic acid (2-thiophen-2-ylethyl) amide |
| "A87" | 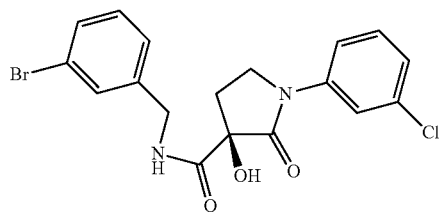<br>(R)-1-(3-Chlorophenyl)-3-hydroxy-2-oxopyrrolidine-3-carboxylic acid 3-bromobenzyl amide |
| "A88" | 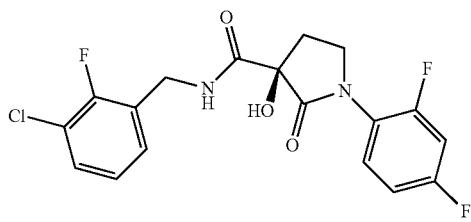<br>(R)-1-(2,4-Difluorophenyl)-3-hydroxy-2-oxopyrrolidine-3-carboxylic acid 3-chloro-2-fluorobenzyl amide |
| "A89" | 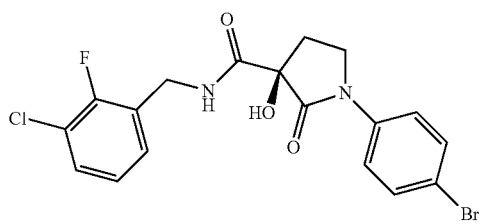<br>(R)-1-(4-Bromophenyl)-3-hydroxy-2-oxopyrrolidine-3-carboxylic acid 3-chloro-2 fluorobenzyl amide |

| Compound No. | Structure/name |
|---|---|
| "A90" | 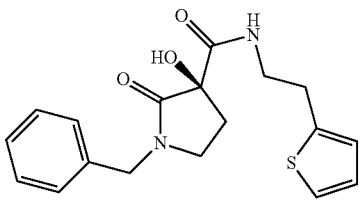<br>(R)-1-Benzyl-3-hydroxy-2-oxopyrrolidine-3-carboxylic acid (2-thiophen-2-ylethyl) amide |
| "A91" | 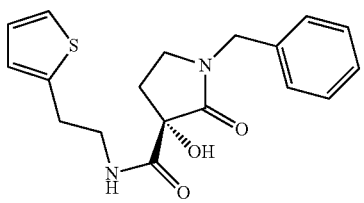<br>(S)-1-Benzyl-3-hydroxy-2-oxopyrrolidine-3-carboxylic acid (2-thiophen-2-ylethyl) amide |
| "A91a" | (S)-3-Amino-2-oxo-1-phenylpyrrolidine-3-carboxylic acid (3-chloro-5-fluorobenzyl) amide |
| "A92" | 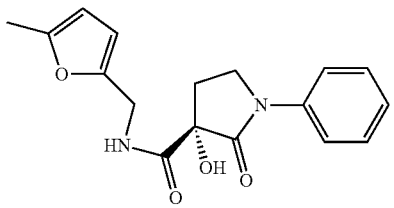<br>(S)-3-Hydroxy-2-oxo-1-phenylpyrrolidine-3-carboxylic acid (5-methylfuran-2-ylmethyl) amide |
| "A93" | 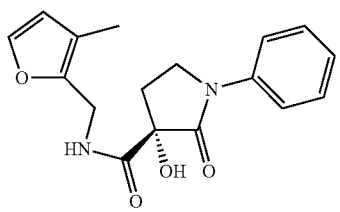<br>(S)-3-Hydroxy-2-oxo-1-phenylpyrrolidine-3-carboxylic acid (3-methylfuran-2-ylmethyl) amide |
| "A94" | 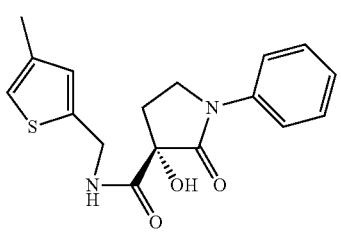<br>(S)-3-Hydroxy-2-oxo-1-phenylpyrrolidine-3-carboxylic acid (4-methylthiophen-2-ylmethyl) amide |

-continued

| Compound No. | Structure/name |
|---|---|
| "A95" | 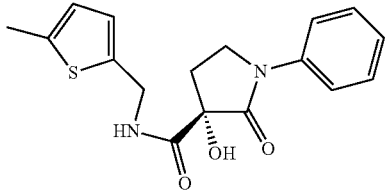<br>(S)-3-Hydroxy-2-oxo-1-phenylpyrrolidine-3-carboxylic acid (5-methylthiophen-2-ylmethyl) amide |
| "A96" | 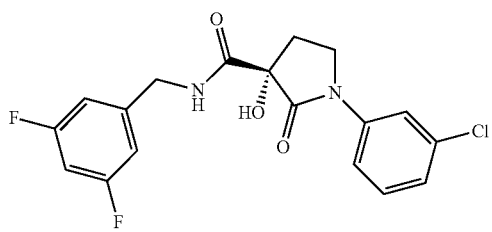<br>(S)-1-(3-Chlorophenyl)-3-hydroxy-2-oxopyrrolidine-3-carboxylic acid 3,5-difluorobenzyl amide |
| "A97" | 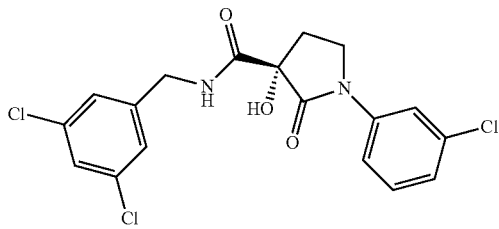<br>(S)-1-(3-Chlorophenyl)-3-hydroxy-2-oxopyrrolidine-3-carboxylic acid 3,5-dichlorobenzyl amide |
| "A98" | 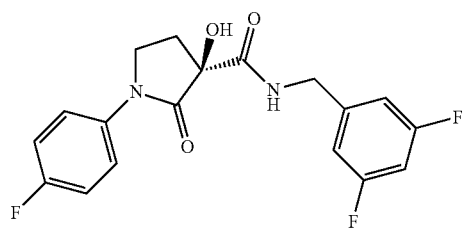<br>(S)-1-(4-Fluorophenyl)-3-hydroxy-2-oxopyrrolidine-3-carboxylic acid 3,5-difluorobenzyl amide |
| "A99" | 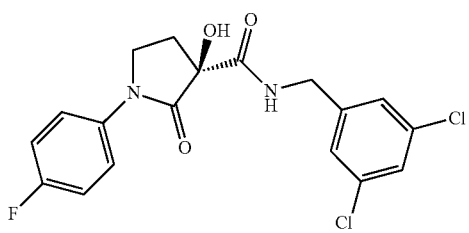<br>(S)-1-(4-Fluorophenyl)-3-hydroxy-2-oxopyrrolidine-3-carboxylic acid 3,5-dichlorobenzyl amide |

-continued

| Compound No. | Structure/name |
|---|---|
| "A100" | 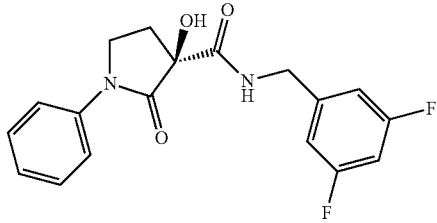<br>(S)-3-Hydroxy-2-oxo-1-phenylpyrrolidine-3-carboxylic acid 3,5-difluorobenzyl amide |
| "A101" | 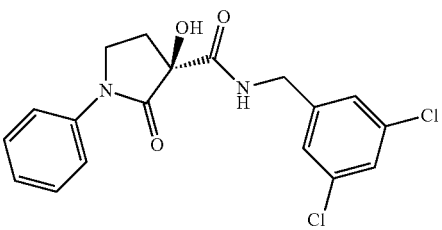<br>(S)-3-Hydroxy-2-oxo-1-phenylpyrrolidine-3-carboxylic acid 3,5-dichlorobenzyl amide |
| "A102" | 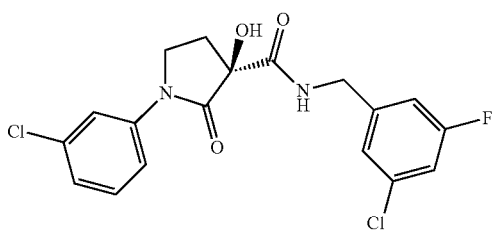<br>(S)-1-(3-Chlorophenyl)-3-hydroxy-2-oxopyrrolidine-3-carboxylic acid 3-chloro-5-fluorobenzyl amide |
| "A103" | 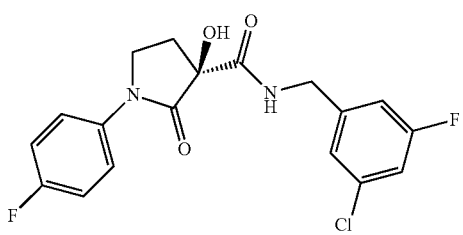<br>(S)-1-(4-Fluorophenyl)-3-hydroxy-2-oxopyrrolidine-3-carboxylic acid 3-chloro-5-fluorobenzyl amide |
| "A104" | 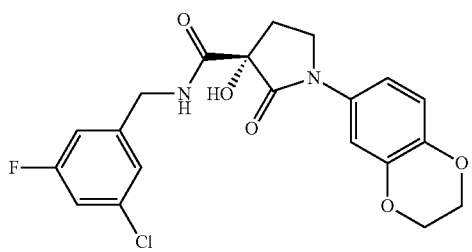<br>(S)-1-(2,3-Dihydrobenzo-1,4-dioxin-6-yl)-3-hydroxy-2-oxo-pyrrolidine-3-carboxylic acid 3-chloro-5-fluorobenzyl amide |

| Compound No. | Structure/name |
|---|---|
| "A105" | 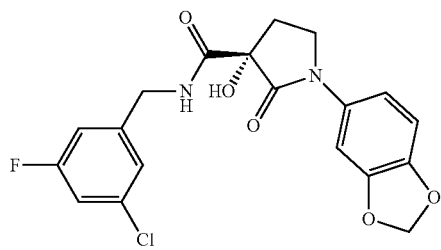<br>(S)-1-Benzo-1,3-dioxol-5-yl-3-hydroxy-2-oxopyrrolidine-3-carboxylic acid 3-chloro-5-fluorobenzyl amide |
| "A106" | 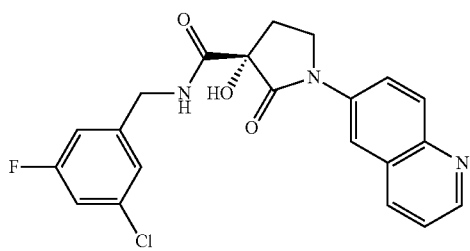<br>(S)-3-Hydroxy-2-oxo-1-quinolin-6-ylpyrrolidine-3-carboxylic acid 3-chloro-5-fluorobenzyl amide |
| "A107" | 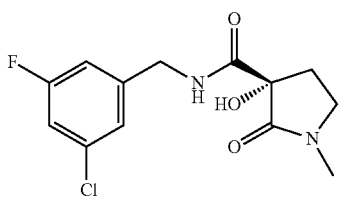<br>(S)-3-Hydroxy-1-methyl-2-oxopyrrolidine-3-carboxylic acid 3-chloro-5-fluorobenzyl amide |
| "A108" | 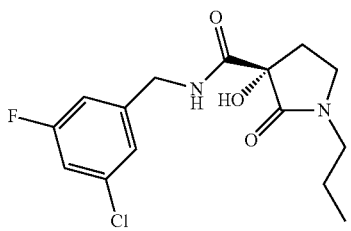<br>(S)-3-Hydroxy-2-oxo-1-propylpyrrolidine-3-carboxylic acid 3-chloro-5-fluorobenzyl amide |
| "A109" | 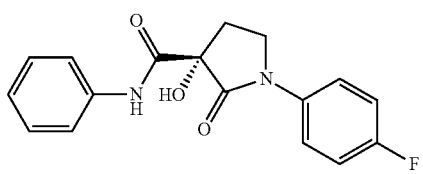<br>(S)-1-(4-Fluorophenyl)-3-hydroxy-2-oxopyrrolidine-3-carboxylic acid phenyl amide |

| Compound No. | Structure/name |
|---|---|
| "A110" | 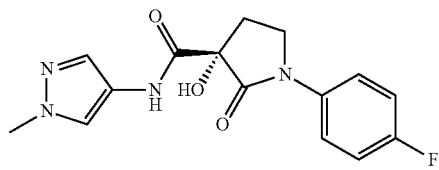<br>(S)-1-(4-Fuorophenyl)-3-hydroxy-2-oxopyrrolidine-<br>3-carboxylic acid (1-methyl-1H-pyrazol-4-yl) amide |
| "A111" | 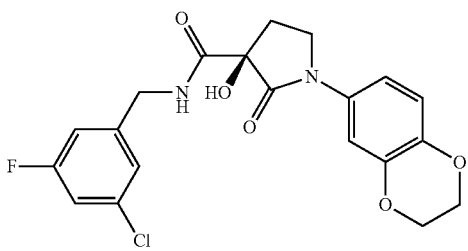<br>(R)-1-(2,3-Dihydrobenzo-1,4-dioxin-6-yl)-3-hydroxy-2-oxo-<br>pyrrolidine-3-carboxylic acid 3-chloro-5-fluorobenzyl amide |
| "A112" | 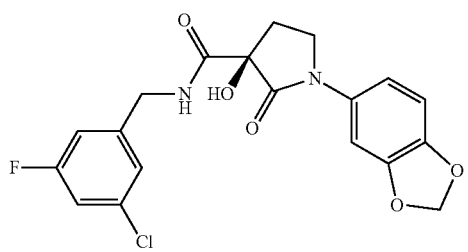<br>(R)-1-Benzo-1,3-dioxol-5-yl-3-hydroxy-<br>2-oxopyrrolidine-3-carboxylic acid<br>3-chloro-5-fluorobenzyl amide |
| "A113" | 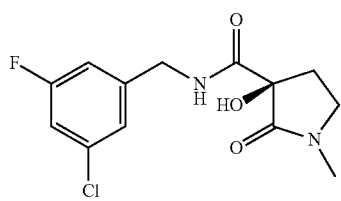<br>(R)-3-Hydroxy-1-methyl-<br>2-oxopyrrolidine-3-carboxylic acid<br>3-chloro-5-fluorobenzyl amide |
| "A114" | 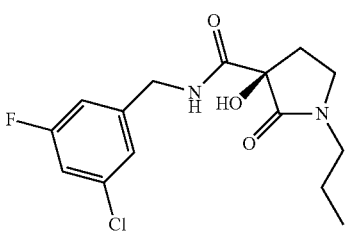<br>(R)-3-Hydroxy-2-oxo-1-<br>propylpyrrolidine-3-carboxylic<br>acid 3-chloro-5-fluorobenzyl amide |

-continued

| Compound No. | Structure/name |
|---|---|
| "A115" | 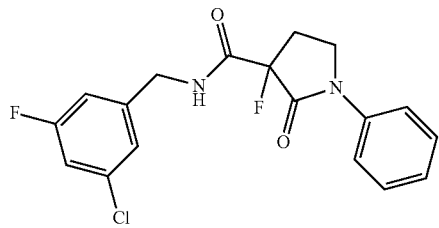<br>3-Fluoro-2-oxo-1-phenylpyrrolidine-3-carboxylic acid 3-chloro-5-fluorobenzyl amide |
| "A116" | 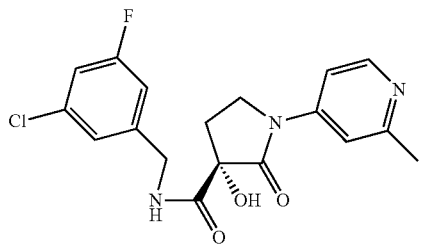<br>(S)-3-Hydroxy-1-(2-methylpyridin-4-yl)-2-oxopyrrolidine-3-carboxylic acid 3-chloro-5-fluorobenzyl amide |
| "A117" | 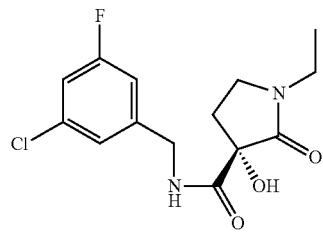<br>(S)-1-Ethyl-3-hydroxy-2-oxopyrrolidine-3-carboxylic acid 3-chloro-5-fluorobenzyl amide |
| "A118" | 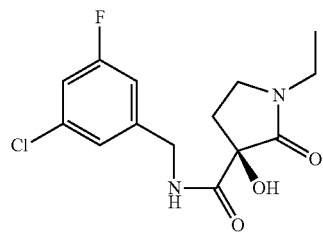<br>(R)-1-Ethyl-3-Hydroxy-2-oxopyrrolidine-3-carboxylic acid 3-chloro-5-fluorobenzyl amide |
| "A119" | 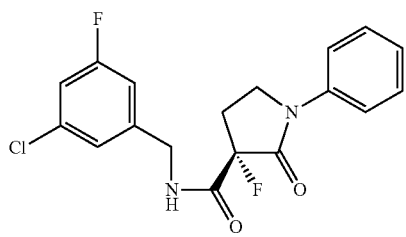<br>(S)-3-Fluoro-2-oxo-1-phenylpyrrolidine-3-carboxylic acid 3-chloro-5-fluorobenzyl amide |

-continued

| Compound No. | Structure/name |
|---|---|
| "A120" | 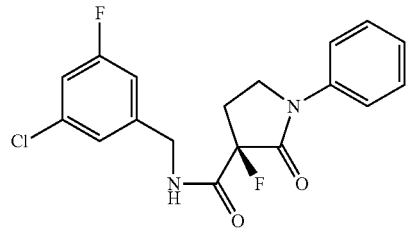<br>(R)-3-Fluoro-2-oxo-1-phenylpyrrolidine-3-carboxylic acid 3-chloro-5-fluorobenzyl amide |
| "A150" | 3-Azido-2-oxo-1-phenylpyrrolidine-3-carboxylic acid (3-chloro-5-fluorobenzyl) amide |
| "A151" | 3-Amino-2-oxo-1-phenylpyrrolidine-3-carboxylic acid (3-chloro-5-fluorobenzyl) amide |
| "A162" | 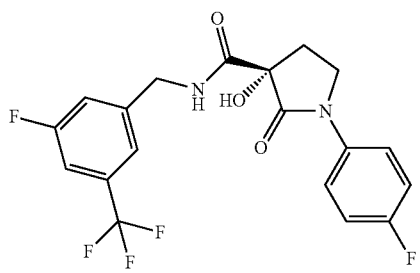<br>(S)-1-(4-Fluorophenyl)-3-hydroxy-2-oxopyrrolidine-3-carboxylic acid 3-fluoro-5-trifluoromethylbenzyl amide |
| "A163" | 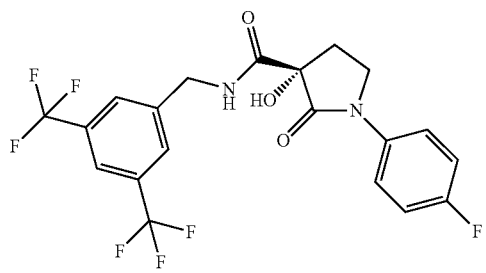<br>(S)-1-(4-Fluorophenyl)-3-hydroxy-2-oxopyrrolidine-3-carboxylic acid 3,5-bistrifluoromethylbenzyl amide |
| "A164" | 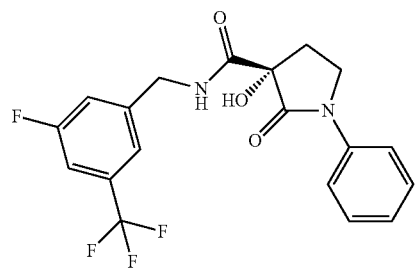<br>(S)-3-Hydroxy-2-oxo-1-phenylpyrrolidine-3-carboxylic acid 3-fluoro-5-trifluoromethylbenzyl amide |

| Compound No. | Structure/name |
|---|---|
| "A165" | 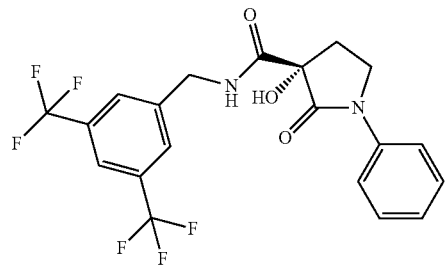<br>(S)-3-Hydroxy-2-oxo-1-phenylpyrrolidine-3-carboxylic acid 3,5-bistrifluoromethylbenzyl amide |
| "A166" | 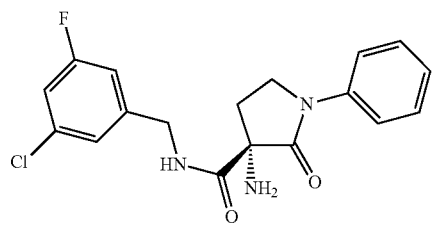<br>(S)-3-Amino-2-oxo-1-phenylpyrrolidine-3-carboxylic acid 3-chloro-5-fluorobenzyl amide |
| "A167" | 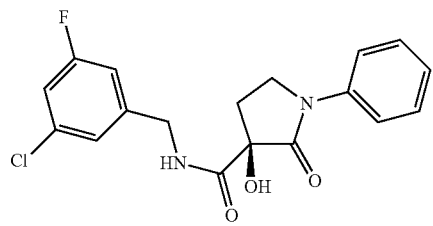<br>(R)-3-Hydroxy-2-oxo-1-phenylpyrrolidine-3-carboxylic acid 3-chloro-5-fluorobenzyl amide |
| "A168" | 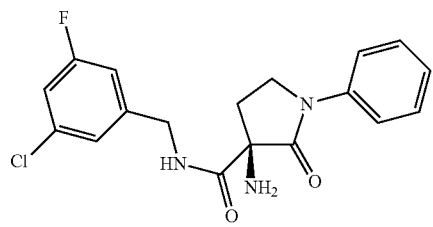<br>(R)-3-Amino-2-oxo-1-phenylpyrrolidine-3-carboxylic acid 3-chloro-5-fluorobenzyl amide |
| "A169" | 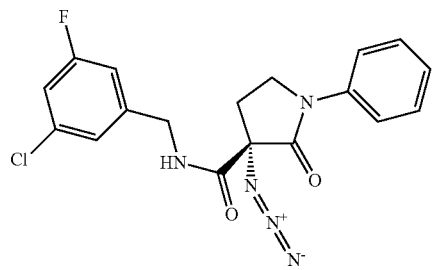<br>(S)-3-Azido-2-oxo-1-phenylpyrrolidine-3-carboxylic acid 3-chloro-5-fluorobenzyl amide |

| Compound No. | Structure/name |
|---|---|
| "A170" | 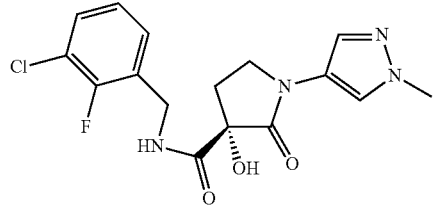<br>(S)-3-Hydroxy-1-(1-methyl-1H-pyrazol-4-yl)-2-oxopyrrolidine-3-carboxylic acid 3-chloro-2-fluorobenzyl amide |
| "A171" | 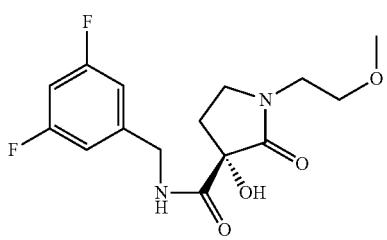<br>(S)-3-Hydroxy-1-(2-methoxyethyl)-2-oxopyrrolidine-3-carboxylic acid 3,5-difluorobenzyl amide |
| "A172" | 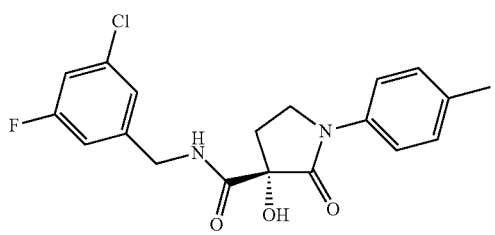<br>(S)-3-Hydroxy-2-oxo-1-p-tolylpyrrolidine-3-carboxylic acid 3-chloro-5-fluorobenzyl amide |
| "A173" | 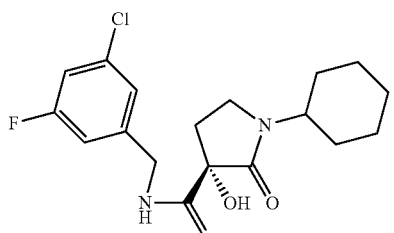<br>(S)-1-Cyclohexyl-3-hydroxy-2-oxopyrrolidine-3-carboxylic acid 3-chloro-5-fluorobenzyl amide |
| "A174" | 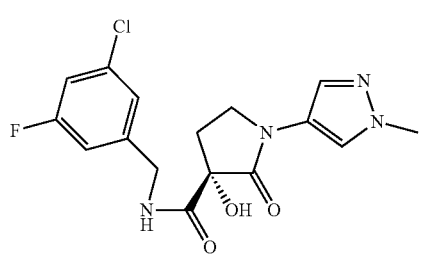<br>(S)-3-Hydroxy-1-(1-methyl-1H-pyrazol-4-yl)-2-oxopyrrolidine-3-carboxylic acid 3-chloro-5-fluorobenzyl amide |

| Compound No. | Structure/name |
|---|---|
| "A175" | 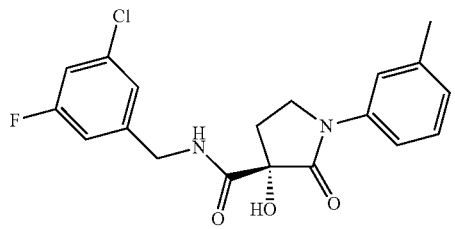<br>(S)-3-Hydroxy-2-oxo-1-m-tolylpyrrolidine-3-carboxylic acid 3-chloro-5-fluorobenzyl amide |
| "A176" | 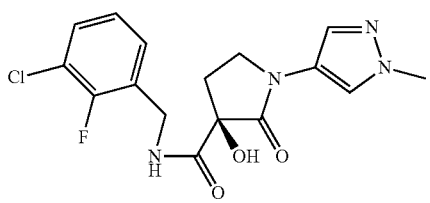<br>(R)-3-Hydroxy-1-(1-methyl-1H-pyrazol-4-yl)-2-oxopyrrolidine-3-carboxylic acid 3-chloro-2-fluorobenzyl amide |
| "A177" | 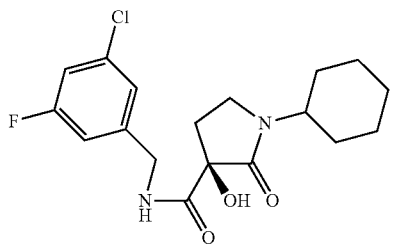<br>(R)-1-Cyclohexyl-3-hydroxy-2-oxopyrrolidine-3-carboxylic acid 3-chloro-5-fluorobenzyl amide |
| "A178" | 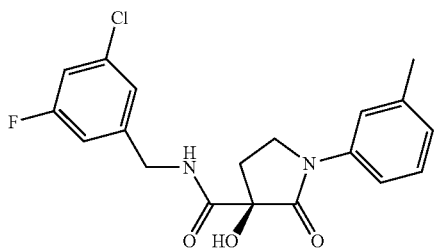<br>(R)-3-Hydroxy-2-oxo-1-m-tolylpyrrolidine-3-carboxylic acid 3-chloro-5-fluorobenzyl amide |
| "A179" | 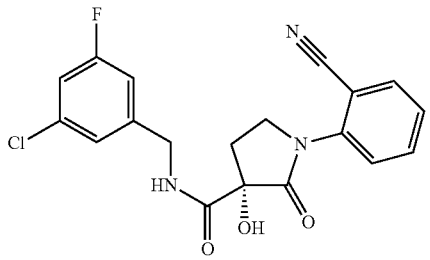<br>(S)-1-(2-Cyanophenyl)-3-hydroxy-2-oxopyrrolidine-3-carboxylic acid 3-chloro-5-fluorobenzyl amide |

| Compound No. | Structure/name |
|---|---|
| "A180" | 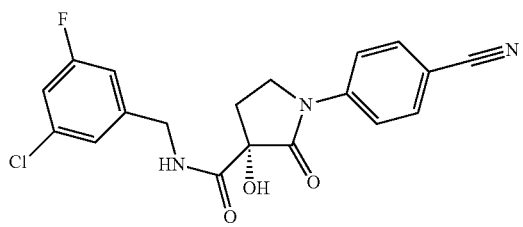<br>(S)-1-(4-Cyanophenyl)-3-hydroxy-2-oxopyrrolidine-3-carboxylic acid 3-chloro-5-fluorobenzyl amide |
| "A181" | 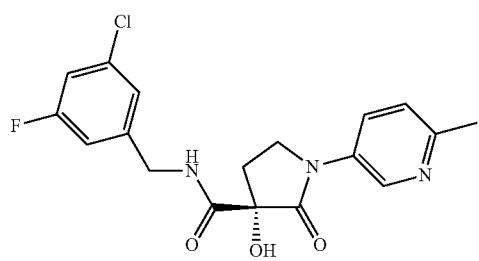<br>(S)-3-Hydroxy-1-(6-methylpyridin-3-yl)-2-oxopyrrolidine-3-carboxylic acid 3-chloro-5-fluorobenzyl amide |
| "A182" | 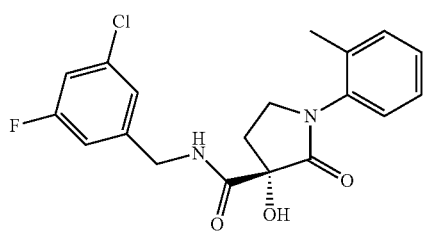<br>(S)-3-Hydroxy-2-oxo-1-o-tolylpyrrolidine-3-carboxylic acid 3-chloro-5-fluorobenzyl amide |
| "A183" | 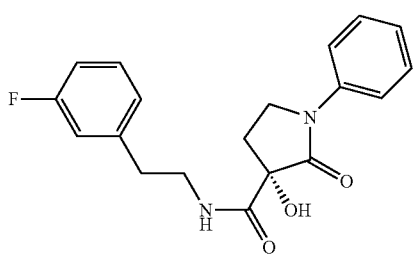<br>(S)-3-Hydroxy-2-oxo-1-phenylpyrrolidine-3-carboxylic acid [2-(3-fluorophenyl)ethyl] amide |
| "A184" | 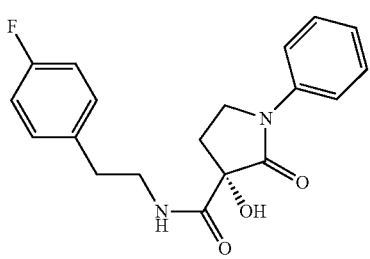<br>(S)-3-Hydroxy-2-oxo-1-phenylpyrrolidine-3-carboxylic acid [2-(4-fluorophenyl)ethyl] amide |

| Compound No. | Structure/name |
|---|---|
| "A185" | 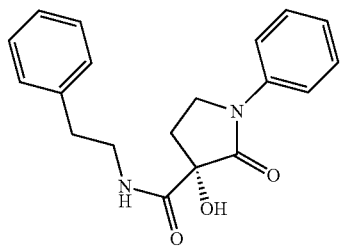<br>(S)-3-Hydroxy-2-oxo-1-phenylpyrrolidine-3-carboxylic acid phenethyl amide |
| "A186" | 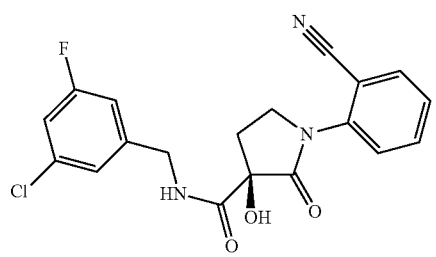<br>(R)-1-(2-Cyanophenyl)-3-hydroxy-2-oxopyrrolidine-3-carboxylic acid 3-chloro-5-fluorobenzyl amide |
| "A187" | 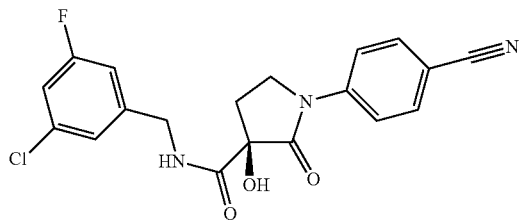<br>(R)-1-(4-Cyanophenyl)-3-hydroxy-2-oxopyrrolidine-3-carboxylic acid 3-chloro-5-fluorobenzyl amide |
| "A188" | 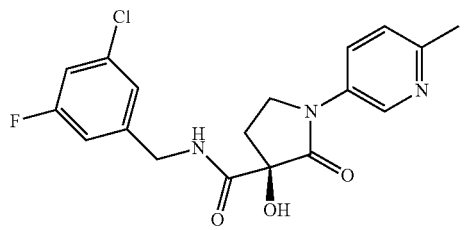<br>(R)-3-Hydroxy-1-(6-methylpyridin-3-yl)-2-oxopyrrolidine-3-carboxylic acid 3-chloro-5-fluorobenzyl amide |
| "A189" | 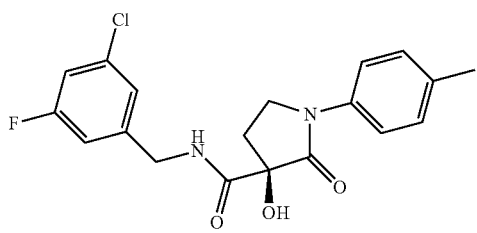<br>(R)-3-Hydroxy-2-oxo-1-p-tolylpyrrolidine-3-carboxylic acid 3-chloro-5-fluorobenzyl amide |

| Compound No. | Structure/name |
|---|---|
| "A190" | 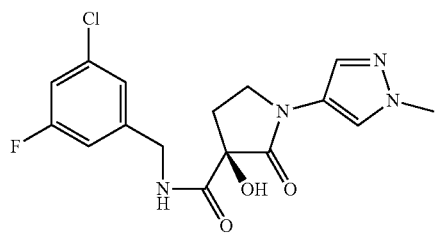<br>(R)-3-Hydroxy-1-(1-methyl-1H-pyrazol-4-yl)-<br>2-oxopyrrolidine-3-carboxylic acid<br>3-chloro-5-fluorobenzyl amide |
| "A191" | 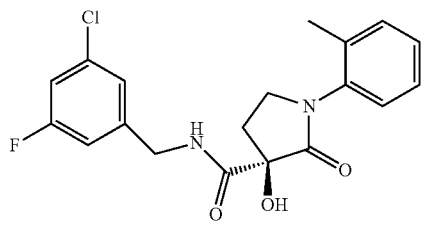<br>(R)-3-Hydroxy-2-oxo-1-o-tolylpyrrolidine-3-<br>carboxylic acid 3-chloro-5-fluorobenzyl amide |
| "A192" | 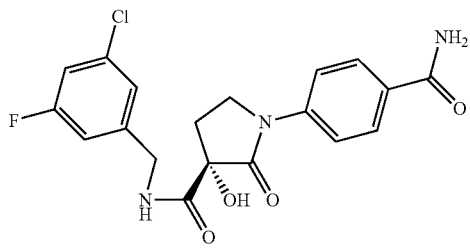<br>(S)-1-(4-Carbamoylphenyl)-3-hydroxy-<br>2-oxopyrrolidine-3-carboxylic acid<br>3-chloro-5-fluorobenzyl amide |
| "A193" | 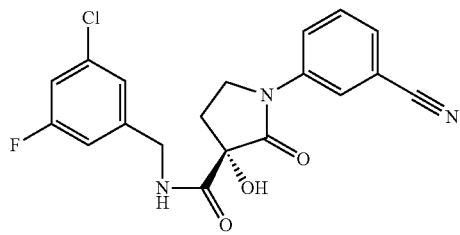<br>(S)-1-(3-Cyanophenyl)-3-hydroxy-<br>2-oxopyrrolidine-3-carboxylic<br>acid 3-chloro-5-fluorobenzyl amide |

| Compound No. | Structure/name |
|---|---|
| "A194" | <br>(R)-1-(3-Cyanophenyl)-3-hydroxy-<br>2-oxopyrrolidine-3-carboxylic<br>acid 3-chloro-5-fluorobenzyl amide |
| "A195" | 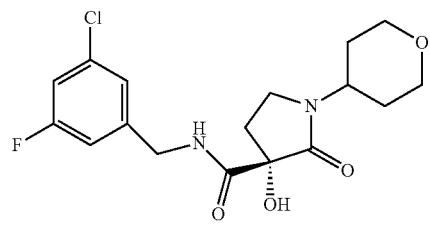<br>(S)-3-Hydroxy-2-oxo-1-(tetrahydropyran-<br>4-yl)pyrrolidine-3-carboxylic acid<br>3-chloro-5-fluorobenzyl amide |
| "A196" | 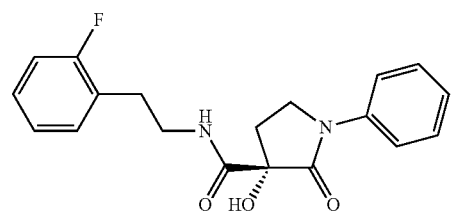<br>(S)-3-Hydroxy-2-oxo-1-phenylpyrrolidine-3-<br>carboxylic acid [2-(2-fluorophenyl)ethyl] amide |
| "A197" | 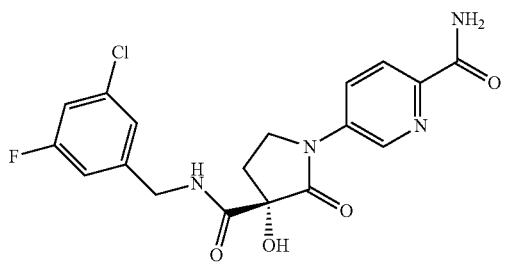<br>5-[(S)-3-(3-Chloro-5-<br>fluorobenzylcarbamoyl)-<br>3-hydroxy-2-oxo-pyrrolidin-1-<br>yl]pyridine-2-carboxylic acid amide |

| Compound No. | Structure/name |
|---|---|
| "A198" | 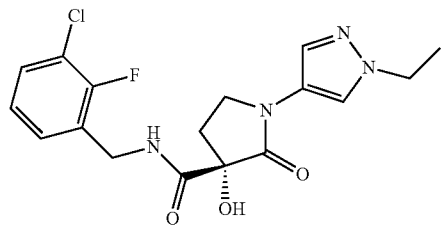<br>(S)-1-(1-Ethyl-1H-pyrazol-4-yl)-3-hydroxy-2-oxopyrrolidine-3-carboxylic acid 3-chloro-2-fluorobenzyl amide |
| "A199" | 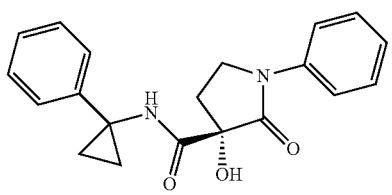<br>(S)-3-Hydroxy-2-oxo-1-phenylpyrrolidine-3-carboxylic acid (1-phenylcyclopropyl) amide |
| "A200" | 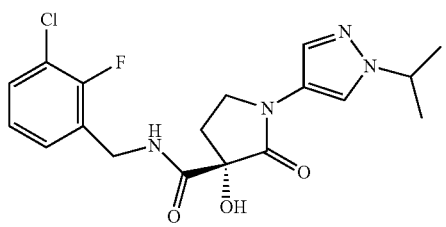<br>(S)-3-Hydroxy-1-(1-isopropyl-1H-pyrazol-4-yl)-2-oxo-pyrrolidine-3-carboxylic acid 3-chloro-2-fluorobenzyl amide |
| "A201" | 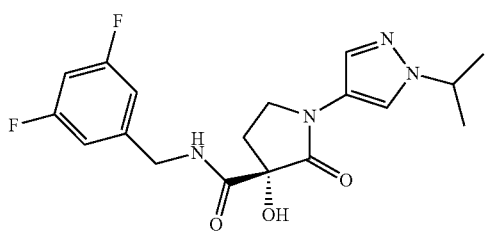<br>(S)-3-Hydroxy-1-(1-isopropyl-1H-pyrazol-4-yl)-2-oxo-pyrrolidine-3-carboxylic acid 3,5-difluorobenzyl amide |
| "A202" | 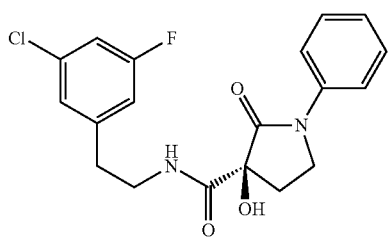<br>(S)-3-Hydroxy-2-oxo-1-phenylpyrrolidine-3-carboxylic acid [2-(3-chloro-5-fluorophenyl)ethyl] amide |

| Compound No. | Structure/name |
|---|---|
| "A203" | 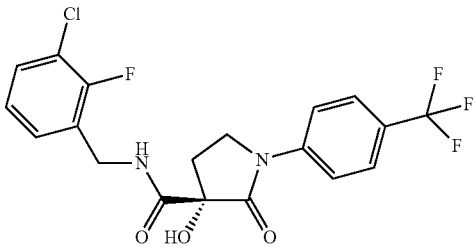<br>(S)-3-Hydroxy-2-oxo-1-(4-trifluoromethylphenyl)pyrrolidine-3-carboxylic acid 3-chloro-2-fluorobenzyl amide |
| "A204" | 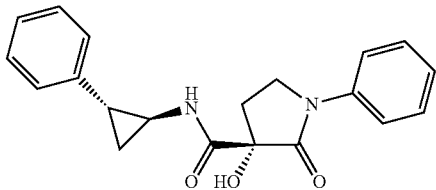<br>(S)-3-Hydroxy-2-oxo-1-phenylpyrrolidine-3-carboxylic acid ((1S,2R)-2-phenylcyclopropyl) amide |
| "A205" | 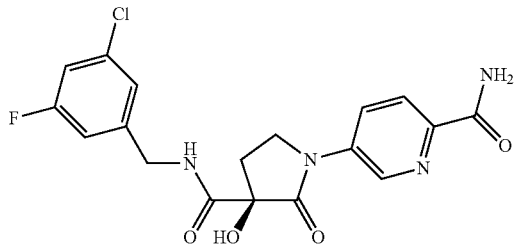<br>5-[(R)-3-(3-Chloro-5-fluorobenzylcarbamoyl)-3-hydroxy-2-oxo-pyrrolidin-1-yl]pyridine-2-carboxylic acid amide |
| "A206" | 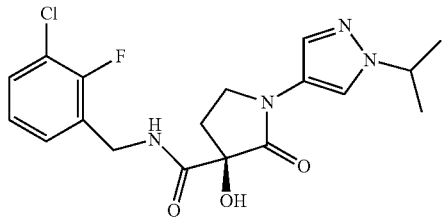<br>(R)-3-Hydroxy-1-(1-isopropyl-1H-pyrazol-4-yl)-2-oxo-pyrrolidine-3-carboxylic acid 3-chloro-2-fluorobenzyl amide |
| "A207" | 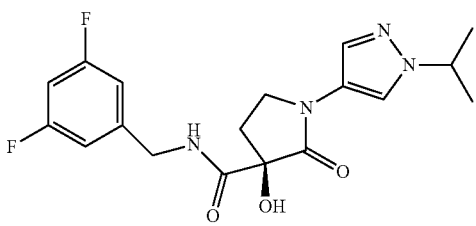<br>(R)-3-Hydroxy-1-(1-isopropyl-1H-pyrazol-4-yl)-2-oxo-pyrrolidine-3-carboxylic acid 3,5-difluorobenzyl amide |

-continued

| Compound No. | Structure/name |
|---|---|
| "A208" | 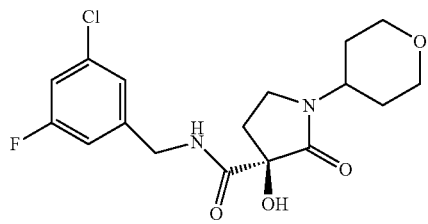
(R)-3-Hydroxy-2-oxo-1-(tetrahydropyran-4-yl)pyrrolidine-3-carboxylic acid 3-chloro-5-fluorobenzyl amide |
| "A209" | 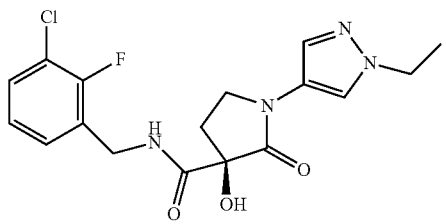
(R)-1-(1-Ethyl-1H-pyrazol-4-yl)-3-hydroxy-2-oxopyrrolidine-3-carboxylic acid 3-chloro-2-fluorobenzyl amide |
| "A210" | 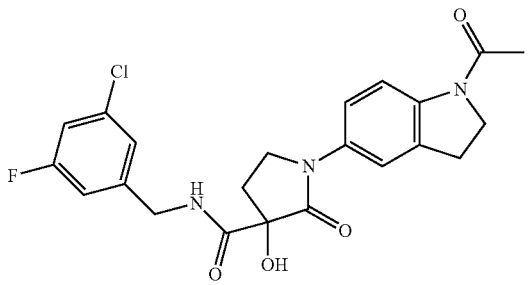
1-(1-Acetyl-2,3-dihydro-1H-indol-5-yl)-3-hydroxy-2-oxo-pyrrolidine-3-carboxylic acid 3-chloro-5-fluorobenzyl amide |
| "A211" | 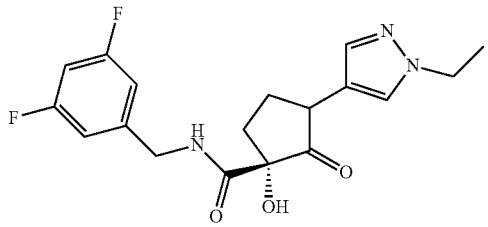
(S)-1-(1-Ethyl-1H-pyrazol-4-yl)-3-hydroxy-2-oxopyrrolidine-3-carboxylic acid 3,5-difluorobenzyl amide |
| "A212" | 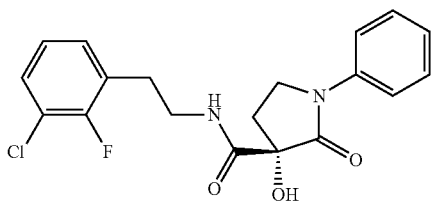
(S)-3-Hydroxy-2-oxo-1-phenylpyrrolidine-3-carboxylic acid [2-(3-chloro-2-fluorophenyl)ethyl] amide |

| Compound No. | Structure/name |
|---|---|
| "A213" | 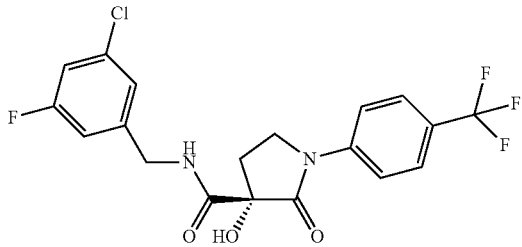
(S)-3-Hydroxy-2-oxo-1-(4-trifluoromethylphenyl)pyrrolidine-3-carboxylic acid 3-chloro-5-fluorobenzyl amide |
| "A214" | 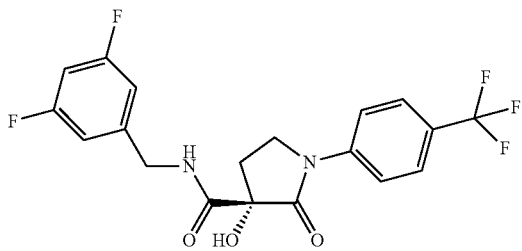
(S)-3-Hydroxy-2-oxo-1-(4-trifluoromethylphenyl)pyrrolidine-3-carboxylic acid 3,5-difluorobenzyl amide |
| "A215" | 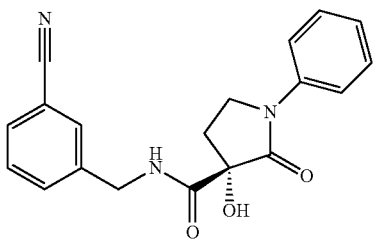
(S)-3-Hydroxy-2-oxo-1-phenylpyrrolidine-3-carboxylic acid 3-cyanobenzyl amide |
| "A216" | 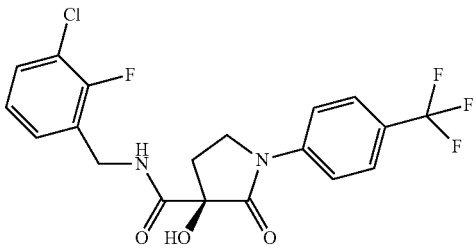
(R)-3-Hydroxy-2-oxo-1-(4-trifluoromethylphenyl)pyrrolidine-3-carboxylic acid 3-chloro-2-fluorobenzyl amide |

| Compound No. | Structure/name |
|---|---|
| "A217" | 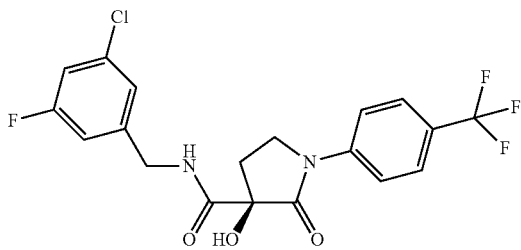<br>(R)-3-Hydroxy-2-oxo-1-(4-trifluoromethylphenyl)pyrrolidine-3-carboxylic acid 3-chloro-5-fluorobenzyl amide |
| "A218" | 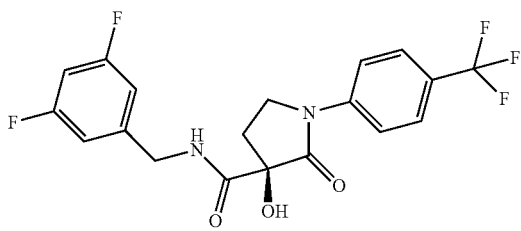<br>(R)-3-Hydroxy-2-oxo-1-(4-trifluoromethylphenyl)pyrrolidine-3-carboxylic acid 3,5-difluorobenzyl amide |
| "A219" | 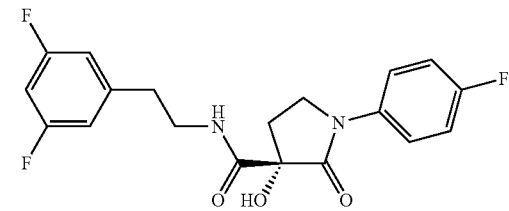<br>(S)-1-(4-Fluorophenyl)-3-hydroxy-2-oxopyrrolidine-3-carboxylic acid [2-(3,5-difluorophenyl)ethyl] amide |
| "A220" | 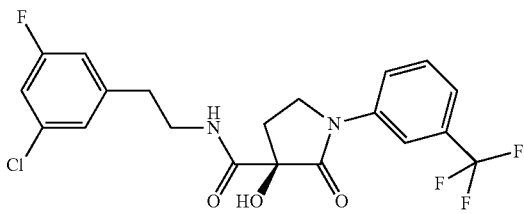<br>(R)-3-Hydroxy-2-oxo-1-(3-trifluoromethylphenyl)pyrrolidine-3-carboxylic acid [2-(3-chloro-5-fluorophenyl)ethyl] amide |
| "A221" | 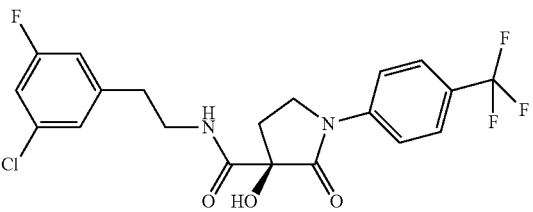<br>(R)-3-Hydroxy-2-oxo-1-(4-trifluoromethylphenyl)pyrrolidine-3-carboxylic acid [2-(3-chloro-5-fluorophenyl)ethyl] amide |

| Compound No. | Structure/name |
|---|---|
| "A222" | 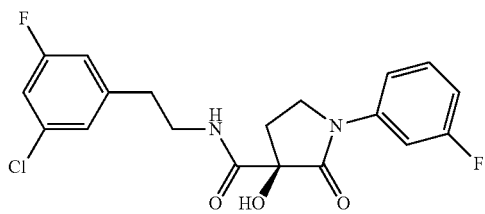<br>(R)-1-(3-Fluorophenyl)-3-hydroxy-<br>2-oxopyrrolidine-3-carboxylic acid<br>[2-(3-chloro-5-fluorophenyl)ethyl] amide |
| "A223" | 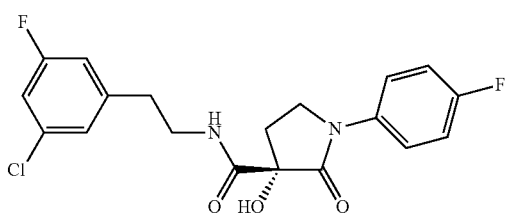<br>(S)-1-(4-Fluorophenyl)-3-hydroxy-<br>2-oxopyrrolidine-3-carboxylic acid<br>[2-(3-chloro-5-fluorophenyl)ethyl] amide |
| "A224" | 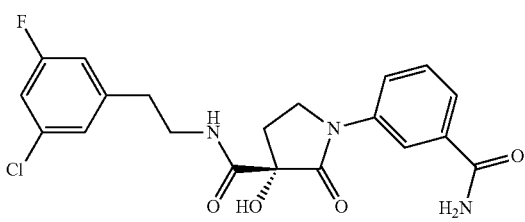<br>(S)-1-(3-Carbamoylphenyl)-3-hydroxy-2-oxopyrrolidine-3-<br>carboxylic acid [2-(3-chloro-5-fluorophenyl)ethyl] amide |
| "A225" | 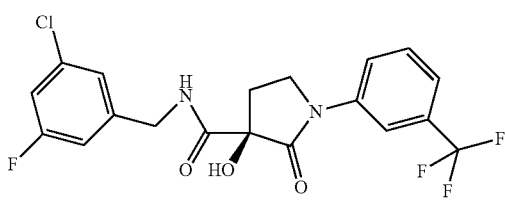<br>(R)-3-Hydroxy-2-oxo-1-<br>(3-trifluoromethylphenyl)pyrrolidine-3-<br>carboxylic acid 3-chloro-5-fluorobenzyl amide |
| "A226" | 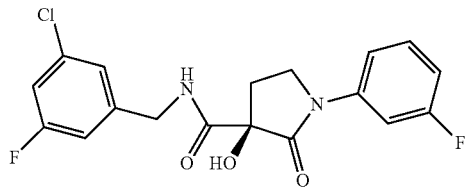<br>(R)-1-(3-Fluorophenyl)-3-hydroxy-<br>2-oxopyrrolidine-3-carboxylic<br>acid 3-chloro-5-fluorobenzyl amide |

| Compound No. | Structure/name |
|---|---|
| "A227" | 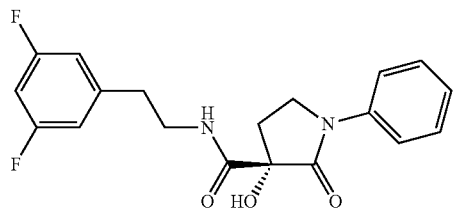<br>(S)-3-Hydroxy-2-oxo-1-phenylpyrrolidine-3-carboxylic acid [2-(3,5-difluorophenyl)ethyl] amide |
| "A228" | 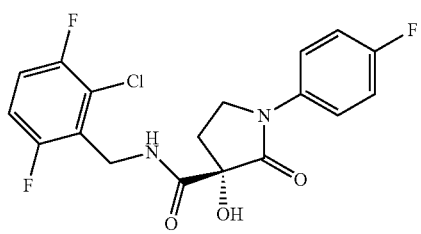<br>(S)-1-(4-Fluorophenyl)-3-hydroxy-2-oxopyrrolidine-3-carboxylic acid 2-chloro-3,6-difluorobenzyl amide |
| "A229" | 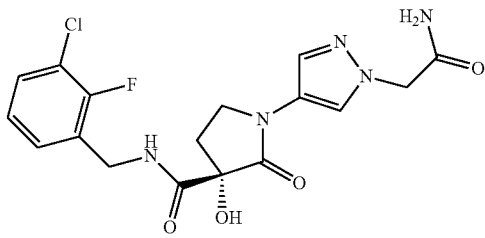<br>(S)-1-(1-Carbamoylmethyl-1H-pyrazol-4-yl)-3-hydroxy-2-oxo-pyrrolidine-3-carboxylic acid 3-chloro-2-fluorobenzyl amide |
| "A230" | 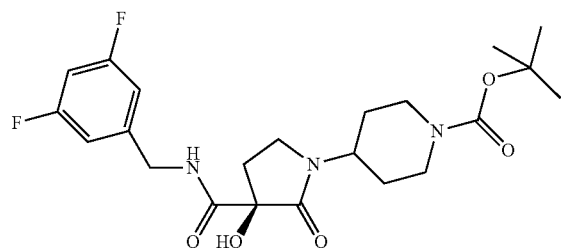<br>Tert-Butyl 4-[(R)-3-(3,5-difluorobenzylcarbamoyl)-3-hydroxy-2-oxopyrrolidin-1-yl]piperidine-1-carboxylate |
| "A231" | 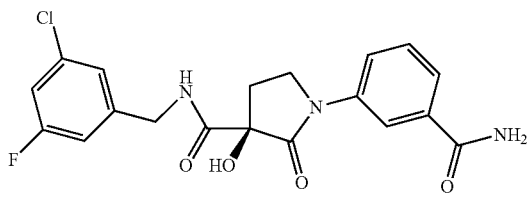<br>(R)-1-(3-Carbamoylphenyl)-3-hydroxy-2-oxopyrrolidine-3-carboxylic acid 3-chloro-5-fluorobenzyl amide |

| Compound No. | Structure/name |
|---|---|
| "A232" | 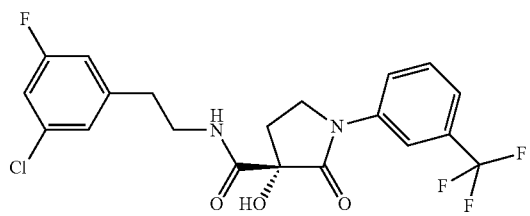<br>(S)-3-Hydroxy-2-oxo-1-(3-trifluoromethylphenyl)pyrrolidine-3-carboxylic acid [2-(3-chloro-5-fluorophenyl)ethyl] amide |
| "A233" | 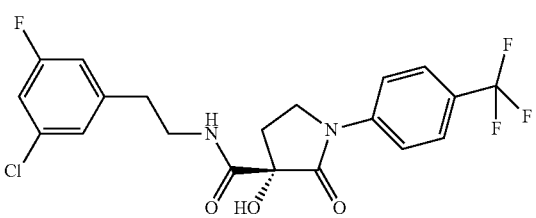<br>(S)-3-Hydroxy-2-oxo-1-(4-trifluoromethylphenyl)pyrrolidine-3-carboxylic acid [2-(3-chloro-5-fluorophenyl)ethyl] amide |
| "A234" | 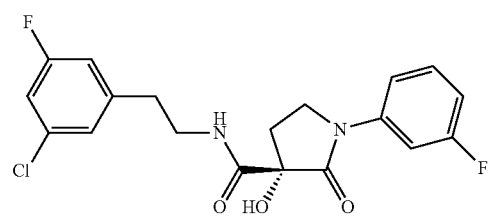<br>(S)-1-(3-Fluorophenyl)-3-hydroxy-2-oxopyrrolidine-3-carboxylic acid [2-(3-chloro-5-fluorophenyl)ethyl] amide |
| "A235" | 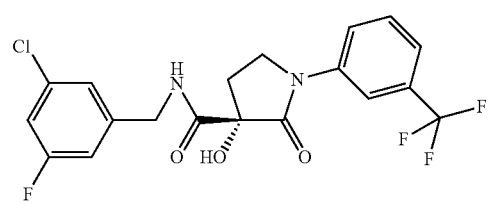<br>(S)-3-Hydroxy-2-oxo-1-(3-trifluoromethylphenyl)pyrrolidine-3-carboxylic acid 3-chloro-5-fluorobenzyl amide |
| "A236" | 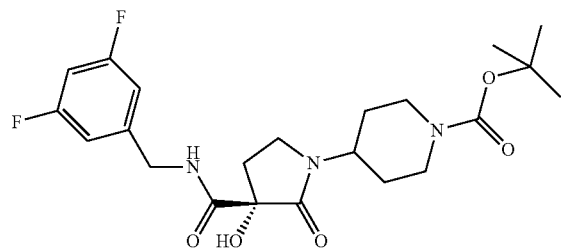<br>Tert-Butyl 4-[(S)-3-(3,5-difluorobenzylcarbamoyl)-3-hydroxy-2-oxopyrrolidin-1-yl]piperidine-1-carboxylate |

| Compound No. | Structure/name |
|---|---|
| "A237" | 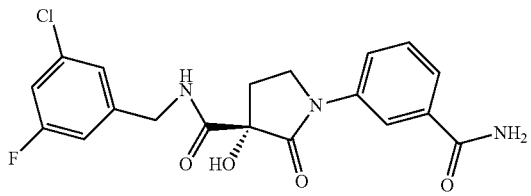<br>(S)-1-(3-Carbamoylphenyl)-3-hydroxy-2-oxopyrrolidine-3-carboxylic acid 3-chloro-5-fluorobenzyl amide |
| "A238" | 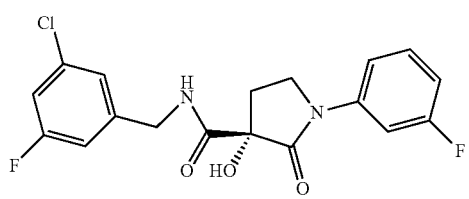<br>(S)-1-(3-Fluorophenyl)-3-hydroxy-2-oxopyrrolidine-3-carboxylic acid 3-chloro-5-fluorobenzyl amide |
| "A239" | 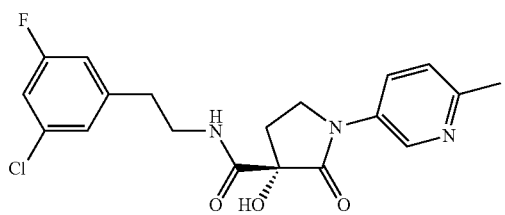<br>(S)-3-Hydroxy-1-(6-methylpyridin-3-yl)-2-oxopyrrolidine-3-carboxylic acid [2-(3-chloro-5-fluorophenyl)ethyl] amide |
| "A240" | 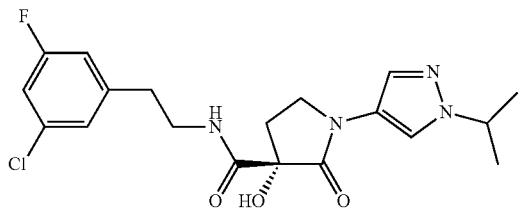<br>(S)-3-Hydroxy-1-(1-isopropyl-1H-pyrazol-4-yl)-2-oxo-pyrrolidine-3-carboxylic acid [2-(3-chloro-5-fluorophenyl)ethyl] amide |
| "A241" | 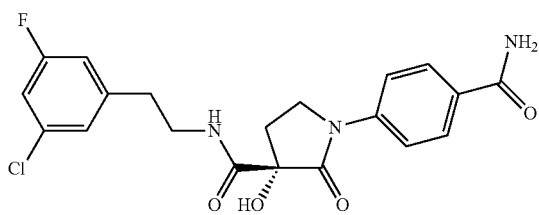<br>(S)-1-(4-Carbamoylphenyl)-3-hydroxy-2-oxopyrrolidine-3-carboxylic acid [2-(3-chloro-5-fluorophenyl)ethyl] amide |

| Compound No. | Structure/name |
|---|---|
| "A242" | 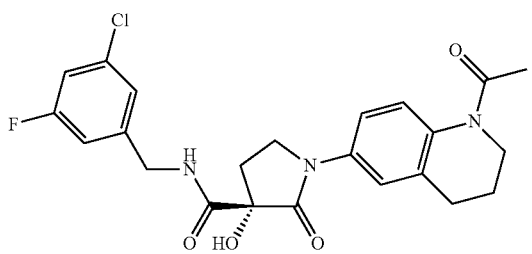<br>(S)-1-(1-Acetyl-1,2,3,4-tetrahydroquinolin-6-yl)-3-hydroxy-2-oxopyrrolidine-3-carboxylic acid 3-chloro-5-fluorobenzyl amide |
| "A243" | 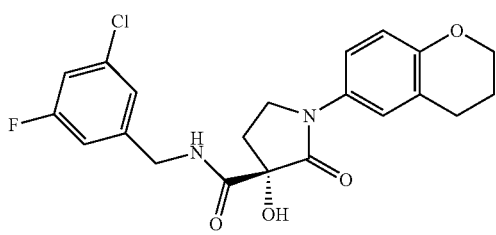<br>(S)-1-Chroman-6-yl-3-hydroxy-2-oxopyrrolidine-3-carboxylic acid 3-chloro-5-fluorobenzyl amide |
| "A244" | 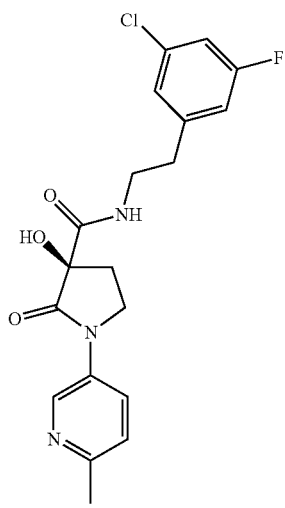<br>(R)-3-Hydroxy-1-(6-methylpyridin-3-yl)-2-oxopyrrolidine-3-carboxylic acid [2-(3-chloro-5-fluorophenyl)ethyl] amide |
| "A245" | 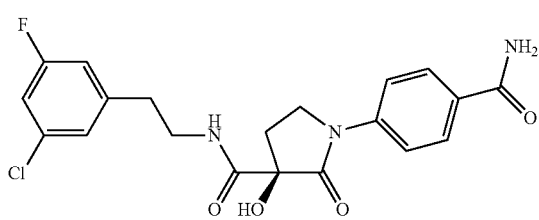<br>(R)-1-(4-Carbamoylphenyl)-3-hydroxy-2-oxopyrrolidine-3-carboxylic acid [2-(3-chloro-5-fluorophenyl)ethyl] amide |

| Compound No. | Structure/name |
|---|---|
| "A246" | 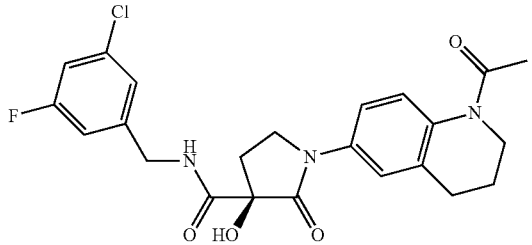<br>(R)-1-(1-Acetyl-1,2,3,4-tetrahydroquinolin-6-yl)-3-hydroxy-2-oxopyrrolidine-3-carboxylic acid 3-chloro-5-fluorobenzyl amide |
| "A247" | 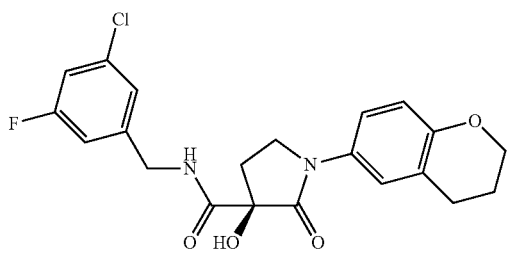<br>(R)-1-Chroman-6-yl-3-hydroxy-2-oxopyrrolidine-3-carboxylic acid 3-chloro-5-fluorobenzyl amide |
| "A248" | 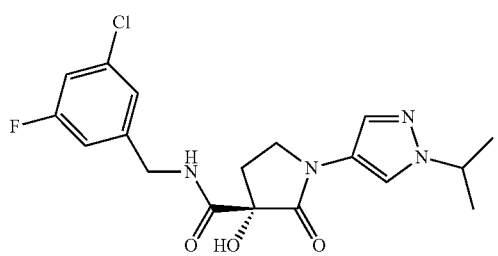<br>(S)-3-Hydroxy-1-(1-isopropyl-1H-pyrazol-4-yl)-2-oxo-pyrrolidine-3-carboxylic acid 3-chloro-5-fluorobenzyl amide |
| "A249" | 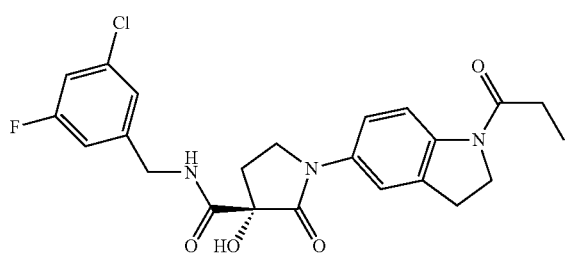<br>(S)-3-Hydroxy-2-oxo-1-(1-propionyl-2,3-dihydro-1H-indol-5-yl)-pyrrolidine-3-carboxylic acid 3-chloro-5-fluorobenzyl amide |

| Compound No. | Structure/name |
|---|---|
| "A250" | 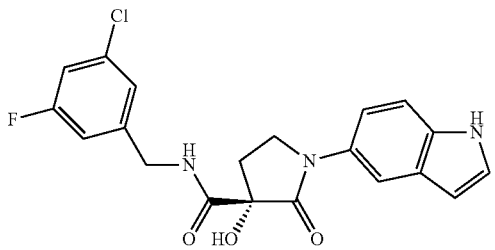<br>(S)-3-Hydroxy-1-(1H-indol-5-yl)-2-oxopyrrolidine-3-carboxylic acid 3-chloro-5-fluorobenzyl amide |
| "A251" | 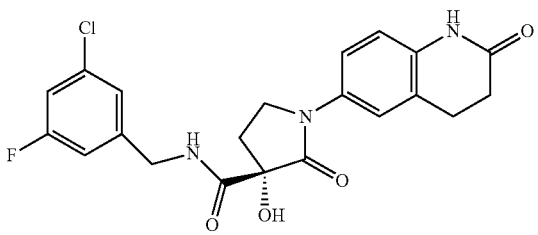<br>(S)-3-Hydroxy-2-oxo-1-(2-oxo-1,2,3,4-tetrahydroquinolin-6-yl)-pyrrolidine-3-carboxylic acid 3-chloro-5-fluorobenzyl amide |
| "A252" | 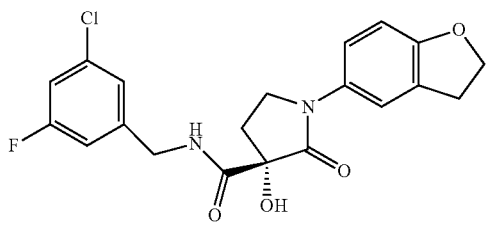<br>(S)-1-(2,3-Dihydrobenzofuran-5-yl)-3-hydroxy-2-oxopyrrolidine-3-carboxylic acid 3-chloro-5-fluorobenzyl amide |
| "A253" | 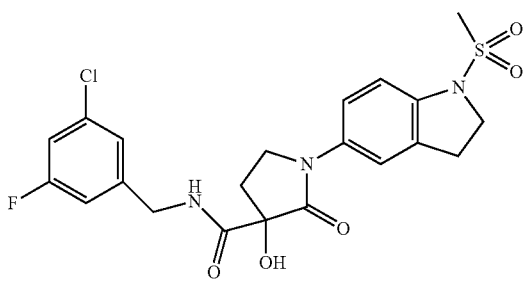<br>3-Hydroxy-1-(1-methanesulfonyl-2,3-dihydro-1H-indol-5-yl)-2-oxopyrrolidine-3-carboxylic acid 3-chloro-5-fluorobenzyl amide |

-continued

| Compound No. | Structure/name |
|---|---|
| "A254" | 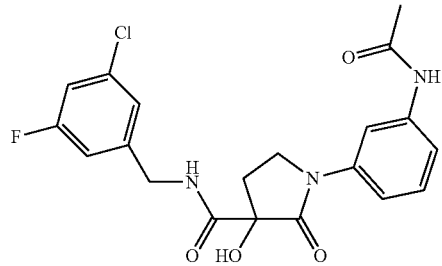<br>1-(3-Acetylaminophenyl)-3-hydroxy-<br>2-oxopyrrolidine-3-carboxylic acid<br>3-chloro-5-fluorobenzyl amide |
| "A255" | 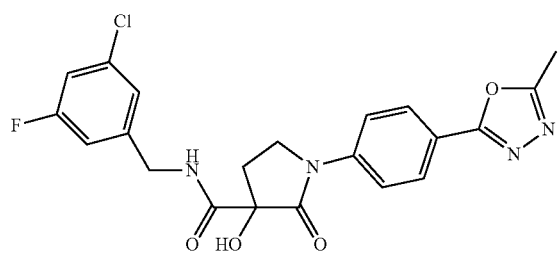<br>3-Hydroxy-1-[4-(5-methyl-1,3,4-oxadiazol-2-yl)-phenyl]-2-oxo-<br>pyrrolidine-3-carboxylic acid 3-chloro-5-fluorobenzyl amide |
| "A256" | 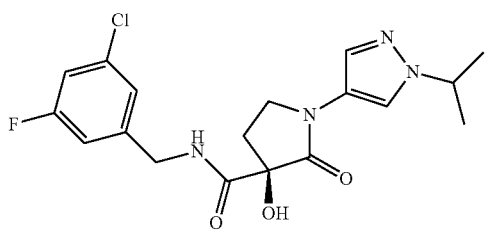<br>(R)-3-Hydroxy-1-(1-isopropyl-1H-pyrazol-<br>4-yl)-2-oxo-pyrrolidine-3-carboxylic acid<br>3-chloro-5-fluorobenzyl amide |
| "A257" | 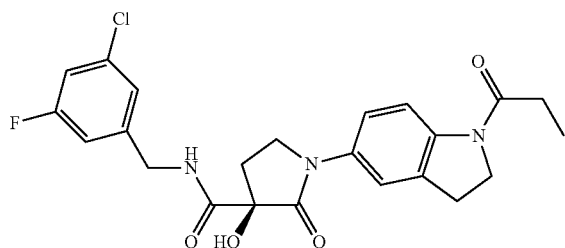<br>(R)-3-Hydroxy-2-oxo-1-(1-propionyl-2,3-dihydro-1H-indol-5-<br>yl)pyrrolidine-3-carboxylic acid 3-chloro-5-fluorobenzyl amide |
| "A258" | 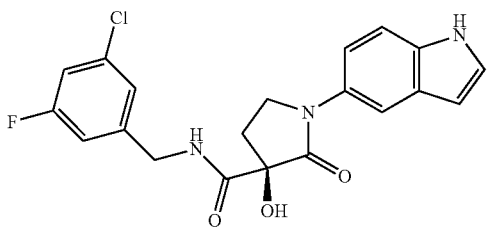<br>(R)-3-Hydroxy-1-(1H-indol-5-yl)-2-oxopyrrolidine-<br>3-carboxylic acid 3-chloro-5-fluorobenzyl amide |

| Compound No. | Structure/name |
|---|---|
| "A259" | 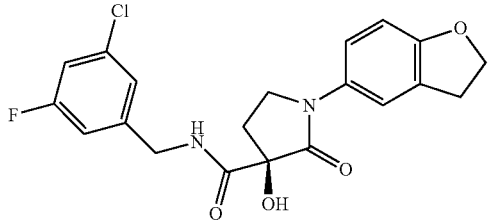<br>(R)-1-(2,3-Dihydrobenzofuran-5-yl)-3-hydroxy-2-oxo-pyrrolidine-3-carboxylic acid 3-chloro-5-fluorobenzyl amide |
| "A260" | 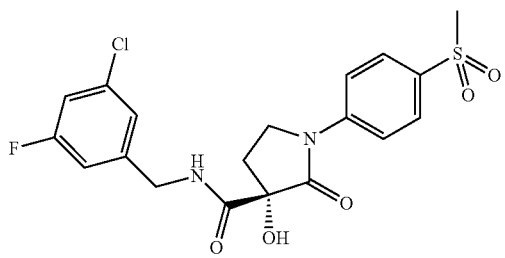<br>(S)-3-Hydroxy-1-(4-methanesulfonylphenyl)-2-oxopyrrolidine-3-carboxylic acid 3-chloro-5-fluorobenzyl amide |
| "A261" | 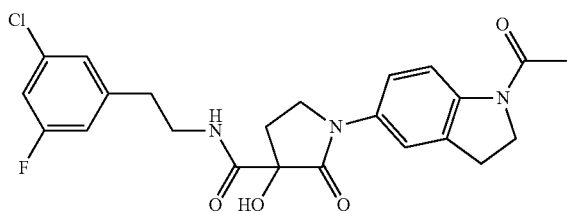<br>1-(1-Acetyl-2,3-dihydro-1H-indol-5-yl)-3-hydroxy-2-oxo-pyrrolidine-3-carboxylic acid [2-(3-chloro-5-fluorophenyl)ethyl] amide |
| "A262" | 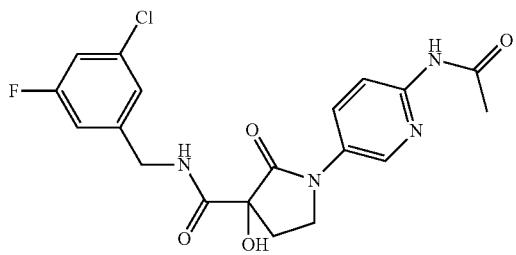<br>1-(6-Acetylaminopyridin-3-yl)-3-hydroxy-2-oxopyrrolidine-3-carboxylic acid 3-chloro-5-fluorobenzyl amide |

| Compound No. | Structure/name |
|---|---|
| "A263" | 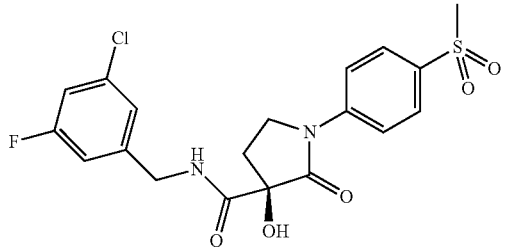<br>(R)-3-Hydroxy-1-(4-methanesulfonylphenyl)-2-oxopyrrolidine-3-carboxylic acid 3-chloro-5-fluorobenzyl amide |
| "A264" | 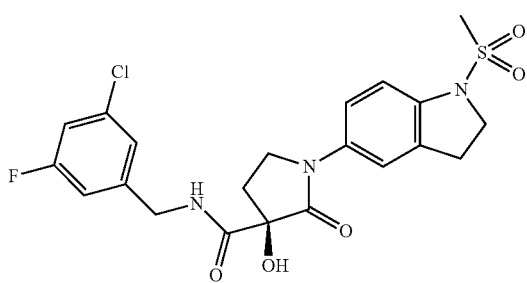<br>(R)-3-Hydroxy-1-(1-methanesulfonyl-2,3-dihydro-1H-indol-5-yl)-2-oxopyrrolidine-3-carboxylic acid 3-chloro-5-fluorobenzyl amide |
| "A265" | 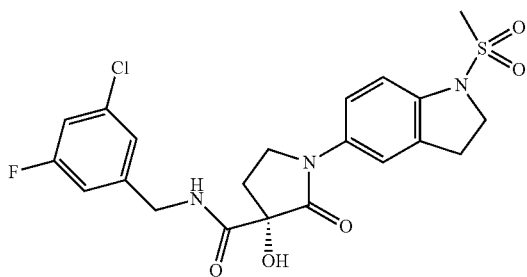<br>(S)-3-Hydroxy-1-(1-methanesulfonyl-2,3-dihydro-1H-indol-5-yl)-2-oxopyrrolidine-3-carboxylic acid 3-chloro-5-fluorobenzyl amide |
| "A266" | 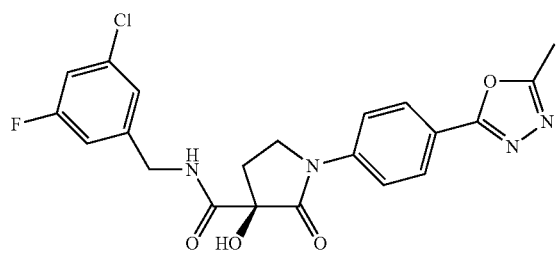<br>(R)-3-Hydroxy-1-[4-(5-methyl-1,3,4-oxadiazol-2-yl)-phenyl]-2-oxopyrrolidine-3-carboxylic acid 3-chloro-5-fluorobenzyl amide |

| Compound No. | Structure/name |
|---|---|
| "A267" | 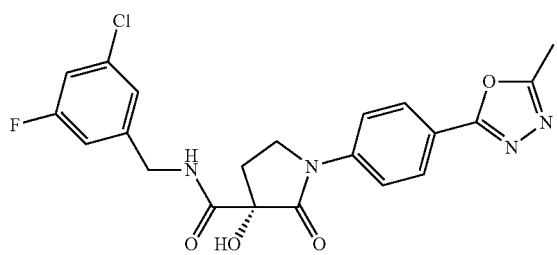<br>(S)-3-Hydroxy-1-(1-methanesulfonyl-2,3-dihydro-1H-indol-5-yl)-2-oxopyrrolidine-3-carboxylic acid 3-chloro-5-fluorobenzyl amide |
| "A268" | 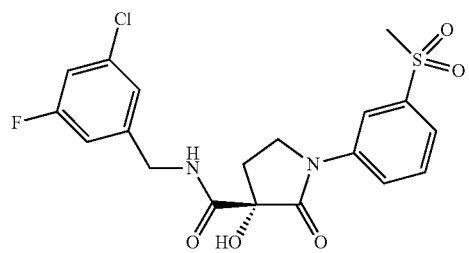<br>(S)-3-Hydroxy-1-(3-methanesulfonylphenyl)-2-oxopyrrolidine-3-carboxylic acid 3-chloro-5-fluorobenzyl amide |
| "A269" | 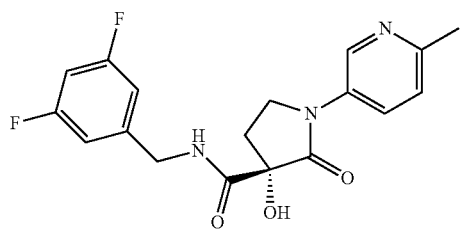<br>(S)-3-Hydroxy-1-(6-methylpyridin-3-yl)-2-oxopyrrolidine-3-carboxylic acid 3,5-difluorobenzyl amide |
| "A270" | 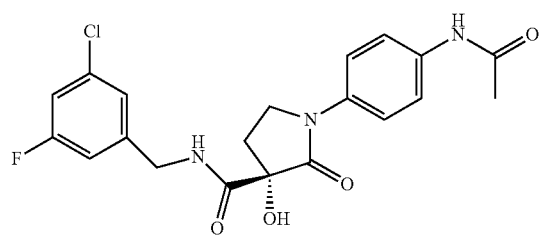<br>(S)-1-(4-Acetylaminophenyl)-3-hydroxy-2-oxopyrrolidine-3-carboxylic acid 3-chloro-5-fluorobenzyl amide |

| Compound No. | Structure/name |
|---|---|
| "A271" | 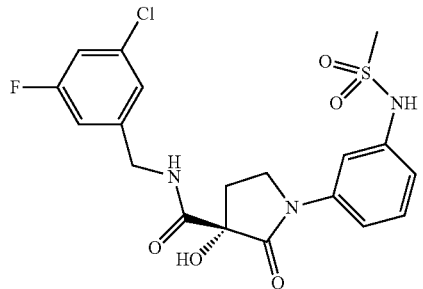<br>(S)-3-Hydroxy-1-(3-methanesulfonylaminophenyl)-2-oxo-pyrrolidine-3-carboxylic acid 3-chloro-5-fluorobenzyl amide |
| "A272" | 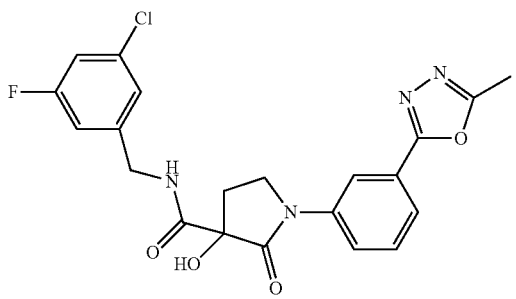<br>3-Hydroxy-1-[3-(5-methyl-1,3,4-oxadiazol-2-yl)-phenyl]-2-oxo-pyrrolidine-3-carboxylic acid 3-chloro-5-fluorobenzyl amide |
| "A273" | 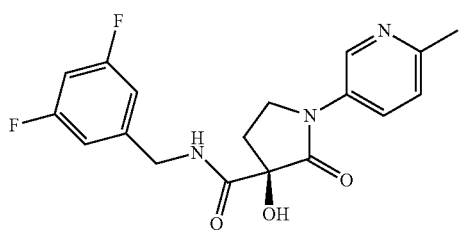<br>(R)-3-Hydroxy-1-(6-methylpyridin-3-yl)-2-oxopyrrolidine-3-carboxylic acid 3,5-difluorobenzyl amide |
| "A274" | 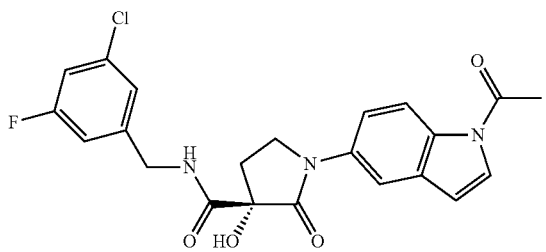<br>(S)-1-(1-Acetyl-1H-indol-5-yl)-3-hydroxy-2-oxopyrrolidine-3-carboxylic acid 3-chloro-5-fluorobenzyl amide |

| Compound No. | Structure/name |
|---|---|
| "A275" | 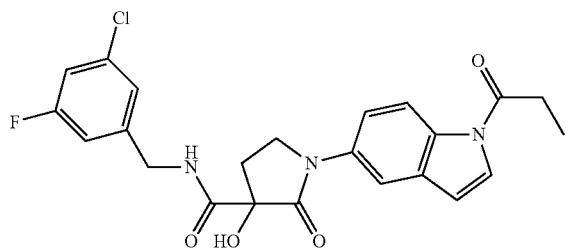<br>3-Hydroxy-2-oxo-1-(1-propionyl-1H-indol-5-yl)pyrrolidine-3-carboxylic acid 3-chloro-5-fluorobenzyl amide |
| "A276" | 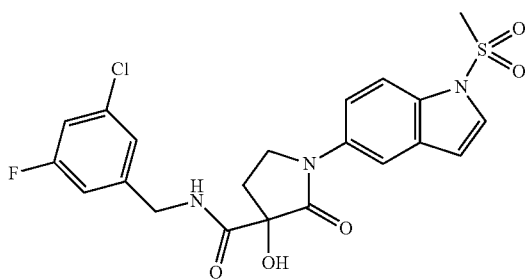<br>3-Hydroxy-1-(1-methanesulfonyl-1H-indol-5-yl)-2-oxo-pyrrolidine-3-carboxylic acid 3-chloro-5-fluorobenzyl amide |
| "A277" | 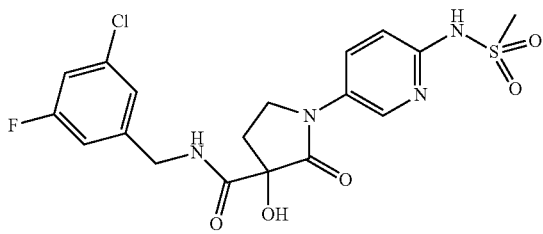<br>3-Hydroxy-1-(6-methanesulfonylaminopyridin-3-yl)-2-oxo-pyrrolidine-3-carboxylic acid 3-chloro-5-fluorobenzyl amide |
| "A278" | 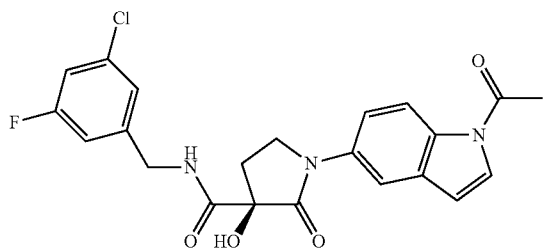<br>(R)-1-(1-Acetyl-1H-indol-5-yl)-3-hydroxy-2-oxopyrrolidine-3-carboxylic acid 3-chloro-5-fluorobenzyl amide |

| Compound No. | Structure/name |
|---|---|
| "A279" | 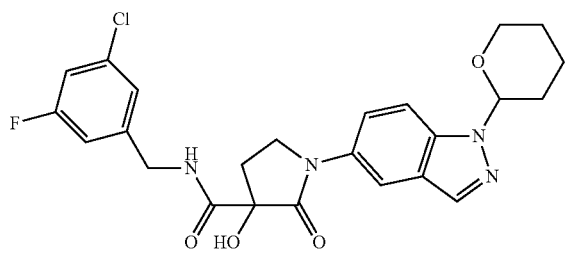<br>3-Hydroxy-2-oxo-1-[1-(tetrahydropyran-2-yl)-1H-indazol-5-yl]-pyrrolidine-3-carboxylic acid 3-chloro-5-fluorobenzyl amide |
| "A280" | 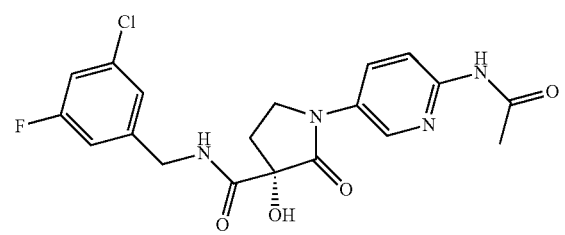<br>(S)-1-(6-Acetylaminopyridin-3-yl)-3-hydroxy-2-oxopyrrolidine-3-carboxylic acid 3-chloro-5-fluorobenzyl amide |
| "A281" | 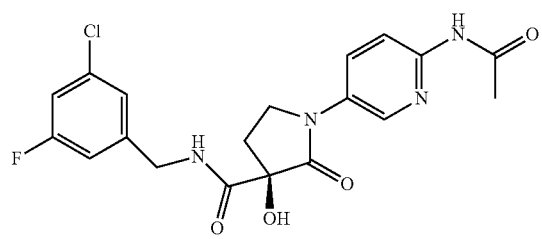<br>(R)-1-(6-Acetylaminopyridin-3-yl)-3-hydroxy-2-oxopyrrolidine-3-carboxylic acid 3-chloro-5-fluorobenzyl amide |
| "A282" | 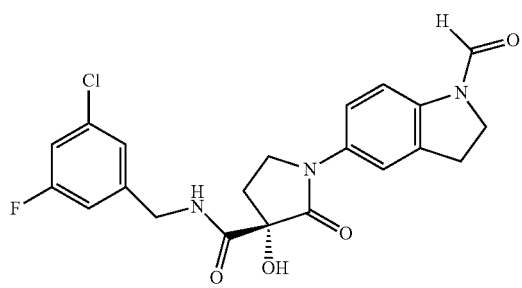<br>(S)-1-(1-Formyl-2,3-dihydro-1H-indol-5-yl)-3-hydroxy-2-oxo-pyrrolidine-3-carboxylic acid 3-chloro-5-fluorobenzyl amide |

| Compound No. | Structure/name |
|---|---|
| "A283" | 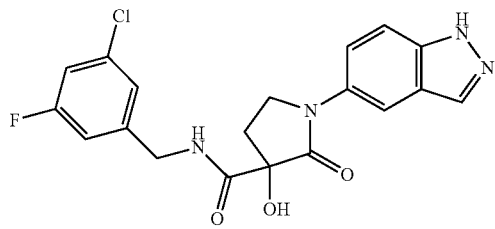<br>3-Hydroxy-1-(1H-indazol-5-yl)-2-oxopyrrolidine-3-carboxylic acid 3-chloro-5-fluorobenzyl amide |
| "A284" | 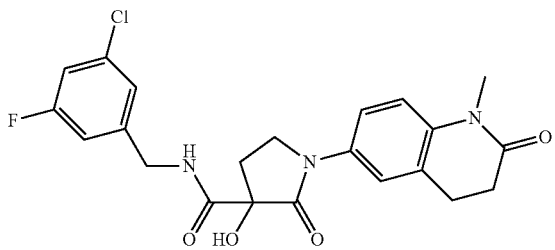<br>3-Hydroxy-1-(1-methyl-2-oxo-1,2,3,4-tetrahydroquinolin-6-yl)-2-oxopyrrolidine-3-carboxylic acid 3-chloro-5-fluorobenzyl amide |
| "A285" | 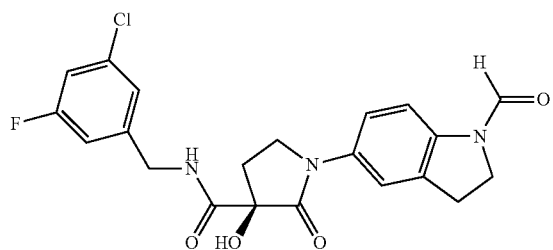<br>(R)-1-(1-Formyl-2,3-dihydro-1H-indol-5-yl)-3-hydroxy-2-oxo-pyrrolidine-3-carboxylic acid 3-chloro-5-fluorobenzyl amide |
| "A286" | 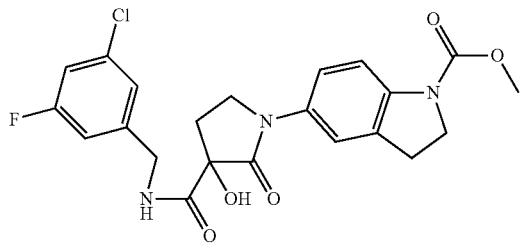<br>Methyl 5-[3-(3-chloro-5-fluorobenzylcarbamoyl)-3-hydroxy-2-oxopyrrolidin-1-yl]-2,3-dihydroindole-1-carboxylate |

| Compound No. | Structure/name |
|---|---|
| "A287" | 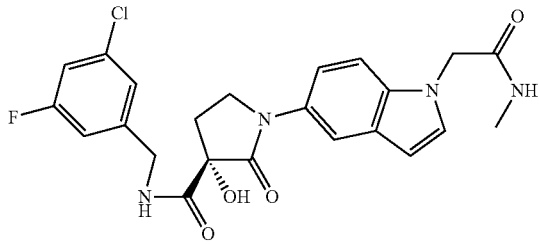<br>(S)-3-Hydroxy-1-(1-methylcarbamoylmethyl-1H-indol-5-yl)-2-oxopyrrolidine-3-carboxylic acid 3-chloro-5-fluorobenzyl amide |
| "A288" | 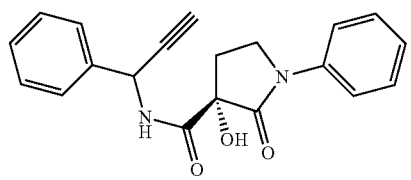<br>(S)-3-Hydroxy-2-oxo-1-phenylpyrrolidine-3-carboxylic acid (1-phenylprop-2-ynyl) amide |
| "A289" | 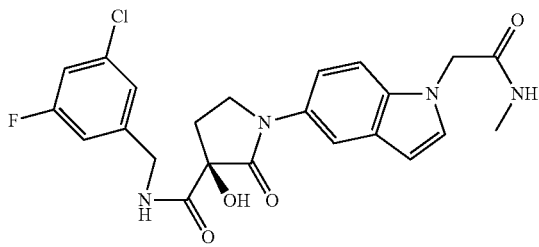<br>(R)-3-Hydroxy-1-(1-methylcarbamoylmethyl-1H-indol-5-yl)-2-oxopyrrolidine-3-carboxylic acid 3-chloro-5-fluorobenzyl amide |
| "A290" | 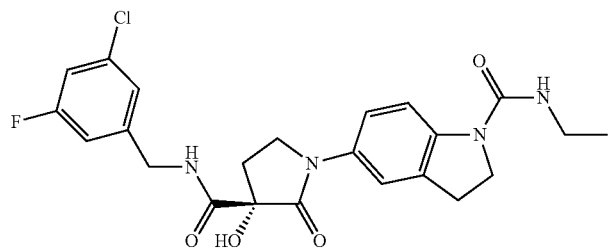<br>5-[(S)-3-(3-Chloro-5-fluorobenzylcarbamoyl)-3-hydroxy-2-oxo-pyrrolidin-1-yl]-2,3-dihydroindole-1-carboxylic acid ethyl amide |
| "A291" | 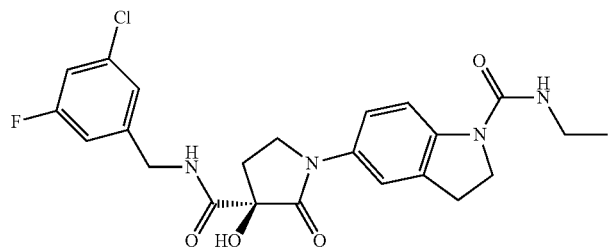<br>5-[(R)-3-(3-Chloro-5-fluorobenzylcarbamoyl)-3-hydroxy-2-oxo-pyrrolidin-1-yl]-2,3-dihydroindole-1-carboxylic acid ethyl amide |

| Compound No. | Structure/name |
|---|---|
| "A292" | 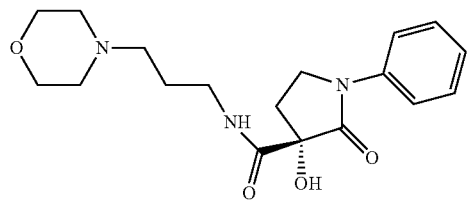<br>(S)-3-Hydroxy-2-oxo-1-phenylpyrrolidine-3-carboxylic acid (3-morpholin-4-ylpropyl) amide |
| "A293" | 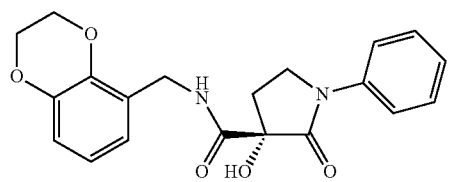<br>(S)-3-Hydroxy-2-oxo-1-phenylpyrrolidine-3-carboxylic acid (2,3-dihydrobenzo-1,4-dioxin-5-ylmethyl) amide |
| "A294" | 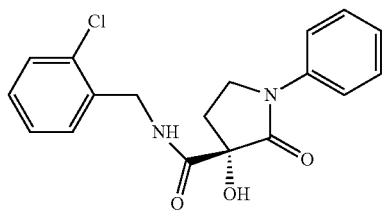<br>(S)-3-Hydroxy-2-oxo-1-phenylpyrrolidine-3-carboxylic acid 2-chlorobenzyl amide |
| "A295" | 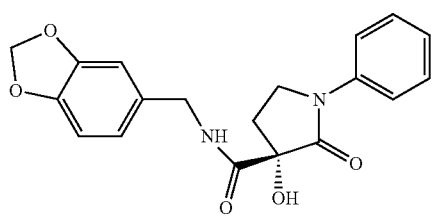<br>(S)-3-Hydroxy-2-oxo-1-phenylpyrrolidine-3-carboxylic acid (benzo-1,3-dioxol-5-ylmethyl) amide |
| "A296" | 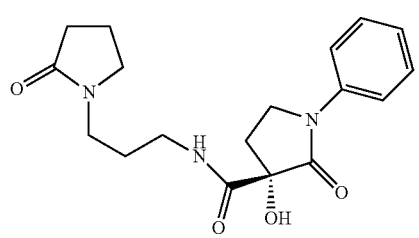<br>(S)-3-Hydroxy-2-oxo-1-phenylpyrrolidine-3-carboxylic acid [3-(2-oxopyrrolidin-1-yl)-propyl] amide |

-continued

| Compound No. | Structure/name |
|---|---|
| "A297" | 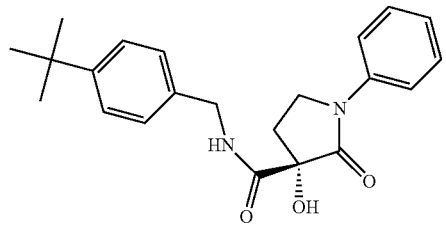
(S)-3-Hydroxy-2-oxo-1-phenylpyrrolidine-3-carboxylic acid 4-tert-butylbenzyl amide |
| "A298" | 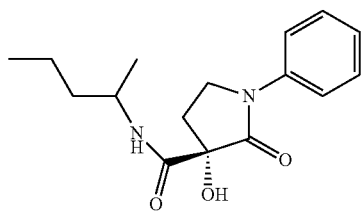
(S)-3-Hydroxy-2-oxo-1-phenylpyrrolidine-3-carboxylic acid (1-methylbutyl) amide |
| "A299" | 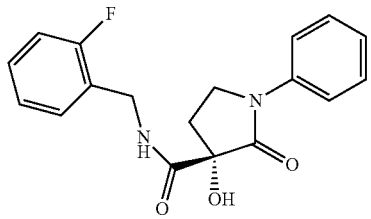
(S)-3-Hydroxy-2-oxo-1-phenylpyrrolidine-3-carboxylic acid 2-fluorobenzyl amide |
| "A300" | 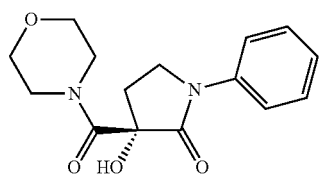
(S)-3-Hydroxy-3-(morpholin-4-carbonyl)-1-phenylpyrrolidin-2-one |
| "A301" | 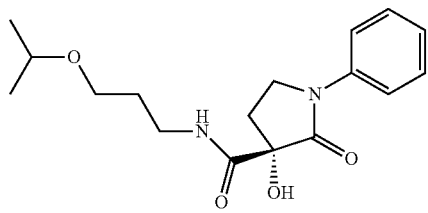
(S)-3-Hydroxy-2-oxo-1-phenylpyrrolidine-3-carboxylic acid (3-isopropoxypropyl) amide |

| Compound No. | Structure/name |
|---|---|
| "A302" | 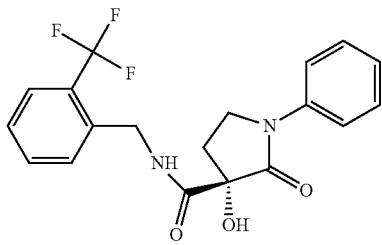<br>(S)-3-Hydroxy-2-oxo-1-phenylpyrrolidine-3-carboxylic acid 2-trifluoromethylbenzyl amide |
| "A303" | 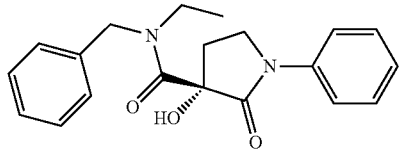<br>(S)-3-Hydroxy-2-oxo-1-phenylpyrrolidine-3-carboxylic acid benzyl ethyl amide |
| "A304" | 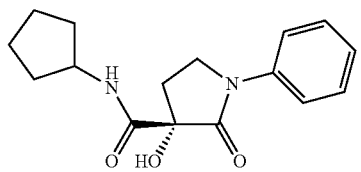<br>(S)-3-Hydroxy-2-oxo-1-phenylpyrrolidine-3-carboxylic acid cyclopentyl amide |
| "A305" | 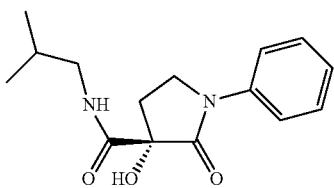<br>(S)-3-Hydroxy-2-oxo-1-phenylpyrrolidine-3-carboxylic acid isobutyl amide |
| "A306" | 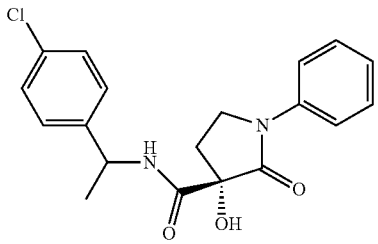<br>(S)-3-Hydroxy-2-oxo-1-phenylpyrrolidine-3-carboxylic acid [1-(4-chlorophenyl)ethyl] amide |

| Compound No. | Structure/name |
|---|---|
| "A307" | 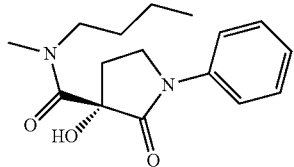<br>(S)-3-Hydroxy-2-oxo-1-phenylpyrrolidine-3-carboxylic acid butyl methyl amide |
| "A308" | 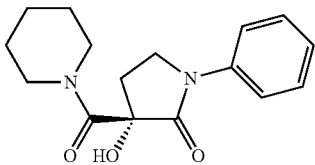<br>(S)-3-Hydroxy-1-phenyl-3-(piperidine-1-carbonyl)pyrrolidin-2-one |
| "A309" | 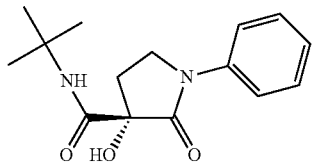<br>(S)-3-Hydroxy-2-oxo-1-phenylpyrrolidine-3-carboxylic acid tert-butyl amide |
| "A310" | 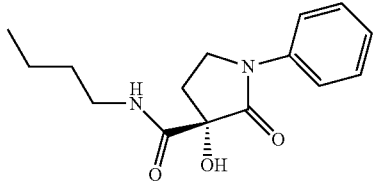<br>(S)-3-Hydroxy-2-oxo-1-phenylpyrrolidine-3-carboxylic acid butyl amide |
| "A311" | 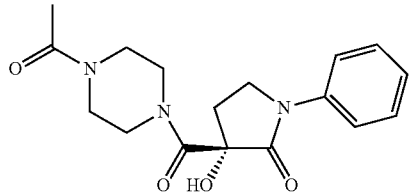<br>(S)-3-(4-Acetylpiperazine-1-carbonyl)-3-hydroxy-1-phenyl-pyrrolidin-2-one |
| "A312" | 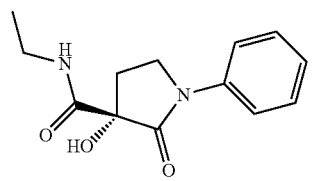<br>(S)-3-Hydroxy-2-oxo-1-phenylpyrrolidine-3-carboxylic acid ethyl amide |

| Compound No. | Structure/name |
|---|---|
| "A313" | 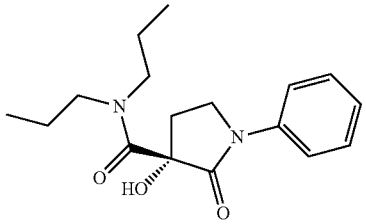<br>(S)-3-Hydroxy-2-oxo-1-phenylpyrrolidine-<br>3-carboxylic acid dipropyl amide |
| "A314" | 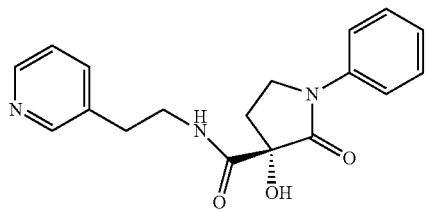<br>(S)-3-Hydroxy-2-oxo-1-phenylpyrrolidine-3-<br>carboxylic acid (2-pyridin-3-ylethyl) amide |
| "A315" | 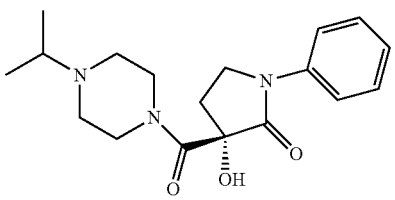<br>(S)-3-Hydroxy-3-(4-isopropylpiperazine-<br>1-carbonyl)-1-phenyl-pyrrolidin-2-one |
| "A316" | 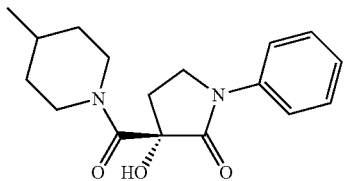<br>(S)-3-Hydroxy-3-(4-methylpiperidine-1-<br>carbonyl)-1-phenyl-pyrrolidin-2-one |
| "A317" | 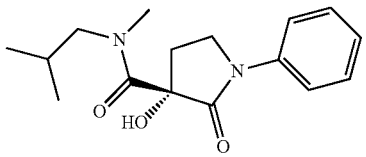<br>(S)-3-Hydroxy-2-oxo-1-phenylpyrrolidine-3-<br>carboxylic acid isobutyl methyl amide |
| "A318" | 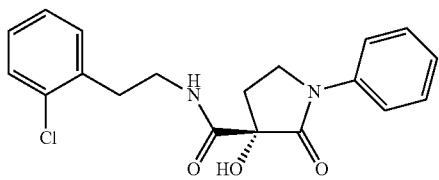<br>(S)-3-Hydroxy-2-oxo-1-phenylpyrrolidine-3-<br>carboxylic acid [2-(2-chlorophenyl)ethyl] amide |

-continued

| Compound No. | Structure/name |
|---|---|
| "A319" | 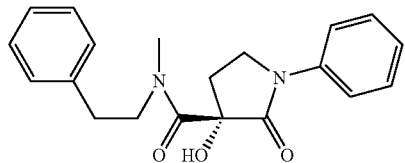<br>(S)-3-Hydroxy-2-oxo-1-phenylpyrrolidine-3-carboxylic acid methyl phenethyl amide |
| "A320" | 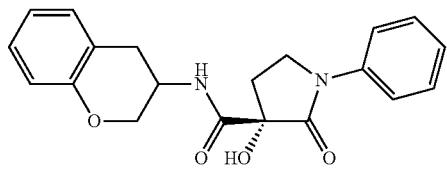<br>(S)-3-Hydroxy-2-oxo-1-phenylpyrrolidine-3-carboxylic acid chroman-3-yl amide |
| "A321" | 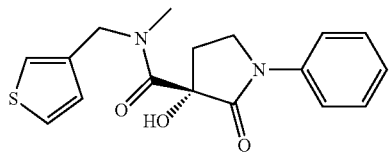<br>(S)-3-Hydroxy-2-oxo-1-phenylpyrrolidine-3-carboxyl methyl thiophen-3-ylmethyl amide |
| "A322" | 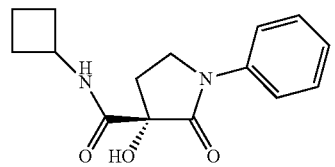<br>(S)-3-Hydroxy-2-oxo-1-phenylpyrrolidine-3-carboxylic acid cyclobutyl amide |
| "A323" | 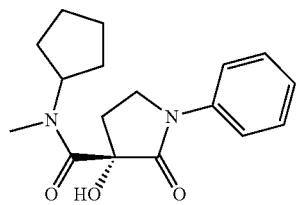<br>(S)-3-Hydroxy-2-oxo-1-phenylpyrrolidine-3-carboxylic acid cyclopentyl methyl amide |
| "A324" | 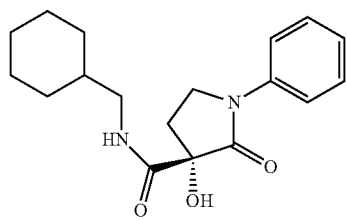<br>(S)-3-Hydroxy-2-oxo-1-phenylpyrrolidine-3-carboxylic acid cyclohexylmethyl amide |

-continued

| Compound No. | Structure/name |
|---|---|

"A325"

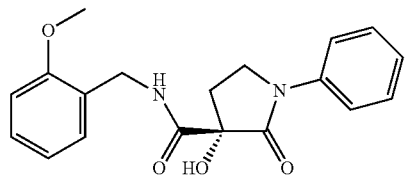

(S)-3-Hydroxy-2-oxo-1-phenylpyrrolidine-
3-carboxylic acid 2-methoxybenzyl amide

"A326"

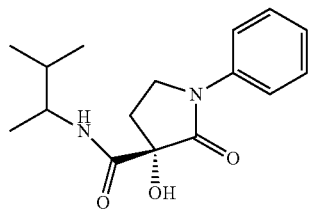

(S)-3-Hydroxy-2-oxo-
1-phenylpyrrolidine-3-
carboxylic acid (1,2-
dimethylpropyl) amide

"A327"

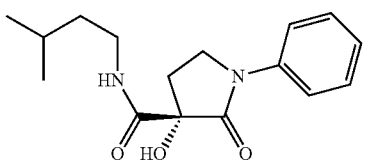

(S)-3-Hydroxy-2-oxo-1-phenylpyrrolidine-3-
carboxylic acid (3-methylbutyl) amide

"A328"

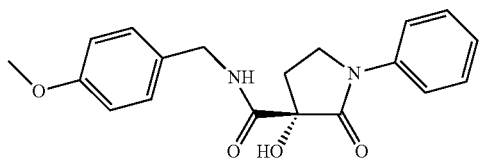

(S)-3-Hydroxy-2-oxo-1-phenylpyrrolidine-
3-carboxylic acid methoxybenzyl amide

"A329"

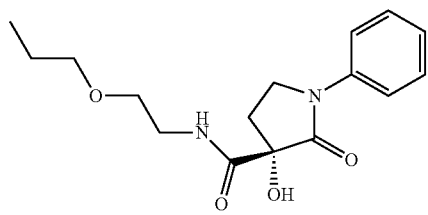

(S)-3-Hydroxy-2-oxo-1-phenylpyrrolidine-
3-carboxylic acid (2-propoxyethyl) amide

| Compound No. | Structure/name |
|---|---|
| "A330" | 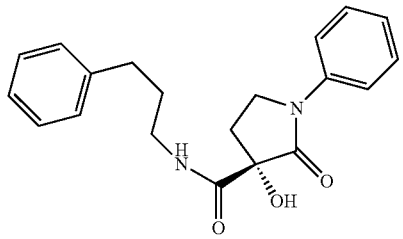<br>(S)-3-Hydroxy-2-oxo-1-phenylpyrrolidine-3-carboxylic acid (3-phenylpropyl) amide |
| "A331" | 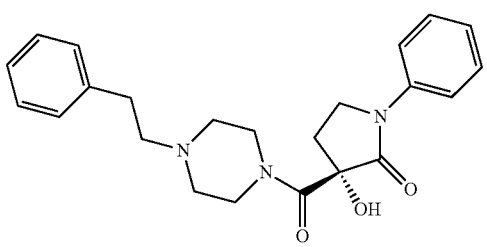<br>(S)-3-Hydroxy-3-(4-phenethylpiperazine-1-carbonyl)-1-phenyl-pyrrolidin-2-one |
| "A332" | 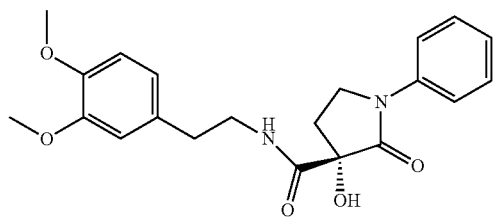<br>(S)-3-Hydroxy-2-oxo-1-phenylpyrrolidine-3-carboxylic acid [2-(3,4-dimethoxyphenyl)ethyl] amide |
| "A333" | 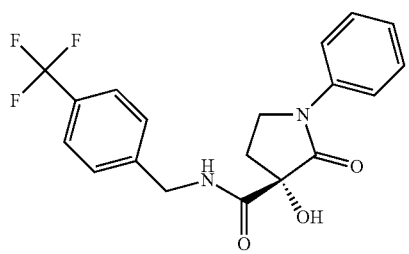<br>(S)-3-Hydroxy-2-oxo-1-phenylpyrrolidine-3-carboxylic acid 4-trifluoromethylbenzyl amide |
| "A334" | 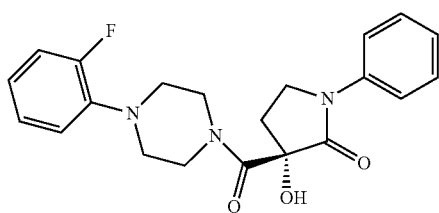<br>(S)-3-[4-(2-Fluorophenyl)piperazine-1-carbonyl]-3-hydroxy-1-phenylpyrrolidin-2-one |

| Compound No. | Structure/name |
|---|---|
| "A335" | 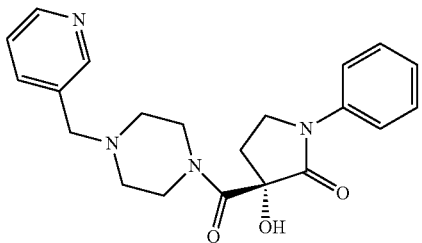<br>(S)-3-Hydroxy-1-phenyl-3-(4-pyridin-3-ylmethylpiperazine-1-carbonyl)pyrrolidin-2-one |
| "A336" | 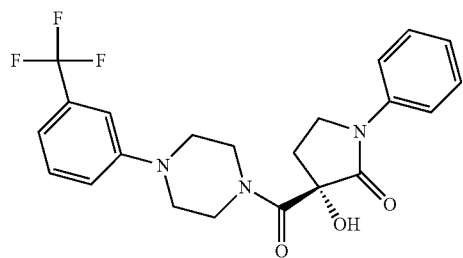<br>(S)-3-Hydroxy-1-phenyl-3-[4-(3-trifluoromethylphenyl)-piperazine-1-carbonyl]pyrrolidin-2-one |
| "A337" | 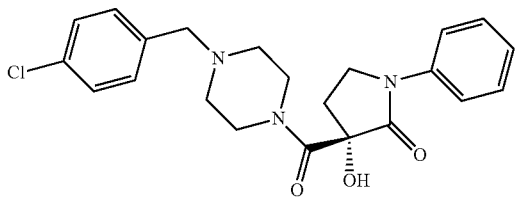<br>(S)-3-[4-(4-Chlorobenzyl)piperazine-1-carbonyl]-3-hydroxy-1-phenylpyrrolidin-2-one |
| "A338" | 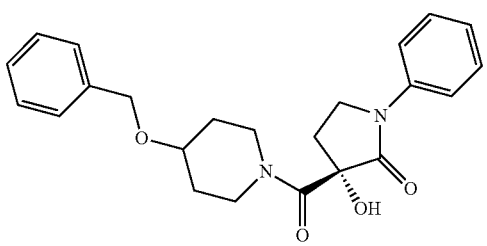<br>(S)-3-(4-Benzyloxypiperidine-1-carbonyl)-3-hydroxy-1-phenyl-pyrrolidin-2-one |
| "A339" | 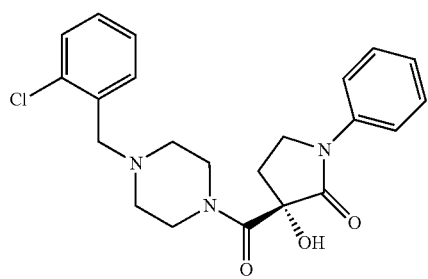<br>(S)-3-[4-(2-Chlorobenzyl)piperazine-1-carbonyl]-3-hydroxy-1-phenylpyrrolidin-2-one |

| Compound No. | Structure/name |
|---|---|
| "A340" | 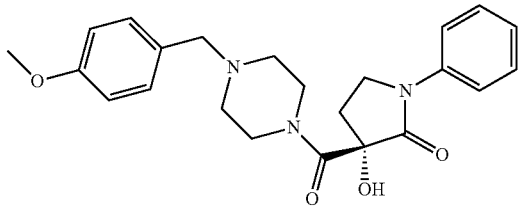<br>(S)-3-Hydroxy-3-[4-(4-methoxybenzyl)piperazine-1-carbonyl]-1-phenylpyrrolidin-2-one |
| "A341" | 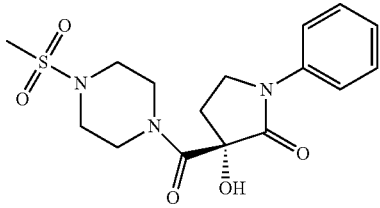<br>(S)-3-Hydroxy-3-(4-methanesulfonylpiperazine-1-carbonyl)-1-phenylpyrrolidin-2-on |
| "A342" | 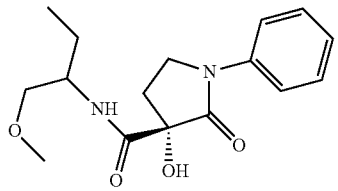<br>(S)-3-Hydroxy-2-oxo-1-phenylpyrrolidine-3-carboxylic acid (1-methoxymethylpropyl) amide |
| "A343" | 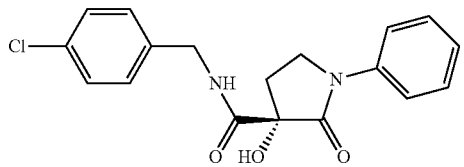<br>(S)-3-Hydroxy-2-oxo-1-phenylpyrrolidine-3-carboxylic acid 4-chlorobenzyl amide |
| "A344" | 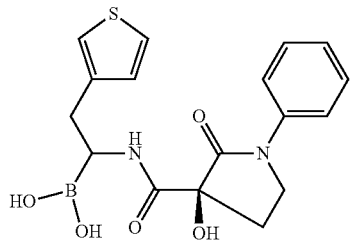<br>[1-[[(3S)-3-hydroxy-2-oxo-1-phenylpyrrolidine-3-carbonyl]amino]-2-(3-thienyl)ethyl]boronic acid |

| Compound No. | Structure/name |
|---|---|
| "A345" | 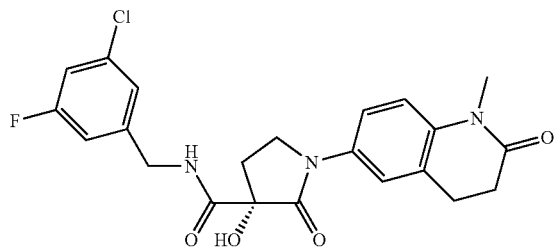<br>(S)-3-Hydroxy-1-(1-methyl-2-oxo-1,2,3,4-tetrahydroquinolin-6-yl)-2-oxopyrrolidine-3-carboxylic acid 3-chloro-5-fluorobenzyl amide |
| | or |
| "A346" | 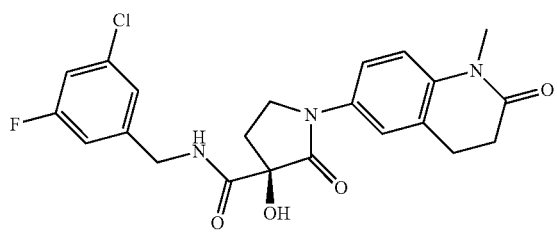<br>(R)-3-Hydroxy-1-(1-methyl-2-oxo-1,2,3,4-tetrahydroquinolin-6-yl)-2-oxopyrrolidine-3-carboxylic acid 3-chloro-5-fluorobenzyl amide | or a pharmaceutically acceptable salt, tautomer or stereoisomer thereof.

9. A process for preparing a compound of formula I according to claim 1 or a pharmaceutically acceptable salt, tautomer or stereoisomer thereof, comprising a) reacting a compound of formula II

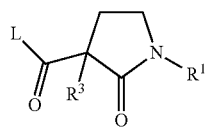   II in which $R^1$ and $R^3$ have the meanings indicated for the compound of formula I, and L denotes Cl, Br, I or a free or reactive functionally-modified OH group, with a compound of formula III

   III in which $R^2$ and $R^4$ have the meanings indicated for the compound of formula I, or b) oxidizing a compound of formula IV

IV in which $R^1$, $R^2$ and $R^4$ have the meanings indicated for the compound of formula I, to give a compound of formula I in which $R^3$ denotes OH, or c) converting a compound of formula I wherein $R^3$ is OH or halogen into a compound of formula I wherein $R^3$ is halogen or $N_3$ by replacing the OH group with a halogen atom, or by replacing the halogen atom with $N_3$, and/or converting a base or acid of the compound of formula I into one of its salts.

10. A pharmaceutical composition comprising at least one compound of the formula I according to claim 1 or a pharmaceutically acceptable salt, tautomer or stereoisomer thereof, and one or more excipients and/or adjuvants.

11. A method for the treatment of a disease whose treatment is effected by the modulation, regulation and/or inhibition of methionine aminopeptidase MetAP-2, which disease is selected from the group consisting of tumours, tumour metastases, proliferative diseases of the mesangial cells, haemangioma, proliferative retinopathy, rheumatoid arthritis, atherosclerotic neovascularisation, psoriasis, ocular neovascularisation, osteoporosis, diabetes, obesity, lymphoid leukaemia, lymphoma, malaria and prostate hypertrophy, comprising administering to a subject in need thereof an effective amount of a compound of claim 1.

12. A method according to claim 11, where the tumour disease is a tumour of the squamous epithelium, the bladder, the stomach, the kidneys, of head and neck, the oesophagus, the cervix, the thyroid, the intestine, the liver, the brain, the prostate, the urogenital tract, the lymphatic system, the larynx, the lung, or the skin, or is monocytic leukaemia, pancreatic cancer, breast carcinoma, acute myeloid leukaemia, chronic myeloid leukaemia, acute lymphatic leukaemia, chronic lymphatic leukaemia, Hodgkin's lymphoma, or non-Hodgkin's lymphoma.

13. A method according to claim 11, wherein a tumor is treated, and where the effective amount of a compound of formula I is administered in combination with a compound from the following groups 1-10: 1) oestrogen receptor modulator, 2) androgen receptor modulator, 3) retinoid receptor modulator, 4) cytotoxic agent, 5) antiproliferative agent, 6) prenyl-protein transferase inhibitor, 7) HMG-CoA reductase inhibitor, 8) HIV protease inhibitor, 9) reverse transcriptase inhibitor and 10) further angiogenesis inhibitors.

14. A method according to claim 11, wherein a tumor is treated, and where the effective amount of a compound of formula I is administered in combination with radiotherapy and a compound from the following groups 1-10: 1) oestrogen receptor modulator, 2) androgen receptor modulator, 3) retinoid receptor modulator, 4) cytotoxic agent, 5) antiproliferative agent, 6) prenyl-protein transferase inhibitor, 7) HMG-CoA reductase inhibitor, 8) HIV protease inhibitor, 9) reverse transcriptase inhibitor and 10) further angiogenesis inhibitors.

15. A method according to claim 11, where the tumour disease is lung adenocarcinoma, small-cell lung carcinoma or glioblastoma.

* * * * *